United States Patent
Choudhury et al.

(10) Patent No.: US 11,873,533 B2
(45) Date of Patent: Jan. 16, 2024

(54) METHOD OF DETECTING AND QUANTIFYING GEONOMIC AND GENE EXPRESSION ALTERATIONS USING RNA

(71) Applicant: LUCENCE LIFE SCIENCES PTE. LTD., Singapore (SG)

(72) Inventors: Yukti Choudhury, Singapore (SG); Chae Yin Cher, Singapore (SG); Jia Min Ho, Singapore (SG); Min-Han Tan, Singapore (SG); Kao Chin Ngeow, Singapore (SG); Pannapa Pinweha, Singapore (SG)

(73) Assignee: LUCENCE LIFE SCIENCES PTE. LTD., Singapore (SG)

( * ) Notice: Subject to any disclaimer, the term of this patent is extended or adjusted under 35 U.S.C. 154(b) by 78 days.

(21) Appl. No.: 17/825,669

(22) Filed: May 26, 2022

(65) Prior Publication Data
US 2023/0250482 A1 Aug. 10, 2023

(30) Foreign Application Priority Data

Sep. 6, 2021 (SG) .......................... 10202109756V

(51) Int. Cl.
*C12P 19/34* (2006.01)
*C12Q 1/6886* (2018.01)
(Continued)

(52) U.S. Cl.
CPC ....... *C12Q 1/6886* (2013.01); *C12N 15/1065* (2013.01); *C12N 15/1096* (2013.01);
(Continued)

(58) Field of Classification Search
CPC .................................................. C12Q 1/6869
See application file for complete search history.

(56) References Cited

U.S. PATENT DOCUMENTS

| 2013/0210663 A1* | 8/2013 | Coverley | C07K 16/18 435/7.1 |
| 2014/0066317 A1* | 3/2014 | Talasaz | C12N 15/1072 506/2 |

(Continued)

FOREIGN PATENT DOCUMENTS

WO 2020206184 A1 10/2020

OTHER PUBLICATIONS

Hasegawa et al., Cancer Science 112, 4393-4403 (epub Aug. 18, 2021). (Year: 2021).*

(Continued)

*Primary Examiner* — Kenneth R Horlick
(74) *Attorney, Agent, or Firm* — DINSMORE & SHOHL LLP

(57) ABSTRACT

Disclosed is a method of detecting and quantifying genomic and gene expression alterations using RNA in a biological sample. The disclosed method may include determining presence or absence of the genomic alteration and/or determining presence or absence of the gene expression and/or quantifying the level of the gene expression, by performing variant calling of the sequence alignment obtained from the disclosed method. Variant calling may comprise the steps of identifying differences between a consensus read and a reference genome based on the sequence alignment from the disclosed method; and determining the read count of sequence alignments comprising genomic alteration. The genomic alteration may be an insertion (such as a duplication), a deletion, a single nucleotide variant, or combinations thereof. Also disclosed is a kit for detecting and quantifying genomic and gene expression alterations using RNA in a biological sample.

23 Claims, 33 Drawing Sheets

Specification includes a Sequence Listing.

(51) Int. Cl.
*C12N 15/10* (2006.01)
*C12Q 1/6869* (2018.01)
*C12Q 1/6806* (2018.01)

(52) U.S. Cl.
CPC ......... *C12Q 1/6806* (2013.01); *C12Q 1/6869* (2013.01); *C12Q 2600/158* (2013.01); *C12Q 2600/16* (2013.01)

(56) References Cited

U.S. PATENT DOCUMENTS

| | | | |
|---|---|---|---|
| 2014/0272956 A1* | 9/2014 | Huang | C12Q 1/6886 435/6.11 |
| 2015/0044687 A1* | 2/2015 | Schmitt | C12Q 1/6806 435/6.12 |
| 2016/0275240 A1 | 9/2016 | Huelga et al. | |
| 2020/0024644 A1* | 1/2020 | Wang | C40B 40/06 |
| 2020/0048694 A1* | 2/2020 | Godwin | C12Q 1/6869 |

OTHER PUBLICATIONS

International Search Report dated Dec. 28, 2022 in reference to co-pending Singapore Application PCT/SG2022/050354 filed May 26, 2022.
Written Opinion dated Dec. 28, 2022 in reference to co-pending Singapore Application PCT/SG2022/050354 filed May 26, 2022.

* cited by examiner

| Sample | Diagnosis | cfDNA per ml plasma (ng) | cfRNA per ml plasma (ng) |
|---|---|---|---|
| Ca-1 | Metastatic Prostate Cancer | 145 | 43.7 |
| Ca-2 | Metastatic Lung Cancer | 26.6 | 27.1 |
| Ca-3 | Metastatic Pancreatic Cancer | 25.8 | 61.5 |
| Ca-4 | Metastatic Prostate Cancer | 356.5 | 52.1 |
| Ca-5 | Metastatic Lung Cancer | 2156 | 96.8 |
| Hth-1 | Healthy | 7.92 | 8.2 |
| Hth-2 | Healthy | 4.76 | 5.71 |
| Hth-3 | Healthy | 7.37 | 3.33 |

Fig. 4

|  | cfDNA fusion+ | cfDNA fusion- |
|---|---|---|
| cfRNA fusion+ | 12 | 5 |
| cfRNA fusion- | 1 | 27 |

Fig. 14A

| cfDNA and cfRNA fusion+ | Only cfRNA fusion+ | Only cfDNA fusion- |
|---|---|---|
| EML4-ALK (n = 4) | LMNA-NTRK1 (n = 2) | KIF5B-RET (n = 1) |
| MET exon 14 skipping (n = 3) | CD74-NRG1 (n = 1) | |
| CD74-ROS1 (n = 2) | ETV6-MET (n = 1) | |
| NCOA4-RET (n =1) | ETV6-NTRK3 (n = 1) | |
| CCDC6-RET (n=1) | | |
| FGFR3-TACC3 (n=1) | | |
| Co-occurring fusions detected in cfRNA | | |
| EML4-ALK* and EWSR1-FLI1 | | |
| EML4-ALK*, SQSTM1-MET and CCDC6-RET | | |
| CD74-ROS1* and SND1-BRAF | | |

Fig. 14B

| Sample | Sample Type | Diagnosis | Mutation | Mutation Type | Mutant expression (Mutant read counts) | Wild-type expression (Wild-type read counts) | VAF (Mutant read counts)/(Total read counts) |
|---|---|---|---|---|---|---|---|
| F_22-274 | FFPE Tumor Tissue | Metastatic Pancreatic Cancer | KRAS c.35G>A p.G12D | SNV | 9142 | 13373 | 41% |
| F_22-83 | FFPE Tumor Tissue | Metastatic Endometrial Cancer | KRAS c.35G>T p.G12V | SNV | 424 | 885 | 32% |
| F_22-137 | FFPE Tumor Tissue | Metastatic Lung Cancer | EGFR c.2311_2319dup p.N771_H773dup | Insertion | 40628 | 26099 | 61% |
| F_22-55 | FFPE Tumor Tissue | Localised Lung Cancer | EGFR c.2240_2257del p.L747_P753delinsS | Deletion | 4266 | 369 | 92% |

Fig. 18A

| Sample | Sample Type | Diagnosis | Mutation | Mutation Type | Mutant expression (Mutant read counts) | Wild-type expression (Wild-type read counts) | VAF (Mutant read counts)/(Total read counts) |
|---|---|---|---|---|---|---|---|
| P_19-2372 | Plasma | Metastatic Lung Cancer | KRAS c.34G>T p.G12C | SNV | 67 | 1100 | 6% |
| P_20-953 | Plasma | Metastatic Lung Cancer | EGFR c.2573T>G p.L858R | SNV | 78 | 82 | 49% |
| P_22-265 | Plasma | Metastatic Lung Cancer | EGFR c.2573T>G p.L858R | SNV | 112 | 48 | 70% |

Fig. 18B

METHOD OF DETECTING AND QUANTIFYING GEONOMIC AND GENE EXPRESSION ALTERATIONS USING RNA

CROSS-REFERENCE TO RELATED APPLICATIONS

This application claims priority to Singapore Patent Application No. 10202109756V, filed Sep. 6, 2021, the entire contents of which are incorporated by reference.

FIELD OF INVENTION

The present invention relates to the detection and quantification of nucleic acid. In particular, the present invention relates to the detection and quantification of RNA.

BACKGROUND

Circulating biomarkers are promising tools used for cancer detection, prognostication and prediction of cancer treatment response. These circulating biomarkers typically include DNA samples such as cell-free DNA (cfDNA) and circulating-tumor cells. It is known that various RNA molecules are also potential biomarkers for the diagnosis and prognosis of various diseases such as cancer and are useful for early cancer diagnosis, tumor progression monitor, and prediction of therapy response. It is also known that cancer cells release cell-free RNA (cfRNA) into the body circulation. These cancer-associated cfRNA, also known as circulating-tumor RNA (ctRNA) can be found in the serum and blood plasma of cancer patients. While both cfDNA and cfRNA are promising cancer biomarkers, the measurement of cfDNA is traditionally preferred due to its stability in biological fluids. Despite the discovery of RNA in blood plasma and serum over 20 years ago, there is still a general perception that extracellular RNA in blood is extremely unstable and highly fragmented, given the relative instability of RNA compared to DNA, which in itself is unstable when fragmented in the blood, due to the presence of a high concentration of ribonucleases in the blood circulation. Multiple studies have documented the presence of tumor-specific circulating RNA (ctRNA) in serum and plasma in cancer patients. Current non-oncology clinical applications of cfRNA include the measurement of maternal and fetal cfRNA transcripts to monitor longitudinal phenotypic changes in both the mother and the fetus and to assess fetal gestational age. It is known that in blood circulation, cfRNA occur in free form, bound to proteins or lipids, or as exosomes protected in various types of membrane-derived microvesicles, making them highly stable. It is plausible that plasma cfRNA is a mixture of RNA protected by RNA binding proteins and RNA contained within extracellular vesicles. The wide availability of cfRNA in plasma, serum and many other bodily fluids and their paradoxical stability makes them potential candidates for the development of biomarkers for rapid, sensitive and inexpensive diagnostics. Furthermore, detection of ctRNA provides the same mutational information as ctDNA, but additionally, it can also provide quantitative information about the expression levels of target genes of interest, and can potentially increase the sensitivity of detection of variants with low allelic frequencies due to the overexpression of tumor-specific transcripts. Lastly, the expression of various ctRNA species is dysregulated due to uncontrolled cell proliferation, rendering it a potential valuable tool for cancer detection. At present, the most common technique for detection of cfRNA is using quantitative Real-time Polymerase Chain Reaction (qRT-PCR). However, methods involving qRT-PCR are often limited by their sensitivity when assaying low input samples. NGS may be more well-suited due the ability to detect novel cfRNAs and differentiate RNA isoforms. With hybridization-based library preparation methods, sequence-specific biases due to enzymatic ligation during library construction step leads to biased representation of transcripts, particularly during analysis of small RNA. Targeted NGS assays such as hybridization capture or amplicon sequencing may also allow for sensitive quantification of cfRNAs (as opposed to whole transcriptome analysis with low conversion efficiency).

Many cancer genes exhibit genomic alterations, and these genomic alteration events have been discovered in a wide variety of tumors. Targeted DNA-based next generation sequencing techniques specifically designed to detect rearrangements in kinases can effectively detect oncogenic kinase fusions with high confidence. However, there are technical limitations to the ability of such DNA-based assays to detect certain genomic alterations, such as gene fusions. DNA-based assays can only identify fusions in genes where the genomic rearrangements occur in typically short introns effectively covered in the panel. Some clinically important fusions arise from rearrangements in very long introns, the complete coverage of which would significantly compromise coverage of the remainder of the genes on the panel. Hence, there are gaps in the coverage of certain introns resulting in blind spots in the detection of potential rearrangement breakpoint. Fusion detection using DNA does not provide direct evidence that the rearrangement produces a fusion expressed at the mRNA level, a particular problem for rearrangements that appear non-canonical at the genomic DNA level. In fact, in one study in lung cancer tissue samples, it was shown that by using RNA sequencing, alterations were detected in 14% (36/254) cases which were otherwise negative for clinically actionable mutations by DNA sequencing. For example, gene fusion events involving Neurotrophic Receptor Tyrosine Kinase (NTRK) gene (NTRK1/2/3) and neuregulin-1 (NRG1) gene cannot be effectively covered in a targeted DNA sequencing panel without compromising on the cost of sequencing and the coverage of the remaining genes in the sequencing panel.

Apart from detecting genomic alterations events, the ability to accurately quantify genomic expression of relevant cancer biomarkers non-invasively is important for predicting the response to cancer therapies and making the appropriate treatment decision. For example, the gene expression level of Programmed death-ligand 1 (PD-L1) is a predictive cancer biomarker used to identify cancer patients with a greater likelihood of responding to immunotherapy. PD-L1 is also a potential predictive biomarker to measure the sensitivity of tumors to immune checkpoint blockade drug inhibitors such as anti-PD-1 inhibitors (pembrolizumab and nivolumab), anti-cytotoxic T-lymphocyte-associated protein 4 (CTLA-4) inhibitors, (ipilimumab and tremelimumab) and anti-programmed death protein 1 (PD-1) (atezolizumab, durvalumab and avelumab). Other genetic biomarkers that are useful for predicting the likelihood of responding to immune checkpoint inhibitor therapy include T cell immunoglobulin and mucin domain-containing protein 3 (TIM-3), Lymphocyte Activating 3 (LAG-3) and cytotoxic T-lymphocyte-associated protein 4 (CTLA-4). The ability to quantify the expression of these target biomarkers longitudinally and non-invasively can be very useful for monitoring treatment response and making treatment decisions.

Conventional assays routinely detect for genomic alterations at the DNA level, limiting the scope of detection to DNA genomic alterations such as mutations and quantifying genomic copy number changes.

Thus, there is a need to provide a method for sensitive detection and quantification of genomic alteration events and expression of genes associated with disease (such as cancer) that overcomes, or at least ameliorates, one or more of the disadvantages described above. There is a need to provide a method to simultaneously detect genomic alterations such as structural rearrangements, and gene expression using an alternative sample input such as RNA (such as circulating cell-free RNA (cfRNA)).

SUMMARY

In one aspect, the present disclosure refers to a method of detecting genomic alteration and/or detecting gene expression and/or quantifying a level of gene expression using RNA in a biological sample, comprising:
(a) extracting RNA from the biological sample and converting the RNA to complementary DNA (cDNA);
(b) performing a plurality of multiplexed PCR reactions on the converted cDNA using
 (I) a plurality of forward and reverse primer pairs specific to a plurality of target genes that are capable of undergoing genomic alteration,
  wherein each forward primer of the plurality of forward and reverse primer pairs specific to the plurality of target genes that are capable of undergoing genomic alteration is complementary to a sequence located about base pairs upstream of an exonic junction of each target gene that is capable of undergoing genomic alteration,
  wherein each reverse primer of the plurality of forward and reverse primer pairs specific to the plurality of target genes that are capable of undergoing genomic alteration is complementary to a sequence located about base pairs downstream of an exonic junction of each target gene that is capable of undergoing genomic alteration,
  wherein each reverse primer of the plurality of forward and reverse primer pairs specific to the plurality of target genes that are capable of undergoing genomic alteration comprises a barcode sequence on its 5' end, wherein the barcode sequence of each reverse primer corresponding to each target gene that is capable of undergoing genomic alteration is different, and/or
 (II) a plurality of forward and reverse primer pairs specific to a plurality of control housekeeping genes, wherein:
  (i) each forward primer of the plurality of forward and reverse primer pairs specific to the plurality of control housekeeping genes is complementary to a sequence spanning an exon-exon junction of each control housekeeping gene,
   wherein each reverse primer of the plurality of forward and reverse primer pairs specific to the plurality of control housekeeping genes is complementary to a sequence about 100 base pairs downstream of the sequence spanning the exon-exon junction of each control housekeeping gene,
   wherein each reverse primer of the plurality of forward and reverse primer pairs specific to the plurality of control housekeeping genes comprises a barcode sequence on its 5' end, wherein the barcode sequence of each reverse primer corresponding to each control housekeeping gene is different;
  (ii) each reverse primer of the plurality of forward and reverse primer pairs specific to the plurality of control housekeeping genes is complementary to a sequence spanning an exon-exon junction of each control housekeeping gene,
   wherein each forward primer of the plurality of forward and reverse primer pairs specific to the plurality of control housekeeping genes is complementary to a sequence about 100 base pairs downstream of the sequence spanning the exon-exon junction of each control housekeeping gene,
   wherein each reverse primer of the plurality of forward and reverse primer pairs specific to the plurality of control housekeeping genes comprises a barcode sequence on its 5' end, wherein the barcode sequence of each reverse primer corresponding to each control housekeeping gene is different;
  (iii) each forward and each reverse primer of the plurality of forward and reverse primer pairs specific to the plurality of control housekeeping genes is complementary to consecutive sequences spanning an exon-exon junction of each control housekeeping gene,
   wherein each reverse primer of the plurality of forward and reverse primer pairs specific to the plurality of control housekeeping genes comprises a barcode sequence on its 5' end, wherein the barcode sequence of each reverse primer corresponding to each control housekeeping gene is different, and/or
 (III) a plurality of primer sets specific to a plurality of target genes related to protein expression,
  wherein each primer set comprises a plurality of forward and reverse primer pairs specific to each target gene related to protein expression, wherein:
  (i) each forward primer of the of the plurality of forward and reverse primer pairs specific to each target gene related to protein expression is complementary to a sequence spanning an exon-exon junction of each target gene related to protein expression,
   wherein each reverse primer of the of the plurality of forward and reverse primer pairs specific to each target gene related to protein expression is complementary to a sequence about 100 base pairs downstream of the sequence spanning the exon-exon junction of each target gene related to protein expression,
   wherein each reverse primer of the plurality of forward and reverse primer pairs specific to each target gene related to protein expression comprises a barcode sequence on its 5' end, wherein the barcode sequence of each reverse primer corresponding to each target gene related to protein expression is different,
  (ii) each reverse primer of the plurality of forward and reverse primer pairs specific to the plurality of target genes related to protein expression is complementary to a sequence spanning an exon-exon junction of each target gene related to protein expression, wherein each forward primer of the plurality of forward and reverse primer pairs specific to the plurality of target genes related to protein expression is complementary to a sequence about 100 base pairs downstream of the sequence spanning the exon-exon junction of each target gene related to protein expression, wherein each reverse primer of the plurality of forward and reverse primer pairs specific to the plurality of target genes related to protein expression comprises a barcode sequence on its 5' end, wherein the barcode sequence of each reverse primer corresponding to each target gene related to protein expression is different;

(iii) each forward and each reverse primer of the plurality of forward and reverse primer pairs specific to the plurality of target genes related to protein expression is complementary to consecutive sequences spanning an exon-exon junction of each target gene related to protein expression, wherein each reverse primer of the plurality of forward and reverse primer pairs specific to the plurality of target genes related to protein expression comprises a barcode sequence on its 5' end, wherein the barcode sequence of each reverse primer corresponding to each target gene related to protein expression is different, thereby generating a plurality of amplicons;
(c) purifying the plurality of amplicons from step (b);
(d) amplifying the purified product from step (c) by using universal indexed adapter primers to generate a sequencing library;
(e) purifying the sequencing library obtained from step (d);
(f) subjecting the purified sequencing library from step (e) to multiplex sequencing on a next-generation sequencing platform to obtain a plurality of sequencing reads;
(g) deriving a consensus read of each sequence from the plurality of sequencing reads obtained from step (f);
(h) performing a sequence alignment of the consensus read obtained from step (g) to a reference genome,
  (I) if the sequence alignment results in a partial alignment to the reference genome of an exon from a first gene and a partial alignment to the reference genome of an exon from a second gene, then:
    (i) determining the sequence alignment as a split read,
    (ii) counting/enumerating the number of split reads from step (h)(I)(i) that supports a fusion junction, and
    (iii) if the number of split reads from step (h)(I)(ii) is two or more, then determining the first gene and the second gene as fusion partners,
  (II) if the sequence alignment results in an alignment to the reference genome of the control housekeeping gene, then:
    (i) determining the sequence alignment as a consensus read of the control housekeeping gene,
    (ii) counting/enumerating consensus read pairs of the control housekeeping gene from step (h)(II)(i), and
    (iii) determining the level of gene expression of the control housekeeping gene,
  (III) if the sequence alignment results in an alignment to the reference genome of the target gene related to protein expression,
    (i) determining the sequence alignment as a consensus read of the target gene related to protein expression,
    (ii) counting/enumerating consensus read pairs of the target gene related to protein expression from step (h)(III)(i), and
    (iii) determining the level of gene expression of the target gene related to protein expression;
(i) determining presence or absence of the genomic alteration and/or determining presence or absence of the gene expression and/or quantifying the level of the gene expression based on the sequence alignment from step (h).

In another aspect, the present disclosure refers to a kit for detecting genomic alteration and/or detecting gene expression and/or quantifying a level of gene expression using RNA in a biological sample according to the method disclosed herein, wherein the kit comprises:

a plurality of forward and reverse primer pairs specific to a plurality of target genes that are capable of undergoing genomic alteration as defined in the method disclosed herein, a plurality of forward and reverse primer pairs specific to a plurality of control housekeeping genes as defined in the method disclosed herein, and a plurality of primer sets specific to a plurality of target genes related to protein expression as defined in the method disclosed herein.

BRIEF DESCRIPTION OF THE DRAWINGS

The invention will be better understood with reference to the detailed description when considered in conjunction with the non-limiting examples and the accompanying drawings, in which:

FIGS. 2A-2B illustrate examples of primer design of the disclosed method, wherein FIG. 2A illustrates examples of primer design for capturing control housekeeping genes (left panel) and expression genes (right panel) in cfRNA. At least one primer of a primer pair spans an exon-exon junction, to prevent unintended amplification of cfDNA and the resulting amplicons are approximately 100 base pairs in length. It should be noted that the primer pairs for the housekeeping genes differ from that of the expression genes, and FIG. 2B illustrates an example of a forward primer and a reverse primer designed to bind to two different exons, intervened by an intron >5000 base pairs in length.

FIGS. 3A-3D show the size and concentration analysis of cfRNA from plasma total nucleic acid extracts from cancer patients and healthy individuals, wherein FIG. 3A shows the size and concentration analysis of cfRNA from plasma total nucleic acid extracts from a cancer patient (sample A), FIG. 3B shows the size and concentration analysis of cfRNA from plasma total nucleic acid extracts from another cancer patient (sample B), FIG. 3C shows the size and concentration analysis of cfRNA from plasma total nucleic acid extracts from a healthy individual (sample C), and FIG. 3D shows the size and concentration analysis of cfRNA from plasma total nucleic acid extracts from another healthy individual (sample D). Bioanalyzer RNA 6000 Pico kit or the High Sensitivity RNA Screentape on the 4200 Tapestation were used to quantify and profile the samples. The total concentration of cfRNA (representative of abundance) is generally higher in the representative plasma extracted from cancer patients, relative to those extracted from healthy individuals.

FIG. 4 shows the comparison of yield for cfDNA and cfRNA in total nucleic acid extracts from plasma extracted from cancer patients and healthy individuals.

FIGS. 5A-5C show an example of the fragmentation of extracted H2228 cell line RNA by physical shearing of large size nucleotides (>1500 nucleotides) into smaller size to mimic cfRNA fragment size. Bioanalyzer RNA 6000 Pico kit or the High Sensitivity RNA Screentape on the 4200 Tapestation were used to quantify and profile the samples, wherein FIG. 5A shows the fragmentation profile of extracted H2228 cell line RNA, FIG. 5B shows the resulting fragmentation profile of fragmented H2228 cell line RNA, and FIG. 5C shows the fragmentation profile of plasma cfRNA. The resulting fragmentation profile of H2228 cell line RNA is similar to that of plasma cfRNA, with a dominant RNA peak at 119 nucleotides (represented by arrows).

FIGS. 6A-6B illustrate the detection of EML4-ALK fusion in 1 ng of fragmented H2228 RNA showing the alignment of split reads capturing the fusion break points of exon 6b of EML4 and exon 20 of ALK, wherein FIG. 6A is a visualization of the split read on Integrated Genome Viewer (IGV), and FIG. 6B is a diagrammatic representation showing exonic fusion (from Arriba tool for detection of gene fusions).

FIGS. 8A-8C show detection of TMPRS S2-ERG gene fusion in nucleic acid extracts from a metastatic prostate patient using the cfRNA-based method described herein, compared to a cfDNA-based method, wherein FIG. 8A is an IGV graphic view showing 17 split reads, which supported the presence of intronic breakpoints, detected with the cfDNA-based detection method, FIG. 8B is an IGV graphic report showing 4123 split reads, which supported the presence of corresponding exonic breakpoints, detected with the cfRNA-based method described herein, and FIG. 8C is a diagrammatic representation from Arriba tool showing TMPRS S2-ERG gene fusion.

FIGS. 9A-9C show detection of CCDC6-RET gene fusion in a nucleic acid extract from a metastatic lung cancer patient using the cfRNA-based method described herein, compared to a cfDNA-based method, wherein FIG. 9A is an IGV graphic report showing 12 split reads, which supported the presence of intronic breakpoints, detected with the cfDNA-based detection method, FIG. 9B is an IGV graphic report showing 1474 split reads, which supported the presence of corresponding exonic breakpoints, detected with the cfRNA-based method described herein, and FIG. 9C is a diagrammatic representation from Arriba tool showing CCDC6-RET gene fusion.

FIGS. 10A-10B show the detection of BCR-ABL1 gene fusion in an RNA sample extracted from the peripheral blood cell fraction of an acute lymphoblastic leukaemia clinical sample using the cfRNA-based method described herein, wherein FIG. 10A is an IGV graphic report showing BCR-ABL1 gene fusion, and FIG. 10B is a diagrammatic representation from Arriba tool showing BCR-ABL1 gene fusion.

FIGS. 13A-13C show the identification of actionable driver fusions in untreated lung cancer cases using cfRNA using the method described herein, wherein FIG. 13A shows detection of LMNA-NTRK1 fusion, FIG. 13B shows detection of CD74-NRG1 fusion, and FIG. 13C shows detection of ETV6-NTRK3 fusion in cfRNA in three lung cancer cases, respectively, that were negative for the presence of other driver gene mutations in cfDNA.

FIGS. 14A-14B show fusion detection in 45 lung cancer cases by cfDNA and cfRNA using the method described herein and that additional fusions were identified when cfRNA fraction was used, compared to cfDNA. Clinical samples processed simultaneously using cfRNA and cfDNA were compared for fusion detection, wherein FIG. 14A shows concordance of fusion detection based on cfDNA and cfRNA, showing cfRNA identified additional fusions in 5 cases, and missed 1 fusion detectable by cfDNA. There were 12 cases with concordant fusion detection by both methods, and FIG. 14B lists the range of fusions detected by both cfDNA and cfRNA methods, or by one of the two methods and the detection of multiple co-occurring fusions detected by cfRNA. (*=fusion detected by both cfDNA and cfRNA).

FIGS. 18A-18B show the detection of expressed transcripts containing single nucleotide variation, insertion (e.g. duplication) or deletion mutations using cfRNA-based method described herein, wherein FIG. 18A shows single nucleotide variation, insertion or deletion mutations detected in tissue RNA extracted from FFPE tumor samples, and FIG. 18B shows single nucleotide variation detected in cfRNA extracted from plasma.

DETAILED DESCRIPTION

Figure 1:
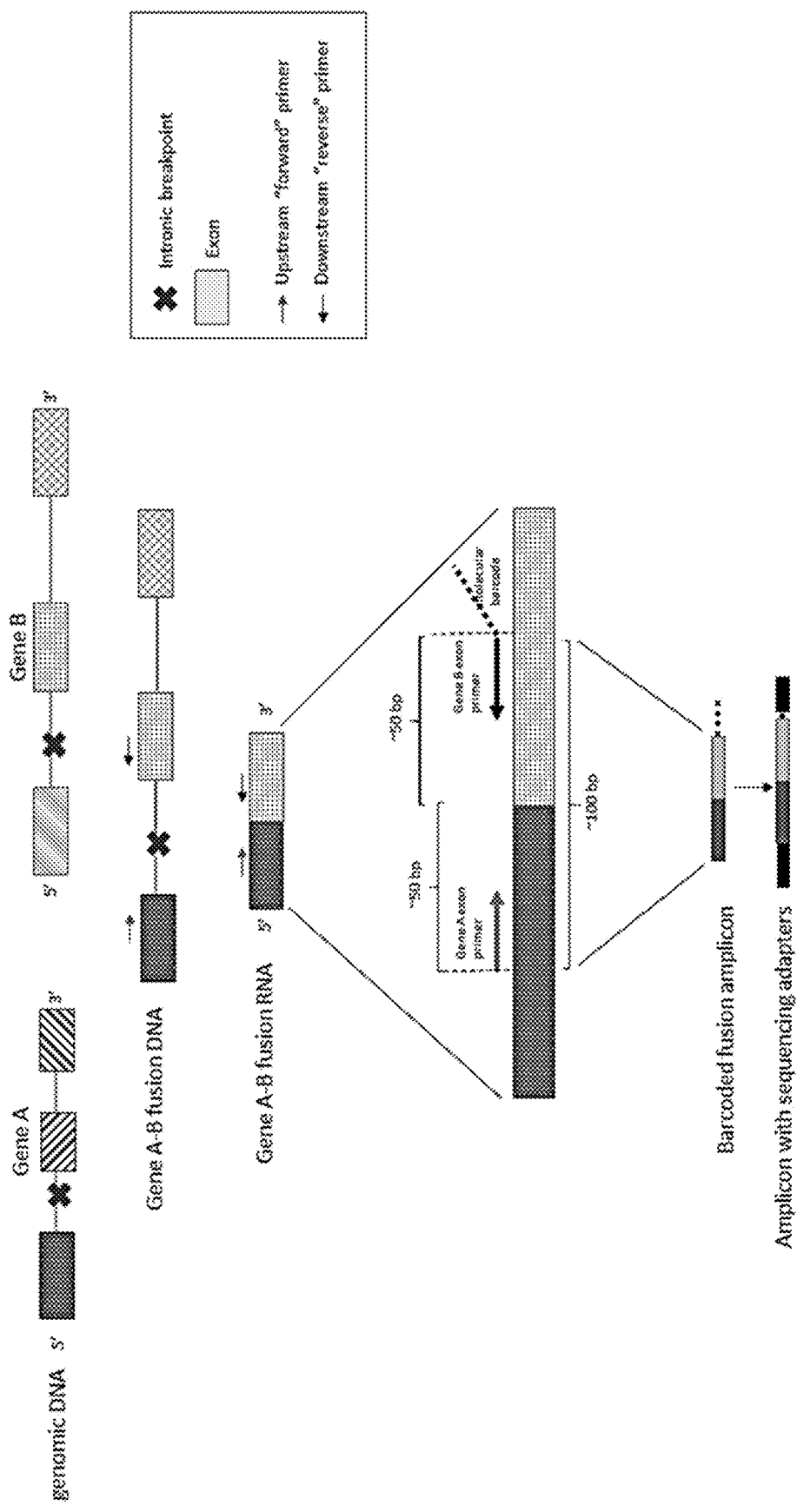
FIG. 1 is a general overview of the cfRNA-based detection method of a gene fusion event resulting from the intronic DNA rearrangement between two genes as described herein. Primers (represented by arrows) are designed to flank exonic junctions of genes known to undergo fusions. Primers (→) are designed such that the if a fusion product is present, the resulting amplicon would be of ~100 base pairs in length to be compatible with the observed cfRNA fragment size in plasma samples.

The disclosed method allows for detection of genomic alteration and gene expression as well as quantifying the level of gene expression of RNA (such as cfRNA) in a biological sample, for the purpose of non-invasive cancer detection, prognostication, and prediction of treatment response. The present disclosure describes a method based on highly multiplexed amplicon-based NGS, that involves the tagging of individual cfRNA molecules using barcode sequences, and the optimized design of amplicons to be compatible with the fragmented nature of cfRNA. The method described herein can be applied to circulating nucleic acid extracts containing both cfDNA and cfRNA, and can detect and quantitate fusion RNA transcript and gene expression simultaneously, in nucleic acid extracts samples. The applicability of cfRNA is extended in the present disclosure with a novel amplicon-based NGS assay combining fusion detection and gene expression monitoring. With hybridization-based library preparation methods sequence-specific biases due to enzymatic ligation during library construction step lead to biased representation of transcripts, particularly during analysis of small amount of input RNA. Targeted NGS assays such as hybridization capture or amplicon sequencing can allow for sensitive quantification of cfRNA. A targeted NGS-based method has a higher conversion efficiency as compared to whole transcriptome analysis, which has disadvantages such as cost and manpower.

In a first aspect, the present disclosure refers to a method of detecting genomic alteration and/or detecting gene expression and/or quantifying a level of gene expression using RNA in a biological sample, comprising:
  (a) extracting RNA from the biological sample and converting the RNA to complementary DNA (cDNA);
  (b) performing a plurality of multiplexed PCR reaction on the converted cDNA using
    (I) a plurality of forward and reverse primer pairs specific to a plurality of target genes that are capable of undergoing genomic alteration,
      wherein each forward primer of the plurality of forward and reverse primer pairs specific to the plurality of target genes that are capable of undergoing genomic alteration is complementary to a sequence located about base pairs upstream of an exonic junction of each target gene that is capable of undergoing genomic alteration,
      wherein each reverse primer of the plurality of forward and reverse primer pairs specific to the plurality of target genes that are capable of undergoing genomic alteration is complementary to a sequence located about base pairs downstream of an exonic junction of each target gene that is capable of undergoing genomic alteration,
      wherein each reverse primer of the plurality of forward and reverse primer pairs specific to the plurality of target genes that are capable of undergoing genomic alteration comprises a barcode sequence on its 5' end,
      wherein the barcode sequence of each reverse primer corresponding to each target gene that is capable of undergoing genomic alteration is different, and/or
    (II) a plurality of forward and reverse primer pairs specific to a plurality of control housekeeping genes, wherein:
      (i) each forward primer of the plurality of forward and reverse primer pairs specific to the plurality of control housekeeping genes is complementary to a sequence spanning an exon-exon junction of each control housekeeping gene,
        wherein each reverse primer of the plurality of forward and reverse primer pairs specific to the plurality of control housekeeping genes is complementary to a sequence about 100 base pairs downstream of the sequence spanning the exon-exon junction of each control housekeeping gene,
        wherein each reverse primer of the plurality of forward and reverse primer pairs specific to the plurality of control housekeeping genes comprises a barcode sequence on its 5' end, wherein the barcode sequence of each reverse primer corresponding to each control housekeeping gene is different;
      (ii) each reverse primer of the plurality of forward and reverse primer pairs specific to the plurality of control housekeeping genes is complementary to a sequence spanning an exon-exon junction of each control housekeeping gene,
        wherein each forward primer of the plurality of forward and reverse primer pairs specific to the plurality of control housekeeping genes is complementary to a sequence about 100 base pairs downstream of the sequence spanning the exon-exon junction of each control housekeeping gene,
        wherein each reverse primer of the plurality of forward and reverse primer pairs specific to the plurality of control housekeeping genes comprises a barcode sequence on its 5' end, wherein the barcode sequence of each reverse primer corresponding to each control housekeeping gene is different;
      (iii) each forward and each reverse primer of the plurality of forward and reverse primer pairs specific to the plurality of control housekeeping genes is complementary to consecutive sequences spanning an exon-exon junction of each control housekeeping gene,
        wherein each reverse primer of the plurality of forward and reverse primer pairs specific to the plurality of control housekeeping genes comprises a barcode sequence on its 5' end, wherein the barcode sequence of each reverse primer corresponding to each control housekeeping gene is different, and/or
    (III) a plurality of primer sets specific to a plurality of target genes related to protein expression,
      wherein each primer set comprises a plurality of forward and reverse primer pairs specific to each target gene related to protein expression, wherein:
      (i) each forward primer of the of the plurality of forward and reverse primer pairs specific to each target gene related to protein expression is complementary to a sequence spanning an exon-exon junction of each target gene related to protein expression
wherein each reverse primer of the of the plurality of forward and reverse primer pairs specific to each target gene related to protein expression is complementary to a sequence about 100 base pairs downstream of the sequence spanning the exon-exon junction of each target gene related to protein expression,
wherein each reverse primer of the plurality of forward and reverse primer pairs specific to each target gene related to protein expression comprises a barcode sequence on its 5' end, wherein the barcode sequence of each reverse primer corresponding to each target gene related to protein expression is different,
(ii) each reverse primer of the plurality of forward and reverse primer pairs specific to the plurality of target genes related to protein expression is complementary to a sequence spanning an exon-exon junction of each target gene related to protein expression,
wherein each forward primer of the plurality of forward and reverse primer pairs specific to the plurality of target genes related to protein expression is complementary to a sequence about 100 base pairs downstream of the sequence spanning the exon-exon junction of each target gene related to protein expression,
wherein each reverse primer of the plurality of forward and reverse primer pairs specific to the plurality of target genes related to protein expression comprises a barcode sequence on its 5' end, wherein the barcode sequence of each reverse primer corresponding to each target gene related to protein expression is different;
(iii) each forward and each reverse primer of the plurality of forward and reverse primer pairs specific to the plurality of target genes related to protein expression is complementary to consecutive sequences spanning an exon-exon junction of each target gene related to protein expression,
wherein each reverse primer of the plurality of forward and reverse primer pairs specific to the plurality of target genes related to protein expression comprises a barcode sequence on its 5' end, wherein the barcode sequence of each reverse primer corresponding to each target gene related to protein expression is different,
thereby generating a plurality of amplicons;
(c) purifying the plurality of amplicons from step (b);
(d) amplifying the purified product from step (c) by using universal indexed adapter primers to generate a sequencing library;
(e) purifying the sequencing library obtained from step (d);
(f) subjecting the purified sequencing library from step (e) to multiplex sequencing on a next-generation sequencing platform to obtain a plurality of sequencing reads;
(g) deriving a consensus read of each sequence from the plurality of sequencing reads obtained from step (f);
(h) performing a sequence alignment of the consensus read obtained from step (g) to a reference genome,
(I) if the sequence alignment results in a partial alignment to the reference genome of an exon from a first gene and a partial alignment to the reference genome of an exon from a second gene, then:
(i) determining the sequence alignment as a split read,
(ii) counting/enumerating the number of split reads from step (h)(I)(i) that supports a fusion junction, and
(iii) if the number of split reads from step (h)(I)(ii) is two or more, then determining the first gene and the second gene as fusion partners,
(II) if the sequence alignment results in an alignment to the reference genome of the control housekeeping gene, then:
(i) determining the sequence alignment as a consensus read of the control housekeeping gene,
(ii) counting/enumerating consensus read pairs of the control housekeeping gene from step (h)(II)(i), and
(iii) determining the level of gene expression of the control housekeeping gene,
(III) if the sequence alignment results in an alignment to the reference genome of the target gene related to protein expression,
(i) determining the sequence alignment as a consensus read of the target gene related to protein expression,
(ii) counting/enumerating consensus read pairs of the target gene related to protein expression from step (h)(III)(i), and
(iii) determining the level of gene expression of the target gene related to protein expression,
(i) determining presence or absence of the genomic alteration and/or determining presence or absence of the gene expression and/or quantifying the level of the gene expression based on the sequence alignment from step (h).

In one example, the disclosed method is used to detect genomic alteration of RNA in a biological sample. For example, the method may be used to detect known and unknown fusions and their quantification, relative to the quantity of control housekeeping genes expression in a given sample. In another example, the disclosed method is used to detect gene expression of RNA in a biological sample. In yet another example, the disclosed method is used to quantify the level of gene expression of RNA in a biological sample. In a further example, the disclosed method is used to simultaneously detect genomic alteration of RNA and detect gene expression of RNA in a biological sample. In a further example, the disclosed method is used to simultaneously detect genomic alteration of RNA and quantify gene expression of RNA in a biological sample. In a further example, the disclosed method is used to simultaneously detect genomic alteration of RNA, detect gene expression of RNA, and quantify gene expression of RNA in a biological sample.

In one example, the disclosed method is used to detect genomic alteration of cfRNA in a biological sample. For example, the method may be used to detect known and unknown fusions and their quantification, relative to the quantity of control housekeeping genes expression in a given sample. In another example, the disclosed method is used to detect gene expression of cfRNA in a biological sample. In yet another example, the disclosed method is used to quantify the level of gene expression of cfRNA in a biological sample. In a further example, the disclosed method is used to simultaneously detect genomic alteration of cfRNA and detect gene expression of cfRNA in a biological sample. In a further example, the disclosed method is used to simultaneously detect genomic alteration of cfRNA and quantify gene expression of cfRNA in a biological sample. In a further example, the disclosed method is used to simultaneously detect genomic alteration of cfRNA, detect gene expression of cfRNA, and quantify gene expression of cfRNA in a biological sample.

In one example, the design of the primers to capture fusion transcripts has two main features—1) the presence of a random barcode sequence in the downstream primers (downstream relative to the target gene (e.g. fusion) transcript) to individually tag each copy of the RNA transcript if present, and 2) the location of each primer approximately 50 base pairs from each exonic junction in the panel, such that the expected total amplicon length would be close to 90-110 base pairs. This was done in order to meet the sample cfRNA size distribution observed which peaked at 110-120 nucleotides.

In one example, the plurality of forward and reverse primer pairs specific to a plurality of target genes that are capable of undergoing genomic alteration as disclosed in step (b)(I) is designed as shown in FIG. 1:
  wherein each forward primer of the plurality of forward and reverse primer pairs specific to the plurality of target genes that are capable of undergoing genomic alteration is complementary to a sequence located about 50 base pairs upstream of an exonic junction of each target gene that is capable of undergoing genomic alteration,
  wherein each reverse primer of the plurality of forward and reverse primer pairs specific to the plurality of target genes that are capable of undergoing genomic alteration is complementary to a sequence located about 50 base pairs downstream of an exonic junction of each target gene that is capable of undergoing genomic alteration,
  wherein each reverse primer of the plurality of forward and reverse primer pairs specific to the plurality of target genes that are capable of undergoing genomic alteration comprises a barcode sequence on its 5' end, wherein the barcode sequence of each reverse primer corresponding to each target gene that is capable of undergoing genomic alteration is different.

Figure 2A:
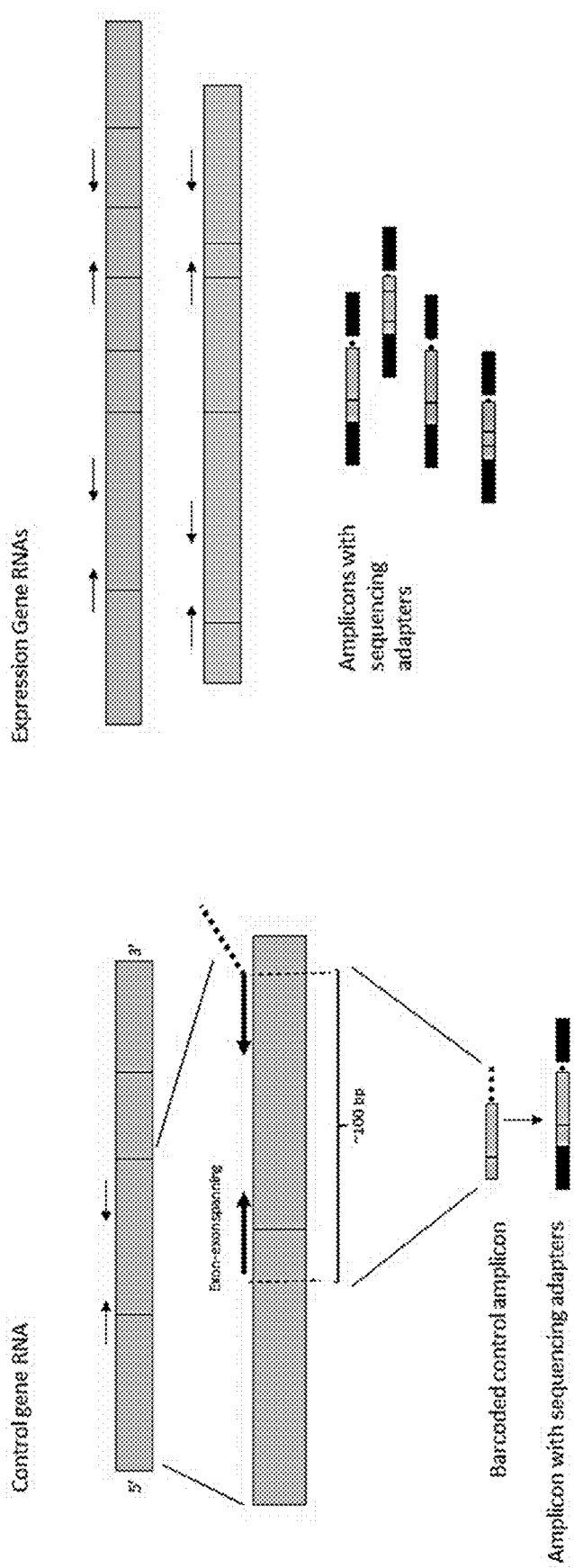

In one example, the plurality of forward and reverse primer pairs specific to a plurality of control housekeeping genes as disclosed in step (b)(II) is designed, wherein:
  (i) each forward primer of the plurality of forward and reverse primer pairs specific to the plurality of control housekeeping genes is complementary to a sequence spanning an exon-exon junction of each control housekeeping gene,
    wherein each reverse primer of the plurality of forward and reverse primer pairs specific to the plurality of control housekeeping genes is complementary to a sequence about 100 base pairs downstream of the sequence spanning the exon-exon junction of each control housekeeping gene,
    wherein each reverse primer of the plurality of forward and reverse primer pairs specific to the plurality of control housekeeping genes comprises a barcode sequence on its 5' end, wherein the barcode sequence of each reverse primer corresponding to each control housekeeping gene is different, as shown in FIG. 2A (left);
  (ii) each reverse primer of the plurality of forward and reverse primer pairs specific to the plurality of control housekeeping genes is complementary to a sequence spanning an exon-exon junction of each control housekeeping gene,
    wherein each forward primer of the plurality of forward and reverse primer pairs specific to the plurality of control housekeeping genes is complementary to a sequence about 100 base pairs downstream of the sequence spanning the exon-exon junction of each control housekeeping gene,
    wherein each reverse primer of the plurality of forward and reverse primer pairs specific to the plurality of control housekeeping genes comprises a barcode sequence on its 5' end, wherein the barcode sequence of each reverse primer corresponding to each control housekeeping gene is different;
  (iii) each forward and each reverse primer of the plurality of forward and reverse primer pairs specific to the plurality of control housekeeping genes is complementary to consecutive sequences spanning an exon-exon junction of each control housekeeping gene,
    wherein each reverse primer of the plurality of forward and reverse primer pairs specific to the plurality of control housekeeping genes comprises a barcode sequence on its 5' end, wherein the barcode sequence of each reverse primer corresponding to each control housekeeping gene is different.

In one example, the plurality primer sets specific to a plurality of target genes related to protein expression as disclosed in step (b)(III) is designed,
  wherein each primer set comprises a plurality of forward and reverse primer pairs specific to each target gene related to protein expression, wherein:
  (i) each forward primer of the of the plurality of forward and reverse primer pairs specific to each target gene related to protein expression is complementary to a sequence spanning an exon-exon junction of each target gene related to protein expression,
    wherein each reverse primer of the of the plurality of forward and reverse primer pairs specific to each target gene related to protein expression is complementary to a sequence about 100 base pairs downstream of the sequence spanning the exon-exon junction of each target gene related to protein expression,
    wherein each reverse primer of the plurality of forward and reverse primer pairs specific to each target gene related to protein expression comprises a barcode sequence on its 5' end, wherein the barcode sequence of each reverse primer corresponding to each target gene related to protein expression is different, as shown in FIG. 2A (right);
  (ii) each reverse primer of the plurality of forward and reverse primer pairs specific to the plurality of target genes related to protein expression is complementary to a sequence spanning an exon-exon junction of each target gene related to protein expression,
    wherein each forward primer of the plurality of forward and reverse primer pairs specific to the plurality of target genes related to protein expression is complementary to a sequence about 100 base pairs downstream of the sequence spanning the exon-exon junction of each target gene related to protein expression,
    wherein each reverse primer of the plurality of forward and reverse primer pairs specific to the plurality of target genes related to protein expression comprises a barcode sequence on its 5' end, wherein the barcode sequence of each reverse primer corresponding to each target gene related to protein expression is different;

(iii) each forward and each reverse primer of the plurality of forward and reverse primer pairs specific to the plurality of target genes related to protein expression is complementary to consecutive sequences spanning an exon-exon junction of each target gene related to protein expression, wherein each reverse primer of the plurality of forward and reverse primer pairs specific to the plurality of target genes related to protein expression comprises a barcode sequence on its 5' end, wherein the barcode sequence of each reverse primer corresponding to each target gene related to protein expression is different.

Figure 2B:
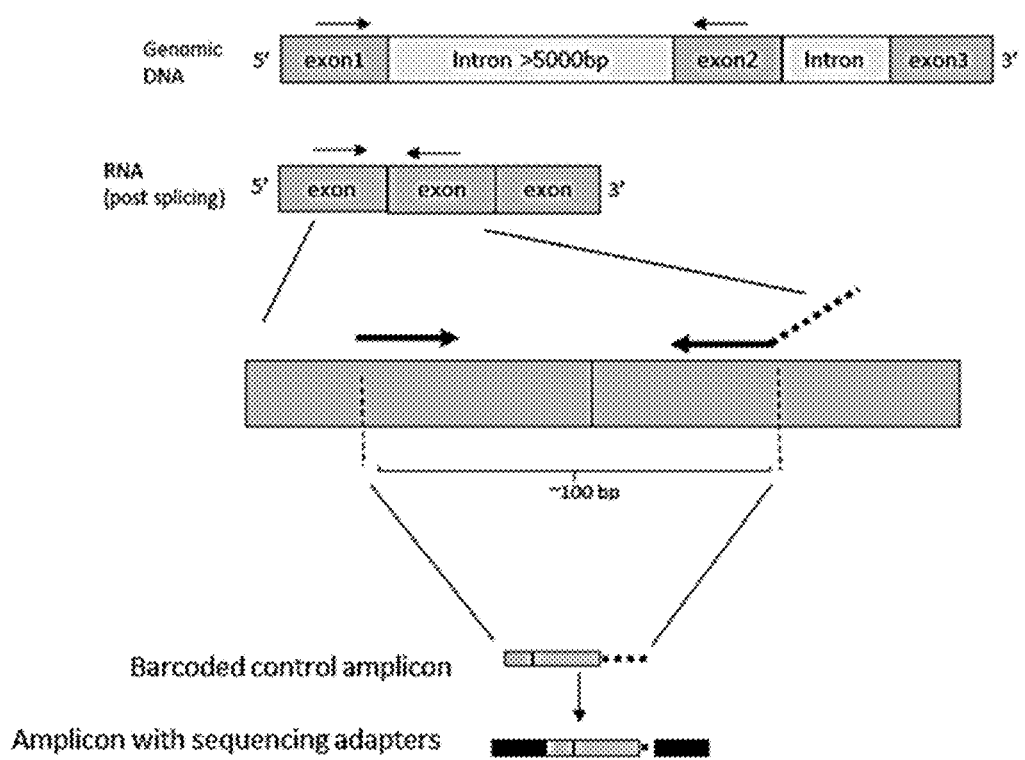

In one example, the forward primer of the plurality of forward and reverse primer pairs specific to a plurality of control housekeeping genes as disclosed in step (b)(II) is complementary to a sequence in a first exon and the reverse primer of the plurality of forward and reverse primer pairs specific to a plurality of control housekeeping genes as disclosed in step (b)(II) is complementary to a sequence in a second exon as shown in FIG. 2B, wherein the first exon and the second exon is intervened by an intron of >5000 base pairs in length, thereby avoiding unintended amplification of any genomic DNA during the plurality of multiplexed PCR reactions.

In one example, at least one of the primers of each forward and reverse primer pair of the plurality of forward and reverse primer pairs specific to a plurality of control housekeeping genes as disclosed in step (b)(II) span an exon-exon junction. In one example, at least one of the primers of each forward and reverse primer pair of the plurality of forward and reverse primer pairs specific to a plurality of target genes related to protein expression as disclosed in step (b)(III) span an exon-exon junction. In one example, at least one of the primers of each forward and reverse primer pair of the plurality of forward and reverse primer pairs specific to a plurality of control housekeeping genes as disclosed in step and/or at least one of the primers of each forward and reverse primer pair of the plurality of forward and reverse primer pairs specific to a plurality of target genes related to protein expression as disclosed in step (b)(III) span an exon-exon junction. In one example, a forward primer or a reverse primer of the plurality of forward and reverse primer pairs specific to a plurality of control housekeeping genes as disclosed in step (b)(II), and/or a forward primer or a reverse primer of the plurality of forward and reverse primer pairs specific to a plurality of target genes related to protein expression as disclosed in step (b)(III) span an exon-exon junction. In another example, both the forward primer and the reverse primer of the plurality of forward and reverse primer pairs specific to a plurality of control housekeeping genes as disclosed in step (b)(II), and/or both the forward primer and the reverse primer of the plurality of forward and reverse primer pairs specific to a plurality of target genes related to protein expression as disclosed in step (b)(III) span an exon-exon junction, wherein the exon length is about 100 base pairs.

In one example, each reverse primer of the plurality of forward and reverse primer pairs specific to a plurality of target genes that are capable of undergoing genetic alteration as disclosed in step (b)(I), each reverse primer of the plurality of forward and reverse primer pairs specific to a plurality of control housekeeping genes as disclosed in step (b)(II), and each reverse primer of the plurality of forward and reverse primer pairs specific to a plurality of target genes related to protein expression as disclosed in step (b)(III) comprise a barcode sequence on its 5' end, wherein each barcode sequence is different. As used herein, the term "barcode sequence" refers to an encoded molecule or barcode that includes variable amount of information within the nucleic acid sequence. For example, the barcode sequence is a tag that can be read out using any of a variety of sequence identification techniques, for example, nucleic acid sequencing, probe hybridization-based assay, and the like. In some examples, the barcode sequence is used in the method as described herein to tag different converted cDNA sequences of target regions of a sample, such that when the barcode sequence tags to the converted DNA sequences of target regions, each different converted cDNA sequence of target region would then have a unique barcode sequence that is attached to it and read out with the converted cDNA sequence of target region from the sample.

The barcode sequence allows the pooled analysis of multiple unique target sequences, where the resulting sequence information from the pool can be later attributed back to each starting target sequence. That is, after the process of amplification, the barcode sequence is used to group amplicons to form a family of amplicons having the same barcode sequence. In some examples, the barcode sequence is an overhang that does not complement any sequence within the target region. As each reverse primer carries on its 5' end a randomly assigned barcode sequence as disclosed herein, the barcode sequence allows individual cDNA molecules to be tagged uniquely in the step of sequencing library formation.

In one example, the barcode sequence is an oligonucleotide comprising 10 to 16 random nucleotides, or 10 to 15 random nucleotides, or 10 to 13 random nucleotides, or 10 random nucleotides, or 11 random nucleotides, or 12 random nucleotides, or 13 random nucleotides, or 14 random nucleotides, or 15 random nucleotides, or 16 random nucleotides. In one example, the barcode sequence is an oligonucleotide comprising 10 to 16 random nucleotides. In one example, the barcode sequence is an oligonucleotide comprising 10 random nucleotides. In one specific example, the barcode sequence is an oligonucleotide comprising 10 random nucleotides which can be represented as NNNNNNNNNN (SEQ ID NO: 615).

In one example, the typical length of each forward primer of the plurality of forward and reverse primers pairs as disclosed in step (b), excluding the barcode sequence and partial adapter sequence, is about 20 base pairs. In one example, the typical length of each reverse primer of the plurality of forward and reverse primers pairs as disclosed in step (b), excluding the barcode sequence and partial adapter sequence, is about 20 base pairs. In one example, the typical length of each forward primer of the plurality of forward and reverse primer pairs as disclosed in step (b), including the barcode sequence and partial adapter sequence, is about 45 base pairs, wherein the length of the barcode sequence is about 10 base pairs, wherein the length of the partial adapter sequence is about 20 base pairs. In one example, the typical length of each reverse primer of the plurality of forward and reverse primer pairs as disclosed in step (b), including the barcode sequence and partial adapter sequence, is about 45 base pairs, wherein the length of the barcode sequence is about 10 base pairs, wherein the length of the partial adapter sequence is about 20 base pairs.

In one example, the biological sample contains RNA. In one example, the RNA is cfRNA. In one example, the cfRNA is present freely in the biological sample and can be converted to cDNA directly as disclosed in step (a) of the disclosed method.

In one example, the cfRNA is extracted from the biological sample prior to step (a) of the disclosed method. In a further example, the RNA may be those that are originally encapsulated within cells and needs to be extracted prior to step (a) of the disclosed method. In one example, the cell may be any type of cell in the body. In one example, the cell is from bone, epithelial, cartilage, adipose tissue, nerves, muscle, connective tissue, esophagus, stomach, liver, gallbladder, pancreas, adrenal glands, bladder, gallbladder, large intestine, small intestine, kidneys, liver, pancreas, colon, stomach, thymus, spleen, brain, spinal cord, heart, lungs, eyes, corneal, skin, or islet tissue or organs. In one example, the cell may be a cancer cell, a stem cell, an endothelial cell, or a fat cell. In one example, the cell is a blood cell. The blood cell may be a white blood cell, or a platelet. In one example, the cell is selected from cancer cells known to harbour genomic alterations. In one example, the cell is selected from cancer cell lines known to harbour fusion genes. In one example, the cancer cell lines harbouring fusion genes may include, but are not limited to, CRL-9591, H-2228, CRL-2724, VCaP, CRL-5813, etc. Various methods for RNA extraction are known in the art and may be used for the purpose of the disclosed method. Various methods for RNA extraction are known in the art and may be used for the purpose of the disclosed method. In one example, the cfRNA is extracted from the biological sample before step (a) using a kit such as, but not limited to Zymo Quick-cfRNA Serum & Plasma Kit (Zymo Research), NextPrep™ Magnazol™ cfRNA Isolation Kit (PerkinElmer), Isopure Plasma cfDNA/RNA Isolation Kit (Aline Biosciences), QIAmp Circulating Nucleic Acid Kit (Qiagen), QIAamp ccfDNA/RNA Kit (Qiagen), MagMAX™ Cell-Free Total Nucleic Acid Isolation Kit (Applied Biosystems), etc.

In one example, the RNA extracted from cells are subjected to ultrasonification to thereby resemble the size of cfRNA more closely. In another example, the ultrasonification is achieved using Covaris, Qsonica, Diagenode Bioruptor, etc. In another example, the RNA extracted from the cells are subjected to heat and divalent cation-based fragmentation. In yet another example, the fragmentation is achieved using NEBNext® Magnesium RNA Fragmentation Module.

In one example, the biological sample contains both cfRNA and cfDNA. As used herein, cfDNA refers to non-encapsulated DNA which is present freely in a liquid sample disclosed herein and not contained within cells. The presence of long intervening introns which have undergone rearrangements prevents rearranged cfDNA from forming sequenceable products.

In the disclosed method, cfRNA present freely in the biological sample or those extracted from the biological sample, is first converted to cDNA as disclosed in step (a) of the method of the first aspect. In one example, cfRNA is converted to cDNA by reverse transcription. The term "reverse transcription" and its grammatical variants as used herein refers to the enzyme-mediated synthesis of a DNA molecule from an RNA template. The resulting DNA, known as complementary DNA (cDNA), can be used as a template for PCR amplification. Methods of reverse transcription, which typically involve the use of non-target specific primers (random primers), are well known in the art. In one example, cfRNA is converted to cDNA using a reverse transcription kit, wherein the reverse transcription kit comprises a reverse transcriptase enzyme and a plurality of random primers. In one example, the random primers are 6-mer primers, 7-mer primers, 8-mer primers, 9-mer primers or combinations thereof. In one example, the random primers are 6-mer (hexamer/hexanucleotide) primers. In one example, the reverse transcription kit is selected from, but is not limited to, High-Capacity cDNA Reverse Transcription Kit (Thermo Fisher Scientific), SuperScript IV One-Step RT-PCR System (Invitrogen), etc.

In one example, the biological sample containing the RNA is a liquid sample, a tissue sample, or a cell sample. In yet another example, the tissue sample is a frozen tissue sample or a fixed tissue sample. In another example, the fixed tissue sample is a Formalin-Fixed Paraffin-Embedded (FFPE) tissue sample. In another example, the liquid sample is a bodily fluid. In one example, the bodily fluid is selected from the group consisting of blood, bone marrow, cerebral spinal fluid, peritoneal fluid, pleural fluid, lymph fluid, ascites, serous fluid, sputum, lacrimal fluid, stool, urine, saliva, ductal fluid from breast, gastric juice, and pancreatic juice. In one example, the bodily fluid is blood. In one example, the blood is plasma.

In another example, the biological sample is obtained from a subject having and/or suspected of having a disease. In another example, the disease is cancer. In yet another example, the cancer is selected from the group consisting of leukemia, lung cancer, colorectal cancer, breast cancer, pancreatic cancer, prostate cancer, nasopharyngeal cancer, liver cancer, cholangiocarcinoma, esophageal cancer, urothelial cancer, and gastrointestinal cancer. In one example, the cancer is an early-stage cancer. In another example, the cancer is a late-stage or metastatic cancer. In one example, the cancer is selected from the group consisting of metastatic prostate cancer, metastatic lung cancer, metastatic breast cancer and leukemia.

In one example, the genomic alteration(s) detected using the disclosed method comprise(s) structural rearrangement(s). In one example, the term "rearrangement" refers to—rearrangement in the order of sections of the DNA. In one example, the structural rearrangement is a fusion, such as a gene fusion. In one example, the term "fusion" refers to structural variations produced through structural rearrangements, such as interchromosomal or intrachromosomal rearrangements. In one example, the structural rearrangement may include, but are not limited to, deletion, insertion (such as duplication), inversion, transversion, translocation, alternative splicing, and the like. In one example, the structural rearrangement results in formation of a fusion gene, such as one that is detectable using the methods disclosed herein. In one example, the "deletion" is a sequence change where at least one nucleotide is removed. In one example, the "deletion" is a sequence change where more than 10 nucleotides are removed. In one example, the "deletion" is a sequence change where more than 20 nucleotides are removed. In one example, the "deletion" is a sequence change where more than 30 nucleotides are removed. In one example, the "deletion" is a sequence change where more than 40 nucleotides are removed. In one example, the "deletion" is a sequence change where more than 50 nucleotides are removed. In one example, the "deletion" may be a "small deletion" where less than 50 nucleotides are removed. In one example, the "insertion" is a sequence change where at least one nucleotide is inserted between two nucleotides. In one example, the "insertion" is a sequence change where more than 10 nucleotides are inserted between two nucleotides. In one example, the "insertion" is a sequence change where more than 20 nucleotides are inserted between two nucleotides. In one example, the "insertion" is a sequence change where more than 30 nucleotides are inserted between two nucleotides. In one example, the "insertion" is a sequence change where more than 40 nucleotides are inserted between two nucleotides. In one example, the "insertion" is a sequence change where more than 50 nucleotides are inserted between two nucleotides. In one example, the "insertion" may be a "small insertion" where less than 50 nucleotides are inserted between two nucleotides. In one example, the "insertion" is a "duplication". In one example, the "duplication" is a sequence change where a copy of one or more nucleotides are inserted directly 3'-flanking of the original copy. In one example, the term "inversion" refers to a sequence change where more than one nucleotide replacing the original sequence are the reverse complement of the original sequence. In one example, the term "translocation" refers to rearrangement of parts between non-homologous chromosomes, which can result in "fusion". In one example, "altered splicing" refers to aberrant splicing of a single gene transcript that may cause one or more exons in sequence to be spliced out of the RNA, bringing usually more distant exons of the same gene in juxtaposition. Altered splicing involves the same gene, compared to fusion which is a definition reserved for two genes. In one example, altered splicing included MET exon 14 skipping where exon 14 of MET gene is spliced out bringing exon 13 and exon 15 in proximity, which is detectable using the method described herein (FIGS. 14A-14B). In one example, the genomic alteration(s) detected using the disclosed method comprise(s) single nucleotide variations. In one example, "single nucleotide variations" refer to variation in a single nucleotide that occurs at a specific position in the genome, differing from the nucleotide defining the position in the reference genome.

In one example, "housekeeping genes" refer to highly conserved genes which are essential for maintaining cellular function. In one example, the control housekeeping gene comprises Glucose-6-phosphate isomerase (GPI), FERM domain containing 8 (FRMD8), Small nuclear ribonucleoprotein D3 (SNRPD3), Proteasome subunit, beta type, 2 (PSMB2), TATA box binding protein (TBP), REL protooncogene, NF-kB subunit (REL), synaptosome associated protein 29 (SNAP29), Tubulin gamma complex associated protein 2 (TUBGCP2), Receptor accessory protein 5 (REEP5), Solute carrier family 4 member 1 adaptor protein (SLC4A1AP), Integrin subunit beta 7 (ITGB7), Protein-O-mannose kinase (POMK), ER membrane protein complex subunit 7 (EMC7), Nuclear autoantigenic sperm protein (NASP), Checkpoint with forkhead and ring finger domains (CHFR), Ribosomal RNA processing 1 (RRP1), Cytosolic iron-sulfur assembly component 1 (CIAO1), Pumilio RNA binding family member 1 (PUM1), Retention in endoplasmic reticulum sorting receptor 1 (RER1), Serine and arginine rich splicing factor 4 (SRSF4) (see FIG. 12B). The expression of housekeeping genes is assumed to be relatively constant across samples. For example, for samples containing the same amount of RNA, the number and expression of housekeeping genes will be similar. For example, for samples containing a smaller amount of RNA, the number and expression of housekeeping genes will be fewer than samples containing a larger amount of RNA, or vice versa. Therefore, the enumeration of RNA molecules of housekeeping genes on average can be used for the normalisation of RNA molecules of gene alteration targets and target genes related to protein expression.

In one example, the amount of cfRNA used in the method disclosed herein is at least 6 ng. In another example, the amount of cfRNA used in the method disclosed herein is about 6 ng to about 100 ng, or about 10 ng, or about 20 ng, or about 30 ng, or about 40 ng, or about 50 ng, or about 60 ng, or about 70 ng, or about 80 ng, or about 90 ng, or about 100 ng. In one example, the amount of cfRNA used in the method disclosed herein is 20 ng to 50 ng.

A multiplexed PCR reaction is then performed on the converted cDNA as disclosed in step (b) of the first aspect, using a plurality of forward and reverse primers pairs specific to a plurality of target genes that are capable of undergoing genomic alteration as disclosed in (b)(I), and/or a plurality of forward and reverse primer pairs specific to a plurality of control housekeeping genes as disclosed in (b)(II), and/or a plurality of forward and reverse primer pairs specific to a plurality of target genes related to protein expression as disclosed in (b)(III), wherein the plurality of forward and reverse primer pairs specific to a plurality of target genes that are capable of undergoing genomic alteration differ from that of a plurality of control housekeeping genes, and differ from that of a plurality of target genes related to protein expression.

In one example, the plurality of multiplexed PCR reaction on the converted cDNA in step (b) is performed using a plurality of forward and reverse primer pairs specific to a plurality of target genes that are capable of undergoing genomic alteration as disclosed in step (b)(I), a plurality of forward and reverse primer pairs specific to a plurality of control housekeeping genes as disclosed in step (b)(II), and a plurality of primer sets specific to a plurality of target genes related to protein expression as disclosed in step (b)(III). In one example, the plurality of multiplexed PCR reactions on the converted cDNA in step (b) is performed using a plurality of forward and reverse primer pairs specific to a plurality of target genes that are capable of undergoing genomic alteration disclosed in step (b)(I) and a plurality of forward and reverse primer pairs specific to a plurality of control housekeeping genes as disclosed in step (b)(II). In another example, the plurality of multiplexed PCR reactions on the converted cDNA in step (b) is performed using a plurality of forward and reverse primers specific to a plurality of control housekeeping genes as disclosed in step (b)(II) and a plurality of primer sets specific to a plurality of target genes related to protein expression as disclosed in step (b)(III). In one example, the plurality of multiplexed PCR reactions on the converted cDNA in step (b) is performed using a plurality of forward and reverse primer pairs specific to a plurality of target genes that are capable of undergoing genomic alteration as disclosed in step (b)(I) and a plurality of forward and reverse primer pairs specific to a plurality of target genes related to protein expression as disclosed in step (b)(III).

In one example, the multiplexed PCR reaction is performed on the converted cDNA using Platinum SuperFi II DNA Polymerase (Invitrogen), KAPA HiFi DNA Polymerase (Roche), Platinum Taq DNA Polymerase or Platinum SuperFi DNA Polymerase (Invitrogen) and Q5 High-Fidelity DNA Polymerase (NEB), etc.

In one example, the plurality of multiplexed PCR reactions performed on the converted cDNA comprises 3 to 15 PCR cycles. In one example, the PCR amplification comprises 3 PCR cycles. In one example, the PCR amplification comprises 4 PCR cycles. In one example, the PCR amplification comprises 5 PCR cycles. In one example, the PCR amplification comprises 6 PCR cycles. In one example, the PCR amplification comprises 7 PCR cycles. In one example, the PCR amplification comprises 8 PCR cycles. In one example, the PCR amplification comprises 9 PCR cycles. In one example, the PCR amplification comprises 10 PCR cycles. In one example, the PCR amplification comprises 11 PCR cycles. In one example, the PCR amplification comprises 12 PCR cycles. In one example, the PCR amplification comprises 13 PCR cycles.

In one example, the number of the forward and reverse primer pairs specific to the plurality of target genes that are capable of undergoing genomic alteration as disclosed in step (b)(I) is at least 100. In another example, the number of the plurality of forward and reverse primer pairs specific to the plurality of target genes that are capable of undergoing genomic alteration as disclosed in step (b)(I) is from 100 to 2000. In one example, the number of the forward and reverse primer pairs specific to the plurality of target genes that are capable of undergoing genomic alteration as disclosed in step (b)(I) is from 200 to 1900, or from 300 to 1800, or from 400 to 1700, or from 500 to 1600, or from 600 to 1500, or from 700 to 1400, or from 800 to 1300, or from 900 to 1200, or from 1000 to 1100. In one example, the number of the plurality of forward and reverse primer pairs specific to the plurality of target genes that are capable of undergoing genomic alteration as disclosed in step (b)(I) is about 100, about 200, about 300, or about 400, or about 500, or about 600, or about 700, or about 800, or about 900, or about 1000, or about 1100, or about 1200, or about 1300, or about 1400, or about 1500, or about 1600, or about 1700, or about 1800, or about 1900, or about 2000. In one example, there is no upper limit on the number of the plurality of forward and reverse primer pairs specific to the plurality of target genes that are capable of undergoing genomic alteration as disclosed in step (b)(I).

In one example, the number of the plurality of forward and reverse primer pairs specific to the plurality of control housekeeping genes as disclosed in step (b)(II) is at least 20. In one example, the number of the plurality of forward and reverse primer pairs specific to the plurality of control housekeeping genes as disclosed in step (b)(II) is from 20 to 300. In one example, the number of the plurality of forward and reverse primer pairs specific to the plurality of control housekeeping genes as disclosed in step (b)(II) is from 30 to 290, or from 40 to 280, or from 50 to 260, or from 60 to 250, or from 70 to 240, or from 80 to 230, or from 90 to 220, or from 100 to 210, or from 110 to 200, or from 120 to 190, or from 130 to 180, or from 140 to 170. In one example, the number of the plurality of forward and reverse primer pairs specific to the plurality of control housekeeping genes as disclosed in step (b)(II) is about 20, or about or about 40, or about 50, or about 60, or about 70, or about 80, or about 90, or about 100, or about 110, or about 120, or about 130, or about 140, or about 150, or about 160, or about 170, or about 180, or about 190, or about 200, or about 210, or about 220, or about 230, or about 240, or about 250, or about 260, or about 270, or about 280, or about 290, or about 300. In one example, there is no upper limit on the number of the plurality of forward and reverse primer pairs specific to the plurality of control housekeeping genes as disclosed in step (b)(II).

In one example, the number of the plurality of forward and reverse primer pairs specific to the plurality of target genes related to protein expression as disclosed in step (b)(III) is at least 10. In one example, the number of the plurality of forward and reverse primer pairs specific to the plurality of target genes related to protein expression as disclosed in step (b)(III) is from 10 to 1700. In one example, the number of the plurality of forward and reverse primer pairs specific to the plurality of target genes related to protein expression as disclosed in step (b)(III) is from 10 to 1700, or from 100 to 1600, or from 200 to 1500, or from 300 to 1400, or from 400 to 1300, or from 500 to 1200, or from 600 to 1100, or from 700 to 1000. In one example, the number of the plurality of forward and reverse primer pairs specific to the plurality of target genes related to protein expression as disclosed in step (b)(III) is about or about 100, or about 200, or about 300, or about 400, or about 500, or about 600, or about 700, or about 800, or about 900, or about 1000, or about 1100, or about 1200, or about 1300, or about 1400, or about 1500, or about 1600, or about 1700. In one example, there is no upper limit on the number of the plurality of forward and reverse primer pairs specific to the plurality of target genes related to protein expression as disclosed in step (b)(III).

In another example, the maximum total number of plurality of forward and reverse primer pairs in the multiplexed PCR reaction is about 4000, wherein the number of plurality of forward and reverse primer pairs specific to a plurality of target genes that are capable of undergoing genomic alteration as disclosed in step (b)(I) is about 2000, wherein the number of plurality of forward and reverse primer pairs specific to a plurality of control housekeeping genes as disclosed in step (b)(II) is about 300, and wherein the number of plurality of forward and reverse primer pairs specific to a plurality of target genes related to protein expression as disclosed in step (b)(III) is about 1700.

In one example, the plurality of target genes that are capable of undergoing genomic alterations comprise an exon from a gene known to undergo fusion fused to an exon from a partner gene of the gene known to undergo fusion. In one example, the gene known to undergo fusion is selected from the group consisting ALK receptor tyrosine kinase, RET proto-oncogene, ROS proto-oncogene 1, fibroblast growth factor receptor 1 (FGFR1), fibroblast growth factor receptor 2 (FGFR2), fibroblast growth factor receptor 3 (FGFR3), neurotrophic receptor tyrosine kinase 1 (NTRK1), neurotrophic receptor tyrosine kinase 2 (NTRK2), neurotrophic receptor tyrosine kinase 3 (NTRK3), neuregulin 1 (NRG1), B-Raf proto-oncogene, serine/threonine kinase (BRAF), transmembrane serine protease 2 (TMPRSS2), MET proto-oncogene, receptor tyrosine kinase (MET), epidermal growth factor receptor (EGFR), estrogen receptor 1 (ESR1), platelet derived growth factor receptor alpha (PDGFRA), androgen receptor (AR), BCR activator of RhoGEF and GTPase (BCR), core-binding factor subunit beta (CBFB), lysine methyltransferase 2A (KMT2A), nucleophosmin 1 (NPM1), PML nuclear body scaffold (PML), and RUNX family transcription factor 1 (RUNX1). In one example, the partner gene of the gene known to undergo fusion is selected from the group consisting of EMAP like 4 (EML4), kinesin family member 5B (KIFSB), coiled-coil domain containing 6 (CCDC6), CD74 molecule (CD74), transforming acidic coiled-coil containing protein 3 (TACC3), ezrin (EZR), ETS transcription factor ERG (ERG), ArfGAP with GTPase domain, ankyrin repeat and PH domain 3 (AGAP3), A-kinase anchoring protein 9 (AKAP9), KIAA1549, tropomyosin 3 (TMP3), translocated promoter region, nuclear basket protein (TPR), trafficking from ER to golgi regulator (TFG), lamin A/C (LMNA), BicC family RNA binding protein 1 (BICC1), RAD51 recombinase (RAD51), CD47 molecule (CD47), Yes 1 associated transcriptional regulator (YAP1), ETS variant transcription factor 1 (ETV1), ETS variant transcription factor 4 (ETV4), ETS variant transcription factor 5 (ETV5), ETS variant transcription factor 6 (ETV6), factor interacting with PAPOLA and CPSF1 (FIP1L1), centriolin (CNTRL), ABL proto-oncogene 1, non-receptor tyrosine kinase (ABL1), AF4/FMR2 family member 1 (AFF1), MDS1 and EVI1 complex locus (MECOM), MLLT3 super elongation complex subunit (MLLT3), myosin heavy chain 11 (MYH11), PBX homeobox 1 (PBX1), retinoic acid receptor alpha (RARA), and RUNX1 partner transcriptional co-repressor 1 (RUNX1T1).

The method of the present disclosure is optimized for generating amplicons having certain sizes. The chosen length of 90-110 base pairs was considered optimal because products of shorter amplicons (<80 base pairs) would be less effectively retained through the multi-step library preparation method for amplicon sequencing. In one example, the length of the plurality of amplicons derived from cDNA in step (b) is 90 to 110 base pairs. In one example, the length of the plurality of amplicons derived from cDNA in step (b) is about 90 base pairs, or about 100 base pairs, or about 110 base pairs.

The plurality of amplicons derived from the cDNA in step (b) are then purified, as disclosed in step (c) of the first aspect.

The method of the present disclosure is designed to involve size-based separation (magnetic bead based) of smaller primer dimer artefacts to be removed and desired products to be retained, and excess primers to be enzymatically digested (e.g. using endonucleases and exonucleases). In one example, the purification of DNA is performed using an agent such as paramagnetic beads. In one example, the paramagnetic beads are selected from the group consisting of AMPure XP beads, SPRI beads, and Dynabeads. In one example, the paramagnetic beads are AMPure XP beads.

Next, the purified plurality of amplicons is amplified using universal indexed adapter primers to generate a plurality of sequencing library, as disclosed in step (d) of the first aspect.

In one example, the amplification is performed by using KAPA Hifi HotStart ReadyMix, Phusion U Hot Start DNA Polymerase (Thermo Scientific), ZymoTaq DNA Polymerase (Zymo Research) and Q5U Hot Start High-Fidelity DNA Polymerase (NEB), etc.

In one example, each universal indexed adapter primer as disclosed in step (d) comprises an adapter sequence. In one example, the term "adapter sequence" refers to any nucleotide sequence which can be added to an oligonucleotide of interest to prepare said oligonucleotide of interest for various purposes. The adapter sequences are complementary to the plurality of oligonucleotides present on the surface of the flow cells of the sequencing tools thereby allowing the DNA fragment to attach to the sequencing tool. In some examples, an adapter sequence allows for the sequencing of the oligonucleotide of interest. Sequencing platform specific adapter sequences are known in the art, and include, for example, the Illumina P5/P7 adapter sequences.

In one example, the universal indexed adapter primers as disclosed in step (d) of the method of the first aspect comprise:
  a forward primer comprising the sequence of
    AATGATACGGCGACCACCGAGATCTA-
      CACCTAGCGCTACACTCTTTCCCTACACG
      ACGCTCTTCCGATC*T (SEQ ID NO: 616); and
  a reverse primer comprising the sequence of
    CAAGCAGAAGACGGCATACGAGA-
      TAACCGCGGGTGACTGGAGTTCAGACGTGTG
      CTCTTCCGATC*T, (SEQ ID NO: 617),
    wherein "*" represents a phosphorothioate bond, and wherein the underlined sequences are the barcode sequences. The plurality of sequencing library formed is then purified, as disclosed in step (e) of the first aspect.

In one example, the purification of the plurality of sequencing library is performed using an agent such as paramagnetic beads. In one example, the paramagnetic beads are selected from the group consisting of AMPure XP beads, SPRI beads, and Dynabeads. In one example, the paramagnetic beads are AMPure XP beads.

The purified plurality of sequencing library is then subjected to multiplex sequencing on a next-generation sequencing platform, as disclosed in step (f) of the first aspect, to obtain a plurality of sequencing reads.

In one example, the plurality of sequencing library is sequenced on NextSeq 550, NovaSeq 6000, or BGI MGISEQ-2000, DNBSEQ-G400, DNB SEQ-T7.

Figure 15:
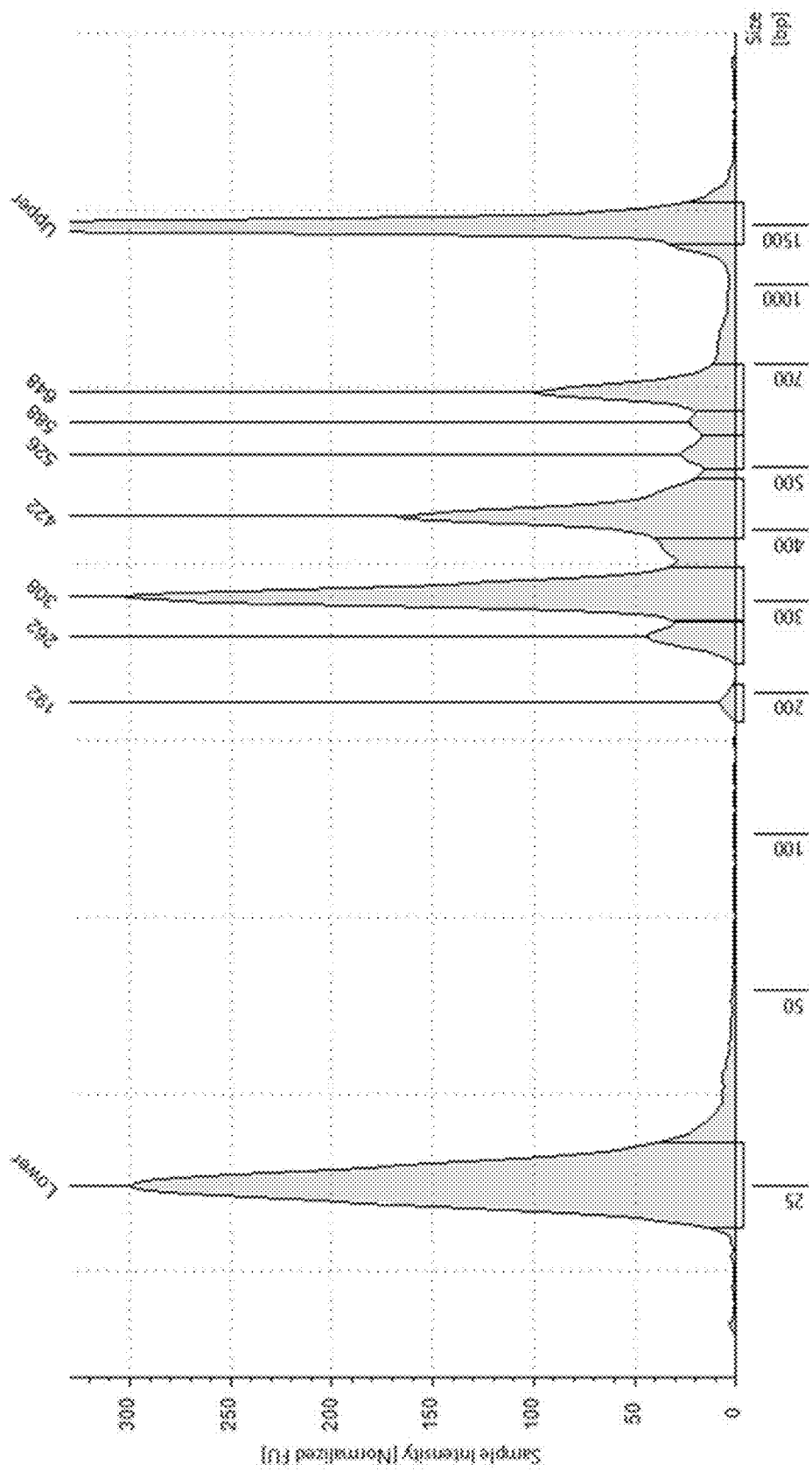
FIG. 15 illustrates a typical library profile for a cfRNA sample converted to a sequencing library as seen on the High Sensitivity DNA Screentape. The multiple peaks >200 base pairs correspond to the multiple products encompassing potential fusion products, control gene products and other gene expression products for which the multiplicity of forward and reverse primers are included. Qualified libraries will have prominent peaks of size >200 base pairs.

In one example, the plurality of sequencing library is qualified using the Agilent High Sensitivity DNA Screentape and quantified using KAPA Library Quantification Kit. In one example, the plurality of sequencing library is qualified by determining the size profile of the sequencing library which if successful will have a typical size profile of multiple prominent peaks greater than 200 base pairs (for example, as shown in FIG. 15).

Subsequently, a plurality of consensus reads is derived from each sequence of the plurality of sequencing reads obtained from step (f), as disclosed in step (g) of the first aspect. In one example, step (g) of the first aspect further comprises:
  (g)(I) detecting the presence of the barcode sequence from each sequencing read,
  (g)(II) performing cluster reassignment for the plurality of sequencing reads having the same barcode sequence to generate a plurality of barcode clusters, wherein each barcode cluster contains reads from the same amplicon and with the same barcode sequence, and
  (g)(III) performing consensus calling for each barcode cluster to obtain the consensus read of each sequence.

The derived consensus sequence is aligned to the reference genome, as disclosed in step (h) of the first aspect. In one example, the term "reference genome" refers to DNA sequences known in the art that may be obtainable from public databases. In one example, the term "consensus read" refers to a nucleotide sequence obtained from consensus calling. In one example, consensus calling is performed by identifying the nucleotide at each position for each sequencing result within the subgroup, comparing the identity for the nucleotide at each position across the plurality of sequencing results, and determining a majority nucleotide at each position. If the majority nucleotide count is above a threshold set for determining majority for a specific position, the assignment for said position is the majority nucleotide. If the majority nucleotide count is below this threshold, no assignment is made for said position. The threshold is variable for every position and is a function of the total number of sequencing results corresponding to a specific position.

In one example, step (h) of the disclosed method further comprises, if the sequence alignment results in a partial alignment to the reference genome of an exon from a first gene and a partial alignment to the reference genome of an exon from a second gene as disclosed in step (h)(I), then the result is used to (i) determine the sequence alignment as a split read, (ii) count/enumerate the number of split reads from step (h)(I)(i) that supports a fusion junction, and (iii) if the number of split reads from step (h)(I)(ii) is two or more, determine the first gene and the second gene as fusion partners. In one example, step (h) of the disclosed method further comprises, if the sequence alignment results in an alignment to the reference genome of the control housekeeping gene as disclosed in step (h)(II), then the result is used to (i) determine the sequence alignment as a consensus read of the control housekeeping gene and (ii) count/enumerate consensus read pairs of the control housekeeping gene from step (h)(II)(i) to determine the level of gene expression of the control housekeeping gene. In one example, step (h) of the disclosed method further comprises, if the sequence alignment results in an alignment to the reference genome of the target gene related to protein expression as disclosed in step (h)(III), then the result is used to (i) determine the sequence alignment as a consensus read of the target gene related to protein expression and (ii) count/enumerate consensus read pairs of the target gene related to protein expression from step (h)(III)(i) to determine the level of gene expression of the target gene related to protein expression.

In one example, "consensus read pairs" refers to the consensus sequence called after collapsing all sequencing reads containing the same barcode sequence and primer pair. Each consensus read pair, for example, is presumed to belong to an original RNA molecule converted to cDNA. In one example, counting/enumerating as disclosed in step (h) is achieved based on the barcode sequence-based consensus counting, wherein each RNA molecule comprising the same barcode sequence and primer pair combination represents a unique RNA molecule. In one example, all reverse primers of the plurality of forward and reverse primer pairs as disclosed in step (b) of the first aspect comprise a barcode sequence. Therefore, all RNA molecules captured by a given barcode sequence and primer pair combination can be detected and counted/enumerated.

In one example, the alignment of the derived plurality of consensus sequence to the reference genome is performed using a sequence alignment tool. In one example, the alignment tool is STAR, HISAT2, bwa, CLC, RSEM, kallisto, salmon, etc.

The results of sequence alignment from step (h) is used to determine presence or absence of the genomic alteration and/or determine presence or absence of gene expression and/or quantify the level of gene expression as disclosed in step (i) of the first aspect.

In one example, the disclosed method further comprises visualisation and fusion calling of the sequence alignment from step (h)(I). In one example, the visualisation is performed using Integrated Genome Viewer, or Savant Genome Browser, etc. In one example, the fusion calling is performed using Arriba and Fusion Catcher, etc.

In one example, the step of determining presence or absence of the genomic alteration and/or determining presence or absence of the gene expression and/or quantifying the level of the gene expression, further comprises performing variant calling of the sequence alignment from step (h). In one example, the step of determining presence or absence of the genomic alteration and/or determining presence or absence of the gene expression and/or quantifying the level of the gene expression, further comprises performing variant calling of the sequence alignment from step (h)(II). In one example, the step of determining presence or absence of the genomic alteration and/or determining presence or absence of the gene expression and/or quantifying the level of the gene expression, further comprises performing variant calling of the sequence alignment from step (h)(III). In one example, the step of variant calling comprises: (i) identifying differences between a consensus read and a reference genome based on the sequence alignment from step (h); and ii) determining the read count of sequence alignments comprising genomic alteration. In one example, the step of variant calling comprises: (i) identifying differences between a consensus read and a reference genome based on the sequence alignment from step (h)(II); and ii) determining the read count of sequence alignments comprising genomic alteration. In one example, the step of variant calling comprises: (i) identifying differences between a consensus read and a reference genome based on the sequence alignment from step (h)(III); and ii) determining the read count of sequence alignments comprising genomic alteration. In one example, the genomic alteration is selected from the group comprising of insertions (e.g., duplications), deletions, and single nucleotide variants. In one example, the variant calling is performed using Mutect2 and a custom variant caller.

In one example, wherein the disclosed method of the first aspect is used to simultaneously detect gene expression, structural rearrangements and quantify gene expression in cfRNA from a biological sample, the expression level of genes that are known to be overexpressed in cancer cells is quantified. In one example, wherein the disclosed method of the first aspect is used to simultaneously detect genomic alteration in cfRNA and quantify gene expression in cfRNA from a biological sample, the expression level of target genes that have undergone genomic alterations is quantified. In one example, wherein the disclosed method of the first aspect is used to simultaneously detect gene expression and quantify gene expression of cfRNA, the expression level of target genes related to protein expression is quantified.

In one example, the statistical modelling technique used to visualise the level of expression of genes related to protein expression is heatmap visualisation, principal component analysis, hierarchical clustering, etc.

In a second aspect, the present disclosure refers to a kit for detecting genomic alteration and/or detecting gene expression and/or quantifying the level of gene expression using RNA in a biological sample according to the method of the first aspect, wherein the kit comprises:
  (a) a plurality of forward and reverse primer pairs specific to a plurality of target genes that are capable of undergoing genomic alteration as defined in step (b)(I) of the method of the first aspect;
  (b) a plurality of forward and reverse primer pairs specific to a plurality of control housekeeping genes as defined in step (b)(II) of the method of the first aspect; and
  (c) a plurality of primer sets specific to a plurality of genes related to protein expression as defined in step (b)(III) of the method of the first aspect.

In one example, a person skilled in the art would be able to design the plurality of primer pairs and primer sets in (a), (b) and (c) of the kit of the second aspect based on the disclosure herein, for example, as described in steps (b)(I), (b)(II) and (b)(III) of the method of the first aspect. In one example, the plurality of primer sets specific to a plurality of genes related to protein expression as defined in step (b)(III) of the method of the first aspect provided in the kit as described herein may be used for determining presence or absence of the genomic alteration. In one example, the plurality of primer sets specific to a plurality of genes related to protein expression as defined in step (b)(III) of the method of the first aspect provided in the kit as described herein may be used for determining presence or absence of the genomic alteration such as deletions, insertions (e.g., duplications) and single nucleotide variations. In one example, the plurality of primer sets specific to a plurality of genes related to protein expression as defined in step (b)(III) of the method of the first aspect provided in the kit as described herein may be used for determining presence or absence of the genomic alteration by further performing the step of variant calling as described herein. In one example, the genomic alteration may be single nucleotide variation, insertion (e.g., duplications) or deletion. In one example, the kit for detecting genomic alteration and/or detecting gene expression and/or quantifying the level of gene expression of cfRNA in a biological sample according to the method of the first aspect further comprises a buffer for performing a plurality of multiplexed PCR reactions, a reverse transcriptase, a DNA polymerase, and a plurality of deoxynucleotide triphosphates (dNTPs). In some examples, the reagents provided in the kit as described herein may be provided in separate containers comprising the components independently distributed in one or more containers. As the method as described herein relates to sequencing (such as high-throughput sequencing), further components required in sequencing process could be easily determined by the person skilled in the art.

As used in this application, the singular form "a," "an," and "the" include plural references unless the context clearly dictates otherwise. For example, the term "a primer" includes a plurality of primers, including mixtures and combinations thereof.

As used herein, the terms "increase" and "decrease" refer to the relative alteration of a chosen trait or characteristic in a subset of a population in comparison to the same trait or characteristic as present in the whole population. An increase thus indicates a change on a positive scale, whereas a decrease indicates a change on a negative scale. The term "change", as used herein, also refers to the difference between a chosen trait or characteristic of an isolated population subset in comparison to the same trait or characteristic in the population as a whole. However, this term is without valuation of the difference seen.

As used herein, the term "about" in the context of concentration of a substance, size of a substance, length of time, or other stated values means +/−5% of the stated value, or +/−4% of the stated value, or +/−3% of the stated value, or +/−2% of the stated value, or +/−1% of the stated value, or +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The present disclosure illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the present disclosure has been specifically disclosed by preferred embodiments and optional features, modification and variation of the present disclosure embodied therein herein disclosed may be resorted to by those skilled in the art, and that such modifications and variations are considered to be within the scope of this present disclosure.

The invention has been described broadly and generically herein. Each of the narrower species and subgeneric groupings falling within the generic disclosure also form part of the present disclosure. This includes the generic description of the present disclosure with a proviso or negative limitation removing any subject matter from the genus, regardless of whether or not the excised material is specifically recited herein.

Other embodiments are within the following claims and non-limiting examples.

Examples

Methods
Sample Collection and Processing
Blood collected into Streck Cell-free DNA BCT® was shipped at ambient temperature before plasma separation. Briefly, blood plasma was prepared using a 2-step centrifugation process: first centrifugation was done at 1500×g for 10 min at 4° C. to separate plasma. The plasma layer was transferred to a separate tube and centrifuged at 15,000×g for 10 min at 4° C. to further remove cellular contaminants, and immediately processed for nucleic acid extraction or stored at −80° C. until used for extraction. If frozen, the plasma was fully thawed at room temperature before extraction.

Plasma cell-free total nucleic acids were extracted using the QIAamp Circulating Nucleic Acids kit (Qiagen). The nucleic acid extract contains co-eluted cfDNA and cfRNA fractions. The cfDNA was quantified using the Qubit Fluorometer (Thermo Fisher Scientific), and sized using the Genomic DNA ScreenTape on the 4200 TapeStation (Agilent). cfRNA was quantified and profiled using the Bioanalyzer RNA 6000 Pico kit or the High Sensitivity RNA Screentape on the 4200 Tapestation.

Design of Primers for Fusions and Expression in a Sequencing Library
A highly multiplex amplicon-based NGS assay was designed to capture potential fusions in cfRNA sample. Depending on the expected orientation of a partner exon in a fusion gene, a primer upstream of the exonic fusion junction ("forward" primer) or downstream of the fusion junction ("reverse" primer) was designed for the target gene's exon. Broadly, multiple exon-flanking primers were designed for target genes that are known to participate in fusion events in cancer. For all downstream primers, a random 10-base pairs barcode sequence was incorporated upstream of the gene-specific sequence for consensus calling and unique molecule enumeration. A pool of >300 "forward" primers and >300 "reverse" primers was prepared. A multiplicity of "upstream" and "downstream" primers were included in the multiplex PCR to optimally capture potential fusions known to occur between genes. The design of primers included exons of well-characterized genes known to undergo fusions and the addition of barcode sequence primers allowed for accurate enumeration of copies of RNA transcript as per method of enumeration (FIG. 1).

For the capture of transcripts corresponding to control genes and other genes for which expression was to be quantified, primers were designed such that at least one primer of a pair landed on an exon-exon junction, or the primer pairs were within two exons intervened by an intron >5000 base pairs in length. These primers were also included in the final primer pools. The specificity of cfRNA amplification was verified by performing the whole cfRNA sequencing workflow, but with leaving out the reverse transcriptase enzyme during the complementary DNA preparation. Any sequencing for intended regions, particularly control and expression genes, when no reverse transcription was performed, could then be attributed to the primers amplifying cfDNA. Any such primers were redesigned to improve specificity for RNA by reducing the 3' exon span of the exon-exon spanning primer. The design of primers for target genes related to expression were similar to the control gene targets, and at least one primer of primer pair spanned an exon-exon junction, and two or more primer pairs were designed per target gene covering both 5' and 3' end exons, to more reliably capture expression of target genes for expression, by allowing one or more amplicons to represent a given target gene. A highly multiplexed primer pool was employed with a plurality of upstream and downstream primers, some of which are expected to generate sequenceable targets in most samples depending on expression variability, and some primers which are expected to generate a product only when a sample is positive for structural rearrangement, generating a fusion gene that is productively expressed. The primers additionally carried the appropriate extensions necessary for generating sequenceable libraries with sequencing adapters for Illumina sequencing (FIGS. 2A and 2B).

Preparation of cfRNA Sequencing Library

Between 20-50 ng of cfRNA was converted to complementary DNA (cDNA) using the High-Capacity cDNA Reverse Transcription Kit (Thermo Fisher Scientific) in a total volume of 20 ul using random primers. The converted cDNA was used as a template in a highly multiplexed PCR reaction for target capture using the Platinum™ SuperFi II DNA Polymerase (Thermo Fisher Scientific). Briefly, cDNA was combined with primers and DNA Polymerase in a single reaction, and subjected to 3 to 15 cycles of PCR with the following conditions: 98° C., 1 min; 60° C., 1 min; 72° C., 1 min, followed by a final extension for 5 min at 72° C. The amplification product was subjected to one round of enzymatic digestion (using exonucleases, ExoI and ExoT) and two rounds of clean-up using 1.8× volume of AMPure XP beads and eluted in Buffer EB or nuclease-free water. The purified PCR products were then amplified with universal indexed adapter primers, compatible for sequencing with Illumina platform, with primers using KAPA HiFi HotStart ReadyMix. The final amplified library was purified with two rounds of 0.8× volume AMPure XP beads to remove excess adapters and size-select the final sequencing library. Library was quantified using the High Sensitivity DNA Screentape and quantified using KAPA Library Quantification Kit. Each library was sequenced on a Nextseq 550 to a depth of 3 million paired-end reads per sample.

Data Analysis

FASTQ files were processed using a custom pipeline. First, sequenced amplicons were identified and labelled in the FASTQ files based on the presence of any potential primer sequences in the right directionality, upstream or downstream (from a predetermined list of primer sequences based on panel design) in Read 1 and paired Read 2. Barcode sequence sequences in read 1 were identified upstream of primer in Read 1 and trimmed using cutadapt. The extracted molecular tag sequences were used to derive the consensus read sequence for all duplicate reads of a sequence identifiable by a given primer pair and unique barcode sequence. The consensus reads were then written to a new FASTQ file and aligned to human genome reference hg19 using STAR aligner. Fusion reads in which non-contiguous regions of the genome are captured within a read were identified as split reads and fusion partners were identified based on the sequence alignment. The presence of split read sequences mapping to two reciprocal partner genes were additionally confirmed to have been captured by primers specific to identified genes. Number of split reads (read pairs) supporting a fusion junction were enumerated. Visualization and fusion calling were also performed using Arriba and Fusion-Catcher. At least 2 supporting split reads were required for calling fusion and exon skipping variants (transcript variants). With molecular barcoding, the sequencing is error-free and increases confidence fusion calls due to the high quality of sequencing data.

Expression-level analysis was done by enumerating consensus read pairs which supported a given amplicon pre-defined by primer pairs for expression. Read pair counts were enumerated and tabulated for downstream analysis as control genes or target genes. Variant calling was performed on consensus BAM files using Mutect2 and a custom variant caller to identify single nucleotide variations, insertion and deletion mutations relative to the reference sequence. Expression of mutant transcripts comprising single nucleotide variations, insertion and deletion was quantified based on the number of reads containing the particular single nucleotide variation, insertion or deletion mutation and mapping to the intended target region. Expression of wild-type transcripts was quantified based on the number of reads matching the reference sequence and mapping to the intended target region. The relative expression of each mutation was also determined based on the proportion of mutant read counts relative to total read counts.

Results

The present disclosure describes a method for the simultaneous detection and quantification of clinically relevant genomic and gene expression alteration using cfRNA, with high sensitivity, specificity, and minimal invasive procedures.

Figure 3A:
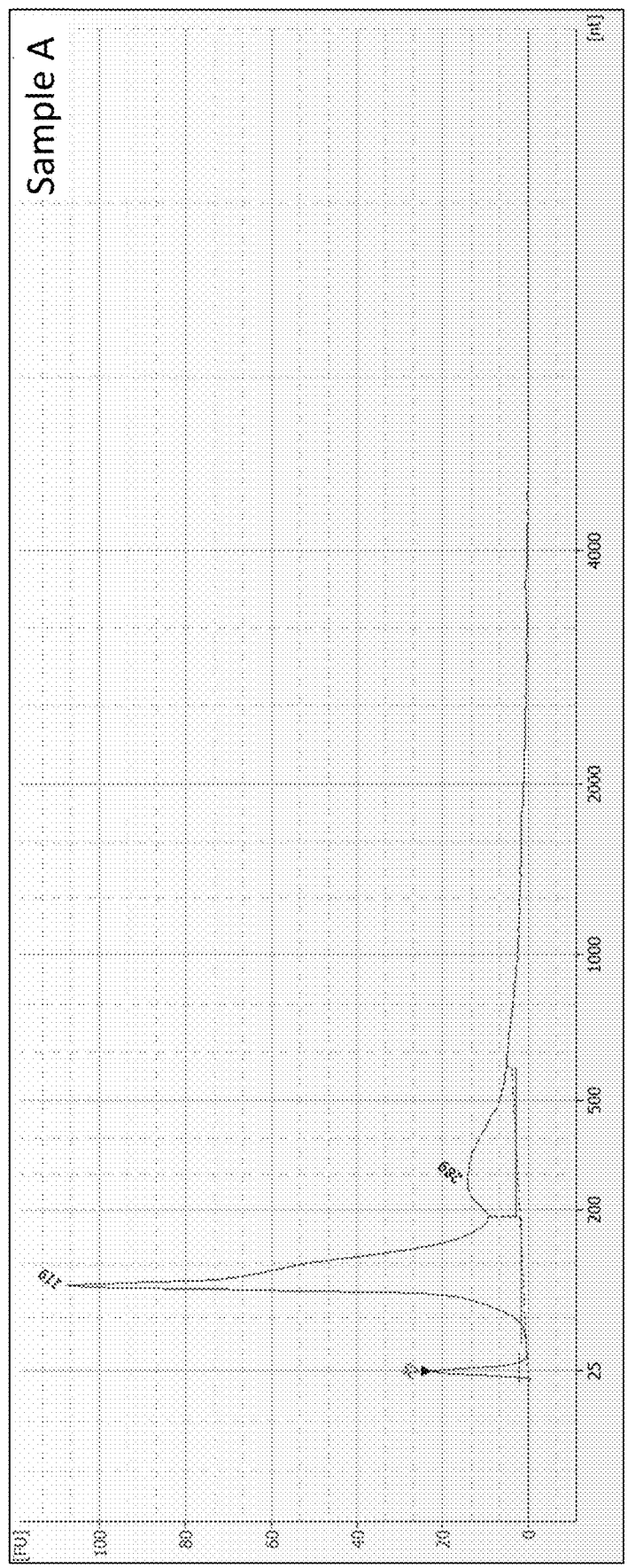
Figure 3B:
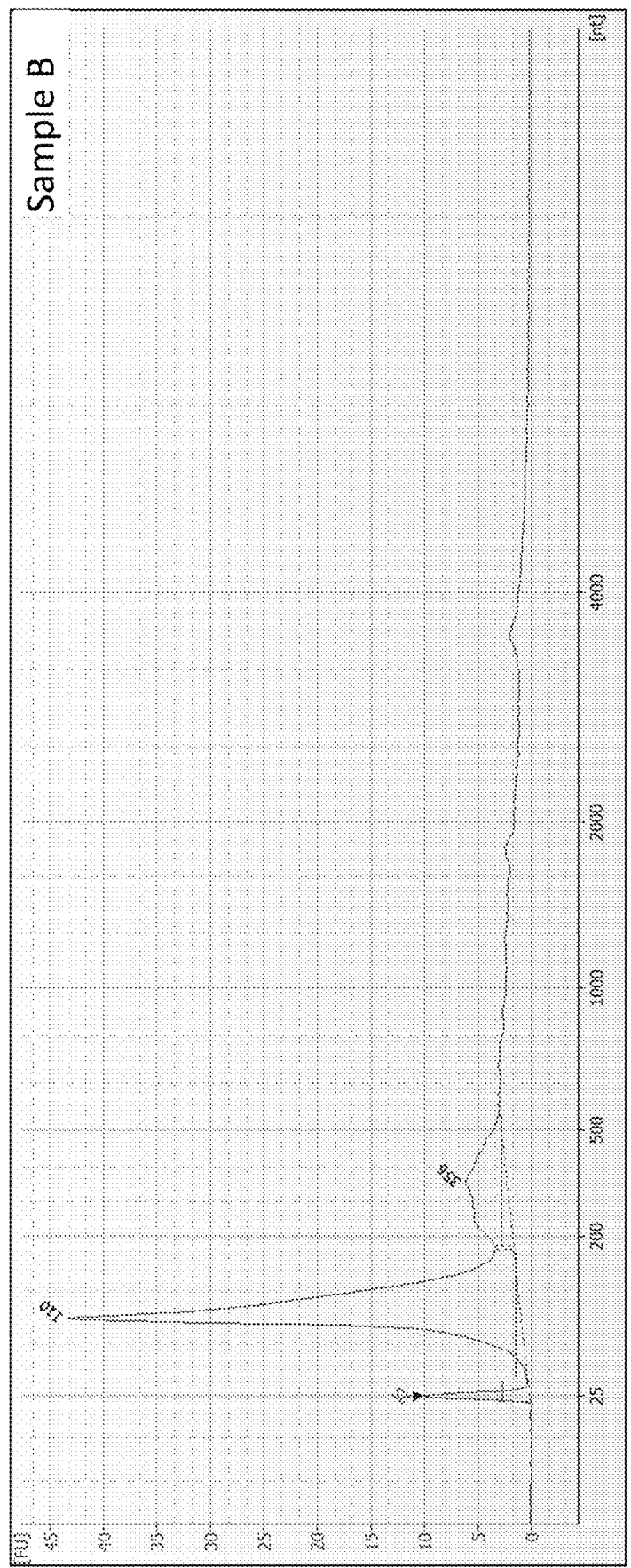
Figure 3C:
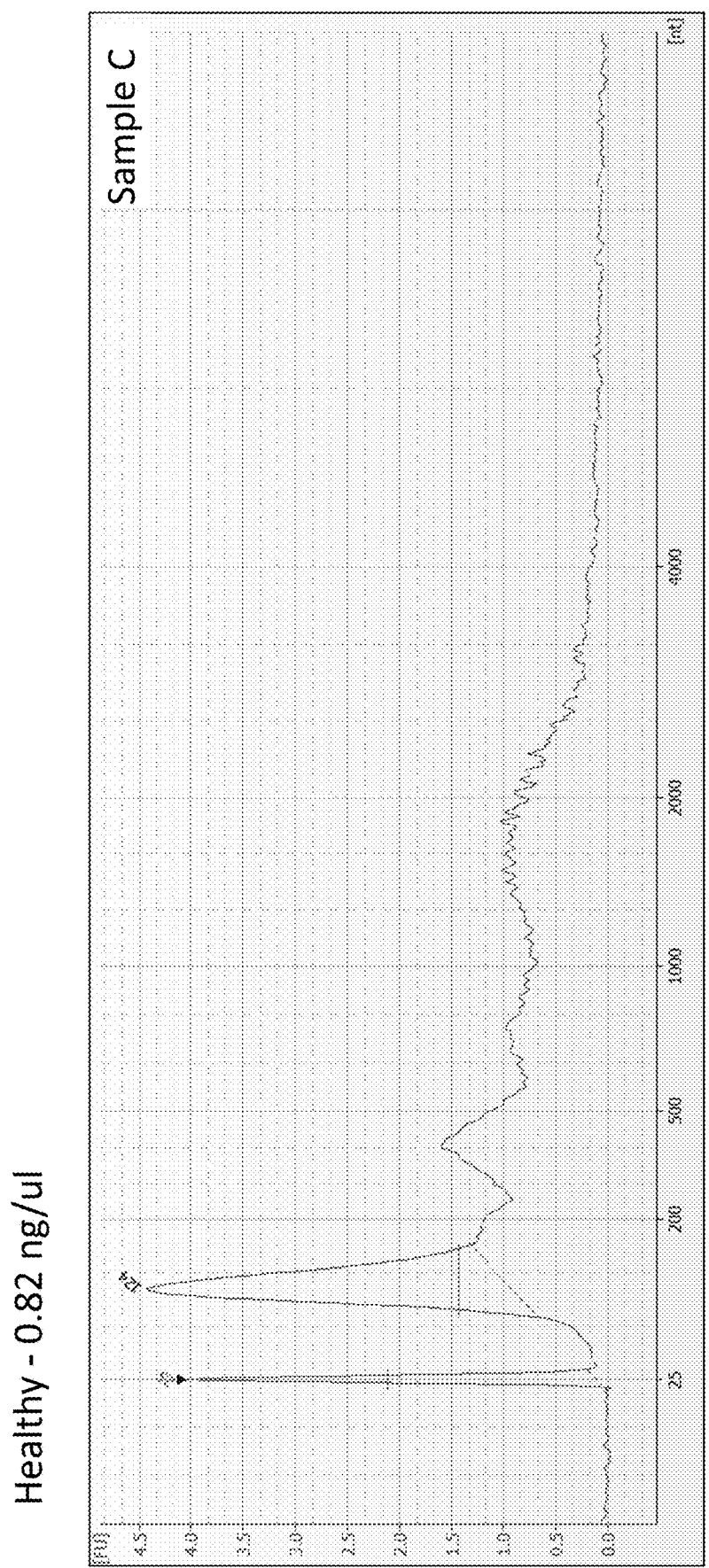
Figure 3D:
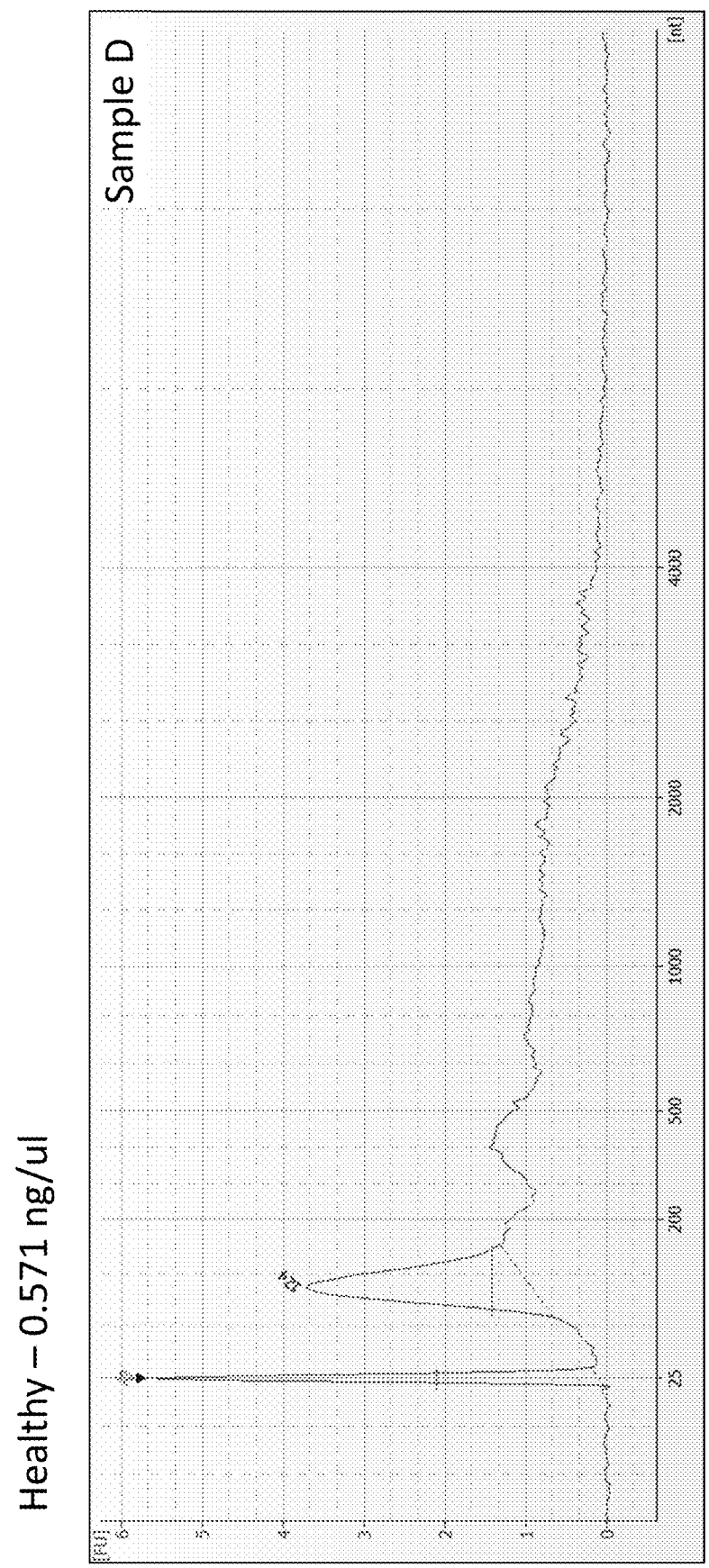

Validation of cfRNA-Based Detection Assay: Relative Abundance of Cell-Free Nucleic Acid in Plasma Total cfRNA concentration from plasma of healthy individuals and cancer patients were characterized for presence of cfRNA and analyzed for fragment size distribution using Bioanalyzer RNA 6000 Pico assay. cfRNA was present in all cancer samples and showed a predominant peak at 110 to 120 nucleotides in size and a second population of RNA in the 200 to 300 nucleotides range (FIGS. 3A and 3B). In terms of relative abundance, the shorter fragments (110 to 120 nucleotides) were about 5 to 10 times more abundant than the larger size RNA fragments (200 to 300 nucleotides). cfRNA from healthy individuals also showed the same pattern of size distribution, but at significantly lower cfRNA concentrations (FIGS. 3C and 3D).

Total nucleic acid extracts comprising cfDNA and cfRNA from plasma of healthy and cancer individuals were analyzed. Relative to each extract's cfDNA concentration, cfRNA concentrations were generally lower, and differed most significantly when the concentration of cfDNA exceeded 10 ng/ml plasma (FIG. 4).

Figure 5A:
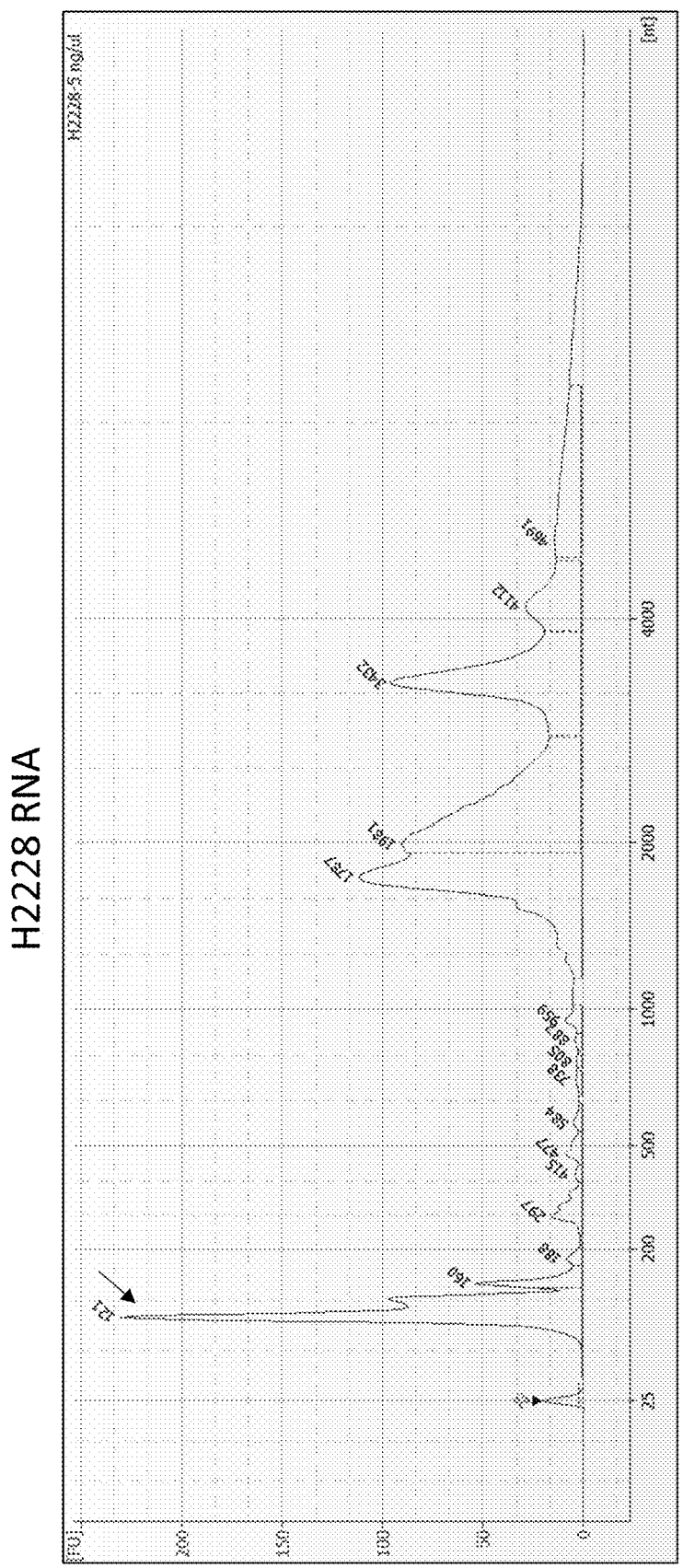
Figure 5B:
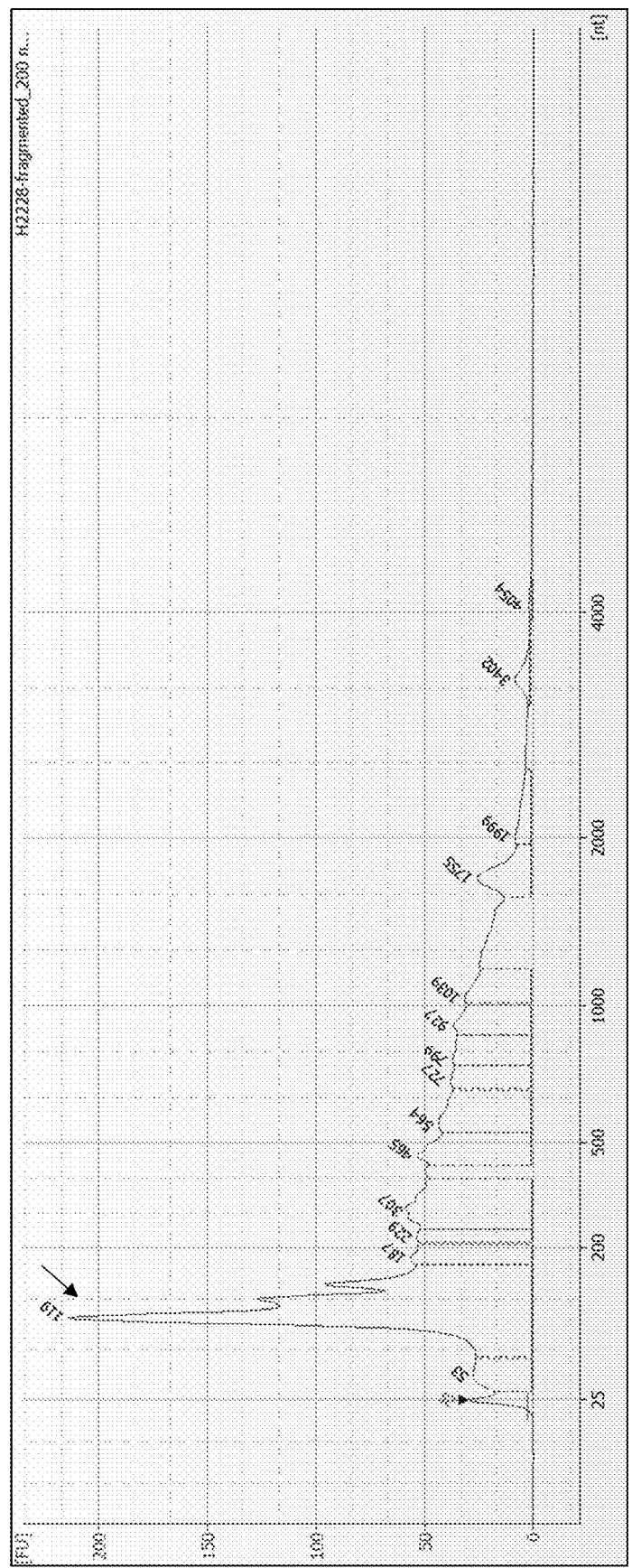
Figure 5C:
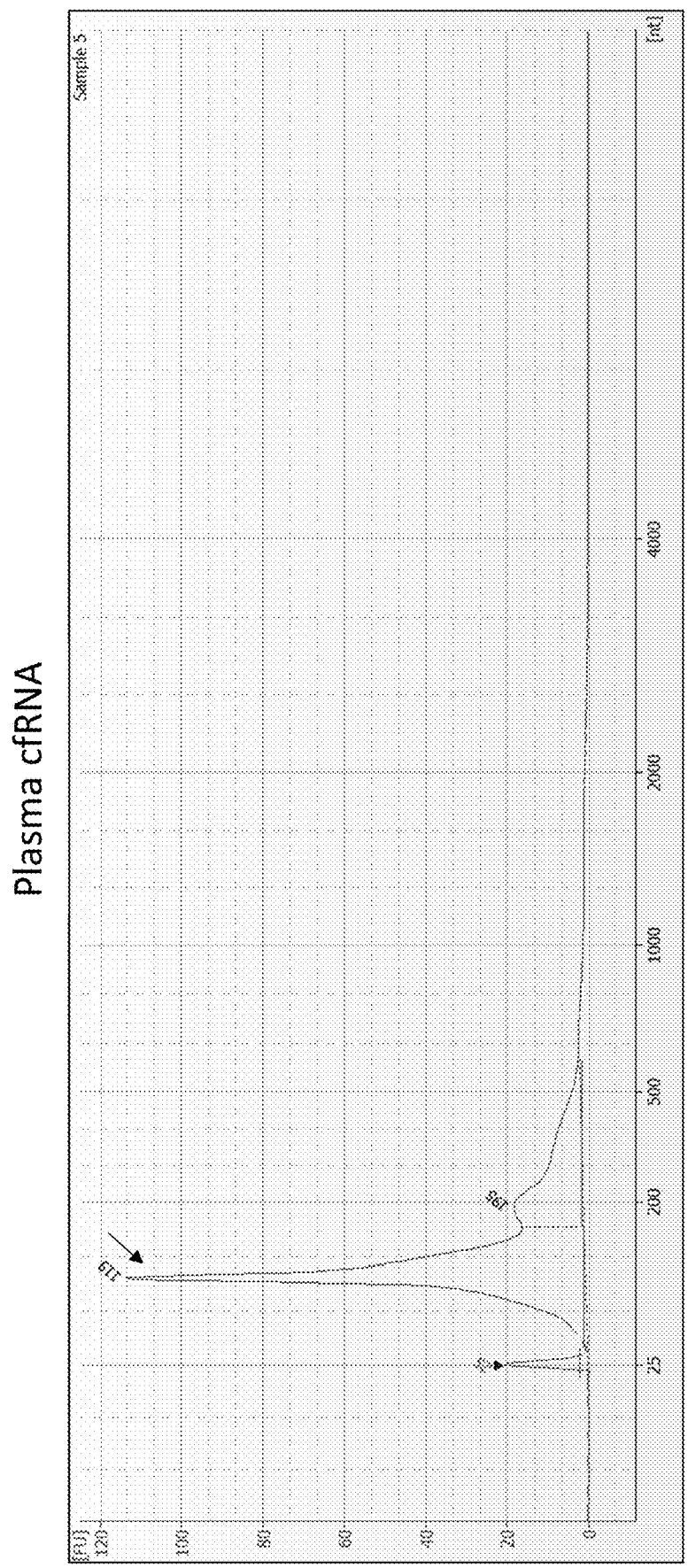
Figure 7:
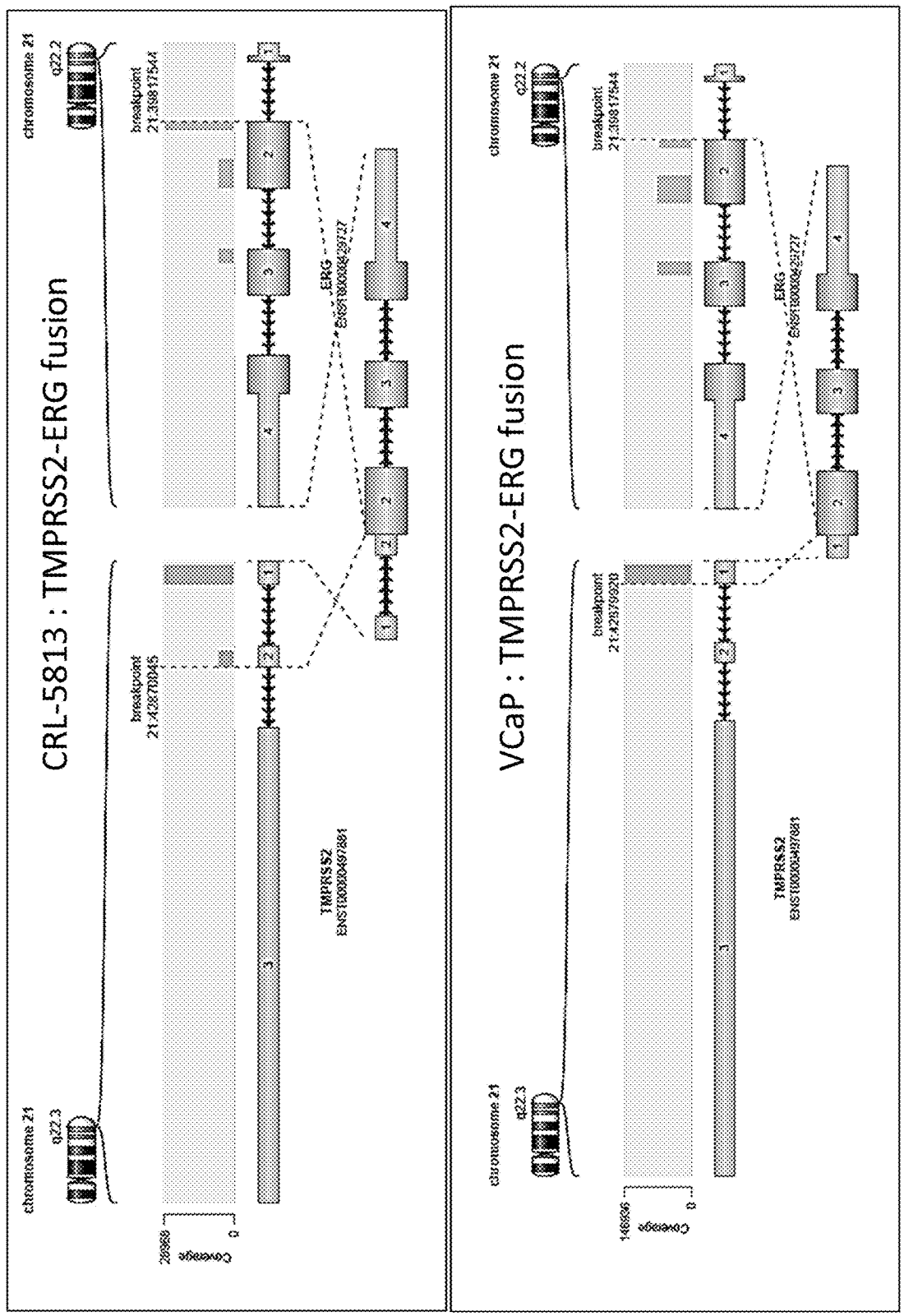
FIG. 7 is a diagrammatic representation from Arriba tool showing the detection of various exonic fusion in cancer cell lines: NCI-H660 cell line (CRL-5813, ATCC), VCaP cell line (CRL-2876, ATCC), MV-4-11 cell line (CRL-9591, ATCC) and Kasumi-1 cell line (CRL-2724, ATCC), using the multiplex amplicon sequencing method as described herein for fragmented RNA samples.
Figure 7:
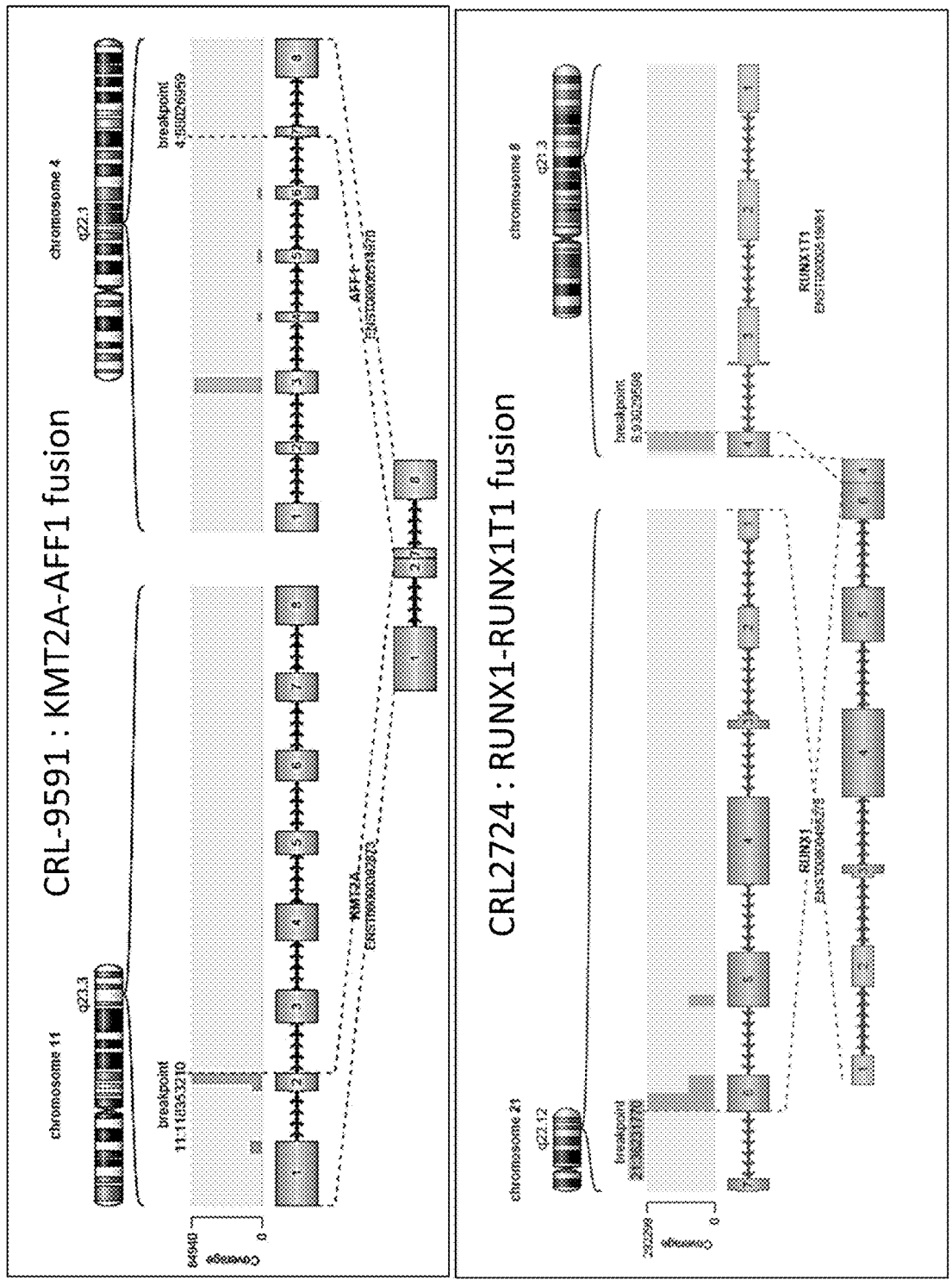

Technical Validation of cfRNA-Based Multiplex Amplicon Sequencing Detection with RNA Extracted from Cancerous Cell Lines The method described herein showed the ability to detect fusions using RNA extracted from cultured cancer cell lines known to harbor fusion genes, such as CRL-9591 (KMT2A-AFF1), H2228 (EML4-ALK), CRL-2724 (RUNX1-RUNX1T1), VCaP (TMPRS S2-ERG) and CRL-5813 (TM-PRSS2-ERG). As RNA from cultured cells is relatively intact compared for plasma cfDNA, the cell line RNA was subjected to ultrasonication (using Covaris) in order to more closely resemble the size of cfRNA. The resulting fraction as used to mimic cfRNA to demonstrate the performance of the multiplex amplicon sequencing for the detection of a variety of known fusions (FIGS. 5A, 5B and 5C), This was used to provide adequate material to mimic cfRNA to demonstrate the performance of the multiplex amplicon sequencing for the detection of a variety of known fusions. RNA-based detection of fusions in all five cancer cell lines was successful (FIG. 7). The plurality of sequencing library obtained can be qualified using the Agilent High Sensitivity DNA Screentape as shown in FIG. 15, which illustrates a typical library profile for a cfRNA sample converted to a sequencing library as seen on the High Sensitivity DNA Screentape. The multiple peaks >200 base pairs correspond to the multiple products encompassing potential fusion products, control gene products and other gene expression products for which the multiplicity of forward and reverse primers are included. Qualified libraries will have prominent peaks of size >200 base pairs.

Figure 6A:
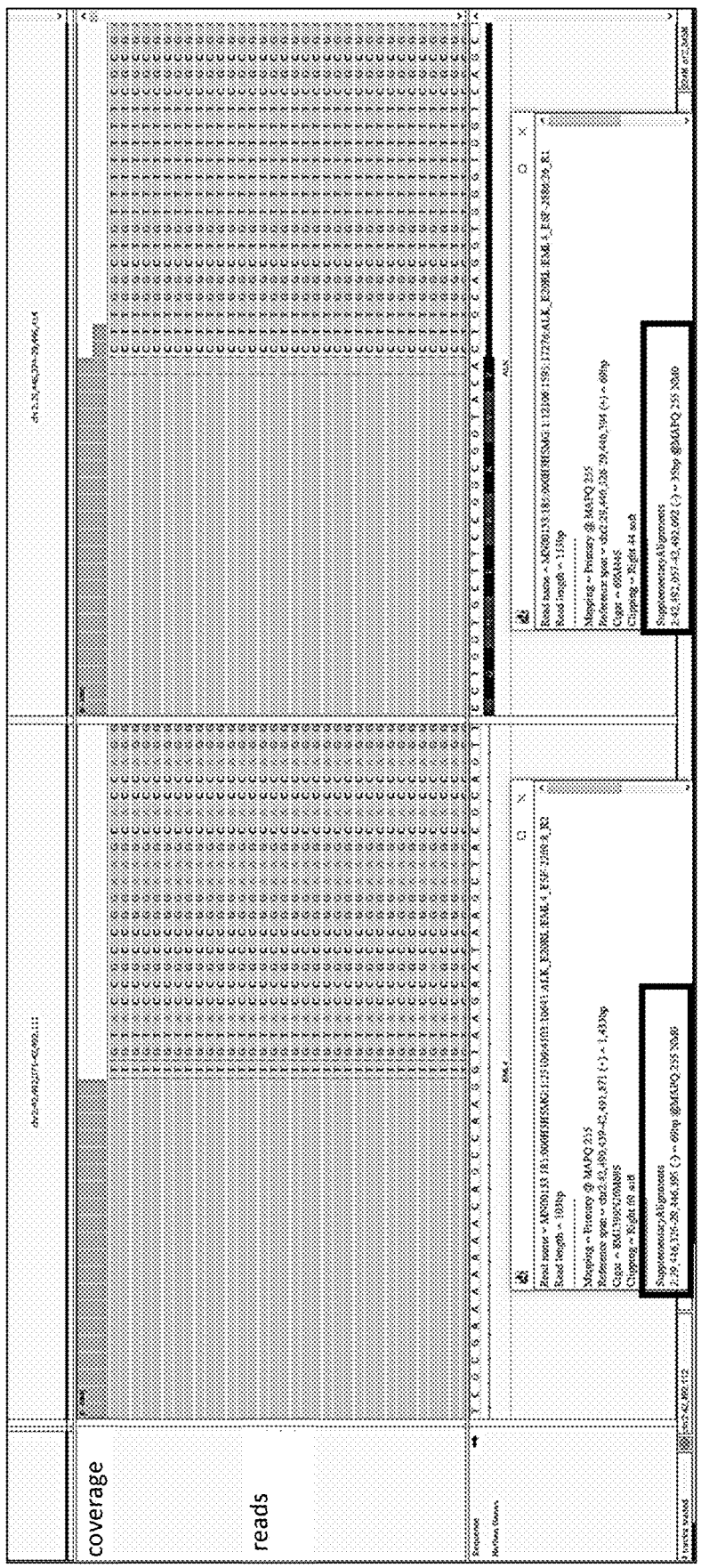
Figure 6B:
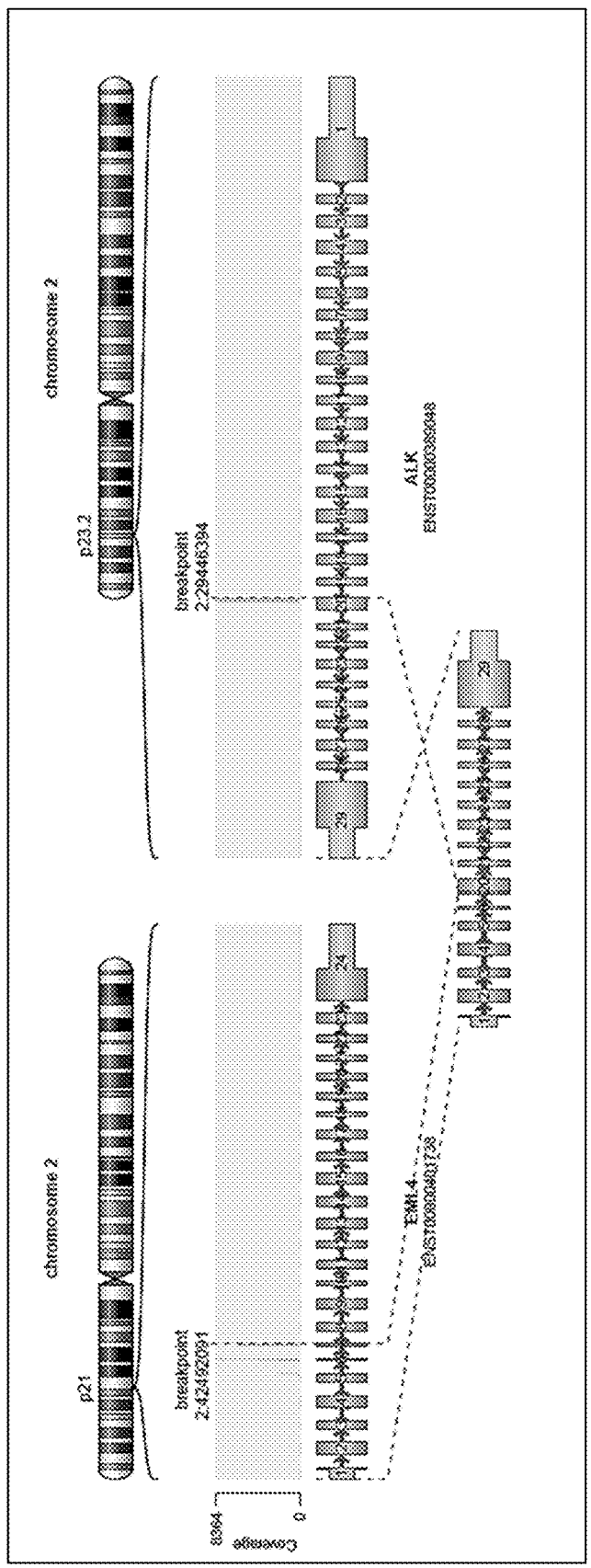

Sequence alignments to the reference genome showed the capture of sequencing reads with partial alignment to the target exon, and partial alignment to another part of the genome sequence of which corresponds to the partner gene exon, known as a split read, and confirmed the detection of the EML4-ALK fusion transcript in H2228 cell line with as little as 1 ng of fragmented RNA with 8364 reads supporting the split configuration. (FIGS. 6A and 6B). The alignment of split reads showed that fusions in cancer cell lines: NCI-H660 cell line (CRL-5813, ATCC), VCaP cell line (CRL-2876, ATCC), Human MV-4-11 cell line (CRL-9591, ATCC) and Kasumi-1 (CRL-2724, ATCC), were accurately detected as visualized by Arriba tool for detection of fusions in RNA sequencing data using the multiplex amplicon sequencing method in fragmented RNA. (FIG. 7).

Data Comparison Between cfDNA and cfRNA-Based Detection Assay

Figure 8A:
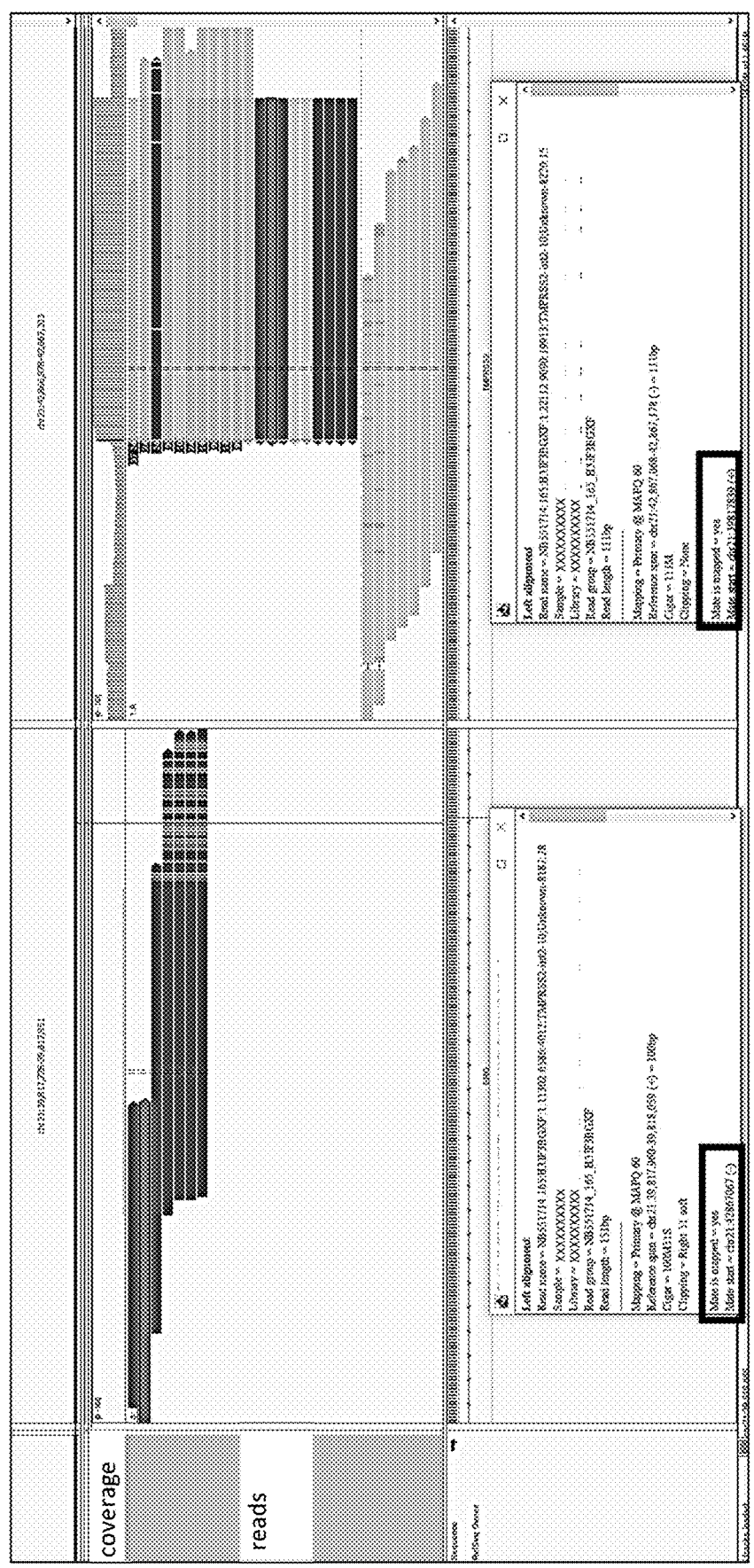
Figure 8B:
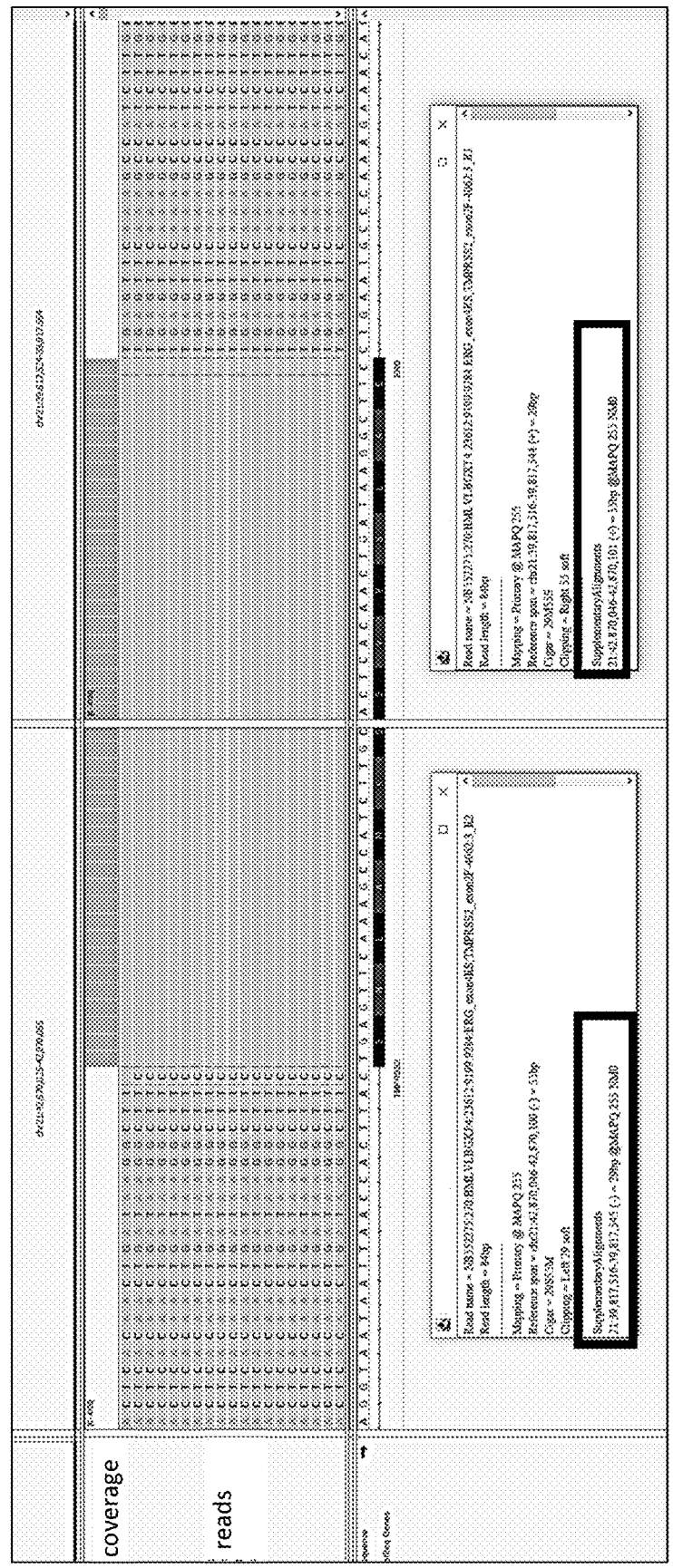
Figure 8C:
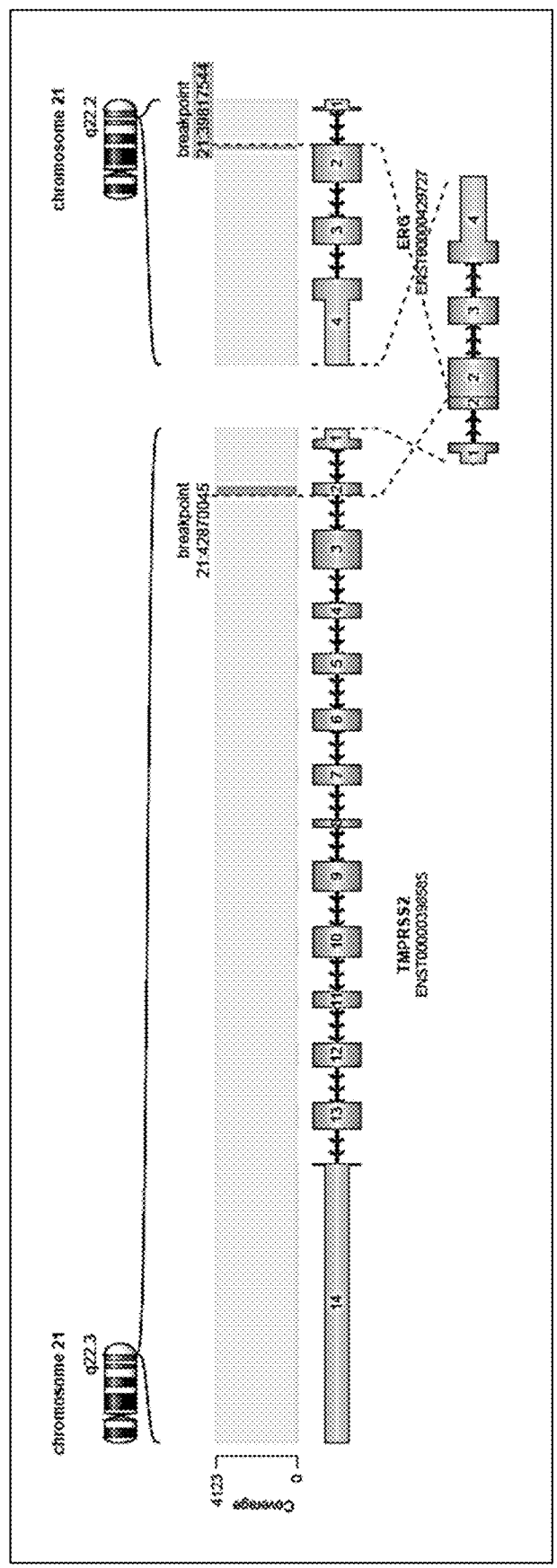

Nucleic acid extracts from plasma of two cancer patients previously characterized to be positive for fusions using a DNA-based method (Liquid Hallmark) were tested. In the first case of a metastatic prostate cancer, TMPRSS2-ERG fusion was detected in cfDNA (using 70 ng of cfDNA) supported by 17 split reads mapping to intronic position chr21:42867069 within TMPRSS2 (intron 2 of TMPRSS2-NM_005656.4) and intronic position chr21:39818058 within ERG (intron 3 of ERG-NM_001291391.1) (FIG. 8A). Using the same circulating nucleic acid extract, fusion in the cfRNA (equivalent of just 24 ng cfRNA) was detected with 4123 supporting split reads, fusing exon 2 of TMPRSS2 (chr21: 21:42870045) with exon 4 of NM_001291391.1 (or exon 2 of ERG NM_182918.4) (chr 21:39817544) (FIG. 8B).

Figure 9A:
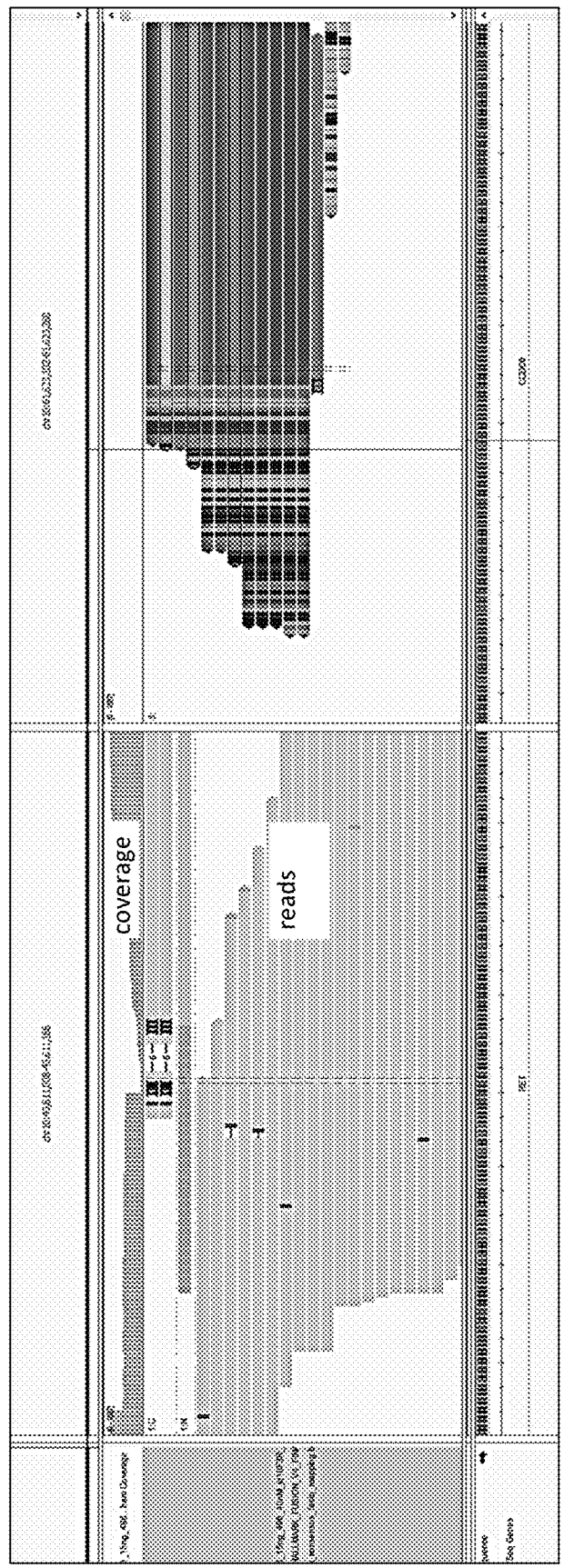
Figure 9B:
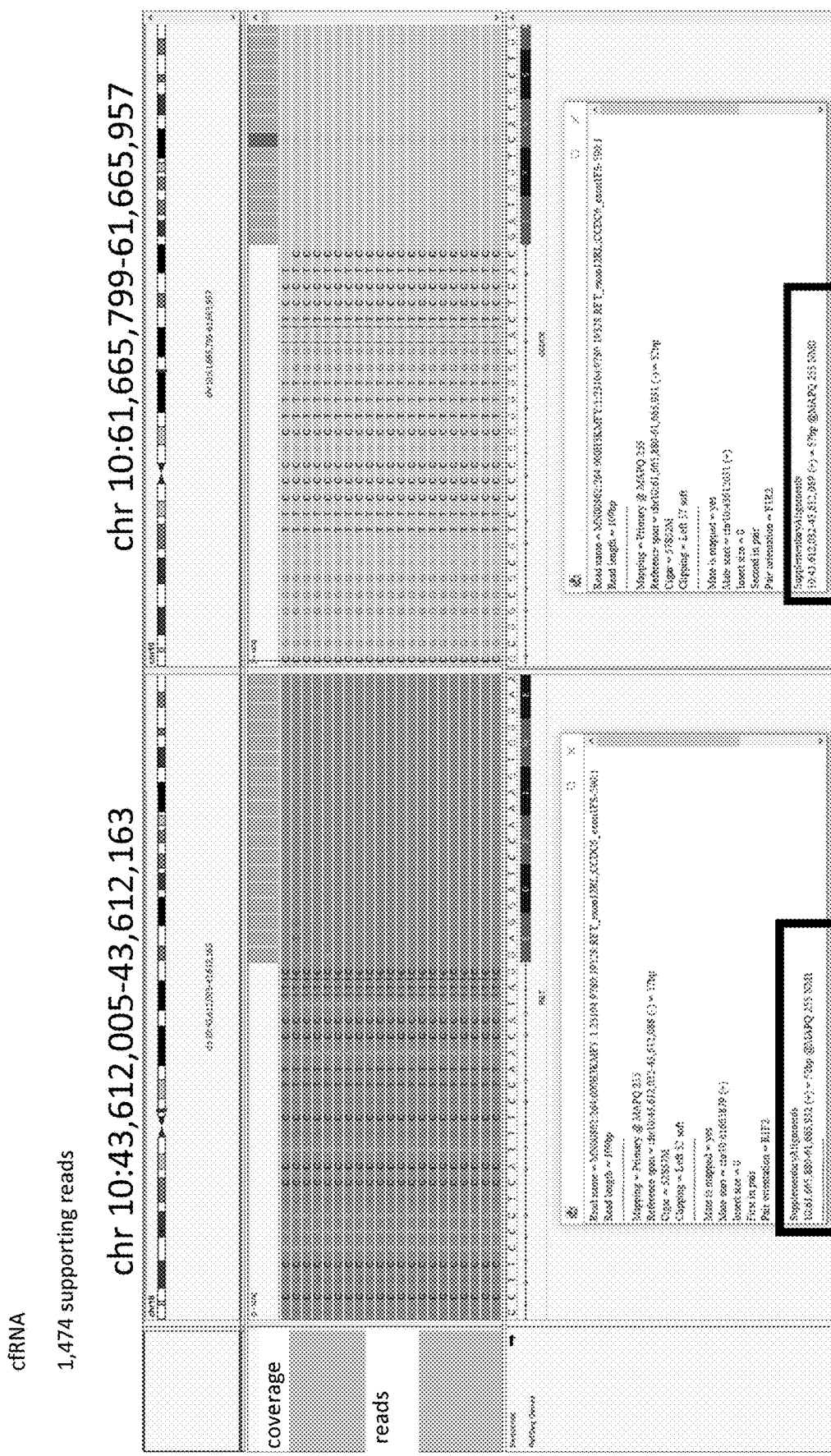
Figure 9C:
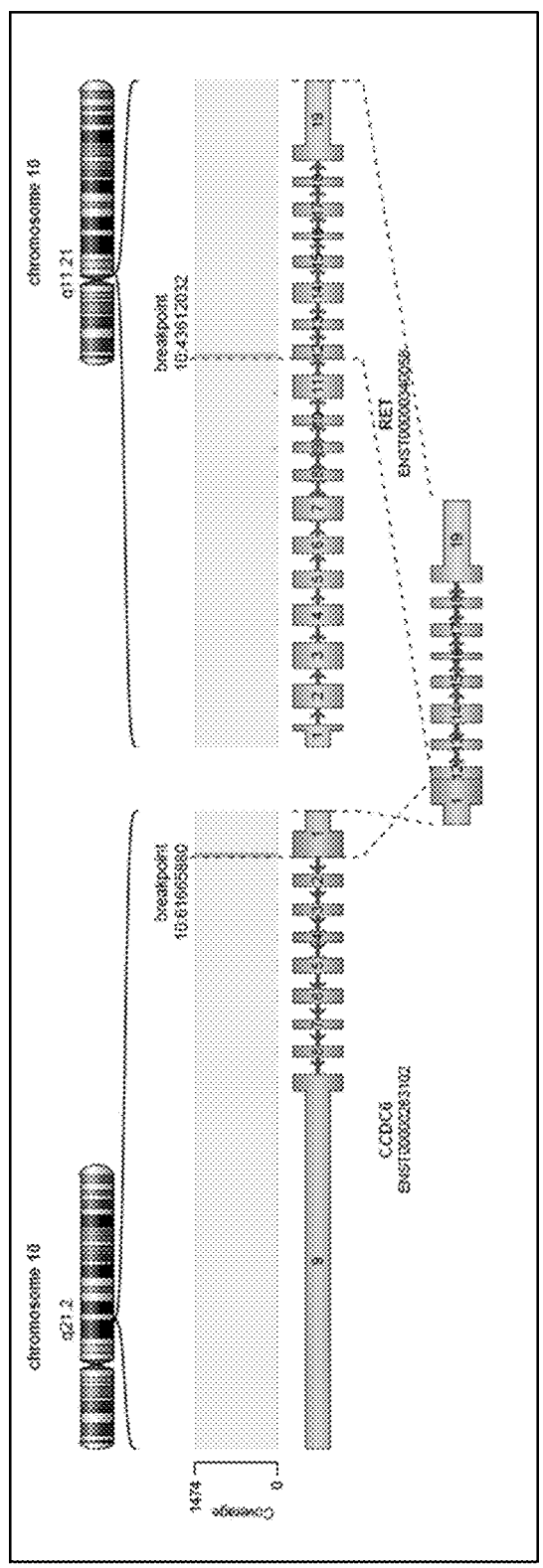

In a second case of metastatic lung cancer, a CCDC6-RET fusion detected using cfDNA (breakpoints CCDC6 Intron 1 (chr10:61623181) and RET intron 11 (chr10:43611035) and cfRNA CCDC6 exon 1 (10:61665879) and RET exon 12 (10:43612031). cfDNA was detected with 12 supporting reads, while fusion in cfRNA was supported by 13 split reads (FIGS. 9A and 9B).

Figure 10A:
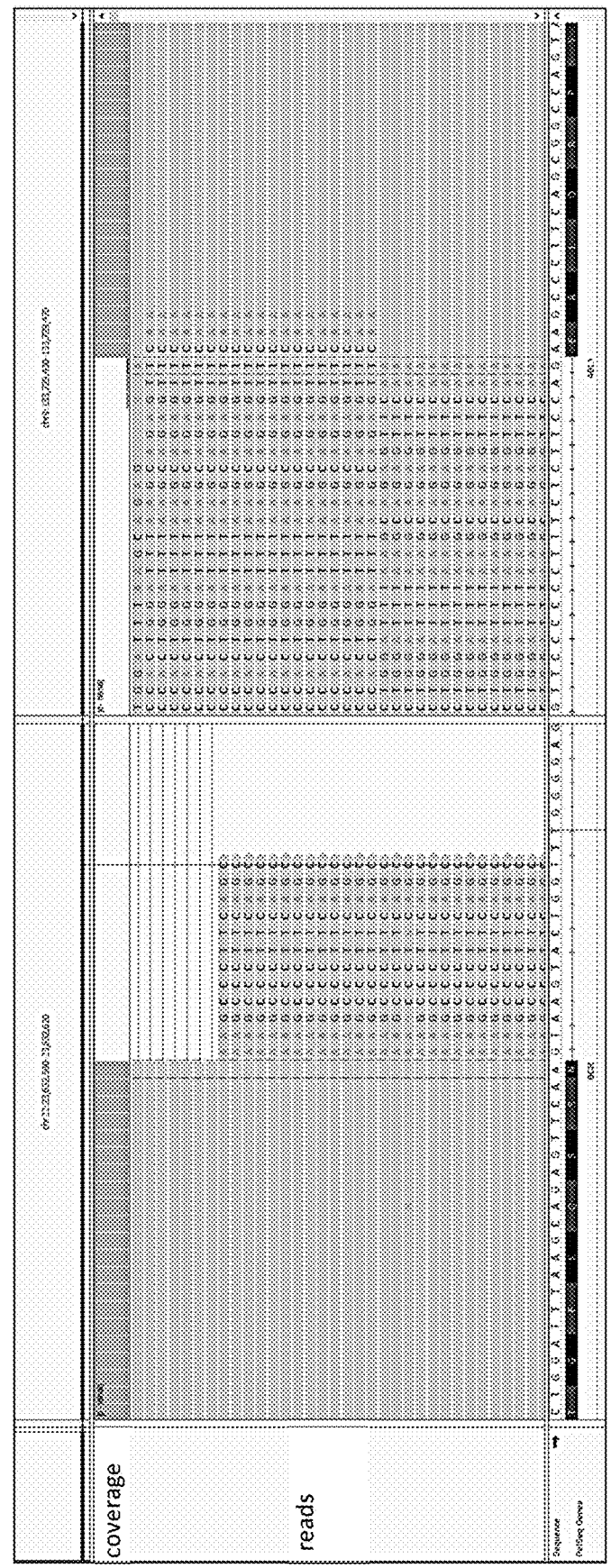
Figure 10B:
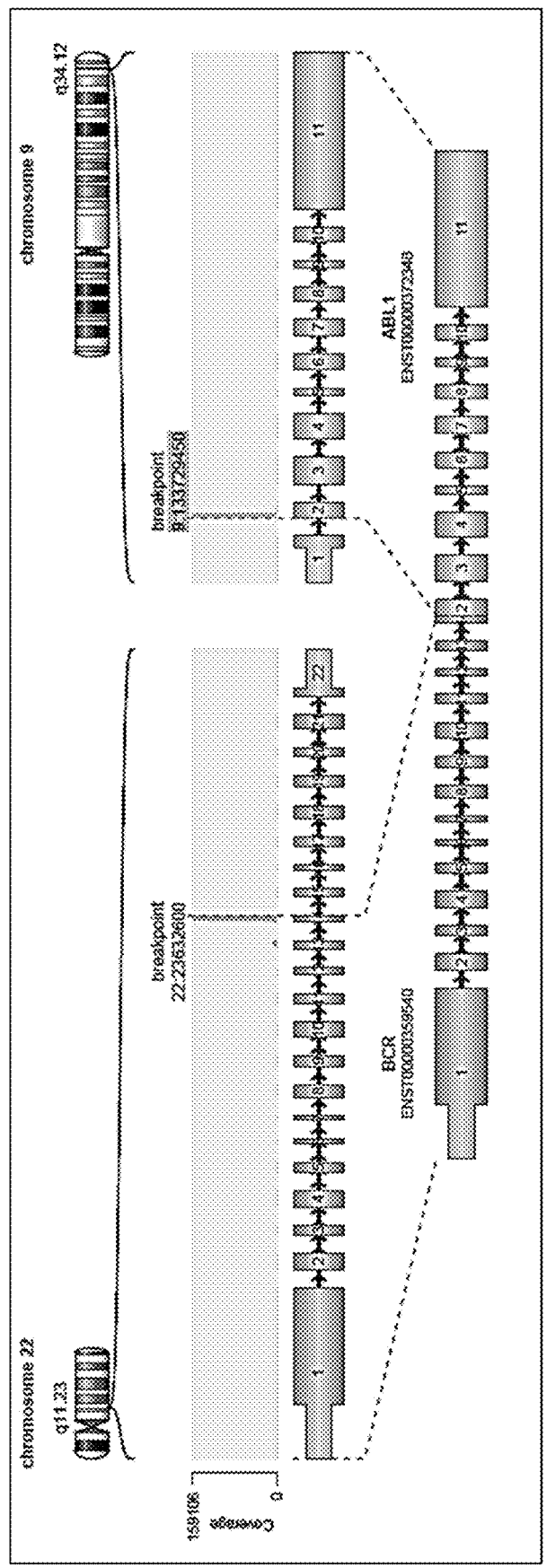

In a third clinical sample from a hematological malignancy (acute lymphoblastic leukemia) with BCR-ABL1 rearrangement confirmed in DNA from the peripheral blood cells, RNA was extracted from another fraction of archived buffy coat and tested with the multiplex amplicon sequencing method described here. The fusion between exon 14 of BCR, and exon 2 of ABL1 was readily detectable in the RNA fraction with an abundant 159,106 supporting reads. The large number of supporting reads is indicative of the enrichment of transcripts with BCR-ABL1 fusion, due to increased expression and secondary enrichment of cancer cells positive for the fusion in sample tested (buffy coat RNA) (FIG. 10A and FIG. 10B).

Figure 13A:
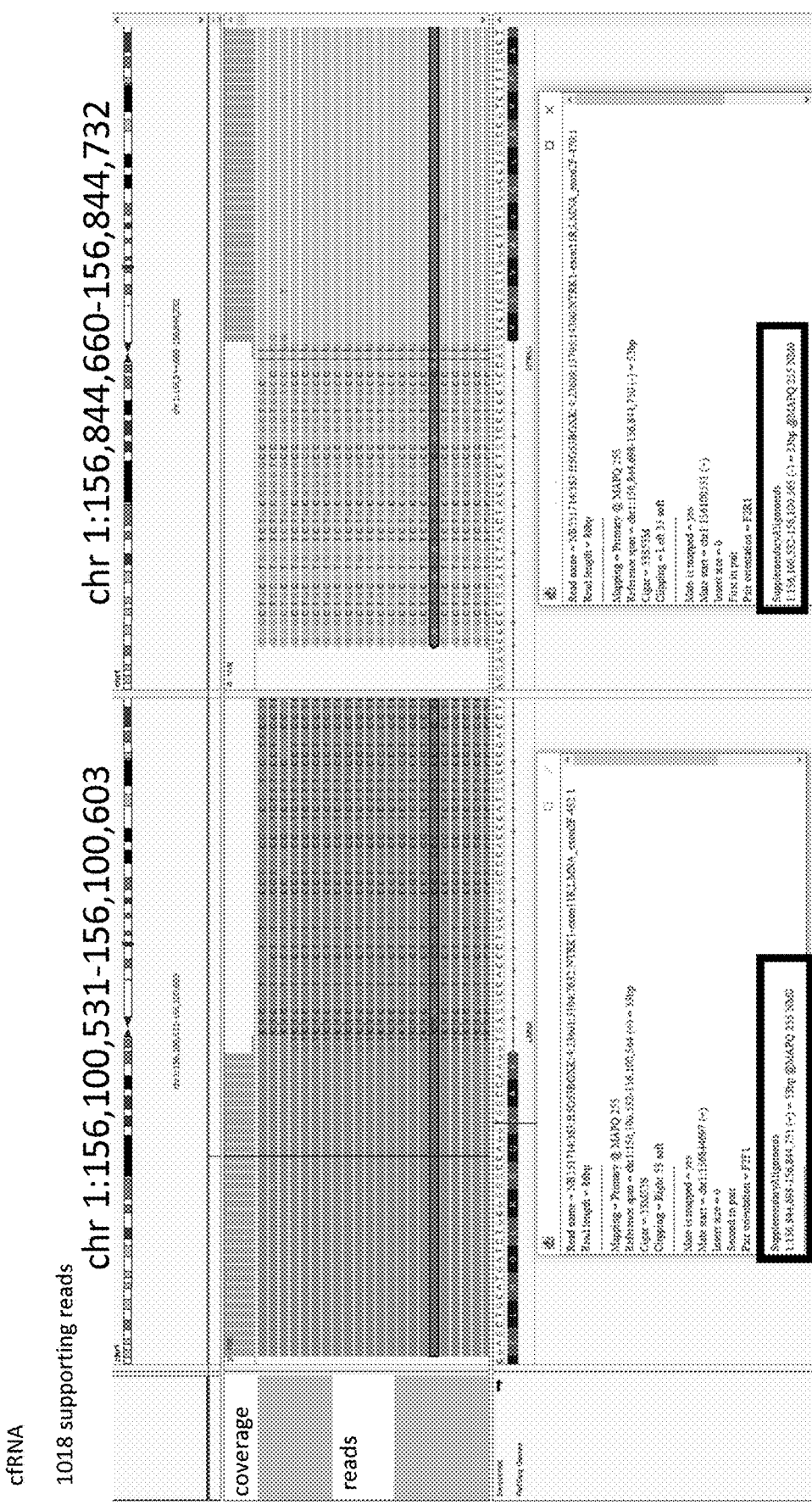
Figure 13B:
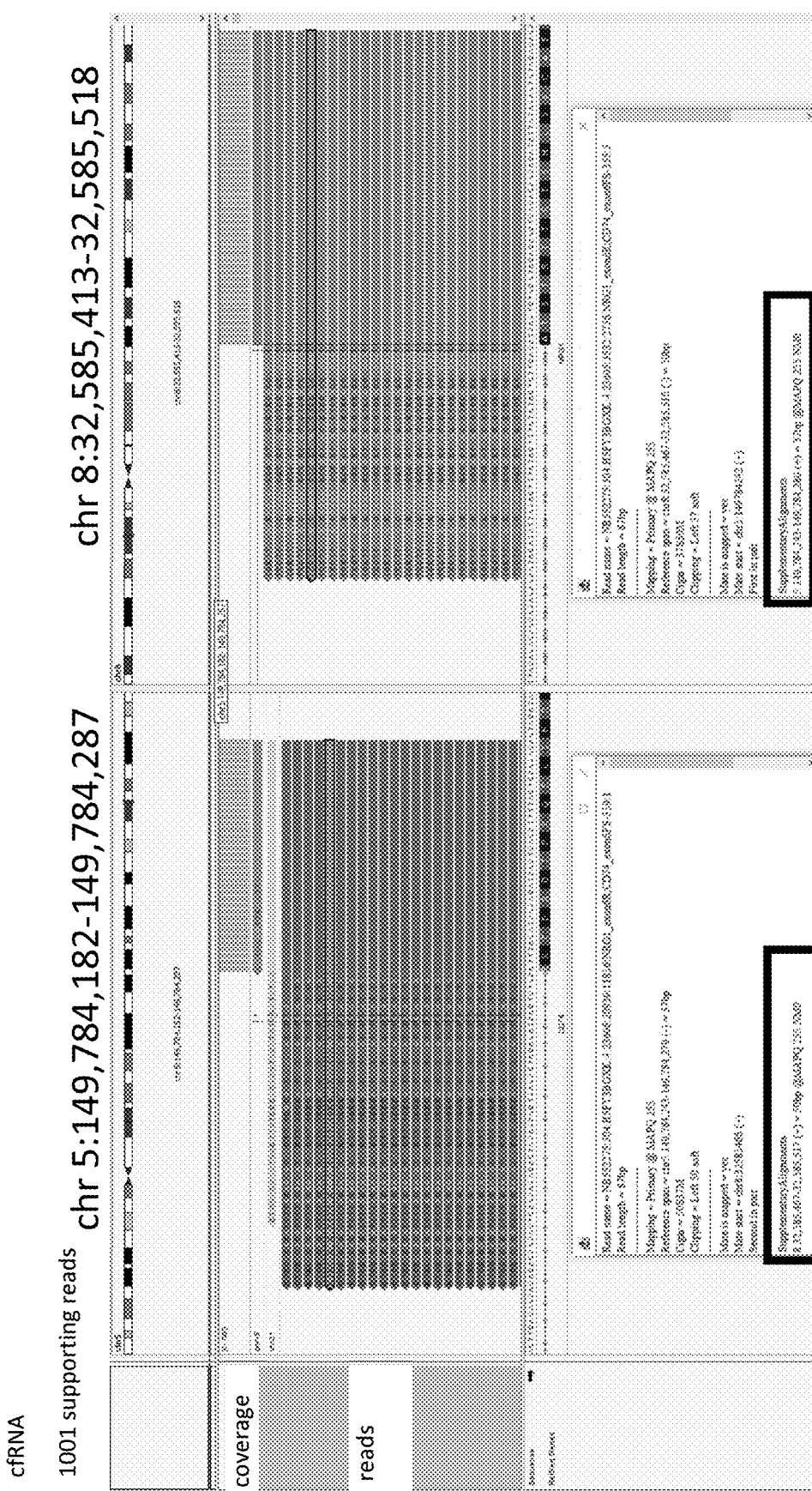
Figure 13C:
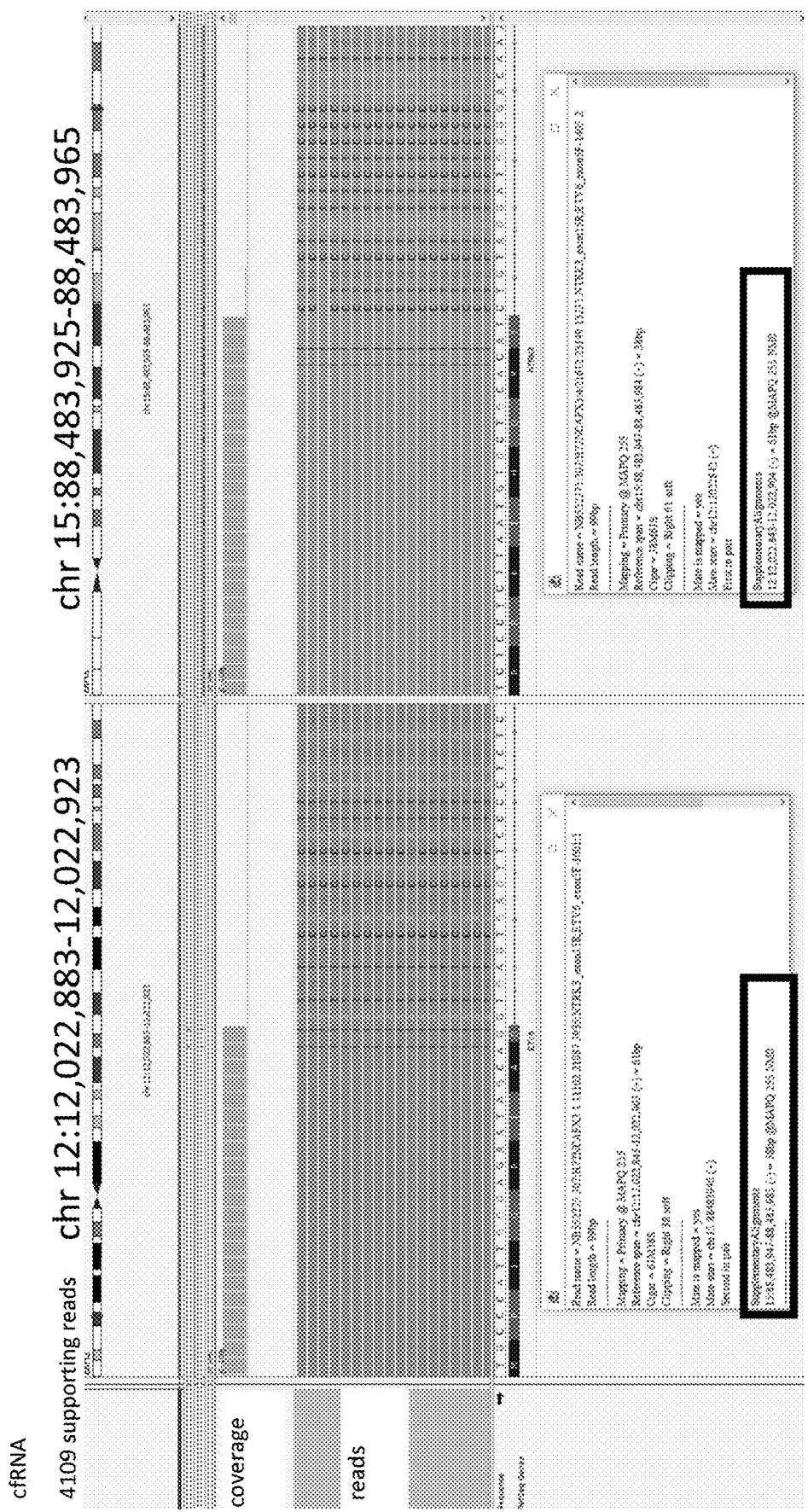

Additional fusion events are shown in FIGS. 13A-13C illustrating the identification of actionable driver fusions in untreated lung cancer cases using cfRNA using the method described herein. FIG. 13A, FIG. 13B and FIG. 13C show the detection of various gene fusion events namely LMNA-NTRK1 fusion, CD74-NRG1 and ETV6-NTRK3 fusion in cfRNA samples in three lung cancer cases, respectively. These mutations were otherwise undetectable using a DNA-based assay and appear as negative for the presence of other driver gene mutations in cfDNA. In addition, when the method described used cfDNA and cfRNA for fusion detection in 45 lung cancer cases, additional fusions were identified when cfRNA fraction was used compared to cfDNA (FIGS. 14A-14B). When testing for fusion was performed with DNA and RNA as sample input orthogonally, there were 12 cases with concordant fusion detection based on cfDNA and cfRNA as sample input. There were additional fusions detected in 5 cases and 1 fusion that was missed and not detected when cfRNA was used as sample input instead of cfDNA. The list of range of fusions detected by both cfDNA and cfRNA methods or by one of the two methods shown in FIG. 14B.

Limit of Detection

Figure 11:
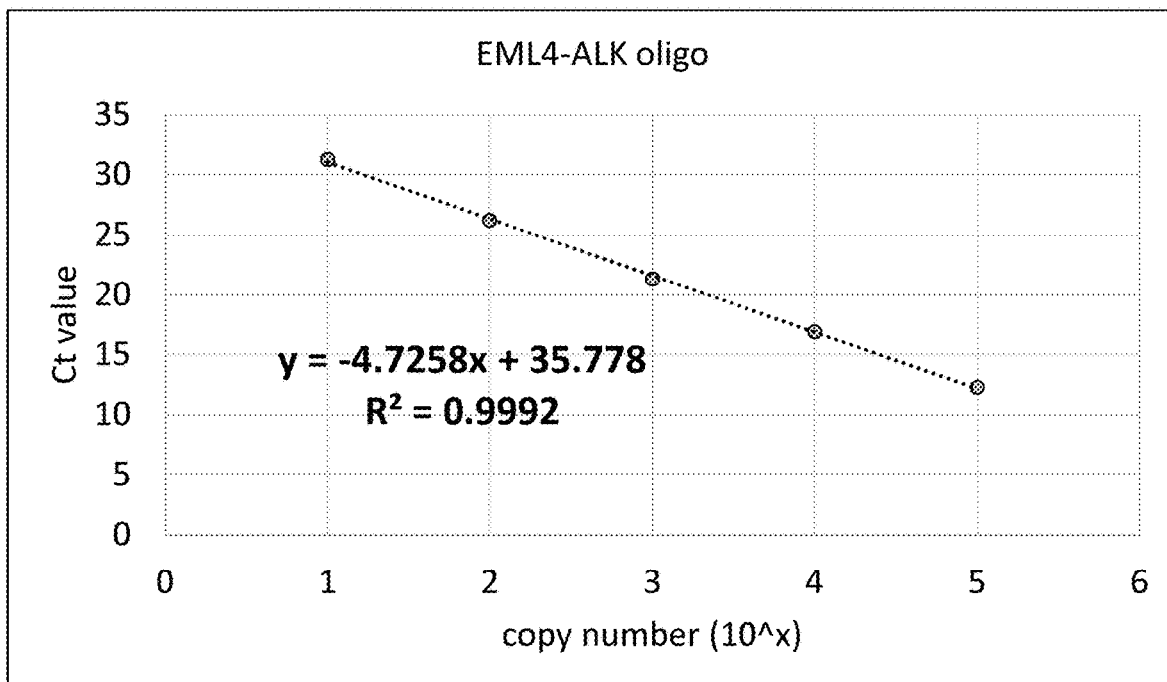
FIG. 11 shows the result from quantitating the number of EML4-ALK fusion transcript copies per nanogram RNA from H2228 cell line, for determining the sensitivity limits of detection of the cfRNA-based method described herein.

The limit of detection is defined as the lowest RNA concentration at which fusion events can be readily detectable. Initial determination of limit of detection of RNA-based fusion was done by quantitating the number of EML4-ALK fusion transcripts present in 1 ng of H2228 cell line RNA, from which EML4-ALK fusion was readily detectable using the method described herein (FIGS. 6A-6B and FIG. 7). The number of EML4-ALK fusion RNA transcripts was determined to be ~13.7 copies per 5 ng of RNA using a qRT-PCR assay designed specifically for the EML4-ALK transcript present in H2228 cells (FIG. 11). Therefore, the method described herein is shown to be able to detect down to 2.72 copies of EML4-ALK fusion (in 1 ng of H2228 RNA), suggesting a very sensitive detection for RNA-based fusions.

Figure 12:
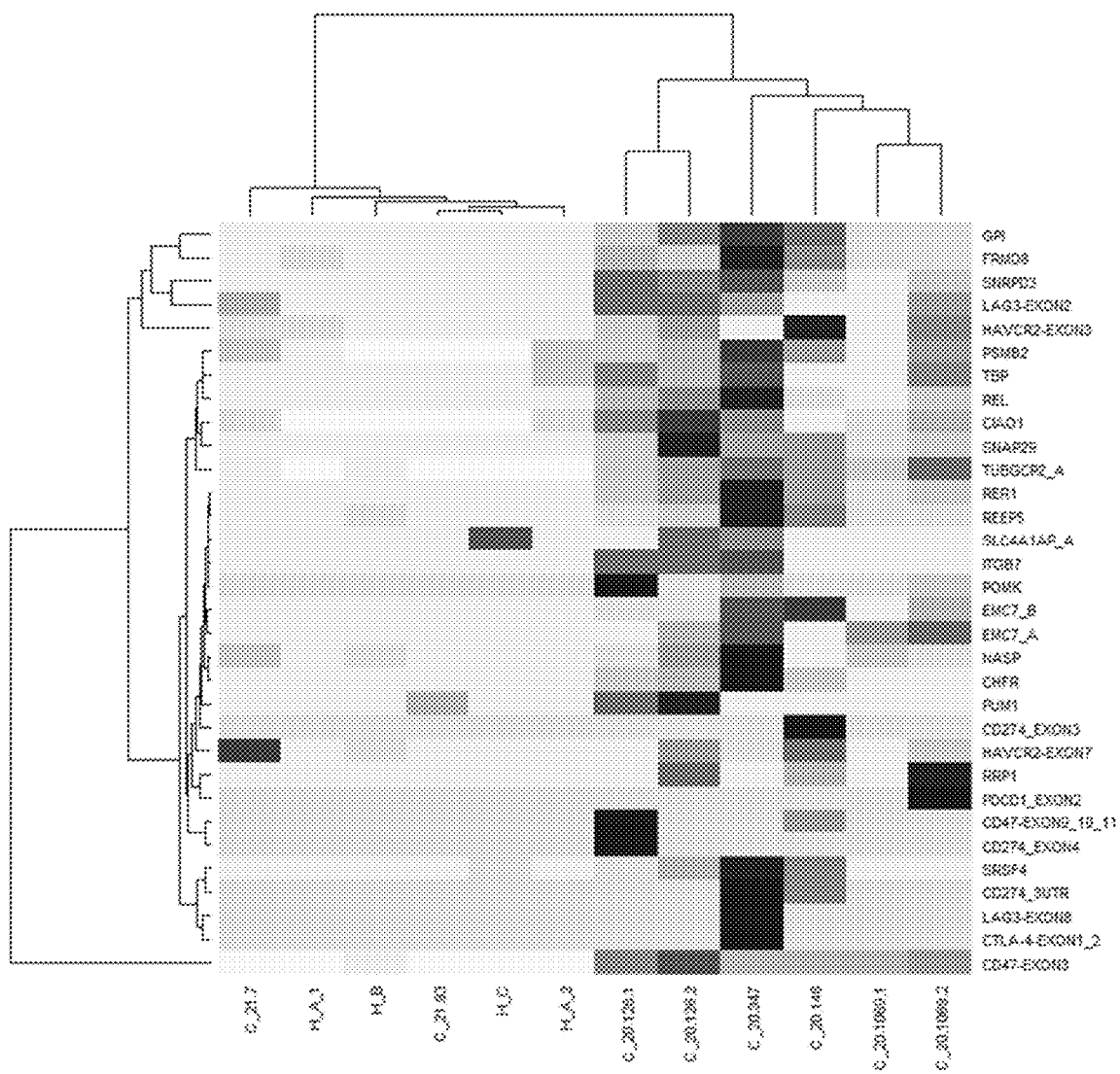
FIG. 12 shows the detection and quantification of expression of control genes and other target genes in cfRNA from both cancer and healthy samples, using the method described herein. The table (top panel) describes the amount of cfRNA input for each sample tested, including repeats of two samples with differing input cfRNA amounts. The expression heatmap (bottom panel) demonstrates the distribution of the expression read counts, as derived from the method described herein, for each sample. Fusion detection in the same sample is feasible and shown for C_20-347, and C_20-146, which were simultaneously positive for CCDC6-RET and TMPRSS2-ERG fusion, respectively, as depicted in FIG. 8 and FIG. 9.

Simultaneous Detection and Quantification of Expression cfRNA-Based Fusion Events Besides the detection of fusions in cfRNA, simultaneous detection of targets genes intended for non-invasive expression monitoring was also done for cfRNA from cancer and healthy samples. In the same multiplex reaction, primers for 22 control genes and 13 amplicons for 6 genes related to immunotherapy response (CD274, PDCD1, CTLA4, LAG3, HAVCR2 and CD47) were included, and the combined target capture was performed. Based on read counts mapping to the intended target regions, the determination of expression level of each target was done. The range of expression levels were visualized in an expression heatmap (FIG. 12).

As healthy samples typically had very low yields of both cfRNA and cfDNA, the expression was low for control genes and immunotherapy response genes across along healthy samples as expected. However, among cancer samples, a range of expression patterns was observed, with some samples showing limited expression of nearly all targets, despite an equivalent amount of cfRNA material used in the method. The reliability of detection and the quantitative ability of the method was demonstrated by the performing repeats of the same sample with differing amounts of cfRNA, which showed an increase in the expression read count, but similarity in pattern among the sample repeats (FIG. 12). The repeats are represented by C_20.126.1 and C_20.126.2 (sample 20.126 repeated) and C_20.1069.1 and C_20.1069.2 (sample 20.1069 repeated). In the heatmap, the two repeats are closest to each other indicating greater similarity between two repeats of same sample, compared to other samples.

Detection of Expressed Transcripts Comprising Deletion Mutation in RNA Sample

Figure 16:
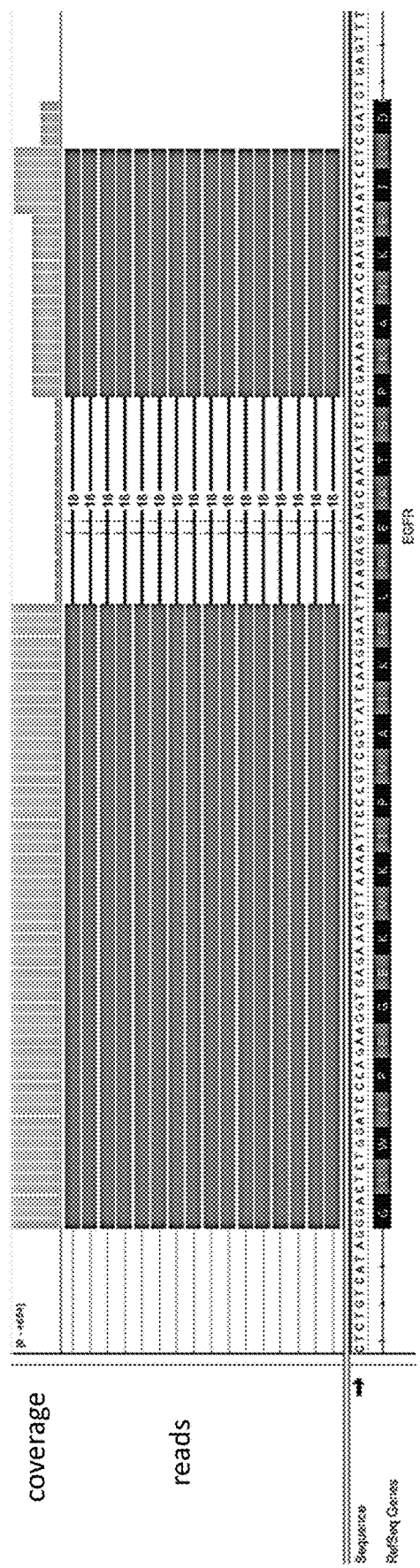
FIG. 16 is an IGV graphic report showing the detection of an 18-bp deletion in RNA extracted from FFPE lung tumor tissue using cfRNA-based method described herein. The expression of EGFR c.2240_2257del p.L747_P753delinsS mutant transcript (comprising the deletion) was supported by 4266 reads.

The method described herein showed the ability to detect an 18-nucleotide deletion in an RNA sample extracted from FFPE lung tumor tissue. The expression of EGFR c.2240_2257del p.L747_P753delinsS mutant transcript (comprising the deletion) was detected with 4266 supporting reads (FIG. 16).

Figure 17:
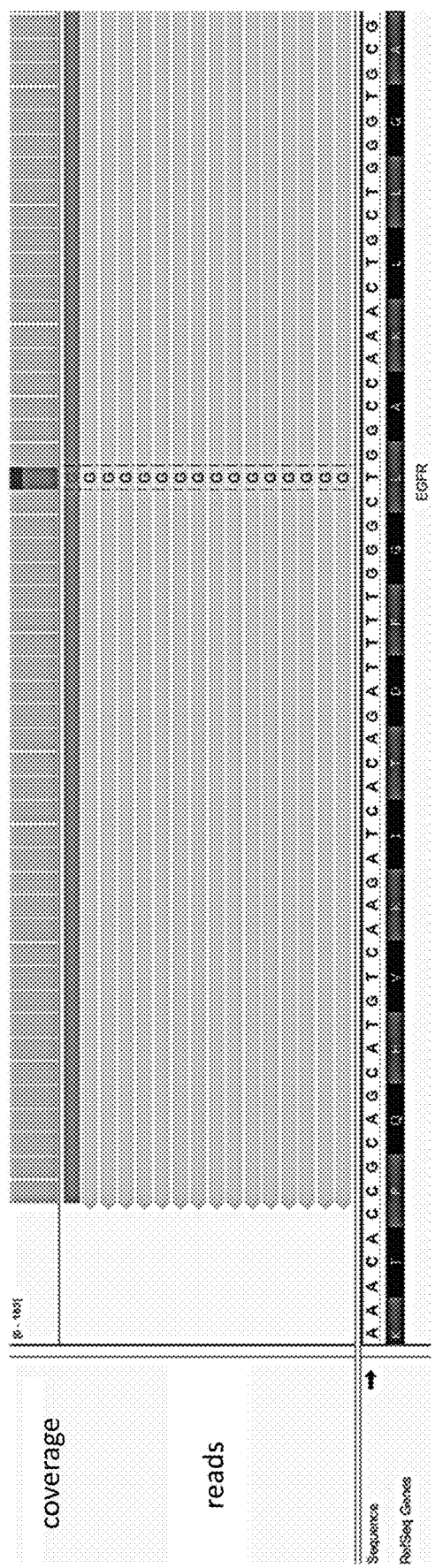
FIG. 17 is an IGV graphic report showing the detection of a single nucleotide variation in cfRNA extracted from the plasma of a metastatic lung cancer patient using cfRNA-based method described herein. Expression of EGFR c.2573T>G p.L858R mutant transcript (comprising the single nucleotide variation) was supported by 112 reads.

Detection of Expressed Transcripts Comprising Single Nucleotide Variations in RNA Sample The method described herein showed the ability to detect single nucleotide variation in a cfRNA sample extracted from the plasma of a metastatic lung cancer patient. The expression of EGFR c.2573T>G p.L858R mutant transcript (comprising the single nucleotide variation) was supported by 112 reads. (FIG. 17)

Detection of Expressed Transcripts Comprising Single Nucleotide Variations, Insertion and Deletion Mutation in RNA Sample The method described herein showed the ability to detect single nucleotide variations, insertion and deletion mutations in tissue RNA extracted from FFPE tumor samples (FIG. 18A) and cfRNA extracted from plasma (FIG. 18B). Simultaneous detection of target genes intended for detection of expressed transcripts containing single nucleotide variations, insertion (e.g., duplications) and deletion mutations was performed for tumor tissue RNA from 4 cancer samples and plasma cfRNA from 3 cancer samples. In the same multiplex PCR reaction, primers for desired targets were included, and combined target capture was performed. The variant allele frequency (VAF) was determined based on the proportion of mutant read counts relative to total read counts detected from the method described herein. The validity of the RNA-based method described herein is shown by the VAF percentage depicted in FIGS. 18A and 18B.

Discussion

In the present disclosure, a method to simultaneously detect genomic alterations such as structural rearrangements, and gene expression using circulating cell-free RNA (cfRNA) is described. Such detection and quantification non-invasively is envisioned to allow the detection of cancer, determination of prognosis and prediction of therapy response. The method is based on highly multiplexed amplicon-based NGS, and involves the tagging of individual cfRNA molecules using barcode sequences, and the optimized design of amplicons to be compatible with the fragmented nature of cfRNA. The inventors have shown that the method can be applied to circulating nucleic acid extracts containing both cfDNA and cfRNA, and can detect and quantitate fusion RNA transcript and gene expression simultaneously, in such samples.

In order to detect structural rearrangements, such as gene fusions—that result in the juxtaposition of exons from different genes, resulting in a fusion transcript—from cfRNA analyte, a targeted multiplex amplicon panel for detection of fusions by next-generation sequencing (NGS) was designed. The juxtaposition of gene exons was exploited to amplify fusion transcripts, by a pair of primers flanking the exonic junctions involved in the fusion. Primers specific for exons of fusion and partner genes known to undergo fusions were designed just flanking the exonic junction sites. Such juxtaposition of exons from different genes can only happen when processed mRNA is generated (by splicing) bringing fused exons together, and so equivalent DNA sequences are unlikely to contribute to productive amplification with the same primers, because of the intervening fused relatively long introns separating the exons in the DNA.

The design of the primers to capture fusion transcripts had two main features—1) the presence of a random barcode sequence in the downstream primers (downstream relative to the fusion transcript) to individually tag each copy of the RNA fusion transcript if present, and 2) the location of each primer approximately 50 base pairs from each exonic junction in the panel, such that the expected total amplicon length would be close to 90-110 base pairs. This was done in order to meet the sample cfRNA size distribution observed which peaked at 110-120 nucleotides. The chosen length of 90-110 base pairs was considered optimal because products of shorter amplicons (<80 base pairs) would be less effectively retained through the multi-step library preparation method for amplicon sequencing, involving size-based separation (magnetic bead based) of smaller primer dimer artefacts to be removed and desired products to be retained. A multiplicity of "upstream" and "downstream" primers were included in the multiplex PCR to optimally capture potential fusions known to occur between genes. The design of primers includes exons of well-characterized genes known to undergo fusions, such as ALK, RET, ROS1, FGFR2, FGFR3 and exons of their partner genes, such as EML4, KIF5B, CCDC6, CD74, TACC3, among others. Potential fusions between any upstream and any downstream exon (not limited to gene pairs for which design was intended) can theoretically be detected if present in a sample, if the capture reaction simultaneously includes the multiplicity of primers. Broadly, primers to capture all exonic junctions known to undergo fusions (and intervening exons which may not have been previously reported to be involved in fusions) in target and partner genes were designed. The barcode sequence primers allow for accurate enumeration of copies of RNA transcript as per method of enumeration.

The first step in the process of preparing a cfRNA NGS library based on this method is the conversion of cfRNA (naturally fragmented) into complementary DNA (cDNA) using reverse transcriptase enzyme with random primers. The result of the reverse transcription reaction is a total complement of the cfRNA molecules present in the sample. In addition to the exon flanking primers for fusion detection, and in order to provide a quantitative measure of amount of cfRNA included in a reaction, primers were also included for several (>20) control housekeeping genes in the multiplex reaction. The purpose of capturing transcripts of genes expressed at some baseline line across all sample types, was to estimate an average abundance of cellular material going into the multiplex PCR reaction, and to serve as a control for the whole process of preparation of cfRNA sequencing libraries, including the sample extraction, reverse transcription, and PCR steps. The design of primers intended for control target genes differed from that of fusion targets, in that at least one primer of a control gene primer pair was designed to span an exon-exon junction, in order to prevent unintended amplification of DNA of the control target gene, and the resulting amplicon was ~100 base pairs in length (FIG. 1). The design of primers for target genes related to expression were similar to the control gene targets, and at least one primer of primer pair spanned an exon-exon junction, and two or more primer pairs were designed per target gene covering both 5' and 3' end exons, to more reliably capture expression of target genes for expression, by allowing one or more amplicons to represent a given target gene. A highly multiplexed primer pool was employed with a plurality of upstream and downstream primers, some of which are expected to generate sequenceable targets in most samples depending on expression variability, and some primers which are expected to generate a product only when a sample is positive for structural rearrangement, generating a fusion gene that is productively expressed. The primers additionally carried the appropriate extensions necessary for generating sequenceable libraries with sequencing adapters for Illumina sequencing.

In this disclosure, the use of cfRNA analyte for the enhanced detection of structural rearrangements and gene expression simultaneously, was demonstrated. This was achieved by the design of multiplex amplicon NGS assay encompassing the exons of genes involved in fusion and the design of amplicons for the expression of target genes, with use of barcode sequences and optimal size selection of amplicons for cfRNA applications. Overall presence of abundance was quantified by read density of accumulated read numbers. In this disclosure, issues related to whole-transcriptome sequencing including cost and manpower were partially overcome with the application of targeted sequencing for plasma cfRNA.

In the present disclosure, clinically relevant altered splicing events such as MET proto-oncogene, receptor tyrosine kinase (MET) exon 14 skipping, Androgen receptor (AR) transcript variants are approached as intra-gene fusions events and are designed to be captured if present using a combination of primers which would capture the aberrant splicing as the juxtaposition of exons of the same gene not normally observed, but that which can occur in cancers. The ability to quantify expression of relevant genes, non-invasively, for the prediction of response to various treatments is valuable, as it allows the longitudinal monitoring of response, and informs clinical decision. However, this has not been routinely implemented in clinical practice, and is largely limited to the detection of DNA level alterations such as mutations and genomic copy number changes. Using sequencing technology such as NGS, mutations are identified by comparing sequencing reads to reference sequences (genomes). Genomic copy number changes are quantified by counting the number of reads corresponding to a gene, and quantifying the deviation from normal copy number count expected from cells or samples having two copies of DNA per gene. In one example, DNA level alterations include single nucleotide variants leading to missense mutations, frameshift mutations, insertion-deletions, splice site mutations. The non-invasive monitoring of expression changes by accessing the cfRNA analyte can exploit the overexpression of tumor-specific transcripts, lead to amplification of tumor-derived RNA signals in blood, thereby increasing sensitivity of detection. For the non-invasive characterization of structural rearrangements, for example, gene fusions in plasma, typically targeted cfRNA-based next-generation sequencing (NGS)-based methods are utilized.

To overcome the issues of stability, appropriate RNA isolation procedures, removing DNA contamination and the use of endogenous housekeeping control genes, has been applied in this disclosure. Combined together, cfRNA can be used to provide precise information related to cancer diagnosis, prognosis and prediction of therapy response.

The novel features of the present disclosure and the reason why they are technologically significant are as follows:
1. The specific design of primers to allow amplification of consistently short amplicons to be able to amplify targets from cfRNA which is usually about 100 nucleotides in length when isolated from plasma.
2. The inclusion of barcode sequences in the primer design for accurate enumeration of specific targets, whether containing fusions or not.
3. The combination of designs for the simultaneous capture of fusions (if any) and target gene expression.
4. The ability to detect novel fusions with any potential primer combination included in the multiplex panel.
5. The design of data analysis workflows which allow the parallel analysis of RNA-based fusions and expression.

The method of the present disclosure has the following advantages:
1. The method of the present disclosure uses cfRNA (which lacks introns) for sample input, thereby allowing the identification of genetic fusions involving long introns which are typically excluded from conventional DNA-based assays.
2. The method of the present disclosure allows for identification of both fully characterised genomic alteration targets and novel genomic alteration targets (i.e. genomic alteration targets which are not previously characterised). Novel genomic alteration targets can be detected with any potential primer combination included in the multiplexed panel. The design of data analysis workflows which allow the parallel analysis of RNA-based fusions and expression.
3. The method of the present disclosure allows for simultaneous detection of structural rearrangement and determination of expression level of cfRNA. For cancer-related genes that are expressed, ctRNA provides the same mutational information as ctDNA; additionally, it can provide quantitative information about the expression levels of target genes of interest, and can potentially increase the sensitivity of detection of variants with low allelic frequencies due to the overexpression of tumor-specific transcripts. The ability to quantitate the expression of these targets non-invasively can be very useful for the monitoring treatment response and making treatment decisions.
4. The method of the present disclosure may be used on a blood-based test (for example, to detect fusion targets in cfRNA in the blood) that is fast and non-invasive (only one draw of blood is needed). In addition, the method is scalable for the detection of multiple cancers in a single test and is suitable for cancer screening in an asymptomatic population.
5. The method of the present disclosure is highly sensitive compared to conventional methods of genomic structural alteration detection. Smaller starting material (cfRNA) is required for equivalent or better detection capabilities. For example, only 24 ng of cfRNA is required for detection of TMPRSS2-ERG fusion in a metastatic prostate cancer sample, as compared to using 70 ng of cfDNA to generate similar sequencing reads.

6. The technological significance lies in the generalizable use of primers for target capture, which allows working with smaller, limiting amounts of input of nucleic acid sample. In addition, the unique combination of targets is selected for the sensitivity and specific detection of multiple cancers.
7. The method of the present disclosure is scalable and allows the capture of multiple genomic regions for the identification of several cancer types in a single assay. The target gene coverage can be expanded by the addition of forward and reverse primer pairs.
8. The method of the present disclosure may be used in the following applications:
   Detection, identification and quantification of well-characterised genomic alterations (such as gene fusions) that are clinically relevant, for example those associated with to cancers.
   Identification of novel genomic alterations specific to cancers.
   Cancer screening in healthy individuals and individuals at high risk for the tested cancers.
   Disease monitoring in cancer patients, including monitoring response to treatment, such as immunotherapy.
9. Shorter fragments are more challenging as starting material for sequencing-based assays, due to restrictions on primer design and the sequence information that can be optimally captured. The method of the present disclosure uses cfRNA, which is shorter (about 100 nucleotides) in length compared to cfDNA (about 160 base pairs) in length. The primers described herein have been optimally designed to capture fragmented cfRNA of about 100 nucleotides in length to maximize sensitivity of detection of fusions and expression changes.
10. The method of the present disclosure uses RNA and not DNA as the sample input for detection of genomic alteration events. This allows for detection of genomic alteration events that would have been excluded in a typical DNA-based detection assay. Examples of such genomic alterations include:
    Copy number gains in DNA leading to overexpression of RNA;
    Structural rearrangements involving very long introns of two or more genes; and
    Changes in gene expression patterns corresponding to drug response or resistance.

Sequence Listing

Table of forward primers specific to genes that are capable of undergoing genomic alteration.

| SEQ ID NO | Primer name | Sequence |
| --- | --- | --- |
| 1 | AGAP3_exon9F | AGAAGAAGGCTGCCGAGTG |
| 2 | AGK_exon2F | GCTCTGCCTGCTGACCTG |
| 3 | AGTRAP_exon5F | CAGAGCACAGCATTAAAGTTTGG |
| 4 | AKAP9_exon21F | AGGCATCTGTAAAGTCATGTGTC |
| 5 | AKAP9_exon8F | GAGCAACTCAACCAAGTGAAAATG |
| 6 | ARMC10_exon4F | GCACTAAATAACCTGAGTGTGAATG |
| 7 | ATIC_exon7F | GTACACACTGCAGCCCAAG |
| 8 | BCR_E1_F | GCAGATCTGGCCCAACGAT |
| 9 | BCR_E13_F | CTGACCAACTCGTGTGTGAAACTCC |
| 10 | BCR_E14_F | CGGGGCTCTATGGGTTTCTG |
| 11 | BCR_E18_F | GTCTTCGGAGTCAAGATTGCTG |
| 12 | BCR_E19_F | ATCTACCGCGTGTCCGGT |
| 13 | BCR_E2_F_rdsgn | ACATTGATGACTCGCCCTCC |
| 14 | BCR_E6_F | AAGATGCCAAGGATCCAACGAC |
| 15 | BCR_E8_F | CAATGAGGAGATCACACCCCG |
| 16 | BRAF_exon1F | TCTTCGGCTGCGGACCCT |
| 17 | BRAF_exon2F | GAACATATAGAGGCCCTATTGGAC |
| 18 | BRAF_exon3F | GAGCAACCCCAAGTCACCA |
| 19 | BRAF_exon4F | TGAGAGGTCTAATCCCAGAGT |
| 20 | BTF3L4_exon3F | CAGAGTTCTCTAAAAAAACTGGCTG |
| 21 | CARS_exon17F | GAGAAGGAGTGCGGAAGATTG |
| 22 | CBFB_E4_F | TGGTATGGGCTGTCTGGAGT |
| 23 | CBFB_E5_F | CGGAGAAGGACACGCGAAT |

-continued

| SEQ ID NO | Primer name | Sequence |
|---|---|---|
| 24 | CCDC6_exon1FS | CAAGGCACTGCAGGAGGAGAAC |
| 25 | CCDC6_exon2F | GAATTCCTCACTAATGAGCTCTCCAG |
| 26 | CCDC6_exon8F | CTTCACGTGCAGCACATGG |
| 27 | CCDC91_exon11F | GGCAGTGAAAAGAACAAGAGATG |
| 28 | CD74_exon6FS | TCCTTGGAGCAAAAGCCCACTG |
| 29 | CDC27_exon16F | TTGATCCCAAGAACCCTCTATG |
| 30 | CLTC_exon30F | CATGCCCTATTTCATCCAGGT |
| 31 | CLTC_exon31F | GAAGAAGAACAAGCTACAGAGACAC |
| 32 | CUX1_exon10F_new | GCCAATCACTCCCTCCAG |
| 33 | DCTN1_exon16F | ATGACTGCGTTCTGGTGCTG |
| 34 | DCTN1_exon26F | CATTGCTACTCTGGTCTCTGG |
| 35 | EML4_exon13F | CTACTGTAGAGCCCACACCTG |
| 36 | EML4_exon14F | ATTAACTGGAGGAGGGAAAGACAG |
| 37 | EML4_exon15F | CGAGGAACATTTAATGATGGCTTC |
| 38 | EML4_exon16F | TGCTCTTGACATGTGCTCAGGACAG |
| 39 | EML4_exon17F | CTGTGCAGATTTTCATCCAAGTGGC |
| 40 | EML4_exon18F | TCTATCCACACAGACGGGAATGAAC |
| 41 | EML4_exon20FS | ATAATGTCTAACTCGGGAGACTATG |
| 42 | EML4_exon2F | GCAATCTCTGAAGATCATGTGG |
| 43 | EML4_exon5F | GCAGACAAGCATAAAGATGTCATCATC |
| 44 | EPS15_exon22F | AATCATTTGGAGGTGGATTTGCTG |
| 45 | ERC1_exon12F | GAGGTGGAAAATGAGAAGAATGAC |
| 46 | EWSR1_exon7F | CTACAGCCAAGCTCCAAGTC |
| 47 | EWSR1_exon9_10F | GCTTCAATAAGCCTGGTGGA |
| 48 | EZR_exon10F | GGCTGCAGGACTATGAGG |
| 49 | FAM131B_exon2F | CATGGACAGCACCAGCTCA |
| 50 | FCHSD1_exon13F | GATGAGGTGGAGCAGGAG |
| 51 | FGFR1OP_exon12FS | GTGGAAATAGATGACATCAATACCAGTG |
| 52 | GHR_exon1F | CGAACCCGCGCTCTCTGA |
| 53 | GOLGA5_exon7F | GGCCAGATACATCAGCTCAG |
| 54 | GOPC_exon4F | TGTTCTCCAGGCTGAAGTATATG |
| 55 | GOPC_exon8F | CAAGTGGGGAAATCAAAGTATTACAAG |
| 56 | GTF2I_exon4F | CAGTTGAGGACTATTTCTGCTTTTG |
| 57 | HIP1_exon21F | ACCACCTGCCTCAGAGCC |
| 58 | HIP1_exon28F | CTCAACCATTTCCGGCAAATCAC |
| 59 | HIP1_exon30F | CTTGCTGGTGTTGCTGAGG |
| 60 | IRF2BP2_E1a_F | GAGCAAGTTTAAGAAGGAGCCG |
| 61 | IRF2BP2_E1b_F | GCAGGTTGTTGGGTTTCGAG |

-continued

| SEQ ID NO | Primer name | Sequence |
|---|---|---|
| 62 | IRF2BP2_E2_F | GGAGAGGTCTATTGTCCCAGTG |
| 63 | KIAA1468_exon10FS | CTGCCTGCCACACATTGTTC |
| 64 | KIAA1549_exon12F | ACGCAGGAGATAAGACGCC |
| 65 | KIAA1549_exon13F | CTTATCGCCATGCAGCCGA |
| 66 | KIAA1549_exon14F | ACAAGATCCTGGACCCCAC |
| 67 | KIAA1549_exon15F | AGCGATGGCACCTACAGGA |
| 68 | KIAA1549_exon16F | AAGAGAGGCGAGCCACCC |
| 69 | KIAA1549_exon18F | GGAGGAGATGCCGTCGGT |
| 70 | KIAA1549_exon19F | AAGCAGAGGCAGCCAGTAT |
| 71 | KIF5B_exon15F | CTTGCAGAAATAGGAATTGCTGTGG |
| 72 | KIF5B_exon16FS | TGAAAAGGAGTTAGCAGCATGTCAG |
| 73 | KIF5B_exon17F | ATGCCCTCAGTGAAGAACTAGTCC |
| 74 | KIF5B_exon22F | GAACTTCAGACTTTACACAACCTGCG |
| 75 | KIF5B_exon23FS | ATCTTGAACAGCTCACTAAAGTGC |
| 76 | KIF5B_exon24F_new | GAAGCAGTCAGGTCAAAGAATATGG |
| 77 | KLC1_exon9F | TGCACATGAAAGGGAGTTTGGTTC |
| 78 | KMT2A_E10_F | CCA_GGG_TGG_TTT_GCT_TTC_TCT |
| 79 | KMT2A_E11_F | TCT_GTC_ACG_TTT_GTG_GAA_GG |
| 80 | KMT2A_E5_F | AAG_CCC_AAG_TTT_GGT_GGT_CG |
| 81 | KMT2A_E6_F | CAATGGATGCCTTCCAAAGCC |
| 82 | KMT2A_E7_F | AAACCACTCCTAGTGAGCCC |
| 83 | KMT2A_E8_F | GCT_CCC_CGC_CCA_AGT_ATC |
| 84 | KMT2A_E9_F | GCAGATGGAGTCCACAGGAT |
| 85 | KTN1_exon29F | CATGCTAAAAGAGAGGGAGAGTG |
| 86 | LRIG3_exon16F | TTCTTACCACAACATGACAGTAGTG |
| 87 | MKRN1_exon4F | ATCCAATGGATGCTGCCCAGA |
| 88 | MSN_exon11F | GACAGAAGAAGGAGAGTGAGG |
| 89 | NCOA4_exon6FS | TTGAAGCTGACACAATTACTCTGC |
| 90 | NCOA4_exon7F | CCTGGAGAAGAGAGGCTGTATC |
| 91 | NCOA4_exon8F_new | AGGACTGGCTTACCCAAAAGCAG |
| 92 | NPM1_E4_F | AAGTGTGGTTCAGGGCCAGT |
| 93 | NPM1_E5_F | TATCTGGAAAGCGGTCTGCC |
| 94 | NUP214_exon21F | AAGACCCCACCAGTGAGAT |
| 95 | PAPSS1_exon5F | CTCCTGTGATGTAAATGACTGTG |
| 96 | PML_E3_F | AGTTCAAGGTGCGCCTGC |
| 97 | PML_E6a_F | CTTCCTGCCCAACAGCAAC |
| 98 | PML_E6b_F | TGCCCCAGGAAGGTCATCAAG |
| 99 | PPFIBP1_exon12F | ATGCAAGACACGGTGGTACTG |

| SEQ ID NO | Primer name | Sequence |
|---|---|---|
| 100 | PPFIBP1_exon8F | GGACAGTGAGAGACTTCAGTATG |
| 101 | PPFIBP1_exon9F | TGGTTTGCAAGATGAAAGGAGAAG |
| 102 | PRKARIA_7F | CATCGACCGAGACAGCTATAGAAG |
| 103 | PWWP2A_exon1F | TTGTCGTGTCGTTCCGCTT |
| 104 | RANBP2_exon18F | GGGTCACAGACATTTCATGGG |
| 105 | RUNX1_E5_F | ATGACCTCAGGTTTGTCGGTC |
| 106 | RUNX1_E6_F | ACCTACCACAGAGCCATCAAA |
| 107 | RUNX1_E7_F | ACTGCCTTTAACCCTCAGCC |
| 108 | SDC4_exon2F | ATCTGATGACTTTGAGCTGTCTGGC |
| 109 | SDC4_exon4F | GCAGCAACATCTTTGAGAGAACGG |
| 110 | SLC34A2_exon13delF | TGTCAAGGCTCCTGAGACCTTTGAT |
| 111 | SLC34A2_exon4F | TCGTGTGCTCCCTGGATATTCTTAG |
| 112 | SND1_exon10F | GATTCACCTGTCCAGCATCC |
| 113 | SND1_exon11F | CCTTACATGTTTGAGGCCC |
| 114 | SND1_exon14F | AGGATTGCATAGCAAGAAGGAAG |
| 115 | SND1_exon16F | CTTGGTGCAGGAAGGAGAG |
| 116 | SND1_exon9F | GCTCCCACAGCTAATTGGAC |
| 117 | SQSTM1_exon5F | CGAGTGTGAATTTCCTGAAGAAC |
| 118 | STAT5B_E15_F | GTGACTCAGAAATTGGCGGC |
| 119 | STRN_exon3F | TGAATCAGGGAGATATGAAGCCTCC |
| 120 | TAXIBP1_exon8F | GCAGTTATGTTTGGCTGAAAAGG |
| 121 | TFG_exon3F | GTGCAGTAGGATACTGAAACTGAC |
| 122 | TFG_exon4F | GAGAACCAGGACCTTCCAC |
| 123 | TFG_exon5F_new | ATGTTATGTCAGCGTTTGGCTTAAC |
| 124 | TFG_exon6F_new | CAGCAGCCACCATATACAGG |
| 125 | TMPRSS2_exon1F | TAAGCAGGAGGCGGAGGC |
| 126 | TMPRSS2_exon2F | CAGATACCTATCATTACTCGATGCTG |
| 127 | TMPRSS2_exon3F | TCCTGACGCAGGCTTCCA |
| 128 | TMPRSS2_exon5F | CTCTAACTGGTGTGATGGCGT |
| 129 | TPM3_exon2F | GCAAAAGCTGGAAGAAGCTGA |
| 130 | TPM3_exon8F | AGTTTGCTGAGAGATCGGTAGC |
| 131 | TPM4_exon8F | GGAAAAGACAATTGATGACCTGGA |
| 132 | TPR_exon15F | CAAACAACAGGAGTTGCCATTCC |
| 133 | TRIM24_exon3F | GTTCACAAAAGACCACACTGTC |
| 134 | TRIM24_exon8F | TCACTGTGATCCTAGTTTCTGG |
| 135 | TRIM24_exon9F | TCCCAACACAGATCAGCCT |
| 136 | VCL_exon16F | CGATGGTGATGGATGCAAAAG |
| 137 | ZBTB16_E2_F | TGGGGTCGAGCTTCCTGATA |

-continued

| SEQ ID NO | Primer name | Sequence |
|---|---|---|
| 138 | ZBTB16_E3_F | GTTCCTGGATAGTTTGCGGC |
| 139 | ZBTB16_E4_F | TTTCGAAGGAGGATGCCCTG |
| 140 | ZC3HAVI_exon3F | CATCTGCAACAGCAAGCACA |
| 141 | AGBL4_exon5_6F | CCAGAGTGTGCAACAACGAAAG |
| 142 | AR_exon2_F_rdsgn | TGTGGAAGCTGCAAGGTCTTC |
| 143 | AR_exon3_F | CCATCTTGTCGTCTTCGGAAATG |
| 144 | BAG4_exon1_F | ATGGCTACTATCCCTCGGGAG |
| 145 | BAG4_exon2_F | GCTCCTTACCCAAGTACATATCCTG |
| 146 | BAIAP2L1_exon9_F | CGATATGTTTAATAACCCAGCCAC |
| 147 | BCAN_exon13F | AAGAGAACGGTCGTTGGGAG |
| 148 | BCR_exon4_F | TTCTATGATGGGCTCTTCCCCC |
| 149 | BCR_exon7_F | CTCTGCTCTACAAGCCTGTGGAC |
| 150 | BCR_exon9_F | CGTCTTCCTGTTCACCGACCT |
| 151 | BTBD1_exon4F | AAGCACTTTCCTTAATCCGGTTC |
| 152 | HMGN2P46_exon1_F | AGGTGAATCTTTTGGTTGGTGA |
| 153 | HMGN2P46_exon2_F | CATGCTTGTCAAAAATCAGAGGC |
| 154 | C8orf34_exon2_F_rdsgn | GGAACCGTGGACAACTTCAAA |
| 155 | CAPZA2_exon4_F | GCATTTGCACAGTATAACTTGGAC |
| 156 | CD47_exon7F | GGTTTGAGTATCTTAGCTCTAGCAC |
| 157 | CD74_exon8F | GAAAGAGTCACTGGAACTGGAGG |
| 158 | CNTRL_exon15_F | GCCAACCAGCTCAAGGAAGAGTT |
| 159 | CNTRL_exon38_F | GCAGGAAGAGGAGAGGTGG |
| 160 | CNTRL_exon39_F | CCAGCCTGAAGGAAGCACTTAA |
| 161 | CNTRL_exon40_F | AGCTCAACCAGATGCAGTATGAG |
| 162 | CTNNB1_exon1_F | AGGTCGAGGACGGTCGG |
| 163 | CUX1_exon1_F_rdsgn | TCTCAAGATGGCGGCCAATGTG |
| 164 | CUX1_exon7_F | ATGTCCACCACCTCAAAGCTGG |
| 165 | CUX1_exon8_9_F | CAAAGGCCGACGAGATTGAAATGAT |
| 166 | CUX1_exon8_F | AACTCGAACAGAATTATTTGACCTGAA |
| 167 | DDX5_exon2_F | GAGAAGAATTTTTATCAAGAGCACCCTG |
| 168 | EGFR_exon15F | TGCCATCCAAACTGCACCTAC |
| 169 | EGFR_exon24F_rdsgn | TCTCCAAAATGGCCCGAGAC |
| 170 | ERBB2_exon14_15_F | TTTGGACCGGAGGCTGACC |
| 171 | ERBB2_exon15F | GAAGTTTCCAGATGAGGAGGG |
| 172 | ERBB2_exon7-8_F | CCTGTCCCTACAACTACCTTTCTAC |
| 173 | ESR1_exon3_F | AACGAGCCCAGCGGCTAC |
| 174 | ESR1_exon4_F | CCATTATGGAGTCTGGTCCTGT |
| 175 | ESR1_exon5_F | GGCTCCGTAAATGCTACGAAGTG |

-continued

| SEQ ID NO | Primer name | Sequence |
|---|---|---|
| 176 | ESR1_exon6_F_rdsgn | CAGACAGGGAGCTGGTTCACA |
| 177 | ESR1_exon7_F | ACCCAGGGAAGCTACTGTTTG |
| 178 | ETV6_exon4F | TGGAAACTCTATACACACAGCC |
| 179 | ETV6_exon5F | CACATCATGGTCTCTGTCTCCC |
| 180 | ETV6_exon7F | ACATTATCAGGAAGGAGCCAGG |
| 181 | FGFR1_exon1_F | ACAAGCCACGGCGGACTCT |
| 182 | FGFR1_exon17_F | TTCAAGCAGCTGGTGGAAGAC |
| 183 | FGFR1_exon18_F | CACAAATTTCCCCAAAGACTGCG |
| 184 | FGFR1_exon2_F | GTCACAGCCACACTCTGCAC |
| 185 | FGFR1OP_exon5_F | TTAGAAGTGATCAGGCGCTGTC |
| 186 | FGFR1OP_exon6_F | TCCACCAAAGTCACCAGAGG |
| 187 | FGFR1OP_exon7_F | GACAAGGTAAGAAGAAGACAAGCG |
| 188 | FGFR2_exon17F | AGAAGACTTGGATCGAATTCTCAC |
| 189 | FGFR2_exon18F | CGAACCATGCCTTCCTCAGTATCC |
| 190 | FGFR3_exon17F | TCCTTACCGTGACGTCCA |
| 191 | FIP1L1_exon10_F | GTTGGGAAGTGGCAGGATCGA |
| 192 | FIP1L1_exon11_F | CTATAACTATCAGCCGAGTAGAAGGCAG |
| 193 | FIP1L1_exon12_F | TCTTCCACCTCCTCCGACTGT |
| 194 | FIP1L1_exon14_F | TTTTCCTCCTCCACCAGGCG |
| 195 | FIP1L1_exon15_F | GGACATTCCTCTGGTTATGATAGTCG |
| 196 | FIP1L1_exon16_F | GACAGAGAAAGAGAACGCACCA |
| 197 | FIP1L1_exon17_F | ACGACACAGGGAGAAAGAGG |
| 198 | FIP1L1_exon18_F | AGAAGGAAAAGAAGCGGGCA |
| 199 | FIP1L1_exon9_F | TGCCCTTCCATCTACAAAAGC |
| 200 | HERV-K_F | GATTCCCGAGTACGTCTACAGTGA |
| 201 | HERVK17_F | TTTCCACACTCTCATTCCGGA |
| 202 | HNRNPA2B1_exon1_F | TGCGGGAAATCGGGCTGAA |
| 203 | LMNA_exon2F | GAGCTGCATGATCTGCGG |
| 204 | MDK_exon4F | CCCAAGACCAAAGCAAAGG |
| 205 | MET_exon13F | ACAGCACTGTTATTACTACTTGGG |
| 206 | MPRIP_exon21F | AGAAGTCCCCTGACAGTGCC |
| 207 | NACC2_exon4F_rdsgn | GACTGGCATCCGCTCGTC |
| 208 | NFASC_exon21F | TCCAGGCTGAAAATGACTTCGGG |
| 209 | PAX8_exon10F | ACATCCCCACCAGCGGAC |
| 210 | PAX8_exon7F | GAGTGCCCATTTGAGCGG |
| 211 | PAX8_exon8F | CTTCCAACACGCCACTGG |
| 212 | PAX8_exon9F | CGCCCTTCAATGCCTTTCC |
| 213 | PCM1_E23_F | CTCCCAAGTCAAAAAGTAAGAAGAGGA |

| SEQ ID NO | Primer name | Sequence |
|---|---|---|
| 214 | PCM1_E24_F | CAGCAGAAAGAATCATGAGCAACTGGAAA |
| 215 | PCM1_E25_F | CCATGAGCTGCAGCTACTAAAC |
| 216 | PCM1_E26_F | ATAGCATCAAACTCAGAACTTACTCCT |
| 217 | PCM1_E36_F | ACTCCTGAAAGCTCTCTGGCTG |
| 218 | PCM1_E37_F | GATTTTGTAAAAGTTGAAGATTTACCACTG |
| 219 | QKI_exon6F | ACACATTGGCACCAGCTACATC |
| 220 | RBPMS_exon5F | CAAACTCGTAGGGACTCCAAAC |
| 221 | SLC45A3_exon1_F | AACCAGCCTGCACGCGCT |
| 222 | SEC61G_5'UTRF_rdsgn | CTCCAGTGCTACGTGTCCCTG |
| 223 | TCF3_exon16_F | ACCCTCCCTGACCTGTCTC |
| 224 | TPM4_exon6F | CTGAAAAGGAGGACAAATATGAAGAAG |
| 225 | TPR_exon21F | TTGAAACAGCACCTCAGTAATATGG |
| 226 | TPR_exon6F | GGGAATGAGATTCTAGAGCTTAAATG |
| 227 | UBTF_exon2_F | AACGGAGAAGCCGACTGC |
| 228 | ZMYM2_exon16_F | TGTATATCCCAGTTCCTATGCACATG |
| 229 | ZMYM2_exon17_F | AGTTGCTTACAATGACGGATATGATGAGT |
| 230 | AFAP1_exon13_F | AGCAGTCAGCCAAAGAAAGC |
| 231 | AFAP1_exon14_F | GCTCCGCAAGGAAAGAAAAGA |
| 232 | AKAP9_exon18F | CAGCTACAAGAAGAGATTAAGAGACTT |
| 233 | AKAP9_exon7F | GACTTCACAATGCAAATTAGTTTCTTG |
| 234 | AKAP9_exon9F | GAACTTCAGAAAATACACCAGTTAGAACT |
| 235 | AXL_exon20_F | TGCTGATAGGGGCTCCCCA |
| 236 | BCR_exon10_F | TGGACGCTTTGAAGATCAAGATC |
| 237 | BCR_exon11_F | CTGCTTATGTCTCCCAGCATG |
| 238 | BCR_exon12_F | CGTGCAGAGTGGAGGGAGAA |
| 239 | BCR_exon15_F | GCAAAGACGCGCGTCTACAG |
| 240 | BCR_exon16_F | AAGGAGGACGGCGAGAGC |
| 241 | BCR_exon17_F | AGGACAGAGACTGGCAGCG |
| 242 | BCR_exon20_F | TTCACTGACGAGTTCTACCCCAA |
| 243 | BCR_exon3_F | CTAGCGAGGAGACTTACCTGAG |
| 244 | BCR_exon5_F | AAATGGCTGAGAAGTGCTGTC |
| 245 | HMGN2P46_exon2_F_rdsgn | GGAACCACACTTCGAGAATCAC |
| 246 | CCDC6_exon3F | GGAGAATGACACCATTTCTAAGCA |
| 247 | CCDC6_exon4F | AGCACTAGTTAATCGCCTCTGGAAA |
| 248 | CCDC6_exon5F | TGAAGTGGAACGGCTGAAGA |
| 249 | CCDC6_exon6F | TCTCCGAGAGTGAGTCCAGC |
| 250 | CCDC6_exon7F | CAGCCCGATCCCTTACACAC |
| 251 | DCBLD1_exon2_F | CCAGACCTGTGCTTCTGACTAT |

-continued

| SEQ ID NO | Primer name | Sequence |
|---|---|---|
| 252 | EGFR_exon1_F | AGTCGGGCTCTGGAGGAAAAG |
| 253 | EML4_exon10F | GGACTTGGCACTTTTGAGCG |
| 254 | EML4_exon11F | GCTTACTGTATGGGACTGGCA |
| 255 | EML4_exon12F | TTTCTTCTGGACCTGGAGCG |
| 256 | EML4_exon19F | CTATGTAGTCTCTGAAAATGGAAGAAAATA |
| 257 | EML4_exon1F | CGCTTTCCCCGCAAGATGGA |
| 258 | EML4_exon21F | AAGGACATTGATTGGACGACA |
| 259 | EML4_exon22F | CGATGACTTTTGTAAAGTCCATCTGTTTCA |
| 260 | EML4_exon23F | AAAGCCACCCTTCTGGAGGA |
| 261 | EML4_exon3F | GTGCTGTCTCAATTGCAGGAAAAG |
| 262 | EML4_exon4F | CACAGACAAACTCCAGAAAGCA |
| 263 | EML4_exon7F | ATCAGAACGGAACTGCCTCC |
| 264 | EML4_exon8F | GAACTCAGCGACACTACCTGG |
| 265 | EML4_exon9F | GCAACTGGACAGATAGCTGG |
| 266 | ESR1_exon8_F | GGAGAGGAGTTTGTGTGCCT |
| 267 | ESR1_exon9_F | GCCCAGCTCCTCCTCATC |
| 268 | ETV6_exon6F | GATCCCAACGGACTGGCTC |
| 269 | EWSR1_exon8_F | TGGAGGCATGAGCAGAGGT |
| 270 | EZR_exon11F | CTAAGGAGGAGCTGGAGAGACA |
| 271 | EZR_exon12F | GAGGCGCAAGGAGGATGAA |
| 272 | FIP1L1_exon8_F | ATGGAAGTTACACCAGGTGCAGAG |
| 273 | FRMD4A_exon2_F | ATGGGAATCGGAGACCATG |
| 274 | GOPC_exon5F | TGCAGAGGACGTAATGACTTGA |
| 275 | GOPC_exon6F | GGTCCAATTAGAAAAGTTCTCCTCCTTA |
| 276 | GOPC_exon7F | ACCTAAGGGACACAAAGCATA |
| 277 | GOPC_exon8F_rdsgn | AGGTGGTAACCCTGGTGCTAGTT |
| 278 | HIP1_exon29F | AAGCATGACGCTGACACAGA |
| 279 | IRF2BP2_exon1_F | CAGGCAGGTTGTTGGGTTTCG |
| 280 | KIAA1549_exon17F | GATACGAAGACTATGGAATGACTCC |
| 281 | KIF5B_exon18F | CATGAAATGGAAAAGGAGCACTTA |
| 282 | KIF5B_exon19F | AGTTTGAGAGATGAAGTAGAAGCA |
| 283 | KIF5B_exon20F | AGTTGAAAGCCACAGATCAGGA |
| 284 | KIF5B_exon21F | ACGAGAACAAGCAAGACAAGAC |
| 285 | MECOM_exon2_F | AGAGCAGAGGTCAAACCTGA |
| 286 | MET_exon11F | AGCCAGTGATGATCTCAATGGG |
| 287 | MYB_exon10_F | AGTTCAACTCCCAAGCGTTCCC |
| 288 | MYB_exon11_F | AACACCATTTCATAGAGACCAGACTG |

-continued

| SEQ ID NO | Primer name | Sequence |
|---|---|---|
| 289 | MYB_exon12_F | TCAAACATGCACTTGCAGCTCAAG |
| 290 | MYB_exon13_F | TGCTGAGTTTCAAGAAAATGGACC |
| 291 | MYB_exon14_F | AGGGGACAGTCTGAATACCCA |
| 292 | MYB_exon15_F | TGTTCTCAAAGCATTTACAGTACCT |
| 293 | MYB_exon8_F | TTAGAATTGCTCCTAATGTCAACCGAGA |
| 294 | MYB_exon9_F | ACCTCTTAGAATTTGCAGAAACACT |
| 295 | NCOA4_exon9F | CAACCTCAGCCAGTTATCTTCTGG |
| 296 | PAN3_exon1_F | AGGCAGTAGCGGGGAC |
| 297 | PAX3_exon7_F | TCCAACCCCATGAACCCCAC |
| 298 | PPFIBP1_exon11F | CAAAAAATGAAAAAAGCTGTGGAGTCC |
| 299 | PPFIBP1_exon9F_rdsgn | GGTCAGATGCAGTATGAAAAGCA |
| 300 | SCAF11_exon1_F | CCTGGGAACCTACTGTGGGG |
| 301 | SDC4_exon3F | TGGAAGACTCCATGATCGGC |
| 302 | SND1_exon12F | GCCTTTTCAGAGCGTACCTG |
| 303 | SND1_exon13F | GACCAGAGATCATCACACTACG |
| 304 | SND1_exon15F | GTCTCAAACTCTATTTGCCAAAGGAAACTT |
| 305 | SPTBN1_exon6_F | AGGGACGGCATGGCCTTC |
| 306 | SS18_exon10_F | AACACAGCCTGGACCACCA |
| 307 | SS18_exon9_F | AGTACCCAGGGCAGCAAGG |
| 308 | TMPRSS2_exon4F | ACCTTCCTCGTGGGAGCT |
| 309 | TPM3_exon2F_rdsgn | TTTGAAGGATGCCCAGGAGAAG |
| 310 | TPM3_exon4F | CTAAGCACATTGCAGAAGAGGC |
| 311 | TPM3_exon5F | AGGAGACTTGGAACGCACAG |
| 312 | TPM3_exon6F | GTCACCAACAACCTCAAGTCTC |
| 313 | TPM3_exon7F_rdsgn | GAAGATAAATATGAGGAAGAAATCAAGATT |
| 314 | TRIM24_exon12_F | CAGAACGGTCCAGTCACCAA |
| 315 | FGFR3_exon17F_new | GAGGCCCACCTTCAAGCAG |

50

Table of reverse primers specific to genes that are capable of undergoing genomic alteration.

| SEQ ID NO | Primer name | Sequence |
|---|---|---|
| 316 | ABL1_E2a_R | CTTCACTCAGACCCTGAGGC |
| 317 | ABL1_E2b_R | CAACGAAAAGGTTGGGGTCA |
| 318 | ABL1_E3_R | GCTTCACACCATTCCCCATTG |
| 319 | ABL1_E4_R | GATGATGAACCAACTCGGCCA |
| 320 | AFF1_E11_R | ATGTGCTGATGCCACTGGTT |
| 321 | AFF1_E6_R | GGCTCAGCTGTACTAGGCG |

| SEQ ID NO | Primer name | Sequence |
|---|---|---|
| 322 | AFF1_E9-10_R_rdsgn | GCTTCTCTGGGGTTTGTTCACT |
| 323 | ALK_exon19R | AGAGAGGATCAGCGAGAGTG |
| 324 | ALK_exon20RL | TCAGCTTGTACTCAGGGCTCT |
| 325 | ALK_exon21R | CTTGGGTCGTTGGGCATTC |
| 326 | BRAF_exon10R | CGTTAGTTAGTGAGCCAGGT |
| 327 | BRAF_exon11R | CAGGAATCTCCCAATCATCACTC |
| 328 | BRAF_exon8R | AGGGCTGTGGAATTGGAATG |
| 329 | BRAF_exon9R | CTCCATCACCACGAAATCCTTG |
| 330 | ERG_exon10R | AAGGCGGCTACTTGTTGGTC |
| 331 | ERG_exon11R | GAGGAACTGCCAAAGCTGGAT |
| 332 | ERG_exon2R | CTTTCCTCGGGTCTCCAAAG |
| 333 | ERG_exon3R | CCCATCTACCAGCTGTTCAG |
| 334 | ERG_exon4RS | TGGTCCTCACTCACAACTGATAAGG |
| 335 | ERG_exon5RS | CCACCATCTTCCCGCCTTTG |
| 336 | ERG_exon8R | CAGGAGATCAGCCTGGAC |
| 337 | ERG_exon9R | GGTCTTCAGTTTTGGGCACTG |
| 338 | MECOM_E2_R | TGCATCTGGCATTTCTTCCAAAG |
| 339 | MLLT3_E10_R | ATGTCATTAACCTTCTGTGAAGCTCTAC |
| 340 | MLLT3_E5_R | TGCTGCTGCTGCTGGTATGAATAC |
| 341 | MLLT3_E7_R | TCTGATTCCTCCTCATTGTCATCA |
| 342 | MLLT3_E9_R | TTTGCTTATCTGATTTGCTTTGCTTTATTG |
| 343 | MYH11_E28_R | TCTCTTTCTCCAGCGTCTGC |
| 344 | MYH11_E29_R | CTCGGCCTCGTTAAGCATCC |
| 345 | MYH11_E30_R | GCAGCTTCGTAGACACGTTG |
| 346 | MYH11_E32_R | CCTCTCATCCGCGTATTTGGA |
| 347 | MYH11_E33_R | TCCATCTGGGTCTCCAGGG |
| 348 | MYH11_E34_R | GTTGCTTTCGCTCGTCTTCC |
| 349 | RARA_E3_R | GGCTGGGCACTATCTCTTCA |
| 350 | RET_exon11RS | ATGAAGGAGAAGAGGACAGCGG |
| 351 | RET_exon12RL | TCCTAGAGTTTTTCCAAGAACCAAG |
| 352 | RET_exon7R | GGACGTTGATGCCACTGAAT |
| 353 | RET_exon8R | CTCTTGCTGACTGCACAGGACAG |
| 354 | ROS1_exon34R | GGTCAGTGGGATTGTAACAACCAGA |
| 355 | ROS1_exon35R | CTTCGTTTATAAGCACTGTCACC |
| 356 | ROS1_exon36R | GAGGGAAGGCAGGAAGATT |
| 357 | RUNX1T1_E2_R | GCGTCTTCACATCCACAGGT |
| 358 | ACTRIA_exon3_R | AAGATGTCGCCTTCAAGGGCT |
| 359 | AHCYL1_exon2R | GTTTTGGTGGGAATTTGGTGAAC |

| SEQ ID NO | Primer name | Sequence |
|---|---|---|
| 360 | AKAP12_exon4_R | AGTAGCCATCTCTTTATCGGAGTCTC |
| 361 | AR_CE3_R | GGTCTGGTCATTTTGAGATGCTTG |
| 362 | AR_CE5_R | ACAACGTGATCCCAAAAGATGTG |
| 363 | AR_CE4_R | ATGCAGTATGGCTTGGGGTT |
| 364 | BAIAP2L1_exon2_3R | AGGATCATAGCGTTTACAGCTTTCT |
| 365 | BICC1_exon2_3R | TGCGTATTTGTTTCCTCCATGATC |
| 366 | CCDC170_exon2_R | AGTGGTTTAACTGCTCCCGC |
| 367 | CLDN7_exon2_R | GCACCAGGGAGACCACCATT |
| 368 | EGFR_exon14R | GGCACTGTATGCACTCAGAGTT |
| 369 | EGFR_exon15R | CAGGTCTTGACGCAGTGG |
| 370 | EGFR_exon18R | GCTTGGTTGGGAGCTTCTC |
| 371 | ERBB2_exon17R | AAGACCACGACCAGCAGAAT |
| 372 | ERBB2_ex8-int8_R | TGAGTGGGTACCTCACACC |
| 373 | ETV1_exon4_R | CTTCTGCAAGCCATGTTTCCT |
| 374 | ETV1_exon6_R | TGAACATGGACTGTGGGGTTCTTTC |
| 375 | ETV1_exon7_R | GGAGGGCCTCATTCCCACTT |
| 376 | ETV1_exon2_R | TGGTGACCATGTAAGGCACT |
| 377 | ETV1_exon2b_R | AGCATTTAGCTGGAGATTTCCTCA |
| 378 | ETV1_exon5_R | AACTTTCAGCCTGATAGTCTGGTACAA |
| 379 | ETV1_exon3_R | TTTTCTTTTCCTGACATTTGTTGGTTTC |
| 380 | ETV1_exon11_R | AGTTCATAGCTGGCCTGTTTTTCTG |
| 381 | ETV1_exon12_R | AGAAAAGGGCTTCTGGATCACACA |
| 382 | ETV4_exon1_2_R | CGAGACCTGCTCCCAGGA |
| 383 | ETV4_exon3_R | CATGAGCTTCCCCAGCGG |
| 384 | ETV4_exon5_R | CTGAATGGAAATCAGGAACAAACTGC |
| 385 | ETV4_exon4_R | AGCGAGCCACGTCTCCTG |
| 386 | ETV5_exon2_R | CAGCATTGAGTAATTTCTGGGGG |
| 387 | ETV5_exon8_R | AACTCCTGGCTGAGGAGGGAA |
| 388 | FGFR1_exon8_R | AGCACCTCCATCTCTTTGTCG |
| 389 | FGFR1_exon6_R | TGTCAGAGGGCACCACAGAG |
| 390 | FGFR1_exon9_R | AGATGATGATCTCCAGGTACAGG |
| 391 | FGFR1_exon10_R | GAACCAGAAGAACCCCAGAGTTC |
| 392 | JAK2_exon9_R | CCATCAATTAATGACACGAAAGACAAAGC |
| 393 | JAK2_exon10_R | ACAGTCCAGTCTGATTACCTGC |
| 394 | JAK2_exon11_R | TGTCCCACTGAGGTTGTACT |
| 395 | JAK2_exon12_R | TGGTGAGGTTGGTACATCAGAA |
| 396 | JAK2_exon13_R | TGACCGTAGTCTCCTACTTCTCT |
| 397 | JAK2_exon14_R | TTAAAACCAAATGCTTGTGAGAAAGCT |

-continued

| SEQ ID NO | Primer name | Sequence |
|---|---|---|
| 398 | JAK2_exon15_R | TCTTTTTCAGATATGTATCTAGTGATCCAA |
| 399 | JAK2_exon16_R | TCTCTGATAAGCAGAATATTTTGGCACA |
| 400 | JAK2_exon17_R | GCATTCAGGTGGTACCCATGGTATT |
| 401 | JAK2_exon18_R | CCACTTTGGTGCAGGAAGCTGA |
| 402 | JAK2_exon19_R | AGGGCACCTATCCTCATATTTGGTAAC |
| 403 | MET_exon11R | GGAGTGGTACAACAGATTATCTCTG |
| 404 | MET_exon15R | CTGCACTTGTCGGCATGAAC |
| 405 | NOP2_exon_16_R | GGATGACCTGAGGCAAGTCTA |
| 406 | NRG1_exon6R | CTCCGCACATTTTACAAGATGG |
| 407 | NRG1_exon5_6R | GTGGTGGATGTAGATGTAGATGAAGAAG |
| 408 | NRG1_exon2R | AACCTGCAGCCGATTCCTG |
| 409 | NRG1_exon3R | GAATCAGCCAGTGATGCTTTGT |
| 410 | NRG1_exon4R | TGCTCCTTCAGTTGAGGCTG |
| 411 | NTRK1-exon10R_rdsgn | GTGTTTCGTCCTTCTTCTCCACC |
| 412 | NTRK1-exon12R | TGTCATGAAATGCAGGGACATGG |
| 413 | NTRK_1-exon9R | ACCAGTGGTGCATCTCCA |
| 414 | NTRK1-exon11R | AGCGTAGAAAGGAAGAGGCAGG |
| 415 | NTRK2_exon13_R_rdsgn | TGGTGTCCCCGATGTCATTC |
| 416 | NTRK2_exon16_R_rdsgn | GCTGGCAGAGTCATCATCATTG |
| 417 | NTRK3_exon14R | GTCCTCCTCACCACTGATGAC |
| 418 | NTRK3_exon15R | CTTCAGCACGATGTCTCTCCTCTTA |
| 419 | NTRK3_exon11_12R | GGACTCACTTCGTCAAACAAGAT |
| 420 | PAWR_exon3_R | TAATTGCATCTTCTCGTTTCCGCT |
| 421 | PBX1_exon3_R | CTGGGGGTCTGTGGGTTC |
| 422 | PCDH11X_exon11_R | CTTGAGTGCAGTTGTCAGAGGC |
| 423 | PDGFRA_exon12_R | TGATTCAATGACCCTCCAGCG |
| 424 | PDGFRB_exon11_R | GGATGATAAGGGAGATGATGGTGAG |
| 425 | PDGFRB_exon9_R | TGTCTGTTCCCCACTGTCAGG |
| 426 | PDGFRB_exon10_R | AGCTGGCTCTCCTCTTCGGA |
| 427 | PDGFRB_exon12_R | AGCTCACAGACTCAATCACCTTC |
| 428 | PLAGI_exon4_R | GCTTTAGGTGGCTTCTCAAGTTTC |
| 429 | PLAGI_exon3_R | GACTCTTCGTGGAAGAGAGTGG |
| 430 | PLAGI_exon2_R | GAATGAAGCATTCTGGGTGCC |
| 431 | POLH_exon2_R | GTCCATGTCCACGAGAGCAA |
| 432 | PPARG_exon2R | AATGGCATCTCTGTGTCAACC |
| 433 | PPARGCIA_exon2R | AGGAAGATCTGGGCAAAGAGG |
| 434 | PPHLN1_exon3R | GTCTAGCAGTGGTGGTTTCTTTG |
| 435 | RAD51_exon4R_rdsg | GGTGGAATTCAGTTGCAGTGG |

-continued

| SEQ ID NO | Primer name | Sequence |
|---|---|---|
| 436 | RUNX1_Exon4_R | CCTCGCTCATCTTGCCTGG |
| 437 | SHC1_exon2R_rdsgn | CCCTTCCACCCGAGTCCT |
| 438 | KIAA1598_exon7_R | TTCTCTGTTCAAGAACTTCTGAATTTAA |
| 439 | KIAA1598_exon8_R | GCTCCAGGTTTACTTGCATCTC |
| 440 | KIAA1598_exon9_R | AGCAGAAGGTGGCTTTGTCT |
| 441 | TACC1_exon7_R | TCCACAGGACACCGACACA |
| 442 | TACC3_exon11R | TTCTTCCCGTGGAGCTCCTC |
| 443 | TACC3_exon10R | GAGCAGGTCCACTATAGGTC |
| 444 | TACC3_exon8R | TCTACCAGGACTGTCCCTCA |
| 445 | TACC3_exon14R_rdsgn2 | GGGTGATCCTTGCCAGGTAAT |
| 446 | TACC3_exon6R | TCACTGCCTGGACAGCTTGTG |
| 447 | YAPI_exon4_R | TCCTGAGTCATGGCTTGTTCC |
| 448 | ABL1_E5_R_rdsgn | GCACCAGGTTAGGGTGTTGA |
| 449 | AFF1_E4_R_redsgn | CCAGGCGATGAGTGTGAGAC |
| 450 | AFF1_E8_R | CGTTCCTTGCTGAGAATTTGAGT |
| 451 | CCAR2_exon4_R | AGTCATGCAAGCTGGTAACAA |
| 452 | CCDC170_exon10_R | GGATTTGTTTAGATCTTCAATGGCTTTA |
| 453 | CCDC170_exon6_R | TAACTTCCCTTTCAAGAGCTTCTTTTG |
| 454 | CCDC170_exon7_R | CAACTGTTCAACAAGCTCAGAT |
| 455 | CCDC170_exon8_R | GCCATCTGGTCCAACTTCATTTTCT |
| 456 | CCDC170_exon9_R | GGAGGCTCATGTGTAATTCTTTGCTCT |
| 457 | CIT_exon23_R | AGCTGTTACGAAGAGCATCAA |
| 458 | EGFR_exon17a_R | GTGGCGATGGACGGGATCT |
| 459 | EGFR_exon17b_R | GCATGAAGAGGCCGATCCC |
| 460 | EGFR_exon8_R | TCCTCCATCTCATAGCTGTCG |
| 461 | ERBB4_exon18_R | GAGCTTGATTGGGTGCTGTG |
| 462 | ERG_exon6R | TTCTTTCACCGCCCACTCCAG |
| 463 | ERG_exon7R | CCGTGGAGAGTTTTGTAAGGCTT |
| 464 | ETV1_exon10R | ATCCTCGCCGTTGGTATGTGG |
| 465 | ETV1_exon8R | TCGTCGGCAAAGGAGGAAAG |
| 466 | ETV1_exon9R | GGACAACACAGGTGTCATCAT |
| 467 | FGFR1_exon7R | GCCACTGTTTTGTTGGCGG |
| 468 | FLI1_exon3_R | AGCTTGCTGCATTTGCTAAC |
| 469 | FLI1_exon4_R | TTATGGCCCACTCCAGCCATT |
| 470 | FLI1_exon5_R | ATCGTGAGGATTGGTCGGTG |
| 47 | FLI1_exon6_R | GTTATTGCCCCAAGCTCCTCT |
| 472 | FLI1_exon7_R | TATTCTTACTGATCGTTTGTGCCC |
| 473 | FLI1_exon8_R | GTTGGCTAGGCGACTGCT |

-continued

| SEQ ID NO | Primer name | Sequence |
|---|---|---|
| 474 | FLI1_exon9_R | GAGAGCAGCTCCAGGAGGAATTG |
| 475 | FOXO1_exon2_R | TCTGCACACGAATGAACTTGC |
| 476 | GPHN_exon11_R | GACATGCGATGTCTTCTAGCCAC |
| 477 | MBIP_exon4_R | CATTGATTTCAGCTTGCTTTCTTTC |
| 478 | MLLT3_E6_R_redsgn | TGGTCTGGGATGGTGTGAAG |
| 479 | MX1_exon12_R | CCACGATACTGATTTTCAAATTTCTGG |
| 480 | MX1_exon9_R | AAGTTTTTCTGCCAGGCAGGG |
| 481 | MYH11_E31_R_rdsgn | CTCTTCCAGAGCTTCCACGG |
| 482 | NCOA3_exon14_R | CTGCTCGGTTATATGGAGGACGAA |
| 483 | NCOA3_exon15_R | TAAGCCCCAGTCTCCTGAGGAA |
| 484 | NFIB_exon10_R | GGGCTTAGTCCCACATATCG |
| 485 | NFIB_exon11_R | GGGGTATAAATGCCTGCCGT |
| 486 | NFIB_exon12_R | AGATGGGTGTCCTATTTGACACTTGG |
| 487 | NFIB_exon9_R | GCCAGGCACTTTCCCTACTA |
| 488 | NTRK2_exon14R | AAAGGCAAAATCCCACCACAGA |
| 489 | NTRK2_exon15R | CAACACCTTGTCTTGATTTTACTTTCCC |
| 490 | NTRK2_exon17_R | TTCGCCTAGCTCCCTTTTCA |
| 491 | NTRK3_exon13R | AGAACCACCAACAGGACACAG |
| 492 | PDGFRA_exon2_R | ACAGCCTAAGACCAGGAACGC |
| 493 | PPARG_exon7_R | AGGTTGTCTTGAATGTCTTCAATGGGC |
| 494 | RET_exon10_R | GTGCCATAGCCAGCTTTAATCC |
| 495 | RET_exon9_R | CAGGTCTTGGTGCTGGGAG |
| 496 | ROS1_exon32_R_rdsgn | GAATTTTTACTCCCTTCTAGTAATTTGG |
| 497 | ROSI_exon33R | TTCCATGTGCAAACACTACTGC |
| 498 | SEPT14_exon10_R | GCTTCCTTATCTCCTCCTGTTGA |
| 499 | SSX1_exon4_R | CTGGAAGTCTGTGGCCTGTTT |
| 500 | SSX1_exon5_R | GGGATGATTCTGTGGAGCCT |
| 501 | SSX1_exon6_R | TGCTTCTGACACTCCCTTCG |
| 502 | SSX2_exon3_R | TCATCTTTTCCCACTCTTCCTTAGAGA |
| 503 | SSX2_exon4_R | AGTCTTCGGCCCGTTTATTACA |
| 504 | SSX2_exon5_R | CTTCGGGGAGATTCCCTGGAG |
| 505 | SSX2_exon6_R | CTGGCACTTCCTCCGAATCA |
| 506 | TACC3_exon13a_R | CCTTCTGCTTCTGAACTTCCT |
| 507 | TACC3_exon13b_R | TTGGTCTTTTTCTTTTAGAACTTTCTGGAT |
| 508 | TACC3_exon5_R | TGCCAACTGCACCACAGG |
| 509 | TACC3_exon7R | AGGAAGTTCCAAACTGCTCCAGGTA |

-continued

| SEQ ID NO | Primer name | Sequence |
|---|---|---|
| 510 | TACC3_exon9R | AAGAAATCGAACTCCACAAGC |
| 511 | TACC3_midExon4_R | TCTCCGCTTTGCATTCTTCCT |
| 512 | YAPI_exon5_R | GTGGCTGTTTCACTGGAGCA |

Table of forward primers specific to control housekeeping genes.

| SEQ ID NO | Primer name | Sequence |
|---|---|---|
| 513 | TBP_F_rdsgn | CTTTGCAGTGACCCAGCATCACT |
| 514 | ITGB7-F | GCACGCACCTATGTGGAAAC |
| 515 | PSMB2_F_rdsgn | TCTTCGGAGTCGGACCCCATAT |
| 516 | EMC7_A_F | TCGGTTTCCTTAAGACAGATGG |
| 517 | EMC7_B_F_rdsgn | ACTTTCTAATGAACCCAATGGTTAT |
| 518 | GPI_F | GCATCACAAGATCCTCCTGG |
| 519 | REEP5_F | CCAGCCTACATCTCAATTAAAGC |
| 520 | RRP1_F_rdsgn | CGGGCCGCAGGTGGTTTT |
| 521 | CHFR_F | AGTATTGTGATTACAGGGTCTGG |
| 522 | REL_F | GAATCAATCCATTCAATGTCCCTG |
| 523 | NASP_F_rdsgn | CAGGAAGCAGCTAGTCTTTTAGGTAAG |
| 524 | POMK_F_rdsgn_2 | GAAGGAGCTGTAAAGAGAGTCTT |
| 525 | FRMD8_F | GATAGCAGAGAGAAGCATGTCC |
| 526 | SLC4A1AP_A_F_rdsgn | TCGGCAGGAAGCAGTATCT |
| 527 | SNAP29_F | GATCGACAGCAACCTAGATGAG |
| 528 | TUBGCP2_A_F_rdsgn | CATCCACGACCCATACAGTGAGTTTATG |
| 529 | SNRPD3_F_rdsgn | GACAACATGAACTGCCAGATGTCCAA |
| 530 | PUM1_F | TCAGACCAGCAGGTAATTAATGAGA |
| 531 | CIAO1_F | CGTTTGGGTCTGGGAAGTTGATGA |
| 532 | SRSF4_F | TGGAACTGAAGTCAATGGGAG |
| 533 | VCP_E1-2_F_new | GCTTCTGGAGCCGATTCAAA |
| 534 | RER1_E3_F_new | GGCTAGACAAGTCCACACCC |
| 535 | CHMP2A_E2-3_F | AAGCAAGGCCAGATGGATGC |
| 536 | RAB7A_E1_F | GTTTAGTCTCCTCCTCGGCG |
| 537 | ACTB_F | GAGACCGCGTCCGCC |

Table of reverse primers specific to control housekeeping genes.

| SEQ ID NO | Primer name | Sequence |
|---|---|---|
| 538 | TBP-R | GCATCTCCAGCACACTCTTC |
| 539 | ITGB7-R | AGCCAAACAGGAAACAGACCAG |
| 540 | PSMB2-R | AGGTAGTCCATGTAATACAGCG |
| 541 | EMC7_A-R | ACGGGATCAAATCTGTAAGCTG |
| 542 | EMC7_B-R | GTCTCATGTCAGGATCACTTGT |
| 543 | GPI-R | AAGGTCCTCTGGACTCTTGC |
| 544 | REEP5-R | CCATGACAGGAAGATATCAGAGAAG |
| 545 | RRP1_R | CTGGAGGAGTGGCTTGTC |
| 546 | CHFR-R | CTTTCTGTCTGGGAGAGCTG |
| 547 | REL-R | CATGTTCATCAGGGAGAAAAACTTG |
| 548 | NASP-R | CTTGCCAACTCCAGAAGTGA |
| 549 | POMK-R | CCTTGGAGAGATTTCAGCATCT |
| 550 | FRMD8-R | GAACTCCAGCCACAAGATG |
| 551 | SLC4A1AP_A-R | TCAGACGCTTCTTCTCAATCAG |
| 552 | SNAP29-R | TGTCATCTTGCTCCTCAATTTCTG |
| 553 | TUBGCP2_A-R | ACTTGTCGTTGTAATCCTCCTG |
| 554 | SNRPD3-R | GATTTTGCTGCCACGGATG |
| 555 | PUM1_R | ACCACGTGATTGCCATTCTG |
| 556 | CIAO1_R | GCCAAACCACATGCTTGACA |
| 557 | SRSF4_R | CTTCGAGAGCGAGACCTTGAAT |
| 558 | VCP_E2_R_new | ACAATTAACCGATTGGGACGG |
| 559 | RER1_E3-4_R_new | GTCACAATGTACCAACCCTGC |
| 560 | CHMP2A_E3_R | TTGAGGGACACAGCCTGGAT |
| 561 | RAB7A_E1-2_R | AGGTCATCCTTCAAACGCGG |
| 562 | ACTB_R | ATCATCCATGGTGAGCTGGC |

Table of forward primers specific to target genes related to protein expression

| SEQ ID NO | Primer name | Sequence |
|---|---|---|
| 563 | CD274_3UTR_F | CAAAGAAGCAAAGTGATACACATTTG |
| 564 | CD274_EXON4_F | GTGAAAGTCAATGCCCCATACAAC |
| 565 | CD274_EXON3_F | GGCATTTGCTGAACGCATTTACTG |
| 566 | PDCD1-EXON3_4_5_F | CCGCACGAGGGACAATAGGA |
| 567 | CTLA4-EXON1_2_F | CTTCTCTTCATCCCTGTCTTCTG |
| 568 | CTLA4-EXON4_F | GCTGTTTCTTTGAGCAAAATGCTAAAGA |
| 569 | CD47-EXON3_F | GAAGGTGAAACGATCATCGAGC |
| 570 | CD47-EXON9_10_11_F | GAGGAACCCCTTAATGCATTCAAAG |
| 571 | LAG3-EXON8_F | CTTTGGAGAAGACAGTGGCGAC |
| 572 | LAG3_EXON2-F_rdsgn | TTTGGGTGGCTCCAGTGAAG |
| 573 | HAVCR2_EXON3-F_rdsgn | AGTTGGTCATCAAACCAGCCAAG |
| 574 | HAVCR2_EXON7-F_rdsgn | CAAAGAGAAGATACAGAATTTAAGCCTCAT |
| 575 | PDCD1_EXON2-F_rdsgn | GCCAGGATGGTTCTTAGACTCC |
| 576 | CD14_exon1_1F | GAAGACTTATCGACCATGGAGC |
| 577 | CD27_exon1-2_1F | CAGATGTGTGAGCCAGGAAC |
| 578 | CD39_exon1_1F | CTTGAGAAAGGATTGCTGGTCA |
| 579 | CD40_exon6-7_1F | GACTGATGTTGTCTGTGGTCC |
| 580 | CD70_exon1_2F | CTTGGTGATCTGCCTCGTG |
| 581 | CD80_exon1_1F | TCTCAGAAGTGGAGTCTTACCC |
| 582 | FOXP3_exon6-7_1F | AGAGGACTTCCTCAAGCACTG |
| 583 | ICOS_exon3_1F | TGTGCAGCCTTTGTTGTAGT |
| 584 | ICOS_exon1-2_2F | GCATTAAAGTTTTAACAGGAGA |
| 585 | TIGIT_exon3_1F | AGATTCCATTGCTTGGAGCC |
| 586 | TNFRSF18_exon2-3_1F | TACAGTCCCAGGGGAAATTCAG |
| 587 | VISTA_exon4-5_1F | TGCGGATGGACAGCAACATT |
| 588 | VISTA_exon2-3_2F | CCTCCCAGGATAGTGAAAACATC |

Table of reverse primers specific to target genes related to protein expression

| SEQ ID NO | Primer name | Sequence |
|---|---|---|
| 589 | CD274_3UTR_R | GAACCCCTAAACCACAGGTTGAG |
| 590 | CD274_EXON4_R | CTCAGCCTGACATGTCAGTTCATG |
| 591 | CD274_EXON3_R | CTACTGGGAATTTGCATTCAATTGTC |
| 592 | PDCD1_EXON2_R | AGAAGCTGCAGGTGAAGGTG |
| 593 | PDCD1-EXON3_4_5_R | GGAAATCCAGCTCCCCATAGTC |
| 594 | CTLA4-EXON1_2_R | GCATACTCACACACAAAGCTGG |
| 595 | CTLA4-EXON4_R | TTGCTTTTCACATTCTGGCTCTG |
| 596 | CD47-EXON3_R | CTGTCCCCAGAACAGGAGTATAG |
| 597 | CD47-EXON9_10_11_R | CCTTTCACGTCTTACTACTCTCCA |
| 598 | LAG3-EXON2_R | CAGAAGGCTGAGATCCTGGAG |
| 599 | LAG3-EXON8_R | GGTTCTTGCTCCAGCTCCTC |
| 600 | HAVCR2-EXON3_R | CCATGTCCCCTGGTGGTAAG |
| 601 | HAVCR2-EXON7_R | GGTATAGATGTTTTCTTCTGAGCGA |
| 602 | CD14_exon2_1R | CGCAGCGGAAATCTTCATCG |
| 603 | CD27_exon2_1R | GTCAGGAGAGAAGGAGACCC |
| 604 | CD39_exon1-2_1R | TCACGTTAGACTCTTGAAACCC |
| 605 | CD40_exon7_1R | GATAAAGACCAGCACCAAGAGG |

-continued

| SEQ ID NO | Primer name | Sequence |
|---|---|---|
| 606 | CD70_exon1-2_2R | AGCTACGTCCCACCCAAG |
| 607 | CD80_exon1-2_1R | GTGGATTTAGTTTCACAGCTTGC |
| 608 | FOXP3_exon7_1R | TCTCTCTCTGGAGGAGACATTG |
| 609 | ICOS_exon3-4_1R | GCACACTGGATGAATACTTCTTT |
| 610 | ICOS_exon2_2R | TTTGTACACCTCCGTTGTGA |
| 611 | TIGIT_exon3-4_1R | GGATTCTGAGGGCTTTCTTCTT |
| 612 | TNFRSF18_exon3-4_1R | CAGCAGTCTGTCCAAGGTTTG |
| 613 | VISTA_exon5_1R | AGGACAGGGGGTGCCTGA |
| 614 | VISTA_exon3_2R | CTGCCTTTGCTTGTAGACCA |

Table of other sequences

| SEQ ID NO | Sequence name | Sequence |
|---|---|---|
| 615 | Barcode sequence | NNNNNNNNNN |
| 616 | Universal indexed forward primer | AATGATACGGCGACCACCGAG ATCTACACCTAGCGCTACACT CTTTCCCTACACGACGCTCTTCCGA TC*T |
| 617 | Universal indexed reverse primer | CAAGCAGAAGACGGCATACGA GATAACCGCGGGTGACTGGAG TTCAGACGTGTGCTCTTCCGATC*T |

The invention claimed is:

1. A method of detecting genomic alteration and/or detecting gene expression and/or quantifying a level of gene expression using RNA in a biological sample, comprising:
 (a) extracting RNA from the biological sample and converting the RNA to complementary DNA (cDNA);
 (b) performing a plurality of multiplexed PCR reactions on the converted cDNA using
  (I) a plurality of forward and reverse primer pairs specific to a plurality of target genes that are capable of undergoing genomic alteration,
   wherein each forward primer of the plurality of forward and reverse primer pairs specific to the plurality of target genes that are capable of undergoing genomic alteration is complementary to a sequence located about 50 base pairs upstream of an exonic junction of each target gene that is capable of undergoing genomic alteration,
   wherein each reverse primer of the plurality of forward and reverse primer pairs specific to the plurality of target genes that are capable of undergoing genomic alteration is complementary to a sequence located about 50 base pairs downstream of an exonic junction of each target gene that is capable of undergoing genomic alteration,
   wherein each reverse primer of the plurality of forward and reverse primer pairs specific to the plurality of target genes that are capable of undergoing genomic alteration comprises a barcode sequence on its 5' end, wherein the barcode sequence of each reverse primer corresponding to each target gene that is capable of undergoing genomic alteration is different, and/or
  (II) a plurality of forward and reverse primer pairs specific to a plurality of control housekeeping genes, wherein:
   (i) each forward primer of the plurality of forward and reverse primer pairs specific to the plurality of control housekeeping genes is complementary to a sequence spanning an exon-exon junction of each control housekeeping gene,
    wherein each reverse primer of the plurality of forward and reverse primer pairs specific to the plurality of control housekeeping genes is complementary to a sequence about 100 base pairs downstream of the sequence spanning the exon-exon junction of each control housekeeping gene,
    wherein each reverse primer of the plurality of forward and reverse primer pairs specific to the plurality of control housekeeping genes comprises a barcode sequence on its 5' end, wherein the barcode sequence of each reverse primer corresponding to each control housekeeping gene is different;
   (ii) each reverse primer of the plurality of forward and reverse primer pairs specific to the plurality of control housekeeping genes is complementary to a sequence spanning an exon-exon junction of each control housekeeping gene,
    wherein each forward primer of the plurality of forward and reverse primer pairs specific to the plurality of control housekeeping genes is complementary to a sequence about 100 base pairs downstream of the sequence spanning the exon-exon junction of each control housekeeping gene,
    wherein each reverse primer of the plurality of forward and reverse primer pairs specific to the plurality of control housekeeping genes comprises a barcode sequence on its 5' end, wherein the barcode sequence of each reverse primer corresponding to each control housekeeping gene is different; or
   (iii) each forward and each reverse primer of the plurality of forward and reverse primer pairs specific to the plurality of control housekeeping genes is complementary to consecutive sequences spanning an exon-exon junction of each control housekeeping gene,
    wherein each reverse primer of the plurality of forward and reverse primer pairs specific to the plurality of control housekeeping genes comprises a barcode sequence on its 5' end, wherein the barcode sequence of each reverse primer corresponding to each control housekeeping gene is different, and/or
  (III) a plurality of primer sets specific to a plurality of target genes related to protein expression,
   wherein each primer set comprises a plurality of forward and reverse primer pairs specific to each target gene related to protein expression, wherein:
    (i) each forward primer of the of the plurality of forward and reverse primer pairs specific to each target gene related to protein expression is complementary to a sequence spanning an exon-exon junction of each target gene related to protein expression,
     wherein each reverse primer of the of the plurality of forward and reverse primer pairs specific to each target gene related to protein expression is complementary to a sequence about 100 base pairs downstream of the sequence spanning the exon-exon junction of each target gene related to protein expression,
wherein each reverse primer of the plurality of forward and reverse primer pairs specific to each target gene related to protein expression comprises a barcode sequence on its 5' end, wherein the barcode sequence of each reverse primer corresponding to each target gene related to protein expression is different,
(ii) each reverse primer of the plurality of forward and reverse primer pairs specific to the plurality of target genes related to protein expression is complementary to a sequence spanning an exon-exon junction of each target gene related to protein expression,
wherein each forward primer of the plurality of forward and reverse primer pairs specific to the plurality of target genes related to protein expression is complementary to a sequence about 100 base pairs downstream of the sequence spanning the exon-exon junction of each target gene related to protein expression,
wherein each reverse primer of the plurality of forward and reverse primer pairs specific to the plurality of target genes related to protein expression comprises a barcode sequence on its 5' end, wherein the barcode sequence of each reverse primer corresponding to each target gene related to protein expression is different; or
(iii) each forward and each reverse primer of the plurality of forward and reverse primer pairs specific to the plurality of target genes related to protein expression is complementary to consecutive sequences spanning an exon-exon junction of each target gene related to protein expression,
wherein each reverse primer of the plurality of forward and reverse primer pairs specific to the plurality of target genes related to protein expression comprises a barcode sequence on its 5' end, wherein the barcode sequence of each reverse primer corresponding to each target gene related to protein expression is different,
thereby generating a plurality of amplicons;
(c) purifying the plurality of amplicons from step (b);
(d) amplifying the purified product from step (c) by using universal indexed adapter primers to generate a sequencing library;
(e) purifying the sequencing library obtained from step (d);
(f) subjecting the purified sequencing library from step (e) to multiplex sequencing on a next-generation sequencing platform to obtain a plurality of sequencing reads;
(g) deriving a consensus read of each sequence from the plurality of sequencing reads obtained from step (f);
(h) performing a sequence alignment of the consensus read obtained from step (g) to a reference genome,
(I) if the sequence alignment results in a partial alignment to the reference genome of an exon from a first gene and a partial alignment to the reference genome of an exon from a second gene, then:
(i) determining the sequence alignment as a split read,
(ii) counting/enumerating the number of split reads from step (h)(I)(i) that supports a fusion junction, and
(iii) if the number of split reads from step (h)(I)(ii) is two or more, then determining the first gene and the second gene as fusion partners,
(II) if the sequence alignment results in an alignment to the reference genome of the control housekeeping gene, then:
(i) determining the sequence alignment as a consensus read of the control housekeeping gene,
(ii) counting/enumerating consensus read pairs of the control housekeeping gene from step (h)(II)(i), and
(iii) determining the level of gene expression of the control housekeeping gene,
(III) if the sequence alignment results in an alignment to the reference genome of the target gene related to protein expression,
(i) determining the sequence alignment as a consensus read of the target gene related to protein expression,
(ii) counting/enumerating consensus read pairs of the target gene related to protein expression from step (h)(III)(i), and
(iii) determining the level of gene expression of the target gene related to protein expression;
(i) determining presence or absence of the genomic alteration and/or determining presence or absence of the gene expression and/or quantifying the level of the gene expression based on the sequence alignment from step (h).

2. The method of claim 1, wherein the RNA is selected from the group consisting of cell-free RNA (cfRNA) and RNA encapsulated within tissues and/or cells.

3. The method of claim 1, wherein the biological sample is selected from the group consisting of a liquid sample, a tissue sample, and a cell sample.

4. The method of claim 3, wherein the liquid sample is a bodily fluid, wherein optionally the bodily fluid is selected from the group consisting of blood, bone marrow, cerebral spinal fluid, peritoneal fluid, pleural fluid, lymph fluid, ascites, serous fluid, sputum, lacrimal fluid, stool, urine, saliva, ductal fluid from breast, gastric juice and pancreatic juice, wherein optionally the bodily fluid is blood, and wherein optionally the blood is plasma.

5. The method of claim 3, wherein the tissue sample is a frozen tissue sample or a fixed tissue sample, and wherein optionally the fixed tissue sample is a Formalin-Fixed Paraffin-Embedded (FFPE) tissue sample.

6. The method of claim 1, wherein the biological sample is obtained from a subject having or suspected of having cancer.

7. The method of claim 6, wherein the cancer is selected from the group consisting of leukemia, lung cancer, colorectal cancer, breast cancer, pancreatic cancer, prostate cancer, nasopharyngeal cancer, liver cancer, cholangiocarcinoma, esophageal cancer, urothelial cancer, and gastrointestinal cancer.

8. The method of claim 6, wherein the cancer is selected from the group consisting of metastatic prostate cancer, metastatic lung cancer, metastatic breast cancer, and leukemia.

9. The method of claim 1, wherein the amount of RNA used in step (a) is from 6 ng to 100 ng.

10. The method of claim 1, wherein step (a) is performed using a reverse transcription kit, wherein the reverse transcription kit comprises a buffer for performing reverse transcription, a reverse transcriptase enzyme and a plurality of random primers.

11. The method of claim 1, wherein the plurality of multiplexed PCR reactions performed on the converted cDNA comprises 3 to 15 PCR cycles.

12. The method of claim 1, wherein the barcode sequence is an oligonucleotide comprising 10 to 16 random nucleotides.

13. The method of claim 1, wherein the barcode sequence is an oligonucleotide comprising 10 random nucleotides.

14. The method of claim 1, wherein the target gene that is capable of undergoing genomic alteration comprises an exon from a gene known to undergo fusion fused to an exon from a partner gene of the gene known to undergo fusion.

15. The method of claim 14, wherein the gene known to undergo fusion is selected from the group consisting of ALK receptor tyrosine kinase, RET proto-oncogene, ROS proto-oncogene 1, fibroblast growth factor receptor 1 (FGFR1), fibroblast growth factor receptor 2 (FGFR2), fibroblast growth factor receptor 3 (FGFR3), neurotrophic receptor tyrosine kinase 1 (NTRK1), neurotrophic receptor tyrosine kinase 2 (NTRK2), neurotrophic receptor tyrosine kinase 3 (NTRK3), neuregulin 1 (NRG1), B-Raf proto-oncogene, serine/threonine kinase (BRAF), transmembrane serine protease 2 (TMPRSS2), MET proto-oncogene, receptor tyrosine kinase (MET), epidermal growth factor receptor (EGFR), estrogen receptor 1 (ESR1), platelet derived growth factor receptor alpha (PDGFRA), androgen receptor (AR), BCR activator of RhoGEF and GTPase (BCR), core-binding factor subunit beta (CBFB), lysine methyltransferase 2A (KMT2A), nucleophosmin 1 (NPM1), PML nuclear body scaffold (PML), and RUNX family transcription factor 1 (RUNX1).

16. The method of claim 14, wherein the partner gene of the gene known to undergo fusion is selected from the group consisting of EMAP like 4 (EML4), kinesin family member 5B (KIF5B), coiled-coil domain containing 6 (CCDC6), CD74 molecule (CD74), transforming acidic coiled-coil containing protein 3 (TACC3), ezrin EZR), ETS transcription factor ERG (ERG), ArfGAP with GTPase domain, ankyrin repeat and PH domain 3 (AGAP3), A-kinase anchoring protein 9 (AKAP9), KIAA1549, tropomyosin 3 (TPM3), translocated promoter region, nuclear basket protein (TPR), trafficking from ER to golgi regulator (TFG), lamin A/C (LMNA), BicC family RNA binding protein 1 (BICC1), RAD51 recombinase (RAD51), CD47 molecule (CD47), Yes 1 associated transcriptional regulator (YAP1), ETS variant transcription factor 1 (ETV1), ETS variant transcription factor 4 (ETV4), ETS variant transcription factor 5 (ETV5), ETS variant transcription factor 6 (ETV6), factor interacting with PAPOLA and CPSF1 (FIP1L1), centriolin (CNTRL), ABL proto-oncogene 1, non-receptor tyrosine kinase (ABL1), AF4/FMR2 family member 1 (AFF1), MDS1 and EVI1 complex locus (MECOM), MLLT3 super elongation complex subunit (MLLT3), myosin heavy chain 11 (MYH11), PBX homeobox 1 (PBX1), retinoic acid receptor alpha (RARA), and RUNX1 partner transcriptional co-repressor 1 (RUNX1T1).

17. The method of claim 1, wherein the number of the plurality of forward and reverse primer pairs specific to the plurality of target genes that are capable of undergoing genomic alteration, the plurality of forward and reverse primer pairs specific to the plurality of control housekeeping genes, and the plurality of primer sets specific to a plurality of target genes related to protein expression is at least 300.

18. The method of claim 1, wherein the length of the plurality of amplicons generated in step (b) is 90 to 110 base pairs.

19. The method of claim 1, wherein the purification in step (c) and/or (e) is performed using a plurality of paramagnetic beads; and wherein optionally the paramagnetic beads are selected from the group consisting of AMPure XP beads, SPRI beads, and dynabeads.

20. The method of claim 1, wherein step (g) further comprises:
(g)(I) detecting the presence of the barcode sequence from each sequencing read,
(g)(II) performing cluster reassignment for the plurality of sequencing reads having the same barcode sequence to generate a plurality of barcode clusters, wherein each barcode cluster contains reads from the same amplicon and with the same barcode sequence, and
(g)(III) performing consensus calling for each barcode cluster to obtain the consensus read of each sequence.

21. The method of claim 1, wherein the step of determining presence or absence of the genomic alteration and/or determining presence or absence of the gene expression and/or quantifying the level of the gene expression, further comprises performing variant calling of the sequence alignment from step (h).

22. The method of claim 21, wherein the step of variant calling comprises:
(i) identifying differences between a consensus read and a reference genome based on the sequence alignment from step (h); and
(ii) determining the read count of sequence alignments comprising genomic alteration.

23. The method of claim 21, wherein the genomic alteration is selected from the group consisting of insertions, deletions, and single nucleotide variants, wherein optionally the insertion is a duplication.

* * * * *

UNITED STATES PATENT AND TRADEMARK OFFICE
CERTIFICATE OF CORRECTION

PATENT NO. : 11,873,533 B2
APPLICATION NO. : 17/825669
DATED : January 16, 2024
INVENTOR(S) : Yukti Choudhury et al.

It is certified that error appears in the above-identified patent and that said Letters Patent is hereby corrected as shown below:

On the Title Page

Item (54), title, and in the Specification Column 1, Lines 1-3, delete "METHOD OF DETECTING AND QUANTIFYING GEONOMIC AND GENE EXPRESSION ALTERATIONS USING RNA" and insert --METHOD OF DETECTING AND QUANTIFYING GENOMIC AND GENE EXPRESSION ALTERATIONS USING RNA--, therefor.

Signed and Sealed this
Thirteenth Day of February, 2024

Katherine Kelly Vidal
*Director of the United States Patent and Trademark Office*

SEQUENCE LISTING

<160> NUMBER OF SEQ ID NOS: 617

<210> SEQ ID NO 1
<211> LENGTH: 19
<212> TYPE: DNA
<213> ORGANISM: Artificial Sequence
<220> FEATURE:
<223> OTHER INFORMATION: Forward Primer AGAP3_exon9F

<400> SEQUENCE: 1
agaagaaggc tgccgagtg                                                  19

<210> SEQ ID NO 2
<211> LENGTH: 18
<212> TYPE: DNA
<213> ORGANISM: Artificial Sequence
<220> FEATURE:
<223> OTHER INFORMATION: Forward Primer AGK_exon2F

<400> SEQUENCE: 2
gctctgcctg ctgacctg                                                   18

<210> SEQ ID NO 3
<211> LENGTH: 23
<212> TYPE: DNA
<213> ORGANISM: Artificial Sequence
<220> FEATURE:
<223> OTHER INFORMATION: Forward Primer AGTRAP_exon5F

<400> SEQUENCE: 3
cagagcacag cattaaagtt tgg                                             23

<210> SEQ ID NO 4
<211> LENGTH: 23
<212> TYPE: DNA
<213> ORGANISM: Artificial Sequence
<220> FEATURE:
<223> OTHER INFORMATION: Forward Primer AKAP9_exon21F

<400> SEQUENCE: 4
aggcatctgt aaagtcatgt gtc                                             23

<210> SEQ ID NO 5

```
<211> LENGTH: 24
<212> TYPE: DNA
<213> ORGANISM: Artificial Sequence
<220> FEATURE:
<223> OTHER INFORMATION: Forward Primer AKAP9_exon8F

<400> SEQUENCE: 5
gagcaactca accaagtgaa aatg                                          24

<210> SEQ ID NO 6
<211> LENGTH: 25
<212> TYPE: DNA
<213> ORGANISM: Artificial Sequence
<220> FEATURE:
<223> OTHER INFORMATION: Forward Primer ARMC10_exon4F

<400> SEQUENCE: 6 gcactaaaata acctgagtgt gaatg                                        25

<210> SEQ ID NO 7
<211> LENGTH: 19
<212> TYPE: DNA
<213> ORGANISM: Artificial Sequence
<220> FEATURE:
<223> OTHER INFORMATION: Forward Primer ATIC_exon7F

<400> SEQUENCE: 7
gtacacactg cagcccaag                                                19

<210> SEQ ID NO 8
<211> LENGTH: 19
<212> TYPE: DNA
<213> ORGANISM: Artificial Sequence
<220> FEATURE:
<223> OTHER INFORMATION: Forward Primer BCR_E1_F

<400> SEQUENCE: 8
gcagatctgg cccaacgat                                                19

<210> SEQ ID NO 9
<211> LENGTH: 25
<212> TYPE: DNA
<213> ORGANISM: Artificial Sequence
<220> FEATURE:
<223> OTHER INFORMATION: Forward Primer BCR_E13_F

<400> SEQUENCE: 9
ctgaccaact cgtgtgtgaa actcc                                         25

<210> SEQ ID NO 10
<211> LENGTH: 20
<212> TYPE: DNA
<213> ORGANISM: Artificial Sequence
<220> FEATURE:
<223> OTHER INFORMATION: Forward Primer BCR_E14_F

<400> SEQUENCE: 10
cggggctcta tgggtttctg                                               20

<210> SEQ ID NO 11
<211> LENGTH: 22
<212> TYPE: DNA
<213> ORGANISM: Artificial Sequence
<220> FEATURE:
<223> OTHER INFORMATION: Forward Primer BCR_E18_F

<400> SEQUENCE: 11
```
gtcttcggag tcaagattgc tg                                              22

<210> SEQ ID NO 12
<211> LENGTH: 18
<212> TYPE: DNA
<213> ORGANISM: Artificial Sequence
<220> FEATURE:
<223> OTHER INFORMATION: Forward Primer BCR_E19_F

<400> SEQUENCE: 12
atctaccgcg tgtccggt                                                   18

<210> SEQ ID NO 13
<211> LENGTH: 20
<212> TYPE: DNA
<213> ORGANISM: Artificial Sequence
<220> FEATURE:
<223> OTHER INFORMATION: Forward Primer BCR_E2_F_rdsgn

<400> SEQUENCE: 13
acattgatga ctcgccctcc                                                 20

<210> SEQ ID NO 14
<211> LENGTH: 22
<212> TYPE: DNA
<213> ORGANISM: Artificial Sequence
<220> FEATURE:
<223> OTHER INFORMATION: Forward Primer BCR_E6_F

<400> SEQUENCE: 14
aagatgccaa ggatccaacg ac                                              22

<210> SEQ ID NO 15
<211> LENGTH: 21
<212> TYPE: DNA
<213> ORGANISM: Artificial Sequence
<220> FEATURE:
<223> OTHER INFORMATION: Forward Primer BCR_E8_F

<400> SEQUENCE: 15
caatgaggag atcacacccc g                                               21

<210> SEQ ID NO 16
<211> LENGTH: 18
<212> TYPE: DNA
<213> ORGANISM: Artificial Sequence
<220> FEATURE:
<223> OTHER INFORMATION: Forward Primer BRAF_exon1F

<400> SEQUENCE: 16
tcttcggctg cggaccct                                                   18

<210> SEQ ID NO 17
<211> LENGTH: 24
<212> TYPE: DNA
<213> ORGANISM: Artificial Sequence
<220> FEATURE:
<223> OTHER INFORMATION: Forward Primer BRAF_exon2F

<400> SEQUENCE: 17
gaacatatag aggccctatt ggac                                            24

<210> SEQ ID NO 18
<211> LENGTH: 19
<212> TYPE: DNA

```
<213> ORGANISM: Artificial Sequence
<220> FEATURE:
<223> OTHER INFORMATION: Forward Primer BRAF_exon3F

<400> SEQUENCE: 18
gagcaacccc aagtcacca                                              19

<210> SEQ ID NO 19
<211> LENGTH: 21
<212> TYPE: DNA
<213> ORGANISM: Artificial Sequence
<220> FEATURE:
<223> OTHER INFORMATION: Forward Primer BRAF_exon4F

<400> SEQUENCE: 19
tgagaggtct aatcccagag t                                           21

<210> SEQ ID NO 20
<211> LENGTH: 25
<212> TYPE: DNA
<213> ORGANISM: Artificial Sequence
<220> FEATURE:
<223> OTHER INFORMATION: Forward Primer BTF3L4_exon3F

<400> SEQUENCE: 20
cagagttctc taaaaaaact ggctg                                       25

<210> SEQ ID NO 21
<211> LENGTH: 21
<212> TYPE: DNA
<213> ORGANISM: Artificial Sequence
<220> FEATURE:
<223> OTHER INFORMATION: Forward Primer CARS_exon17F

<400> SEQUENCE: 21
gagaaggagt gcggaagatt g                                           21

<210> SEQ ID NO 22
<211> LENGTH: 20
<212> TYPE: DNA
<213> ORGANISM: Artificial Sequence
<220> FEATURE:
<223> OTHER INFORMATION: Forward Primer CBFB_E4_F

<400> SEQUENCE: 22
tggtatgggc tgtctggagt                                             20

<210> SEQ ID NO 23
<211> LENGTH: 19
<212> TYPE: DNA
<213> ORGANISM: Artificial Sequence
<220> FEATURE:
<223> OTHER INFORMATION: Forward Primer CBFB_E5_F

<400> SEQUENCE: 23
cggagaagga cacgcgaat                                              19

<210> SEQ ID NO 24
<211> LENGTH: 22
<212> TYPE: DNA
<213> ORGANISM: Artificial Sequence
<220> FEATURE:
<223> OTHER INFORMATION: Forward Primer CCDC6_exon1FS

<400> SEQUENCE: 24
caaggcactg caggaggaga ac                                          22
```

```
<210> SEQ ID NO 25
<211> LENGTH: 26
<212> TYPE: DNA
<213> ORGANISM: Artificial Sequence
<220> FEATURE:
<223> OTHER INFORMATION: Forward Primer CCDC6_exon2F

<400> SEQUENCE: 25
gaattcctca ctaatgagct ctccag                                         26

<210> SEQ ID NO 26
<211> LENGTH: 19
<212> TYPE: DNA
<213> ORGANISM: Artificial Sequence
<220> FEATURE:
<223> OTHER INFORMATION: Forward Primer CCDC6_exon8F

<400> SEQUENCE: 26
cttcacgtgc agcacatgg                                                 19

<210> SEQ ID NO 27
<211> LENGTH: 23
<212> TYPE: DNA
<213> ORGANISM: Artificial Sequence
<220> FEATURE:
<223> OTHER INFORMATION: Forward Primer CCDC91_exon11F

<400> SEQUENCE: 27
ggcagtgaaa agaacaagag atg                                            23

<210> SEQ ID NO 28
<211> LENGTH: 22
<212> TYPE: DNA
<213> ORGANISM: Artificial Sequence
<220> FEATURE:
<223> OTHER INFORMATION: Forward Primer CD74_exon6FS

<400> SEQUENCE: 28
tccttggagc aaaagcccac tg                                             22

<210> SEQ ID NO 29
<211> LENGTH: 22
<212> TYPE: DNA
<213> ORGANISM: Artificial Sequence
<220> FEATURE:
<223> OTHER INFORMATION: Forward Primer CDC27_exon16F

<400> SEQUENCE: 29
ttgatcccaa gaaccctcta tg                                             22

<210> SEQ ID NO 30
<211> LENGTH: 21
<212> TYPE: DNA
<213> ORGANISM: Artificial Sequence
<220> FEATURE:
<223> OTHER INFORMATION: Forward Primer CLTC_exon30F

<400> SEQUENCE: 30
catgccctat ttcatccagg t                                              21

<210> SEQ ID NO 31
<211> LENGTH: 25
<212> TYPE: DNA
<213> ORGANISM: Artificial Sequence
<220> FEATURE:
```

```
<223> OTHER INFORMATION: Forward Primer CLTC_exon31F

<400> SEQUENCE: 31
gaagaagaac aagctacaga gacac                                           25

<210> SEQ ID NO 32
<211> LENGTH: 18
<212> TYPE: DNA
<213> ORGANISM: Artificial Sequence
<220> FEATURE:
<223> OTHER INFORMATION: Forward Primer CUX1_exon10F_new

<400> SEQUENCE: 32
gccaatcact ccctccag                                                   18

<210> SEQ ID NO 33
<211> LENGTH: 20
<212> TYPE: DNA
<213> ORGANISM: Artificial Sequence
<220> FEATURE:
<223> OTHER INFORMATION: Forward Primer DCTN1_exon16F

<400> SEQUENCE: 33
atgactgcgt tctggtgctg                                                 20

<210> SEQ ID NO 34
<211> LENGTH: 21
<212> TYPE: DNA
<213> ORGANISM: Artificial Sequence
<220> FEATURE:
<223> OTHER INFORMATION: Forward Primer DCTN1_exon26F

<400> SEQUENCE: 34
cattgctact ctggtctctg g                                               21

<210> SEQ ID NO 35
<211> LENGTH: 21
<212> TYPE: DNA
<213> ORGANISM: Artificial Sequence
<220> FEATURE:
<223> OTHER INFORMATION: Forward Primer EML4_exon13F

<400> SEQUENCE: 35
ctactgtaga gcccacacct g                                               21

<210> SEQ ID NO 36
<211> LENGTH: 24
<212> TYPE: DNA
<213> ORGANISM: Artificial Sequence
<220> FEATURE:
<223> OTHER INFORMATION: Forward Primer EML4_exon14F

<400> SEQUENCE: 36
attaactgga ggagggaaag acag                                            24

<210> SEQ ID NO 37
<211> LENGTH: 24
<212> TYPE: DNA
<213> ORGANISM: Artificial Sequence
<220> FEATURE:
<223> OTHER INFORMATION: Forward Primer EML4_exon15F

<400> SEQUENCE: 37
cgaggaacat ttaatgatgg cttc                                            24
```

```
<210> SEQ ID NO 38
<211> LENGTH: 25
<212> TYPE: DNA
<213> ORGANISM: Artificial Sequence
<220> FEATURE:
<223> OTHER INFORMATION: Forward Primer EML4_exon16F

<400> SEQUENCE: 38
tgctcttgac atgtgctcag gacag                                  25

<210> SEQ ID NO 39
<211> LENGTH: 25
<212> TYPE: DNA
<213> ORGANISM: Artificial Sequence
<220> FEATURE:
<223> OTHER INFORMATION: Forward Primer EML4_exon17F

<400> SEQUENCE: 39
ctgtgcagat tttcatccaa gtggc                                  25

<210> SEQ ID NO 40
<211> LENGTH: 25
<212> TYPE: DNA
<213> ORGANISM: Artificial Sequence
<220> FEATURE:
<223> OTHER INFORMATION: Forward Primer EML4_exon18F

<400> SEQUENCE: 40
tctatccaca cagacgggaa tgaac                                  25

<210> SEQ ID NO 41
<211> LENGTH: 25
<212> TYPE: DNA
<213> ORGANISM: Artificial Sequence
<220> FEATURE:
<223> OTHER INFORMATION: Forward Primer EML4_exon20FS

<400> SEQUENCE: 41
ataatgtcta actcgggaga ctatg                                  25

<210> SEQ ID NO 42
<211> LENGTH: 22
<212> TYPE: DNA
<213> ORGANISM: Artificial Sequence
<220> FEATURE:
<223> OTHER INFORMATION: Forward Primer EML4_exon2F

<400> SEQUENCE: 42
gcaatctctg aagatcatgt gg                                     22

<210> SEQ ID NO 43
<211> LENGTH: 27
<212> TYPE: DNA
<213> ORGANISM: Artificial Sequence
<220> FEATURE:
<223> OTHER INFORMATION: Forward Primer EML4_exon5F

<400> SEQUENCE: 43
gcagacaagc ataaagatgt catcatc                                27

<210> SEQ ID NO 44
<211> LENGTH: 24
<212> TYPE: DNA
<213> ORGANISM: Artificial Sequence
<220> FEATURE:
<223> OTHER INFORMATION: Forward Primer EPS15_exon22F
```

<400> SEQUENCE: 44
aatcatttgg aggtggattt gctg                                          24

<210> SEQ ID NO 45
<211> LENGTH: 24
<212> TYPE: DNA
<213> ORGANISM: Artificial Sequence
<220> FEATURE:
<223> OTHER INFORMATION: Forward Primer ERC1_exon12F

<400> SEQUENCE: 45
gaggtggaaa atgagaagaa tgac                                          24

<210> SEQ ID NO 46
<211> LENGTH: 20
<212> TYPE: DNA
<213> ORGANISM: Artificial Sequence
<220> FEATURE:
<223> OTHER INFORMATION: Forward Primer EWSR1_exon7F

<400> SEQUENCE: 46
ctacagccaa gctccaagtc                                               20

<210> SEQ ID NO 47
<211> LENGTH: 20
<212> TYPE: DNA
<213> ORGANISM: Artificial Sequence
<220> FEATURE:
<223> OTHER INFORMATION: Forward Primer EWSR1_exon9_10F

<400> SEQUENCE: 47
gcttcaataa gcctggtgga                                               20

<210> SEQ ID NO 48
<211> LENGTH: 18
<212> TYPE: DNA
<213> ORGANISM: Artificial Sequence
<220> FEATURE:
<223> OTHER INFORMATION: Forward Primer EZR_exon10F

<400> SEQUENCE: 48
ggctgcagga ctatgagg                                                 18

<210> SEQ ID NO 49
<211> LENGTH: 19
<212> TYPE: DNA
<213> ORGANISM: Artificial Sequence
<220> FEATURE:
<223> OTHER INFORMATION: Forward Primer FAM131B_exon2F

<400> SEQUENCE: 49
catggacagc accagctca                                                19

<210> SEQ ID NO 50
<211> LENGTH: 18
<212> TYPE: DNA
<213> ORGANISM: Artificial Sequence
<220> FEATURE:
<223> OTHER INFORMATION: Forward Primer FCHSD1_exon13F

<400> SEQUENCE: 50
gatgaggtgg agcaggag                                                 18

<210> SEQ ID NO 51
<211> LENGTH: 28

```
<212> TYPE: DNA
<213> ORGANISM: Artificial Sequence
<220> FEATURE:
<223> OTHER INFORMATION: Forward Primer FGFR1OP_exon12FS

<400> SEQUENCE: 51
gtggaaatag atgacatcaa taccagtg                                          28

<210> SEQ ID NO 52
<211> LENGTH: 18
<212> TYPE: DNA
<213> ORGANISM: Artificial Sequence
<220> FEATURE:
<223> OTHER INFORMATION: Forward Primer GHR_exon1F

<400> SEQUENCE: 52
cgaacccgcg ctctctga                                                     18

<210> SEQ ID NO 53
<211> LENGTH: 20
<212> TYPE: DNA
<213> ORGANISM: Artificial Sequence
<220> FEATURE:
<223> OTHER INFORMATION: Forward Primer GOLGA5_exon7F

<400> SEQUENCE: 53
ggccagatac atcagctcag                                                   20

<210> SEQ ID NO 54
<211> LENGTH: 23
<212> TYPE: DNA
<213> ORGANISM: Artificial Sequence
<220> FEATURE:
<223> OTHER INFORMATION: Forward Primer GOPC_exon4F

<400> SEQUENCE: 54
tgttctccag gctgaagtat atg                                               23

<210> SEQ ID NO 55
<211> LENGTH: 27
<212> TYPE: DNA
<213> ORGANISM: Artificial Sequence
<220> FEATURE:
<223> OTHER INFORMATION: Forward Primer GOPC_exon8F

<400> SEQUENCE: 55
caagtgggga aatcaaagta ttacaag                                           27

<210> SEQ ID NO 56
<211> LENGTH: 25
<212> TYPE: DNA
<213> ORGANISM: Artificial Sequence
<220> FEATURE:
<223> OTHER INFORMATION: Forward Primer GTF2I_exon4F

<400> SEQUENCE: 56
cagttgagga ctatttctgc ttttg                                             25

<210> SEQ ID NO 57
<211> LENGTH: 18
<212> TYPE: DNA
<213> ORGANISM: Artificial Sequence
<220> FEATURE:
<223> OTHER INFORMATION: Forward Primer HIP1_exon21F

<400> SEQUENCE: 57
```
accacctgcc tcagagcc                                                           18

<210> SEQ ID NO 58
<211> LENGTH: 23
<212> TYPE: DNA
<213> ORGANISM: Artificial Sequence
<220> FEATURE:
<223> OTHER INFORMATION: Forward Primer HIP1_exon28F

<400> SEQUENCE: 58
ctcaaccatt tccggcaaat cac                                                     23

<210> SEQ ID NO 59
<211> LENGTH: 19
<212> TYPE: DNA
<213> ORGANISM: Artificial Sequence
<220> FEATURE:
<223> OTHER INFORMATION: Forward Primer HIP1_exon30F

<400> SEQUENCE: 59
cttgctggtg ttgctgagg                                                          19

<210> SEQ ID NO 60
<211> LENGTH: 22
<212> TYPE: DNA
<213> ORGANISM: Artificial Sequence
<220> FEATURE:
<223> OTHER INFORMATION: Forward Primer IRF2BP2_E1a_F

<400> SEQUENCE: 60
gagcaagttt aagaaggagc cg                                                      22

<210> SEQ ID NO 61
<211> LENGTH: 20
<212> TYPE: DNA
<213> ORGANISM: Artificial Sequence
<220> FEATURE:
<223> OTHER INFORMATION: Forward Primer IRF2BP2_E1b_F

<400> SEQUENCE: 61
gcaggttgtt gggtttcgag                                                         20

<210> SEQ ID NO 62
<211> LENGTH: 22
<212> TYPE: DNA
<213> ORGANISM: Artificial Sequence
<220> FEATURE:
<223> OTHER INFORMATION: Forward Primer IRF2BP2_E2_F

<400> SEQUENCE: 62
ggagaggtct attgtcccag tg                                                      22

<210> SEQ ID NO 63
<211> LENGTH: 20
<212> TYPE: DNA
<213> ORGANISM: Artificial Sequence
<220> FEATURE:
<223> OTHER INFORMATION: Forward Primer KIAA1468_exon10FS

<400> SEQUENCE: 63
ctgcctgcca cacattgttc                                                         20

<210> SEQ ID NO 64
<211> LENGTH: 19
<212> TYPE: DNA
<213> ORGANISM: Artificial Sequence

```
<220> FEATURE:
<223> OTHER INFORMATION: Forward Primer KIAA1549_exon12F

<400> SEQUENCE: 64
acgcaggaga taagacgcc                                              19

<210> SEQ ID NO 65
<211> LENGTH: 19
<212> TYPE: DNA
<213> ORGANISM: Artificial Sequence
<220> FEATURE:
<223> OTHER INFORMATION: Forward Primer KIAA1549_exon13F

<400> SEQUENCE: 65
cttatcgcca tgcagccga                                              19

<210> SEQ ID NO 66
<211> LENGTH: 19
<212> TYPE: DNA
<213> ORGANISM: Artificial Sequence
<220> FEATURE:
<223> OTHER INFORMATION: Forward Primer KIAA1549_exon14F

<400> SEQUENCE: 66
acaagatcct ggaccccac                                              19

<210> SEQ ID NO 67
<211> LENGTH: 19
<212> TYPE: DNA
<213> ORGANISM: Artificial Sequence
<220> FEATURE:
<223> OTHER INFORMATION: Forward Primer KIAA1549_exon15F

<400> SEQUENCE: 67
agcgatggca cctacagga                                              19

<210> SEQ ID NO 68
<211> LENGTH: 18
<212> TYPE: DNA
<213> ORGANISM: Artificial Sequence
<220> FEATURE:
<223> OTHER INFORMATION: Forward Primer KIAA1549_exon16F

<400> SEQUENCE: 68
aagagaggcg agccaccc                                               18

<210> SEQ ID NO 69
<211> LENGTH: 18
<212> TYPE: DNA
<213> ORGANISM: Artificial Sequence
<220> FEATURE:
<223> OTHER INFORMATION: Forward Primer KIAA1549_exon18F

<400> SEQUENCE: 69
ggaggagatg ccgtcggt                                               18

<210> SEQ ID NO 70
<211> LENGTH: 19
<212> TYPE: DNA
<213> ORGANISM: Artificial Sequence
<220> FEATURE:
<223> OTHER INFORMATION: Forward Primer KIAA1549_exon19F

<400> SEQUENCE: 70
aagcagaggc agccagtat                                              19
```

<210> SEQ ID NO 71
<211> LENGTH: 25
<212> TYPE: DNA
<213> ORGANISM: Artificial Sequence
<220> FEATURE:
<223> OTHER INFORMATION: Forward Primer KIF5B_exon15F

<400> SEQUENCE: 71
cttgcagaaa taggaattgc tgtgg                                  25

<210> SEQ ID NO 72
<211> LENGTH: 25
<212> TYPE: DNA
<213> ORGANISM: Artificial Sequence
<220> FEATURE:
<223> OTHER INFORMATION: Forward Primer KIF5B_exon16FS

<400> SEQUENCE: 72
tgaaaaggag ttagcagcat gtcag                                  25

<210> SEQ ID NO 73
<211> LENGTH: 24
<212> TYPE: DNA
<213> ORGANISM: Artificial Sequence
<220> FEATURE:
<223> OTHER INFORMATION: Forward Primer KIF5B_exon17F

<400> SEQUENCE: 73
atgccctcag tgaagaacta gtcc                                   24

<210> SEQ ID NO 74
<211> LENGTH: 26
<212> TYPE: DNA
<213> ORGANISM: Artificial Sequence
<220> FEATURE:
<223> OTHER INFORMATION: Forward Primer KIF5B_exon22F

<400> SEQUENCE: 74
gaacttcaga ctttacacaa cctgcg                                 26

<210> SEQ ID NO 75
<211> LENGTH: 24
<212> TYPE: DNA
<213> ORGANISM: Artificial Sequence
<220> FEATURE:
<223> OTHER INFORMATION: Forward Primer KIF5B_exon23FS

<400> SEQUENCE: 75
atcttgaaca gctcactaaa gtgc                                   24

<210> SEQ ID NO 76
<211> LENGTH: 25
<212> TYPE: DNA
<213> ORGANISM: Artificial Sequence
<220> FEATURE:
<223> OTHER INFORMATION: Forward Primer KIF5B_exon24F_new

<400> SEQUENCE: 76
gaagcagtca ggtcaaagaa tatgg                                  25

<210> SEQ ID NO 77
<211> LENGTH: 24
<212> TYPE: DNA
<213> ORGANISM: Artificial Sequence
<220> FEATURE:
<223> OTHER INFORMATION: Forward Primer KLC1_exon9F

```
<400> SEQUENCE: 77
tgcacatgaa agggagtttg gttc                                              24

<210> SEQ ID NO 78
<211> LENGTH: 21
<212> TYPE: DNA
<213> ORGANISM: Artificial Sequence
<220> FEATURE:
<223> OTHER INFORMATION: Forward Primer KMT2A_E10_F

<400> SEQUENCE: 78
ccagggtggt ttgctttctc t                                                 21

<210> SEQ ID NO 79
<211> LENGTH: 20
<212> TYPE: DNA
<213> ORGANISM: Artificial Sequence
<220> FEATURE:
<223> OTHER INFORMATION: Forward Primer KMT2A_E11_F

<400> SEQUENCE: 79
tctgtcacgt ttgtggaagg                                                   20

<210> SEQ ID NO 80
<211> LENGTH: 20
<212> TYPE: DNA
<213> ORGANISM: Artificial Sequence
<220> FEATURE:
<223> OTHER INFORMATION: Forward Primer KMT2A_E5_F

<400> SEQUENCE: 80
aagcccaagt ttggtggtcg                                                   20

<210> SEQ ID NO 81
<211> LENGTH: 21
<212> TYPE: DNA
<213> ORGANISM: Artificial Sequence
<220> FEATURE:
<223> OTHER INFORMATION: Forward Primer KMT2A_E6_F

<400> SEQUENCE: 81
caatggatgc cttccaaagc c                                                 21

<210> SEQ ID NO 82
<211> LENGTH: 20
<212> TYPE: DNA
<213> ORGANISM: Artificial Sequence
<220> FEATURE:
<223> OTHER INFORMATION: Forward Primer KMT2A_E7_F

<400> SEQUENCE: 82
aaaccactcc tagtgagccc                                                   20

<210> SEQ ID NO 83
<211> LENGTH: 18
<212> TYPE: DNA
<213> ORGANISM: Artificial Sequence
<220> FEATURE:
<223> OTHER INFORMATION: Forward Primer KMT2A_E8_F

<400> SEQUENCE: 83
gctccccgcc caagtatc                                                     18

<210> SEQ ID NO 84
```

```
<211> LENGTH: 20
<212> TYPE: DNA
<213> ORGANISM: Artificial Sequence
<220> FEATURE:
<223> OTHER INFORMATION: Forward Primer KMT2A_E9_F

<400> SEQUENCE: 84
gcagatggag tccacaggat                                              20

<210> SEQ ID NO 85
<211> LENGTH: 23
<212> TYPE: DNA
<213> ORGANISM: Artificial Sequence
<220> FEATURE:
<223> OTHER INFORMATION: Forward Primer KTN1_exon29F

<400> SEQUENCE: 85
catgctaaaa gagagggaga gtg                                          23

<210> SEQ ID NO 86
<211> LENGTH: 25
<212> TYPE: DNA
<213> ORGANISM: Artificial Sequence
<220> FEATURE:
<223> OTHER INFORMATION: Forward Primer LRIG3_exon16F

<400> SEQUENCE: 86
ttcttaccac aacatgacag tagtg                                        25

<210> SEQ ID NO 87
<211> LENGTH: 21
<212> TYPE: DNA
<213> ORGANISM: Artificial Sequence
<220> FEATURE:
<223> OTHER INFORMATION: Forward Primer MKRN1_exon4F

<400> SEQUENCE: 87
atccaatgga tgctgcccag a                                            21

<210> SEQ ID NO 88
<211> LENGTH: 21
<212> TYPE: DNA
<213> ORGANISM: Artificial Sequence
<220> FEATURE:
<223> OTHER INFORMATION: Forward Primer MSN_exon11F

<400> SEQUENCE: 88
gacagaagaa ggagagtgag g                                            21

<210> SEQ ID NO 89
<211> LENGTH: 24
<212> TYPE: DNA
<213> ORGANISM: Artificial Sequence
<220> FEATURE:
<223> OTHER INFORMATION: Forward Primer NCOA4_exon6FS

<400> SEQUENCE: 89
ttgaagctga cacaattact ctgc                                         24

<210> SEQ ID NO 90
<211> LENGTH: 22
<212> TYPE: DNA
<213> ORGANISM: Artificial Sequence
<220> FEATURE:
<223> OTHER INFORMATION: Forward Primer NCOA4_exon7F

<400> SEQUENCE: 90
```

```
cctggagaag agaggctgta tc                                            22

<210> SEQ ID NO 91
<211> LENGTH: 23
<212> TYPE: DNA
<213> ORGANISM: Artificial Sequence
<220> FEATURE:
<223> OTHER INFORMATION: Forward Primer NCOA4_exon8F_new

<400> SEQUENCE: 91
aggactggct tacccaaaag cag                                           23

<210> SEQ ID NO 92
<211> LENGTH: 20
<212> TYPE: DNA
<213> ORGANISM: Artificial Sequence
<220> FEATURE:
<223> OTHER INFORMATION: Forward Primer NPM1_E4_F

<400> SEQUENCE: 92
aagtgtggtt cagggccagt                                               20

<210> SEQ ID NO 93
<211> LENGTH: 20
<212> TYPE: DNA
<213> ORGANISM: Artificial Sequence
<220> FEATURE:
<223> OTHER INFORMATION: Forward Primer NPM1_E5_F

<400> SEQUENCE: 93
tatctggaaa gcggtctgcc                                               20

<210> SEQ ID NO 94
<211> LENGTH: 19
<212> TYPE: DNA
<213> ORGANISM: Artificial Sequence
<220> FEATURE:
<223> OTHER INFORMATION: Forward Primer NUP214_exon21F

<400> SEQUENCE: 94
aagaccccac cagtgagat                                                19

<210> SEQ ID NO 95
<211> LENGTH: 23
<212> TYPE: DNA
<213> ORGANISM: Artificial Sequence
<220> FEATURE:
<223> OTHER INFORMATION: Forward Primer PAPSS1_exon5F

<400> SEQUENCE: 95
ctcctgtgat gtaaatgact gtg                                           23

<210> SEQ ID NO 96
<211> LENGTH: 18
<212> TYPE: DNA
<213> ORGANISM: Artificial Sequence
<220> FEATURE:
<223> OTHER INFORMATION: Forward Primer PML_E3_F

<400> SEQUENCE: 96
agttcaaggt gcgcctgc                                                 18

<210> SEQ ID NO 97
<211> LENGTH: 19
<212> TYPE: DNA
```

```
<213> ORGANISM: Artificial Sequence
<220> FEATURE:
<223> OTHER INFORMATION: Forward Primer PML_E6a_F

<400> SEQUENCE: 97
cttcctgccc aacagcaac                                               19

<210> SEQ ID NO 98
<211> LENGTH: 21
<212> TYPE: DNA
<213> ORGANISM: Artificial Sequence
<220> FEATURE:
<223> OTHER INFORMATION: Forward Primer PML_E6b_F

<400> SEQUENCE: 98
tgccccagga aggtcatcaa g                                            21

<210> SEQ ID NO 99
<211> LENGTH: 21
<212> TYPE: DNA
<213> ORGANISM: Artificial Sequence
<220> FEATURE:
<223> OTHER INFORMATION: Forward Primer PPFIBP1_exon12F

<400> SEQUENCE: 99
atgcaagaca cggtggtact g                                            21

<210> SEQ ID NO 100
<211> LENGTH: 23
<212> TYPE: DNA
<213> ORGANISM: Artificial Sequence
<220> FEATURE:
<223> OTHER INFORMATION: Forward Primer PPFIBP1_exon8F

<400> SEQUENCE: 100
ggacagtgag agacttcagt atg                                          23

<210> SEQ ID NO 101
<211> LENGTH: 24
<212> TYPE: DNA
<213> ORGANISM: Artificial Sequence
<220> FEATURE:
<223> OTHER INFORMATION: Forward Primer PPFIBP1_exon9F

<400> SEQUENCE: 101
tggtttgcaa gatgaaagga gaag                                         24

<210> SEQ ID NO 102
<211> LENGTH: 24
<212> TYPE: DNA
<213> ORGANISM: Artificial Sequence
<220> FEATURE:
<223> OTHER INFORMATION: Forward Primer PRKAR1A_7F

<400> SEQUENCE: 102
catcgaccga gacagctata gaag                                         24

<210> SEQ ID NO 103
<211> LENGTH: 19
<212> TYPE: DNA
<213> ORGANISM: Artificial Sequence
<220> FEATURE:
<223> OTHER INFORMATION: Forward Primer PWWP2A_exon1F

<400> SEQUENCE: 103
ttgtcgtgtc gttccgctt                                               19
```

<210> SEQ ID NO 104
<211> LENGTH: 21
<212> TYPE: DNA
<213> ORGANISM: Artificial Sequence
<220> FEATURE:
<223> OTHER INFORMATION: Forward Primer RANBP2_exon18F

<400> SEQUENCE: 104
gggtcacaga catttcatgg g                                             21

<210> SEQ ID NO 105
<211> LENGTH: 21
<212> TYPE: DNA
<213> ORGANISM: Artificial Sequence
<220> FEATURE:
<223> OTHER INFORMATION: Forward Primer RUNX1_E5_F

<400> SEQUENCE: 105
atgacctcag gtttgtcggt c                                             21

<210> SEQ ID NO 106
<211> LENGTH: 21
<212> TYPE: DNA
<213> ORGANISM: Artificial Sequence
<220> FEATURE:
<223> OTHER INFORMATION: Forward Primer RUNX1_E6_F

<400> SEQUENCE: 106
acctaccaca gagccatcaa a                                             21

<210> SEQ ID NO 107
<211> LENGTH: 20
<212> TYPE: DNA
<213> ORGANISM: Artificial Sequence
<220> FEATURE:
<223> OTHER INFORMATION: Forward Primer RUNX1_E7_F

<400> SEQUENCE: 107
actgccttta accctcagcc                                               20

<210> SEQ ID NO 108
<211> LENGTH: 25
<212> TYPE: DNA
<213> ORGANISM: Artificial Sequence
<220> FEATURE:
<223> OTHER INFORMATION: Forward Primer SDC4_exon2F

<400> SEQUENCE: 108
atctgatgac tttgagctgt ctggc                                         25

<210> SEQ ID NO 109
<211> LENGTH: 24
<212> TYPE: DNA
<213> ORGANISM: Artificial Sequence
<220> FEATURE:
<223> OTHER INFORMATION: Forward Primer SDC4_exon4F

<400> SEQUENCE: 109
gcagcaacat ctttgagaga acgg                                          24

<210> SEQ ID NO 110
<211> LENGTH: 25
<212> TYPE: DNA
<213> ORGANISM: Artificial Sequence
<220> FEATURE:

<223> OTHER INFORMATION: Forward Primer SLC34A2_exon13delF

<400> SEQUENCE: 110
tgtcaaggct cctgagacct ttgat                                         25

<210> SEQ ID NO 111
<211> LENGTH: 25
<212> TYPE: DNA
<213> ORGANISM: Artificial Sequence
<220> FEATURE:
<223> OTHER INFORMATION: Forward Primer SLC34A2_exon4F

<400> SEQUENCE: 111
tcgtgtgctc cctggatatt cttag                                         25

<210> SEQ ID NO 112
<211> LENGTH: 20
<212> TYPE: DNA
<213> ORGANISM: Artificial Sequence
<220> FEATURE:
<223> OTHER INFORMATION: Forward Primer SND1_exon10F

<400> SEQUENCE: 112
gattcacctg tccagcatcc                                               20

<210> SEQ ID NO 113
<211> LENGTH: 19
<212> TYPE: DNA
<213> ORGANISM: Artificial Sequence
<220> FEATURE:
<223> OTHER INFORMATION: Forward Primer SND1_exon11F

<400> SEQUENCE: 113
ccttacatgt ttgaggccc                                                19

<210> SEQ ID NO 114
<211> LENGTH: 23
<212> TYPE: DNA
<213> ORGANISM: Artificial Sequence
<220> FEATURE:
<223> OTHER INFORMATION: Forward Primer SND1_exon14F

<400> SEQUENCE: 114
aggattgcat agcaagaagg aag                                           23

<210> SEQ ID NO 115
<211> LENGTH: 19
<212> TYPE: DNA
<213> ORGANISM: Artificial Sequence
<220> FEATURE:
<223> OTHER INFORMATION: Forward Primer SND1_exon16F

<400> SEQUENCE: 115
cttggtgcag gaaggagag                                                19

<210> SEQ ID NO 116
<211> LENGTH: 21
<212> TYPE: DNA
<213> ORGANISM: Artificial Sequence
<220> FEATURE:
<223> OTHER INFORMATION: Forward Primer SND1_exon9F

<400> SEQUENCE: 116
gctcccacag ctaatttgga c                                             21

```
<210> SEQ ID NO 117
<211> LENGTH: 23
<212> TYPE: DNA
<213> ORGANISM: Artificial Sequence
<220> FEATURE:
<223> OTHER INFORMATION: Forward Primer SQSTM1_exon5F

<400> SEQUENCE: 117
cgagtgtgaa tttcctgaag aac                                        23

<210> SEQ ID NO 118
<211> LENGTH: 20
<212> TYPE: DNA
<213> ORGANISM: Artificial Sequence
<220> FEATURE:
<223> OTHER INFORMATION: Forward Primer STAT5B_E15_F

<400> SEQUENCE: 118
gtgactcaga aattggcggc                                            20

<210> SEQ ID NO 119
<211> LENGTH: 25
<212> TYPE: DNA
<213> ORGANISM: Artificial Sequence
<220> FEATURE:
<223> OTHER INFORMATION: Forward Primer STRN_exon3F

<400> SEQUENCE: 119
tgaatcaggg agatatgaag cctcc                                      25

<210> SEQ ID NO 120
<211> LENGTH: 23
<212> TYPE: DNA
<213> ORGANISM: Artificial Sequence
<220> FEATURE:
<223> OTHER INFORMATION: Forward Primer TAX1BP1_exon8F

<400> SEQUENCE: 120
gcagttatgt ttggctgaaa agg                                        23

<210> SEQ ID NO 121
<211> LENGTH: 24
<212> TYPE: DNA
<213> ORGANISM: Artificial Sequence
<220> FEATURE:
<223> OTHER INFORMATION: Forward Primer TFG_exon3F

<400> SEQUENCE: 121
gtgcagtagg atactgaaac tgac                                       24

<210> SEQ ID NO 122
<211> LENGTH: 19
<212> TYPE: DNA
<213> ORGANISM: Artificial Sequence
<220> FEATURE:
<223> OTHER INFORMATION: Forward Primer TFG_exon4F

<400> SEQUENCE: 122
gagaaccagg accttccac                                             19

<210> SEQ ID NO 123
<211> LENGTH: 25
<212> TYPE: DNA
<213> ORGANISM: Artificial Sequence
<220> FEATURE:
<223> OTHER INFORMATION: Forward Primer TFG_exon5F_new
```

```
<400> SEQUENCE: 123
atgttatgtc agcgtttggc ttaac                                   25

<210> SEQ ID NO 124
<211> LENGTH: 20
<212> TYPE: DNA
<213> ORGANISM: Artificial Sequence
<220> FEATURE:
<223> OTHER INFORMATION: Forward Primer TFG_exon6F_new

<400> SEQUENCE: 124
cagcagccac catatacagg                                         20

<210> SEQ ID NO 125
<211> LENGTH: 18
<212> TYPE: DNA
<213> ORGANISM: Artificial Sequence
<220> FEATURE:
<223> OTHER INFORMATION: Forward Primer TMPRSS2_exon1F

<400> SEQUENCE: 125
taagcaggag gcggaggc                                           18

<210> SEQ ID NO 126
<211> LENGTH: 26
<212> TYPE: DNA
<213> ORGANISM: Artificial Sequence
<220> FEATURE:
<223> OTHER INFORMATION: Forward Primer TMPRSS2_exon2F

<400> SEQUENCE: 126
cagataccta tcattactcg atgctg                                  26

<210> SEQ ID NO 127
<211> LENGTH: 18
<212> TYPE: DNA
<213> ORGANISM: Artificial Sequence
<220> FEATURE:
<223> OTHER INFORMATION: Forward Primer TMPRSS2_exon3F

<400> SEQUENCE: 127
tcctgacgca ggcttcca                                           18

<210> SEQ ID NO 128
<211> LENGTH: 21
<212> TYPE: DNA
<213> ORGANISM: Artificial Sequence
<220> FEATURE:
<223> OTHER INFORMATION: Forward Primer TMPRSS2_exon5F

<400> SEQUENCE: 128
ctctaactgg tgtgatggcg t                                       21

<210> SEQ ID NO 129
<211> LENGTH: 21
<212> TYPE: DNA
<213> ORGANISM: Artificial Sequence
<220> FEATURE:
<223> OTHER INFORMATION: Forward Primer TPM3_exon2F

<400> SEQUENCE: 129
gcaaaagctg gaagaagctg a                                       21

<210> SEQ ID NO 130
<211> LENGTH: 22
```

```
<212> TYPE: DNA
<213> ORGANISM: Artificial Sequence
<220> FEATURE:
<223> OTHER INFORMATION: Forward Primer TPM3_exon8F

<400> SEQUENCE: 130
agtttgctga gagatcggta gc                                              22

<210> SEQ ID NO 131
<211> LENGTH: 24
<212> TYPE: DNA
<213> ORGANISM: Artificial Sequence
<220> FEATURE:
<223> OTHER INFORMATION: Forward Primer TPM4_exon8F

<400> SEQUENCE: 131
ggaaaagaca attgatgacc tgga                                            24

<210> SEQ ID NO 132
<211> LENGTH: 23
<212> TYPE: DNA
<213> ORGANISM: Artificial Sequence
<220> FEATURE:
<223> OTHER INFORMATION: Forward Primer TPR_exon15F

<400> SEQUENCE: 132
caaacaacag gagttgccat tcc                                             23

<210> SEQ ID NO 133
<211> LENGTH: 22
<212> TYPE: DNA
<213> ORGANISM: Artificial Sequence
<220> FEATURE:
<223> OTHER INFORMATION: Forward Primer TRIM24_exon3F

<400> SEQUENCE: 133
gttcacaaaa gaccacactg tc                                              22

<210> SEQ ID NO 134
<211> LENGTH: 22
<212> TYPE: DNA
<213> ORGANISM: Artificial Sequence
<220> FEATURE:
<223> OTHER INFORMATION: Forward Primer TRIM24_exon8F

<400> SEQUENCE: 134
tcactgtgat cctagtttct gg                                              22

<210> SEQ ID NO 135
<211> LENGTH: 19
<212> TYPE: DNA
<213> ORGANISM: Artificial Sequence
<220> FEATURE:
<223> OTHER INFORMATION: Forward Primer TRIM24_exon9F

<400> SEQUENCE: 135
tcccaacaca gatcagcct                                                  19

<210> SEQ ID NO 136
<211> LENGTH: 21
<212> TYPE: DNA
<213> ORGANISM: Artificial Sequence
<220> FEATURE:
<223> OTHER INFORMATION: Forward Primer VCL_exon16F

<400> SEQUENCE: 136
```
cgatggtgat ggatgcaaaa g    21

<210> SEQ ID NO 137
<211> LENGTH: 20
<212> TYPE: DNA
<213> ORGANISM: Artificial Sequence
<220> FEATURE:
<223> OTHER INFORMATION: Forward Primer ZBTB16_E2_F

<400> SEQUENCE: 137
tggggtcgag cttcctgata    20

<210> SEQ ID NO 138
<211> LENGTH: 20
<212> TYPE: DNA
<213> ORGANISM: Artificial Sequence
<220> FEATURE:
<223> OTHER INFORMATION: Forward Primer ZBTB16_E3_F

<400> SEQUENCE: 138
gttcctggat agtttgcggc    20

<210> SEQ ID NO 139
<211> LENGTH: 20
<212> TYPE: DNA
<213> ORGANISM: Artificial Sequence
<220> FEATURE:
<223> OTHER INFORMATION: Forward Primer ZBTB16_E4_F

<400> SEQUENCE: 139
tttcgaagga ggatgccctg    20

<210> SEQ ID NO 140
<211> LENGTH: 20
<212> TYPE: DNA
<213> ORGANISM: Artificial Sequence
<220> FEATURE:
<223> OTHER INFORMATION: Forward Primer ZC3HAV1_exon3F

<400> SEQUENCE: 140
catctgcaac agcaagcaca    20

<210> SEQ ID NO 141
<211> LENGTH: 22
<212> TYPE: DNA
<213> ORGANISM: Artificial Sequence
<220> FEATURE:
<223> OTHER INFORMATION: Forward Primer AGBL4_exon5_6F

<400> SEQUENCE: 141
ccagagtgtg caacaacgaa ag    22

<210> SEQ ID NO 142
<211> LENGTH: 21
<212> TYPE: DNA
<213> ORGANISM: Artificial Sequence
<220> FEATURE:
<223> OTHER INFORMATION: Forward Primer AR_exon2_F_rdsgn

<400> SEQUENCE: 142
tgtggaagct gcaaggtctt c    21

<210> SEQ ID NO 143
<211> LENGTH: 23
<212> TYPE: DNA
<213> ORGANISM: Artificial Sequence

```
<220> FEATURE:
<223> OTHER INFORMATION: Forward Primer AR_exon3_F

<400> SEQUENCE: 143
ccatcttgtc gtcttcggaa atg                                              23

<210> SEQ ID NO 144
<211> LENGTH: 21
<212> TYPE: DNA
<213> ORGANISM: Artificial Sequence
<220> FEATURE:
<223> OTHER INFORMATION: Forward Primer BAG4_exon1_F

<400> SEQUENCE: 144
atggctacta tccctcggga g                                                21

<210> SEQ ID NO 145
<211> LENGTH: 25
<212> TYPE: DNA
<213> ORGANISM: Artificial Sequence
<220> FEATURE:
<223> OTHER INFORMATION: Forward Primer BAG4_exon2_F

<400> SEQUENCE: 145
gctccttacc caagtacata tcctg                                            25

<210> SEQ ID NO 146
<211> LENGTH: 24
<212> TYPE: DNA
<213> ORGANISM: Artificial Sequence
<220> FEATURE:
<223> OTHER INFORMATION: Forward Primer BAIAP2L1_exon9_F

<400> SEQUENCE: 146
cgatatgttt aataacccag ccac                                             24

<210> SEQ ID NO 147
<211> LENGTH: 20
<212> TYPE: DNA
<213> ORGANISM: Artificial Sequence
<220> FEATURE:
<223> OTHER INFORMATION: Forward Primer BCAN_exon13F

<400> SEQUENCE: 147
aagagaacgg tcgttgggag                                                  20

<210> SEQ ID NO 148
<211> LENGTH: 22
<212> TYPE: DNA
<213> ORGANISM: Artificial Sequence
<220> FEATURE:
<223> OTHER INFORMATION: Forward Primer BCR_exon4_F

<400> SEQUENCE: 148
ttctatgatg ggctcttccc cc                                               22

<210> SEQ ID NO 149
<211> LENGTH: 23
<212> TYPE: DNA
<213> ORGANISM: Artificial Sequence
<220> FEATURE:
<223> OTHER INFORMATION: Forward Primer BCR_exon7_F

<400> SEQUENCE: 149
ctctgctcta caagcctgtg gac                                              23
```

<210> SEQ ID NO 150
<211> LENGTH: 21
<212> TYPE: DNA
<213> ORGANISM: Artificial Sequence
<220> FEATURE:
<223> OTHER INFORMATION: Forward Primer BCR_exon9_F

<400> SEQUENCE: 150
cgtcttcctg ttcaccgacc t                                         21

<210> SEQ ID NO 151
<211> LENGTH: 23
<212> TYPE: DNA
<213> ORGANISM: Artificial Sequence
<220> FEATURE:
<223> OTHER INFORMATION: Forward Primer BTBD1_exon4F

<400> SEQUENCE: 151
aagcactttc cttaatccgg ttc                                       23

<210> SEQ ID NO 152
<211> LENGTH: 22
<212> TYPE: DNA
<213> ORGANISM: Artificial Sequence
<220> FEATURE:
<223> OTHER INFORMATION: Forward Primer HMGN2P46_exon1_F

<400> SEQUENCE: 152
aggtgaatct tttggttggt ga                                        22

<210> SEQ ID NO 153
<211> LENGTH: 23
<212> TYPE: DNA
<213> ORGANISM: Artificial Sequence
<220> FEATURE:
<223> OTHER INFORMATION: Forward Primer HMGN2P46_exon2_F

<400> SEQUENCE: 153
catgcttgtc aaaaatcaga ggc                                       23

<210> SEQ ID NO 154
<211> LENGTH: 21
<212> TYPE: DNA
<213> ORGANISM: Artificial Sequence
<220> FEATURE:
<223> OTHER INFORMATION: Forward Primer C8orf34_exon2_F_rdsgn

<400> SEQUENCE: 154
ggaaccgtgg acaacttcaa a                                         21

<210> SEQ ID NO 155
<211> LENGTH: 24
<212> TYPE: DNA
<213> ORGANISM: Artificial Sequence
<220> FEATURE:
<223> OTHER INFORMATION: Forward Primer CAPZA2_exon4_F

<400> SEQUENCE: 155
gcatttgcac agtataactt ggac                                      24

<210> SEQ ID NO 156
<211> LENGTH: 25
<212> TYPE: DNA
<213> ORGANISM: Artificial Sequence
<220> FEATURE:
<223> OTHER INFORMATION: Forward Primer CD47_exon7F

<400> SEQUENCE: 156
ggtttgagta tcttagctct agcac                                          25

<210> SEQ ID NO 157
<211> LENGTH: 23
<212> TYPE: DNA
<213> ORGANISM: Artificial Sequence
<220> FEATURE:
<223> OTHER INFORMATION: Forward Primer CD74_exon8F

<400> SEQUENCE: 157
gaaagagtca ctggaactgg agg                                            23

<210> SEQ ID NO 158
<211> LENGTH: 23
<212> TYPE: DNA
<213> ORGANISM: Artificial Sequence
<220> FEATURE:
<223> OTHER INFORMATION: Forward Primer CNTRL_exon15_F

<400> SEQUENCE: 158
gccaaccagc tcaaggaaga gtt                                            23

<210> SEQ ID NO 159
<211> LENGTH: 19
<212> TYPE: DNA
<213> ORGANISM: Artificial Sequence
<220> FEATURE:
<223> OTHER INFORMATION: Forward Primer CNTRL_exon38_F

<400> SEQUENCE: 159
gcaggaagag gagaggtgg                                                 19

<210> SEQ ID NO 160
<211> LENGTH: 22
<212> TYPE: DNA
<213> ORGANISM: Artificial Sequence
<220> FEATURE:
<223> OTHER INFORMATION: Forward Primer CNTRL_exon39_F

<400> SEQUENCE: 160
ccagcctgaa ggaagcactt aa                                             22

<210> SEQ ID NO 161
<211> LENGTH: 23
<212> TYPE: DNA
<213> ORGANISM: Artificial Sequence
<220> FEATURE:
<223> OTHER INFORMATION: Forward Primer CNTRL_exon40_F

<400> SEQUENCE: 161
agctcaacca gatgcagtat gag                                            23

<210> SEQ ID NO 162
<211> LENGTH: 17
<212> TYPE: DNA
<213> ORGANISM: Artificial Sequence
<220> FEATURE:
<223> OTHER INFORMATION: Forward Primer CTNNB1_exon1_F

<400> SEQUENCE: 162
aggtcgagga cggtcgg                                                   17

<210> SEQ ID NO 163

```
<211> LENGTH: 22
<212> TYPE: DNA
<213> ORGANISM: Artificial Sequence
<220> FEATURE:
<223> OTHER INFORMATION: Forward Primer CUX1_exon1_F_rdsgn

<400> SEQUENCE: 163
tctcaagatg gcggccaatg tg                                          22

<210> SEQ ID NO 164
<211> LENGTH: 22
<212> TYPE: DNA
<213> ORGANISM: Artificial Sequence
<220> FEATURE:
<223> OTHER INFORMATION: Forward Primer CUX1_exon7_F

<400> SEQUENCE: 164
atgtccacca cctcaaagct gg                                          22

<210> SEQ ID NO 165
<211> LENGTH: 25
<212> TYPE: DNA
<213> ORGANISM: Artificial Sequence
<220> FEATURE:
<223> OTHER INFORMATION: Forward Primer CUX1_exon8_9_F

<400> SEQUENCE: 165
caaaggccga cgagattgaa atgat                                       25

<210> SEQ ID NO 166
<211> LENGTH: 27
<212> TYPE: DNA
<213> ORGANISM: Artificial Sequence
<220> FEATURE:
<223> OTHER INFORMATION: Forward Primer CUX1_exon8_F

<400> SEQUENCE: 166
aactcgaaca gaattatttg acctgaa                                     27

<210> SEQ ID NO 167
<211> LENGTH: 28
<212> TYPE: DNA
<213> ORGANISM: Artificial Sequence
<220> FEATURE:
<223> OTHER INFORMATION: Forward Primer DDX5_exon2_F

<400> SEQUENCE: 167
gagaagaatt tttatcaaga gcaccctg                                    28

<210> SEQ ID NO 168
<211> LENGTH: 21
<212> TYPE: DNA
<213> ORGANISM: Artificial Sequence
<220> FEATURE:
<223> OTHER INFORMATION: Forward Primer EGFR_exon15F

<400> SEQUENCE: 168
tgccatccaa actgcaccta c                                           21

<210> SEQ ID NO 169
<211> LENGTH: 20
<212> TYPE: DNA
<213> ORGANISM: Artificial Sequence
<220> FEATURE:
<223> OTHER INFORMATION: Forward Primer EGFR_exon24F_rdsgn

<400> SEQUENCE: 169
```
tctccaaaat ggcccgagac                                              20

<210> SEQ ID NO 170
<211> LENGTH: 19
<212> TYPE: DNA
<213> ORGANISM: Artificial Sequence
<220> FEATURE:
<223> OTHER INFORMATION: Forward Primer ERBB2_exon14_15_F

<400> SEQUENCE: 170
tttggaccgg aggctgacc                                               19

<210> SEQ ID NO 171
<211> LENGTH: 21
<212> TYPE: DNA
<213> ORGANISM: Artificial Sequence
<220> FEATURE:
<223> OTHER INFORMATION: Forward Primer ERBB2_exon15F

<400> SEQUENCE: 171
gaagtttcca gatgaggagg g                                            21

<210> SEQ ID NO 172
<211> LENGTH: 25
<212> TYPE: DNA
<213> ORGANISM: Artificial Sequence
<220> FEATURE:
<223> OTHER INFORMATION: Forward Primer ERBB2_exon7-8_F

<400> SEQUENCE: 172
cctgtcccta caactacctt tctac                                        25

<210> SEQ ID NO 173
<211> LENGTH: 18
<212> TYPE: DNA
<213> ORGANISM: Artificial Sequence
<220> FEATURE:
<223> OTHER INFORMATION: Forward Primer ESR1_exon3_F

<400> SEQUENCE: 173
aacgagccca gcggctac                                                18

<210> SEQ ID NO 174
<211> LENGTH: 22
<212> TYPE: DNA
<213> ORGANISM: Artificial Sequence
<220> FEATURE:
<223> OTHER INFORMATION: Forward Primer ESR1_exon4_F

<400> SEQUENCE: 174
ccattatgga gtctggtcct gt                                           22

<210> SEQ ID NO 175
<211> LENGTH: 23
<212> TYPE: DNA
<213> ORGANISM: Artificial Sequence
<220> FEATURE:
<223> OTHER INFORMATION: Forward Primer ESR1_exon5_F

<400> SEQUENCE: 175
ggctccgtaa atgctacgaa gtg                                          23

<210> SEQ ID NO 176
<211> LENGTH: 21
<212> TYPE: DNA

```
<213> ORGANISM: Artificial Sequence
<220> FEATURE:
<223> OTHER INFORMATION: Forward Primer ESR1_exon6_F_rdsgn

<400> SEQUENCE: 176
cagacaggga gctggttcac a                                              21

<210> SEQ ID NO 177
<211> LENGTH: 21
<212> TYPE: DNA
<213> ORGANISM: Artificial Sequence
<220> FEATURE:
<223> OTHER INFORMATION: Forward Primer ESR1_exon7_F

<400> SEQUENCE: 177
acccagggaa gctactgttt g                                              21

<210> SEQ ID NO 178
<211> LENGTH: 24
<212> TYPE: DNA
<213> ORGANISM: Artificial Sequence
<220> FEATURE:
<223> OTHER INFORMATION: Forward Primer ETV6_exon4F

<400> SEQUENCE: 178
tggaaactct atacacacac agcc                                           24

<210> SEQ ID NO 179
<211> LENGTH: 22
<212> TYPE: DNA
<213> ORGANISM: Artificial Sequence
<220> FEATURE:
<223> OTHER INFORMATION: Forward Primer ETV6_exon5F

<400> SEQUENCE: 179
cacatcatgg tctctgtctc cc                                             22

<210> SEQ ID NO 180
<211> LENGTH: 22
<212> TYPE: DNA
<213> ORGANISM: Artificial Sequence
<220> FEATURE:
<223> OTHER INFORMATION: Forward Primer ETV6_exon7F

<400> SEQUENCE: 180
acattatcag gaaggagcca gg                                             22

<210> SEQ ID NO 181
<211> LENGTH: 19
<212> TYPE: DNA
<213> ORGANISM: Artificial Sequence
<220> FEATURE:
<223> OTHER INFORMATION: Forward Primer FGFR1_exon1_F

<400> SEQUENCE: 181
acaagccacg gcggactct                                                 19

<210> SEQ ID NO 182
<211> LENGTH: 21
<212> TYPE: DNA
<213> ORGANISM: Artificial Sequence
<220> FEATURE:
<223> OTHER INFORMATION: Forward Primer FGFR1_exon17_F

<400> SEQUENCE: 182
ttcaagcagc tggtggaaga c                                              21
```

```
<210> SEQ ID NO 183
<211> LENGTH: 23
<212> TYPE: DNA
<213> ORGANISM: Artificial Sequence
<220> FEATURE:
<223> OTHER INFORMATION: Forward Primer FGFR1_exon18_F

<400> SEQUENCE: 183
cacaaatttc cccaaagact gcg                                          23

<210> SEQ ID NO 184
<211> LENGTH: 20
<212> TYPE: DNA
<213> ORGANISM: Artificial Sequence
<220> FEATURE:
<223> OTHER INFORMATION: Forward Primer FGFR1_exon2_F

<400> SEQUENCE: 184
gtcacagcca cactctgcac                                              20

<210> SEQ ID NO 185
<211> LENGTH: 22
<212> TYPE: DNA
<213> ORGANISM: Artificial Sequence
<220> FEATURE:
<223> OTHER INFORMATION: Forward Primer FGFR1OP_exon5_F

<400> SEQUENCE: 185
ttagaagtga tcaggcgctg tc                                           22

<210> SEQ ID NO 186
<211> LENGTH: 20
<212> TYPE: DNA
<213> ORGANISM: Artificial Sequence
<220> FEATURE:
<223> OTHER INFORMATION: Forward Primer FGFR1OP_exon6_F

<400> SEQUENCE: 186
tccaccaaag tcaccagagg                                              20

<210> SEQ ID NO 187
<211> LENGTH: 24
<212> TYPE: DNA
<213> ORGANISM: Artificial Sequence
<220> FEATURE:
<223> OTHER INFORMATION: Forward Primer FGFR1OP_exon7_F

<400> SEQUENCE: 187
gacaaggtaa gaagaagaca agcg                                         24

<210> SEQ ID NO 188
<211> LENGTH: 24
<212> TYPE: DNA
<213> ORGANISM: Artificial Sequence
<220> FEATURE:
<223> OTHER INFORMATION: Forward Primer FGFR2_exon17F

<400> SEQUENCE: 188
agaagacttg gatcgaattc tcac                                         24

<210> SEQ ID NO 189
<211> LENGTH: 24
<212> TYPE: DNA
<213> ORGANISM: Artificial Sequence
<220> FEATURE:
```

<223> OTHER INFORMATION: Forward Primer FGFR2_exon18F

<400> SEQUENCE: 189
cgaaccatgc cttcctcagt atcc                                24

<210> SEQ ID NO 190
<211> LENGTH: 18
<212> TYPE: DNA
<213> ORGANISM: Artificial Sequence
<220> FEATURE:
<223> OTHER INFORMATION: Forward Primer FGFR3_exon17F

<400> SEQUENCE: 190
tccttaccgt gacgtcca                                       18

<210> SEQ ID NO 191
<211> LENGTH: 21
<212> TYPE: DNA
<213> ORGANISM: Artificial Sequence
<220> FEATURE:
<223> OTHER INFORMATION: Forward Primer FIP1L1_exon10_F

<400> SEQUENCE: 191
gttgggaagt ggcaggatcg a                                   21

<210> SEQ ID NO 192
<211> LENGTH: 28
<212> TYPE: DNA
<213> ORGANISM: Artificial Sequence
<220> FEATURE:
<223> OTHER INFORMATION: Forward Primer FIP1L1_exon11_F

<400> SEQUENCE: 192
ctataactat cagccgagta gaaggcag                            28

<210> SEQ ID NO 193
<211> LENGTH: 21
<212> TYPE: DNA
<213> ORGANISM: Artificial Sequence
<220> FEATURE:
<223> OTHER INFORMATION: Forward Primer FIP1L1_exon12_F

<400> SEQUENCE: 193
tcttccacct cctccgactg t                                   21

<210> SEQ ID NO 194
<211> LENGTH: 20
<212> TYPE: DNA
<213> ORGANISM: Artificial Sequence
<220> FEATURE:
<223> OTHER INFORMATION: Forward Primer FIP1L1_exon14_F

<400> SEQUENCE: 194
ttttcctcct ccaccaggcg                                     20

<210> SEQ ID NO 195
<211> LENGTH: 26
<212> TYPE: DNA
<213> ORGANISM: Artificial Sequence
<220> FEATURE:
<223> OTHER INFORMATION: Forward Primer FIP1L1_exon15_F

<400> SEQUENCE: 195
ggacattcct ctggttatga tagtcg                              26

<210> SEQ ID NO 196
<211> LENGTH: 22
<212> TYPE: DNA
<213> ORGANISM: Artificial Sequence
<220> FEATURE:
<223> OTHER INFORMATION: Forward Primer FIP1L1_exon16_F

<400> SEQUENCE: 196
gacagagaaa gagaacgcac ca         22

<210> SEQ ID NO 197
<211> LENGTH: 20
<212> TYPE: DNA
<213> ORGANISM: Artificial Sequence
<220> FEATURE:
<223> OTHER INFORMATION: Forward Primer FIP1L1_exon17_F

<400> SEQUENCE: 197
acgacacagg gagaaagagg         20

<210> SEQ ID NO 198
<211> LENGTH: 20
<212> TYPE: DNA
<213> ORGANISM: Artificial Sequence
<220> FEATURE:
<223> OTHER INFORMATION: Forward Primer FIP1L1_exon18_F

<400> SEQUENCE: 198
agaaggaaaa gaagcgggca         20

<210> SEQ ID NO 199
<211> LENGTH: 21
<212> TYPE: DNA
<213> ORGANISM: Artificial Sequence
<220> FEATURE:
<223> OTHER INFORMATION: Forward Primer FIP1L1_exon9_F

<400> SEQUENCE: 199
tgcccttcca tctacaaaag c         21

<210> SEQ ID NO 200
<211> LENGTH: 24
<212> TYPE: DNA
<213> ORGANISM: Artificial Sequence
<220> FEATURE:
<223> OTHER INFORMATION: Forward Primer HERV-K_F

<400> SEQUENCE: 200
gattcccgag tacgtctaca gtga         24

<210> SEQ ID NO 201
<211> LENGTH: 21
<212> TYPE: DNA
<213> ORGANISM: Artificial Sequence
<220> FEATURE:
<223> OTHER INFORMATION: Forward Primer HERVK17_F

<400> SEQUENCE: 201
tttccacact ctcattccgg a         21

<210> SEQ ID NO 202
<211> LENGTH: 19
<212> TYPE: DNA
<213> ORGANISM: Artificial Sequence
<220> FEATURE:
<223> OTHER INFORMATION: Forward Primer HNRNPA2B1_exon1_F

```
<400> SEQUENCE: 202
tgcgggaaat cgggctgaa                                              19

<210> SEQ ID NO 203
<211> LENGTH: 18
<212> TYPE: DNA
<213> ORGANISM: Artificial Sequence
<220> FEATURE:
<223> OTHER INFORMATION: Forward Primer LMNA_exon2F

<400> SEQUENCE: 203
gagctgcatg atctgcgg                                               18

<210> SEQ ID NO 204
<211> LENGTH: 19
<212> TYPE: DNA
<213> ORGANISM: Artificial Sequence
<220> FEATURE:
<223> OTHER INFORMATION: Forward Primer MDK_exon4F

<400> SEQUENCE: 204
cccaagacca aagcaaagg                                              19

<210> SEQ ID NO 205
<211> LENGTH: 24
<212> TYPE: DNA
<213> ORGANISM: Artificial Sequence
<220> FEATURE:
<223> OTHER INFORMATION: Forward Primer MET_exon13F

<400> SEQUENCE: 205
acagcactgt tattactact tggg                                        24

<210> SEQ ID NO 206
<211> LENGTH: 20
<212> TYPE: DNA
<213> ORGANISM: Artificial Sequence
<220> FEATURE:
<223> OTHER INFORMATION: Forward Primer MPRIP_exon21F

<400> SEQUENCE: 206
agaagtcccc tgacagtgcc                                             20

<210> SEQ ID NO 207
<211> LENGTH: 18
<212> TYPE: DNA
<213> ORGANISM: Artificial Sequence
<220> FEATURE:
<223> OTHER INFORMATION: Forward Primer NACC2_exon4F_rdsgn

<400> SEQUENCE: 207
gactggcatc cgctcgtc                                               18

<210> SEQ ID NO 208
<211> LENGTH: 23
<212> TYPE: DNA
<213> ORGANISM: Artificial Sequence
<220> FEATURE:
<223> OTHER INFORMATION: Forward Primer NFASC_exon21F

<400> SEQUENCE: 208
tccaggctga aaatgacttc ggg                                         23

<210> SEQ ID NO 209
<211> LENGTH: 18
```

```
<212> TYPE: DNA
<213> ORGANISM: Artificial Sequence
<220> FEATURE:
<223> OTHER INFORMATION: Forward Primer PAX8_exon10F

<400> SEQUENCE: 209
acatccccac cagcggac                                                 18

<210> SEQ ID NO 210
<211> LENGTH: 18
<212> TYPE: DNA
<213> ORGANISM: Artificial Sequence
<220> FEATURE:
<223> OTHER INFORMATION: Forward Primer PAX8_exon7F

<400> SEQUENCE: 210
gagtgcccat ttgagcgg                                                 18

<210> SEQ ID NO 211
<211> LENGTH: 18
<212> TYPE: DNA
<213> ORGANISM: Artificial Sequence
<220> FEATURE:
<223> OTHER INFORMATION: Forward Primer PAX8_exon8F

<400> SEQUENCE: 211
cttccaacac gccactgg                                                 18

<210> SEQ ID NO 212
<211> LENGTH: 19
<212> TYPE: DNA
<213> ORGANISM: Artificial Sequence
<220> FEATURE:
<223> OTHER INFORMATION: Forward Primer PAX8_exon9F

<400> SEQUENCE: 212
cgcccttcaa tgcctttcc                                                19

<210> SEQ ID NO 213
<211> LENGTH: 27
<212> TYPE: DNA
<213> ORGANISM: Artificial Sequence
<220> FEATURE:
<223> OTHER INFORMATION: Forward Primer PCM1_E23_F

<400> SEQUENCE: 213
ctcccaagtc aaaaagtaag aagagga                                       27

<210> SEQ ID NO 214
<211> LENGTH: 29
<212> TYPE: DNA
<213> ORGANISM: Artificial Sequence
<220> FEATURE:
<223> OTHER INFORMATION: Forward Primer PCM1_E24_F

<400> SEQUENCE: 214
cagcagaaag aatcatgagc aactggaaa                                     29

<210> SEQ ID NO 215
<211> LENGTH: 22
<212> TYPE: DNA
<213> ORGANISM: Artificial Sequence
<220> FEATURE:
<223> OTHER INFORMATION: Forward Primer PCM1_E25_F

<400> SEQUENCE: 215
```
ccatgagctg cagctactaa ac                     22

<210> SEQ ID NO 216
<211> LENGTH: 27
<212> TYPE: DNA
<213> ORGANISM: Artificial Sequence
<220> FEATURE:
<223> OTHER INFORMATION: Forward Primer PCM1_E26_F

<400> SEQUENCE: 216
atagcatcaa actcagaact tactcct                27

<210> SEQ ID NO 217
<211> LENGTH: 22
<212> TYPE: DNA
<213> ORGANISM: Artificial Sequence
<220> FEATURE:
<223> OTHER INFORMATION: Forward Primer PCM1_E36_F

<400> SEQUENCE: 217
actcctgaaa gctctctggc tg                     22

<210> SEQ ID NO 218
<211> LENGTH: 30
<212> TYPE: DNA
<213> ORGANISM: Artificial Sequence
<220> FEATURE:
<223> OTHER INFORMATION: Forward Primer PCM1_E37_F

<400> SEQUENCE: 218
gattttgtaa aagttgaaga tttaccactg              30

<210> SEQ ID NO 219
<211> LENGTH: 22
<212> TYPE: DNA
<213> ORGANISM: Artificial Sequence
<220> FEATURE:
<223> OTHER INFORMATION: Forward Primer QKI_exon6F

<400> SEQUENCE: 219
acacattggc accagctaca tc                     22

<210> SEQ ID NO 220
<211> LENGTH: 22
<212> TYPE: DNA
<213> ORGANISM: Artificial Sequence
<220> FEATURE:
<223> OTHER INFORMATION: Forward Primer RBPMS_exon5F

<400> SEQUENCE: 220
caaactcgta gggactccaa ac                     22

<210> SEQ ID NO 221
<211> LENGTH: 18
<212> TYPE: DNA
<213> ORGANISM: Artificial Sequence
<220> FEATURE:
<223> OTHER INFORMATION: Forward Primer SLC45A3_exon1_F

<400> SEQUENCE: 221
aaccagcctg cacgcgct                          18

<210> SEQ ID NO 222
<211> LENGTH: 21
<212> TYPE: DNA
<213> ORGANISM: Artificial Sequence

```
<220> FEATURE:
<223> OTHER INFORMATION: Forward Primer SEC61G_5'UTRF_rdsgn

<400> SEQUENCE: 222
ctccagtgct acgtgtccct g                                           21

<210> SEQ ID NO 223
<211> LENGTH: 19
<212> TYPE: DNA
<213> ORGANISM: Artificial Sequence
<220> FEATURE:
<223> OTHER INFORMATION: Forward Primer TCF3_exon16_F

<400> SEQUENCE: 223
accctccctg acctgtctc                                              19

<210> SEQ ID NO 224
<211> LENGTH: 27
<212> TYPE: DNA
<213> ORGANISM: Artificial Sequence
<220> FEATURE:
<223> OTHER INFORMATION: Forward Primer TPM4_exon6F

<400> SEQUENCE: 224
ctgaaaagga ggacaaatat gaagaag                                     27

<210> SEQ ID NO 225
<211> LENGTH: 25
<212> TYPE: DNA
<213> ORGANISM: Artificial Sequence
<220> FEATURE:
<223> OTHER INFORMATION: Forward Primer TPR_exon21F

<400> SEQUENCE: 225
ttgaaacagc acctcagtaa tatgg                                       25

<210> SEQ ID NO 226
<211> LENGTH: 26
<212> TYPE: DNA
<213> ORGANISM: Artificial Sequence
<220> FEATURE:
<223> OTHER INFORMATION: Forward Primer TPR_exon6F

<400> SEQUENCE: 226
gggaatgaga ttctagagct taaatg                                      26

<210> SEQ ID NO 227
<211> LENGTH: 18
<212> TYPE: DNA
<213> ORGANISM: Artificial Sequence
<220> FEATURE:
<223> OTHER INFORMATION: Forward Primer UBTF_exon2_F

<400> SEQUENCE: 227
aacggagaag ccgactgc                                               18

<210> SEQ ID NO 228
<211> LENGTH: 26
<212> TYPE: DNA
<213> ORGANISM: Artificial Sequence
<220> FEATURE:
<223> OTHER INFORMATION: Forward Primer ZMYM2_exon16_F

<400> SEQUENCE: 228
tgtatatccc agttcctatg cacatg                                      26
```

<210> SEQ ID NO 229
<211> LENGTH: 29
<212> TYPE: DNA
<213> ORGANISM: Artificial Sequence
<220> FEATURE:
<223> OTHER INFORMATION: Forward Primer ZMYM2_exon17_F

<400> SEQUENCE: 229
agttgcttac aatgacggat atgatgagt                                    29

<210> SEQ ID NO 230
<211> LENGTH: 20
<212> TYPE: DNA
<213> ORGANISM: Artificial Sequence
<220> FEATURE:
<223> OTHER INFORMATION: Forward Primer AFAP1_exon13_F

<400> SEQUENCE: 230
agcagtcagc caaagaaagc                                              20

<210> SEQ ID NO 231
<211> LENGTH: 21
<212> TYPE: DNA
<213> ORGANISM: Artificial Sequence
<220> FEATURE:
<223> OTHER INFORMATION: Forward Primer AFAP1_exon14_F

<400> SEQUENCE: 231
gctccgcaag gaaagaaaag a                                            21

<210> SEQ ID NO 232
<211> LENGTH: 27
<212> TYPE: DNA
<213> ORGANISM: Artificial Sequence
<220> FEATURE:
<223> OTHER INFORMATION: Forward Primer AKAP9_exon18F

<400> SEQUENCE: 232
cagctacaag aagagattaa gagactt                                      27

<210> SEQ ID NO 233
<211> LENGTH: 27
<212> TYPE: DNA
<213> ORGANISM: Artificial Sequence
<220> FEATURE:
<223> OTHER INFORMATION: Forward Primer AKAP9_exon7F

<400> SEQUENCE: 233
gacttcacaa tgcaaattag tttcttg                                      27

<210> SEQ ID NO 234
<211> LENGTH: 29
<212> TYPE: DNA
<213> ORGANISM: Artificial Sequence
<220> FEATURE:
<223> OTHER INFORMATION: Forward Primer AKAP9_exon9F

<400> SEQUENCE: 234
gaacttcaga aaatacacca gttagaact                                    29

<210> SEQ ID NO 235
<211> LENGTH: 19
<212> TYPE: DNA
<213> ORGANISM: Artificial Sequence
<220> FEATURE:
<223> OTHER INFORMATION: Forward Primer AXL_exon20_F

```
<400> SEQUENCE: 235
tgctgatagg ggctcccca                                              19

<210> SEQ ID NO 236
<211> LENGTH: 23
<212> TYPE: DNA
<213> ORGANISM: Artificial Sequence
<220> FEATURE:
<223> OTHER INFORMATION: Forward Primer BCR_exon10_F

<400> SEQUENCE: 236
tggacgcttt gaagatcaag atc                                         23

<210> SEQ ID NO 237
<211> LENGTH: 21
<212> TYPE: DNA
<213> ORGANISM: Artificial Sequence
<220> FEATURE:
<223> OTHER INFORMATION: Forward Primer BCR_exon11_F

<400> SEQUENCE: 237
ctgcttatgt ctcccagcat g                                           21

<210> SEQ ID NO 238
<211> LENGTH: 20
<212> TYPE: DNA
<213> ORGANISM: Artificial Sequence
<220> FEATURE:
<223> OTHER INFORMATION: Forward Primer BCR_exon12_F

<400> SEQUENCE: 238
cgtgcagagt ggagggagaa                                             20

<210> SEQ ID NO 239
<211> LENGTH: 20
<212> TYPE: DNA
<213> ORGANISM: Artificial Sequence
<220> FEATURE:
<223> OTHER INFORMATION: Forward Primer BCR_exon15_F

<400> SEQUENCE: 239
gcaaagacgc gcgtctacag                                             20

<210> SEQ ID NO 240
<211> LENGTH: 18
<212> TYPE: DNA
<213> ORGANISM: Artificial Sequence
<220> FEATURE:
<223> OTHER INFORMATION: Forward Primer BCR_exon16_F

<400> SEQUENCE: 240
aaggaggacg gcgagagc                                               18

<210> SEQ ID NO 241
<211> LENGTH: 19
<212> TYPE: DNA
<213> ORGANISM: Artificial Sequence
<220> FEATURE:
<223> OTHER INFORMATION: Forward Primer BCR_exon17_F

<400> SEQUENCE: 241
aggacagaga ctggcagcg                                              19

<210> SEQ ID NO 242
```

```
<211> LENGTH: 23
<212> TYPE: DNA
<213> ORGANISM: Artificial Sequence
<220> FEATURE:
<223> OTHER INFORMATION: Forward Primer BCR_exon20_F

<400> SEQUENCE: 242
ttcactgacg agttctaccc caa                                          23

<210> SEQ ID NO 243
<211> LENGTH: 22
<212> TYPE: DNA
<213> ORGANISM: Artificial Sequence
<220> FEATURE:
<223> OTHER INFORMATION: Forward Primer BCR_exon3_F

<400> SEQUENCE: 243
ctagcgagga gacttacctg ag                                           22

<210> SEQ ID NO 244
<211> LENGTH: 21
<212> TYPE: DNA
<213> ORGANISM: Artificial Sequence
<220> FEATURE:
<223> OTHER INFORMATION: Forward Primer BCR_exon5_F

<400> SEQUENCE: 244
aaatggctga gaagtgctgt c                                            21

<210> SEQ ID NO 245
<211> LENGTH: 22
<212> TYPE: DNA
<213> ORGANISM: Artificial Sequence
<220> FEATURE:
<223> OTHER INFORMATION: Forward Primer HMGN2P46_exon2_F_rdsgn

<400> SEQUENCE: 245
ggaaccacac ttcgagaatc ac                                           22

<210> SEQ ID NO 246
<211> LENGTH: 24
<212> TYPE: DNA
<213> ORGANISM: Artificial Sequence
<220> FEATURE:
<223> OTHER INFORMATION: Forward Primer CCDC6_exon3F

<400> SEQUENCE: 246
ggagaatgac accatttcta agca                                         24

<210> SEQ ID NO 247
<211> LENGTH: 25
<212> TYPE: DNA
<213> ORGANISM: Artificial Sequence
<220> FEATURE:
<223> OTHER INFORMATION: Forward Primer CCDC6_exon4F

<400> SEQUENCE: 247
agcactagtt aatcgcctct ggaaa                                        25

<210> SEQ ID NO 248
<211> LENGTH: 20
<212> TYPE: DNA
<213> ORGANISM: Artificial Sequence
<220> FEATURE:
<223> OTHER INFORMATION: Forward Primer CCDC6_exon5F

<400> SEQUENCE: 248
```
tgaagtggaa cggctgaaga                                          20

<210> SEQ ID NO 249
<211> LENGTH: 20
<212> TYPE: DNA
<213> ORGANISM: Artificial Sequence
<220> FEATURE:
<223> OTHER INFORMATION: Forward Primer CCDC6_exon6F

<400> SEQUENCE: 249
tctccgagag tgagtccagc                                          20

<210> SEQ ID NO 250
<211> LENGTH: 20
<212> TYPE: DNA
<213> ORGANISM: Artificial Sequence
<220> FEATURE:
<223> OTHER INFORMATION: Forward Primer CCDC6_exon7F

<400> SEQUENCE: 250
cagcccgatc ccttacacac                                          20

<210> SEQ ID NO 251
<211> LENGTH: 22
<212> TYPE: DNA
<213> ORGANISM: Artificial Sequence
<220> FEATURE:
<223> OTHER INFORMATION: Forward Primer DCBLD1_exon2_F

<400> SEQUENCE: 251
ccagacctgt gcttctgact at                                       22

<210> SEQ ID NO 252
<211> LENGTH: 21
<212> TYPE: DNA
<213> ORGANISM: Artificial Sequence
<220> FEATURE:
<223> OTHER INFORMATION: Forward Primer EGFR_exon1_F

<400> SEQUENCE: 252
agtcgggctc tggaggaaaa g                                        21

<210> SEQ ID NO 253
<211> LENGTH: 20
<212> TYPE: DNA
<213> ORGANISM: Artificial Sequence
<220> FEATURE:
<223> OTHER INFORMATION: Forward Primer EML4_exon10F

<400> SEQUENCE: 253
ggacttggca cttttgagcg                                          20

<210> SEQ ID NO 254
<211> LENGTH: 21
<212> TYPE: DNA
<213> ORGANISM: Artificial Sequence
<220> FEATURE:
<223> OTHER INFORMATION: Forward Primer EML4_exon11F

<400> SEQUENCE: 254
gcttactgta tgggactggc a                                        21

<210> SEQ ID NO 255
<211> LENGTH: 20
<212> TYPE: DNA

<213> ORGANISM: Artificial Sequence
<220> FEATURE:
<223> OTHER INFORMATION: Forward Primer EML4_exon12F

<400> SEQUENCE: 255
tttcttctgg acctggagcg                                           20

<210> SEQ ID NO 256
<211> LENGTH: 30
<212> TYPE: DNA
<213> ORGANISM: Artificial Sequence
<220> FEATURE:
<223> OTHER INFORMATION: Forward Primer EML4_exon19F

<400> SEQUENCE: 256
ctatgtagtc tctgaaaatg aagaaaata                                 30

<210> SEQ ID NO 257
<211> LENGTH: 20
<212> TYPE: DNA
<213> ORGANISM: Artificial Sequence
<220> FEATURE:
<223> OTHER INFORMATION: Forward Primer EML4_exon1F

<400> SEQUENCE: 257
cgctttcccc gcaagatgga                                           20

<210> SEQ ID NO 258
<211> LENGTH: 21
<212> TYPE: DNA
<213> ORGANISM: Artificial Sequence
<220> FEATURE:
<223> OTHER INFORMATION: Forward Primer EML4_exon21F

<400> SEQUENCE: 258
aaggacattg attggacgac a                                         21

<210> SEQ ID NO 259
<211> LENGTH: 30
<212> TYPE: DNA
<213> ORGANISM: Artificial Sequence
<220> FEATURE:
<223> OTHER INFORMATION: Forward Primer EML4_exon22F

<400> SEQUENCE: 259
cgatgacttt tgtaaagtcc atctgtttca                                30

<210> SEQ ID NO 260
<211> LENGTH: 20
<212> TYPE: DNA
<213> ORGANISM: Artificial Sequence
<220> FEATURE:
<223> OTHER INFORMATION: Forward Primer EML4_exon23F

<400> SEQUENCE: 260
aaagccaccc ttctggagga                                           20

<210> SEQ ID NO 261
<211> LENGTH: 24
<212> TYPE: DNA
<213> ORGANISM: Artificial Sequence
<220> FEATURE:
<223> OTHER INFORMATION: Forward Primer EML4_exon3F

<400> SEQUENCE: 261
gtgctgtctc aattgcagga aaag                                      24

<210> SEQ ID NO 262
<211> LENGTH: 22
<212> TYPE: DNA
<213> ORGANISM: Artificial Sequence
<220> FEATURE:
<223> OTHER INFORMATION: Forward Primer EML4_exon4F

<400> SEQUENCE: 262
cacagacaaa ctccagaaag ca                                              22

<210> SEQ ID NO 263
<211> LENGTH: 20
<212> TYPE: DNA
<213> ORGANISM: Artificial Sequence
<220> FEATURE:
<223> OTHER INFORMATION: Forward Primer EML4_exon7F

<400> SEQUENCE: 263
atcagaacgg aactgcctcc                                                 20

<210> SEQ ID NO 264
<211> LENGTH: 21
<212> TYPE: DNA
<213> ORGANISM: Artificial Sequence
<220> FEATURE:
<223> OTHER INFORMATION: Forward Primer EML4_exon8F

<400> SEQUENCE: 264
gaactcagcg acactacctg g                                               21

<210> SEQ ID NO 265
<211> LENGTH: 20
<212> TYPE: DNA
<213> ORGANISM: Artificial Sequence
<220> FEATURE:
<223> OTHER INFORMATION: Forward Primer EML4_exon9F

<400> SEQUENCE: 265
gcaactggac agatagctgg                                                 20

<210> SEQ ID NO 266
<211> LENGTH: 20
<212> TYPE: DNA
<213> ORGANISM: Artificial Sequence
<220> FEATURE:
<223> OTHER INFORMATION: Forward Primer ESR1_exon8_F

<400> SEQUENCE: 266
ggagaggagt ttgtgtgcct                                                 20

<210> SEQ ID NO 267
<211> LENGTH: 18
<212> TYPE: DNA
<213> ORGANISM: Artificial Sequence
<220> FEATURE:
<223> OTHER INFORMATION: Forward Primer ESR1_exon9_F

<400> SEQUENCE: 267
gcccagctcc tcctcatc                                                   18

<210> SEQ ID NO 268
<211> LENGTH: 19
<212> TYPE: DNA
<213> ORGANISM: Artificial Sequence
<220> FEATURE:

<223> OTHER INFORMATION: Forward Primer ETV6_exon6F

<400> SEQUENCE: 268
gatcccaacg gactggctc                    19

<210> SEQ ID NO 269
<211> LENGTH: 19
<212> TYPE: DNA
<213> ORGANISM: Artificial Sequence
<220> FEATURE:
<223> OTHER INFORMATION: Forward Primer EWSR1_exon8_F

<400> SEQUENCE: 269
tggaggcatg agcagaggt                    19

<210> SEQ ID NO 270
<211> LENGTH: 22
<212> TYPE: DNA
<213> ORGANISM: Artificial Sequence
<220> FEATURE:
<223> OTHER INFORMATION: Forward Primer EZR_exon11F

<400> SEQUENCE: 270
ctaaggagga gctggagaga ca                22

<210> SEQ ID NO 271
<211> LENGTH: 19
<212> TYPE: DNA
<213> ORGANISM: Artificial Sequence
<220> FEATURE:
<223> OTHER INFORMATION: Forward Primer EZR_exon12F

<400> SEQUENCE: 271
gaggcgcaag gaggatgaa                    19

<210> SEQ ID NO 272
<211> LENGTH: 24
<212> TYPE: DNA
<213> ORGANISM: Artificial Sequence
<220> FEATURE:
<223> OTHER INFORMATION: Forward Primer FIP1L1_exon8_F

<400> SEQUENCE: 272
atggaagtta caccaggtgc agag              24

<210> SEQ ID NO 273
<211> LENGTH: 19
<212> TYPE: DNA
<213> ORGANISM: Artificial Sequence
<220> FEATURE:
<223> OTHER INFORMATION: Forward Primer FRMD4A_exon2_F

<400> SEQUENCE: 273
atgggaatcg gagaccatg                    19

<210> SEQ ID NO 274
<211> LENGTH: 22
<212> TYPE: DNA
<213> ORGANISM: Artificial Sequence
<220> FEATURE:
<223> OTHER INFORMATION: Forward Primer GOPC_exon5F

<400> SEQUENCE: 274
tgcagaggac gtaatgactt ga                22

```
<210> SEQ ID NO 275
<211> LENGTH: 28
<212> TYPE: DNA
<213> ORGANISM: Artificial Sequence
<220> FEATURE:
<223> OTHER INFORMATION: Forward Primer GOPC_exon6F

<400> SEQUENCE: 275
ggtccaatta gaaaagttct cctcctta                                       28

<210> SEQ ID NO 276
<211> LENGTH: 21
<212> TYPE: DNA
<213> ORGANISM: Artificial Sequence
<220> FEATURE:
<223> OTHER INFORMATION: Forward Primer GOPC_exon7F

<400> SEQUENCE: 276
acctaaggga cacaaagcat a                                              21

<210> SEQ ID NO 277
<211> LENGTH: 23
<212> TYPE: DNA
<213> ORGANISM: Artificial Sequence
<220> FEATURE:
<223> OTHER INFORMATION: Forward Primer GOPC_exon8F_rdsgn

<400> SEQUENCE: 277
aggtggtaac cctggtgcta gtt                                            23

<210> SEQ ID NO 278
<211> LENGTH: 20
<212> TYPE: DNA
<213> ORGANISM: Artificial Sequence
<220> FEATURE:
<223> OTHER INFORMATION: Forward Primer HIP1_exon29F

<400> SEQUENCE: 278
aagcatgacg ctgacacaga                                                20

<210> SEQ ID NO 279
<211> LENGTH: 21
<212> TYPE: DNA
<213> ORGANISM: Artificial Sequence
<220> FEATURE:
<223> OTHER INFORMATION: Forward Primer IRF2BP2_exon1_F

<400> SEQUENCE: 279
caggcaggtt gttgggtttc g                                              21

<210> SEQ ID NO 280
<211> LENGTH: 25
<212> TYPE: DNA
<213> ORGANISM: Artificial Sequence
<220> FEATURE:
<223> OTHER INFORMATION: Forward Primer KIAA1549_exon17F

<400> SEQUENCE: 280
gatacgaaga ctatggaatg actcc                                          25

<210> SEQ ID NO 281
<211> LENGTH: 24
<212> TYPE: DNA
<213> ORGANISM: Artificial Sequence
<220> FEATURE:
<223> OTHER INFORMATION: Forward Primer KIF5B_exon18F
```

```
<400> SEQUENCE: 281
catgaaatgg aaaaggagca ctta                                         24

<210> SEQ ID NO 282
<211> LENGTH: 24
<212> TYPE: DNA
<213> ORGANISM: Artificial Sequence
<220> FEATURE:
<223> OTHER INFORMATION: Forward Primer KIF5B_exon19F

<400> SEQUENCE: 282
agtttgagag atgaagtaga agca                                         24

<210> SEQ ID NO 283
<211> LENGTH: 22
<212> TYPE: DNA
<213> ORGANISM: Artificial Sequence
<220> FEATURE:
<223> OTHER INFORMATION: Forward Primer KIF5B_exon20F

<400> SEQUENCE: 283
agttgaaagc cacagatcag ga                                           22

<210> SEQ ID NO 284
<211> LENGTH: 22
<212> TYPE: DNA
<213> ORGANISM: Artificial Sequence
<220> FEATURE:
<223> OTHER INFORMATION: Forward Primer KIF5B_exon21F

<400> SEQUENCE: 284
acgagaacaa gcaagacaag ac                                           22

<210> SEQ ID NO 285
<211> LENGTH: 20
<212> TYPE: DNA
<213> ORGANISM: Artificial Sequence
<220> FEATURE:
<223> OTHER INFORMATION: Forward Primer MECOM_exon2_F

<400> SEQUENCE: 285
agagcagagg tcaaacctga                                              20

<210> SEQ ID NO 286
<211> LENGTH: 22
<212> TYPE: DNA
<213> ORGANISM: Artificial Sequence
<220> FEATURE:
<223> OTHER INFORMATION: Forward Primer MET_exon11F

<400> SEQUENCE: 286
agccagtgat gatctcaatg gg                                           22

<210> SEQ ID NO 287
<211> LENGTH: 22
<212> TYPE: DNA
<213> ORGANISM: Artificial Sequence
<220> FEATURE:
<223> OTHER INFORMATION: Forward Primer MYB_exon10_F

<400> SEQUENCE: 287
agttcaactc ccaagcgttc cc                                           22

<210> SEQ ID NO 288
<211> LENGTH: 26
```

```
<212> TYPE: DNA
<213> ORGANISM: Artificial Sequence
<220> FEATURE:
<223> OTHER INFORMATION: Forward Primer MYB_exon11_F

<400> SEQUENCE: 288
aacaccattt catagagacc agactg                                          26

<210> SEQ ID NO 289
<211> LENGTH: 24
<212> TYPE: DNA
<213> ORGANISM: Artificial Sequence
<220> FEATURE:
<223> OTHER INFORMATION: Forward Primer MYB_exon12_F

<400> SEQUENCE: 289
tcaaacatgc acttgcagct caag                                            24

<210> SEQ ID NO 290
<211> LENGTH: 24
<212> TYPE: DNA
<213> ORGANISM: Artificial Sequence
<220> FEATURE:
<223> OTHER INFORMATION: Forward Primer MYB_exon13_F

<400> SEQUENCE: 290
tgctgagttt caagaaaatg gacc                                            24

<210> SEQ ID NO 291
<211> LENGTH: 21
<212> TYPE: DNA
<213> ORGANISM: Artificial Sequence
<220> FEATURE:
<223> OTHER INFORMATION: Forward Primer MYB_exon14_F

<400> SEQUENCE: 291
aggggacagt ctgaataccc a                                               21

<210> SEQ ID NO 292
<211> LENGTH: 25
<212> TYPE: DNA
<213> ORGANISM: Artificial Sequence
<220> FEATURE:
<223> OTHER INFORMATION: Forward Primer MYB_exon15_F

<400> SEQUENCE: 292
tgttctcaaa gcatttacag tacct                                           25

<210> SEQ ID NO 293
<211> LENGTH: 28
<212> TYPE: DNA
<213> ORGANISM: Artificial Sequence
<220> FEATURE:
<223> OTHER INFORMATION: Forward Primer MYB_exon8_F

<400> SEQUENCE: 293
ttagaattgc tcctaatgtc aaccgaga                                        28

<210> SEQ ID NO 294
<211> LENGTH: 25
<212> TYPE: DNA
<213> ORGANISM: Artificial Sequence
<220> FEATURE:
<223> OTHER INFORMATION: Forward Primer MYB_exon9_F

<400> SEQUENCE: 294
```

```
acctcttaga atttgcagaa acact                                          25

<210> SEQ ID NO 295
<211> LENGTH: 24
<212> TYPE: DNA
<213> ORGANISM: Artificial Sequence
<220> FEATURE:
<223> OTHER INFORMATION: Forward Primer NCOA4_exon9F

<400> SEQUENCE: 295
caacctcagc cagttatctt ctgg                                           24

<210> SEQ ID NO 296
<211> LENGTH: 17
<212> TYPE: DNA
<213> ORGANISM: Artificial Sequence
<220> FEATURE:
<223> OTHER INFORMATION: Forward Primer PAN3_exon1_F

<400> SEQUENCE: 296
aggcagtagc gggggac                                                   17

<210> SEQ ID NO 297
<211> LENGTH: 20
<212> TYPE: DNA
<213> ORGANISM: Artificial Sequence
<220> FEATURE:
<223> OTHER INFORMATION: Forward Primer PAX3_exon7_F

<400> SEQUENCE: 297
tccaacccca tgaaccccac                                                20

<210> SEQ ID NO 298
<211> LENGTH: 27
<212> TYPE: DNA
<213> ORGANISM: Artificial Sequence
<220> FEATURE:
<223> OTHER INFORMATION: Forward Primer PPFIBP1_exon11F

<400> SEQUENCE: 298
caaaaaatga aaaagctgt ggagtcc                                         27

<210> SEQ ID NO 299
<211> LENGTH: 23
<212> TYPE: DNA
<213> ORGANISM: Artificial Sequence
<220> FEATURE:
<223> OTHER INFORMATION: Forward Primer PPFIBP1_exon9F_rdsgn

<400> SEQUENCE: 299
ggtcagatgc agtatgaaaa gca                                            23

<210> SEQ ID NO 300
<211> LENGTH: 20
<212> TYPE: DNA
<213> ORGANISM: Artificial Sequence
<220> FEATURE:
<223> OTHER INFORMATION: Forward Primer SCAF11_exon1_F

<400> SEQUENCE: 300
cctgggaacc tactgtgggg                                                20

<210> SEQ ID NO 301
<211> LENGTH: 20
<212> TYPE: DNA
<213> ORGANISM: Artificial Sequence
```

```
<220> FEATURE:
<223> OTHER INFORMATION: Forward Primer SDC4_exon3F

<400> SEQUENCE: 301
tggaagactc catgatcggc                                               20

<210> SEQ ID NO 302
<211> LENGTH: 20
<212> TYPE: DNA
<213> ORGANISM: Artificial Sequence
<220> FEATURE:
<223> OTHER INFORMATION: Forward Primer SND1_exon12F

<400> SEQUENCE: 302
gccttttcag agcgtacctg                                               20

<210> SEQ ID NO 303
<211> LENGTH: 22
<212> TYPE: DNA
<213> ORGANISM: Artificial Sequence
<220> FEATURE:
<223> OTHER INFORMATION: Forward Primer SND1_exon13F

<400> SEQUENCE: 303
gaccagagat catcacacta cg                                            22

<210> SEQ ID NO 304
<211> LENGTH: 30
<212> TYPE: DNA
<213> ORGANISM: Artificial Sequence
<220> FEATURE:
<223> OTHER INFORMATION: Forward Primer SND1_exon15F

<400> SEQUENCE: 304
gtctcaaact ctatttgcca aaggaaactt                                    30

<210> SEQ ID NO 305
<211> LENGTH: 18
<212> TYPE: DNA
<213> ORGANISM: Artificial Sequence
<220> FEATURE:
<223> OTHER INFORMATION: Forward Primer SPTBN1_exon6_F

<400> SEQUENCE: 305
agggacggca tggccttc                                                 18

<210> SEQ ID NO 306
<211> LENGTH: 19
<212> TYPE: DNA
<213> ORGANISM: Artificial Sequence
<220> FEATURE:
<223> OTHER INFORMATION: Forward Primer SS18_exon10_F

<400> SEQUENCE: 306
aacacagcct ggaccacca                                                19

<210> SEQ ID NO 307
<211> LENGTH: 19
<212> TYPE: DNA
<213> ORGANISM: Artificial Sequence
<220> FEATURE:
<223> OTHER INFORMATION: Forward Primer SS18_exon9_F

<400> SEQUENCE: 307
agtacccagg gcagcaagg                                                19
```

<210> SEQ ID NO 308
<211> LENGTH: 18
<212> TYPE: DNA
<213> ORGANISM: Artificial Sequence
<220> FEATURE:
<223> OTHER INFORMATION: Forward Primer TMPRSS2_exon4F

<400> SEQUENCE: 308
accttcctcg tgggagct                                             18

<210> SEQ ID NO 309
<211> LENGTH: 22
<212> TYPE: DNA
<213> ORGANISM: Artificial Sequence
<220> FEATURE:
<223> OTHER INFORMATION: Forward Primer TPM3_exon2F_rdsgn

<400> SEQUENCE: 309
tttgaaggat gcccaggaga ag                                        22

<210> SEQ ID NO 310
<211> LENGTH: 22
<212> TYPE: DNA
<213> ORGANISM: Artificial Sequence
<220> FEATURE:
<223> OTHER INFORMATION: Forward Primer TPM3_exon4F

<400> SEQUENCE: 310
ctaagcacat tgcagaagag gc                                        22

<210> SEQ ID NO 311
<211> LENGTH: 20
<212> TYPE: DNA
<213> ORGANISM: Artificial Sequence
<220> FEATURE:
<223> OTHER INFORMATION: Forward Primer TPM3_exon5F

<400> SEQUENCE: 311
aggagacttg gaacgcacag                                           20

<210> SEQ ID NO 312
<211> LENGTH: 22
<212> TYPE: DNA
<213> ORGANISM: Artificial Sequence
<220> FEATURE:
<223> OTHER INFORMATION: Forward Primer TPM3_exon6F

<400> SEQUENCE: 312
gtcaccaaca acctcaagtc tc                                        22

<210> SEQ ID NO 313
<211> LENGTH: 30
<212> TYPE: DNA
<213> ORGANISM: Artificial Sequence
<220> FEATURE:
<223> OTHER INFORMATION: Forward Primer TPM3_exon7F_rdsgn

<400> SEQUENCE: 313
gaagataaat atgaggaaga aatcaagatt                                30

<210> SEQ ID NO 314
<211> LENGTH: 20
<212> TYPE: DNA
<213> ORGANISM: Artificial Sequence
<220> FEATURE:
<223> OTHER INFORMATION: Forward Primer TRIM24_exon12_F

<400> SEQUENCE: 314
cagaacggtc cagtcaccaa                                               20

<210> SEQ ID NO 315
<211> LENGTH: 19
<212> TYPE: DNA
<213> ORGANISM: Artificial Sequence
<220> FEATURE:
<223> OTHER INFORMATION: Forward Primer FGFR3_exon17F_new

<400> SEQUENCE: 315
gaggcccacc ttcaagcag                                                19

<210> SEQ ID NO 316
<211> LENGTH: 20
<212> TYPE: DNA
<213> ORGANISM: Artificial Sequence
<220> FEATURE:
<223> OTHER INFORMATION: Reverse Primer ABL1_E2a_R

<400> SEQUENCE: 316
cttcactcag accctgaggc                                               20

<210> SEQ ID NO 317
<211> LENGTH: 20
<212> TYPE: DNA
<213> ORGANISM: Artificial Sequence
<220> FEATURE:
<223> OTHER INFORMATION: Reverse Primer ABL1_E2b_R

<400> SEQUENCE: 317
caacgaaaag gttggggtca                                               20

<210> SEQ ID NO 318
<211> LENGTH: 21
<212> TYPE: DNA
<213> ORGANISM: Artificial Sequence
<220> FEATURE:
<223> OTHER INFORMATION: Reverse Primer ABL1_E3_R

<400> SEQUENCE: 318
gcttcacacc attccccatt g                                             21

<210> SEQ ID NO 319
<211> LENGTH: 21
<212> TYPE: DNA
<213> ORGANISM: Artificial Sequence
<220> FEATURE:
<223> OTHER INFORMATION: Reverse Primer ABL1_E4_R

<400> SEQUENCE: 319
gatgatgaac caactcggcc a                                             21

<210> SEQ ID NO 320
<211> LENGTH: 20
<212> TYPE: DNA
<213> ORGANISM: Artificial Sequence
<220> FEATURE:
<223> OTHER INFORMATION: Reverse Primer AFF1_E11_R

<400> SEQUENCE: 320
atgtgctgat gccactggtt                                               20

<210> SEQ ID NO 321

```
<211> LENGTH: 19
<212> TYPE: DNA
<213> ORGANISM: Artificial Sequence
<220> FEATURE:
<223> OTHER INFORMATION: Reverse Primer AFF1_E6_R

<400> SEQUENCE: 321
ggctcagctg tactaggcg                                            19

<210> SEQ ID NO 322
<211> LENGTH: 22
<212> TYPE: DNA
<213> ORGANISM: Artificial Sequence
<220> FEATURE:
<223> OTHER INFORMATION: Reverse Primer AFF1_E9-10_R_rdsgn

<400> SEQUENCE: 322
gcttctctgg ggtttgttca ct                                        22

<210> SEQ ID NO 323
<211> LENGTH: 20
<212> TYPE: DNA
<213> ORGANISM: Artificial Sequence
<220> FEATURE:
<223> OTHER INFORMATION: Reverse Primer ALK_exon19R

<400> SEQUENCE: 323
agagaggatc agcgagagtg                                           20

<210> SEQ ID NO 324
<211> LENGTH: 21
<212> TYPE: DNA
<213> ORGANISM: Artificial Sequence
<220> FEATURE:
<223> OTHER INFORMATION: Reverse Primer ALK_exon20RL

<400> SEQUENCE: 324
tcagcttgta ctcagggctc t                                         21

<210> SEQ ID NO 325
<211> LENGTH: 19
<212> TYPE: DNA
<213> ORGANISM: Artificial Sequence
<220> FEATURE:
<223> OTHER INFORMATION: Reverse Primer ALK_exon21R

<400> SEQUENCE: 325
cttgggtcgt tgggcattc                                            19

<210> SEQ ID NO 326
<211> LENGTH: 20
<212> TYPE: DNA
<213> ORGANISM: Artificial Sequence
<220> FEATURE:
<223> OTHER INFORMATION: Reverse Primer BRAF_exon10R

<400> SEQUENCE: 326
cgttagttag tgagccaggt                                           20

<210> SEQ ID NO 327
<211> LENGTH: 23
<212> TYPE: DNA
<213> ORGANISM: Artificial Sequence
<220> FEATURE:
<223> OTHER INFORMATION: Reverse Primer BRAF_exon11R

<400> SEQUENCE: 327
```

```
caggaatctc ccaatcatca ctc                                            23
```

<210> SEQ ID NO 328
<211> LENGTH: 20
<212> TYPE: DNA
<213> ORGANISM: Artificial Sequence
<220> FEATURE:
<223> OTHER INFORMATION: Reverse Primer BRAF_exon8R

<400> SEQUENCE: 328

```
agggctgtgg aattggaatg                                                20
```

<210> SEQ ID NO 329
<211> LENGTH: 22
<212> TYPE: DNA
<213> ORGANISM: Artificial Sequence
<220> FEATURE:
<223> OTHER INFORMATION: Reverse Primer BRAF_exon9R

<400> SEQUENCE: 329

```
ctccatcacc acgaaatcct tg                                             22
```

<210> SEQ ID NO 330
<211> LENGTH: 20
<212> TYPE: DNA
<213> ORGANISM: Artificial Sequence
<220> FEATURE:
<223> OTHER INFORMATION: Reverse Primer ERG_exon10R

<400> SEQUENCE: 330

```
aaggcggcta cttgttggtc                                                20
```

<210> SEQ ID NO 331
<211> LENGTH: 21
<212> TYPE: DNA
<213> ORGANISM: Artificial Sequence
<220> FEATURE:
<223> OTHER INFORMATION: Reverse Primer ERG_exon11R

<400> SEQUENCE: 331

```
gaggaactgc caaagctgga t                                              21
```

<210> SEQ ID NO 332
<211> LENGTH: 20
<212> TYPE: DNA
<213> ORGANISM: Artificial Sequence
<220> FEATURE:
<223> OTHER INFORMATION: Reverse Primer ERG_exon2R

<400> SEQUENCE: 332

```
ctttcctcgg gtctccaaag                                                20
```

<210> SEQ ID NO 333
<211> LENGTH: 20
<212> TYPE: DNA
<213> ORGANISM: Artificial Sequence
<220> FEATURE:
<223> OTHER INFORMATION: Reverse Primer ERG_exon3R

<400> SEQUENCE: 333

```
cccatctacc agctgttcag                                                20
```

<210> SEQ ID NO 334
<211> LENGTH: 25
<212> TYPE: DNA

```
<213> ORGANISM: Artificial Sequence
<220> FEATURE:
<223> OTHER INFORMATION: Reverse Primer ERG_exon4RS

<400> SEQUENCE: 334
tggtcctcac tcacaactga taagg                                      25

<210> SEQ ID NO 335
<211> LENGTH: 20
<212> TYPE: DNA
<213> ORGANISM: Artificial Sequence
<220> FEATURE:
<223> OTHER INFORMATION: Reverse Primer ERG_exon5RS

<400> SEQUENCE: 335
ccaccatctt cccgcctttg                                            20

<210> SEQ ID NO 336
<211> LENGTH: 18
<212> TYPE: DNA
<213> ORGANISM: Artificial Sequence
<220> FEATURE:
<223> OTHER INFORMATION: Reverse Primer ERG_exon8R

<400> SEQUENCE: 336
caggagatca gcctggac                                              18

<210> SEQ ID NO 337
<211> LENGTH: 21
<212> TYPE: DNA
<213> ORGANISM: Artificial Sequence
<220> FEATURE:
<223> OTHER INFORMATION: Reverse Primer ERG_exon9R

<400> SEQUENCE: 337
ggtcttcagt tttgggcact g                                          21

<210> SEQ ID NO 338
<211> LENGTH: 23
<212> TYPE: DNA
<213> ORGANISM: Artificial Sequence
<220> FEATURE:
<223> OTHER INFORMATION: Reverse Primer MECOM_E2_R

<400> SEQUENCE: 338
tgcatctggc atttcttcca aag                                        23

<210> SEQ ID NO 339
<211> LENGTH: 28
<212> TYPE: DNA
<213> ORGANISM: Artificial Sequence
<220> FEATURE:
<223> OTHER INFORMATION: Reverse Primer MLLT3_E10_R

<400> SEQUENCE: 339
atgtcattaa ccttctgtga agctctac                                   28

<210> SEQ ID NO 340
<211> LENGTH: 24
<212> TYPE: DNA
<213> ORGANISM: Artificial Sequence
<220> FEATURE:
<223> OTHER INFORMATION: Reverse Primer MLLT3_E5_R

<400> SEQUENCE: 340
tgctgctgct gctggtatga atac                                       24
```

<210> SEQ ID NO 341
<211> LENGTH: 24
<212> TYPE: DNA
<213> ORGANISM: Artificial Sequence
<220> FEATURE:
<223> OTHER INFORMATION: Reverse Primer MLLT3_E7_R

<400> SEQUENCE: 341
tctgattcct cctcattgtc atca                                          24

<210> SEQ ID NO 342
<211> LENGTH: 30
<212> TYPE: DNA
<213> ORGANISM: Artificial Sequence
<220> FEATURE:
<223> OTHER INFORMATION: Reverse Primer MLLT3_E9_R

<400> SEQUENCE: 342
tttgcttatc tgatttgctt tgctttattg                                    30

<210> SEQ ID NO 343
<211> LENGTH: 20
<212> TYPE: DNA
<213> ORGANISM: Artificial Sequence
<220> FEATURE:
<223> OTHER INFORMATION: Reverse Primer MYH11_E28_R

<400> SEQUENCE: 343
tctctttctc cagcgtctgc                                               20

<210> SEQ ID NO 344
<211> LENGTH: 20
<212> TYPE: DNA
<213> ORGANISM: Artificial Sequence
<220> FEATURE:
<223> OTHER INFORMATION: Reverse Primer MYH11_E29_R

<400> SEQUENCE: 344
ctcggcctcg ttaagcatcc                                               20

<210> SEQ ID NO 345
<211> LENGTH: 20
<212> TYPE: DNA
<213> ORGANISM: Artificial Sequence
<220> FEATURE:
<223> OTHER INFORMATION: Reverse Primer MYH11_E30_R

<400> SEQUENCE: 345
gcagcttcgt agacacgttg                                               20

<210> SEQ ID NO 346
<211> LENGTH: 21
<212> TYPE: DNA
<213> ORGANISM: Artificial Sequence
<220> FEATURE:
<223> OTHER INFORMATION: Reverse Primer MYH11_E32_R

<400> SEQUENCE: 346
cctctcatcc gcgtatttgg a                                             21

<210> SEQ ID NO 347
<211> LENGTH: 19
<212> TYPE: DNA
<213> ORGANISM: Artificial Sequence
<220> FEATURE:

<223> OTHER INFORMATION: Reverse Primer MYH11_E33_R

<400> SEQUENCE: 347
tccatctggg tctccaggg                                          19

<210> SEQ ID NO 348
<211> LENGTH: 20
<212> TYPE: DNA
<213> ORGANISM: Artificial Sequence
<220> FEATURE:
<223> OTHER INFORMATION: Reverse Primer MYH11_E34_R

<400> SEQUENCE: 348
gttgctttcg ctcgtcttcc                                         20

<210> SEQ ID NO 349
<211> LENGTH: 20
<212> TYPE: DNA
<213> ORGANISM: Artificial Sequence
<220> FEATURE:
<223> OTHER INFORMATION: Reverse Primer RARA_E3_R

<400> SEQUENCE: 349
ggctgggcac tatctcttca                                         20

<210> SEQ ID NO 350
<211> LENGTH: 22
<212> TYPE: DNA
<213> ORGANISM: Artificial Sequence
<220> FEATURE:
<223> OTHER INFORMATION: Reverse Primer RET_exon11RS

<400> SEQUENCE: 350
atgaaggaga agaggacagc gg                                      22

<210> SEQ ID NO 351
<211> LENGTH: 25
<212> TYPE: DNA
<213> ORGANISM: Artificial Sequence
<220> FEATURE:
<223> OTHER INFORMATION: Reverse Primer RET_exon12RL

<400> SEQUENCE: 351
tcctagagtt tttccaagaa ccaag                                   25

<210> SEQ ID NO 352
<211> LENGTH: 20
<212> TYPE: DNA
<213> ORGANISM: Artificial Sequence
<220> FEATURE:
<223> OTHER INFORMATION: Reverse Primer RET_exon7R

<400> SEQUENCE: 352
ggacgttgat gccactgaat                                         20

<210> SEQ ID NO 353
<211> LENGTH: 23
<212> TYPE: DNA
<213> ORGANISM: Artificial Sequence
<220> FEATURE:
<223> OTHER INFORMATION: Reverse Primer RET_exon8R

<400> SEQUENCE: 353
ctcttgctga ctgcacagga cag                                     23

```
<210> SEQ ID NO 354
<211> LENGTH: 25
<212> TYPE: DNA
<213> ORGANISM: Artificial Sequence
<220> FEATURE:
<223> OTHER INFORMATION: Reverse Primer ROS1_exon34R

<400> SEQUENCE: 354
ggtcagtggg attgtaacaa ccaga                                    25

<210> SEQ ID NO 355
<211> LENGTH: 23
<212> TYPE: DNA
<213> ORGANISM: Artificial Sequence
<220> FEATURE:
<223> OTHER INFORMATION: Reverse Primer ROS1_exon35R

<400> SEQUENCE: 355
cttcgtttat aagcactgtc acc                                      23

<210> SEQ ID NO 356
<211> LENGTH: 19
<212> TYPE: DNA
<213> ORGANISM: Artificial Sequence
<220> FEATURE:
<223> OTHER INFORMATION: Reverse Primer ROS1_exon36R

<400> SEQUENCE: 356
gagggaaggc aggaagatt                                           19

<210> SEQ ID NO 357
<211> LENGTH: 20
<212> TYPE: DNA
<213> ORGANISM: Artificial Sequence
<220> FEATURE:
<223> OTHER INFORMATION: Reverse Primer RUNX1T1_E2_R

<400> SEQUENCE: 357
gcgtcttcac atccacaggt                                          20

<210> SEQ ID NO 358
<211> LENGTH: 21
<212> TYPE: DNA
<213> ORGANISM: Artificial Sequence
<220> FEATURE:
<223> OTHER INFORMATION: Reverse Primer ACTR1A_exon3_R

<400> SEQUENCE: 358
aagatgtcgc cttcaagggc t                                        21

<210> SEQ ID NO 359
<211> LENGTH: 24
<212> TYPE: DNA
<213> ORGANISM: Artificial Sequence
<220> FEATURE:
<223> OTHER INFORMATION: Reverse Primer AHCYL1_exon2R

<400> SEQUENCE: 359
gttttggtgg ggaatttggt gaac                                     24

<210> SEQ ID NO 360
<211> LENGTH: 26
<212> TYPE: DNA
<213> ORGANISM: Artificial Sequence
<220> FEATURE:
<223> OTHER INFORMATION: Reverse Primer AKAP12_exon4_R
```

```
<400> SEQUENCE: 360
agtagccatc tctttatcgg agtctc                                          26

<210> SEQ ID NO 361
<211> LENGTH: 24
<212> TYPE: DNA
<213> ORGANISM: Artificial Sequence
<220> FEATURE:
<223> OTHER INFORMATION: Reverse Primer AR_CE3_R

<400> SEQUENCE: 361
ggtctggtca ttttgagatg cttg                                            24

<210> SEQ ID NO 362
<211> LENGTH: 23
<212> TYPE: DNA
<213> ORGANISM: Artificial Sequence
<220> FEATURE:
<223> OTHER INFORMATION: Reverse Primer AR_CE5_R

<400> SEQUENCE: 362
acaacgtgat cccaaaagat gtg                                             23

<210> SEQ ID NO 363
<211> LENGTH: 20
<212> TYPE: DNA
<213> ORGANISM: Artificial Sequence
<220> FEATURE:
<223> OTHER INFORMATION: Reverse Primer AR_CE4_R

<400> SEQUENCE: 363
atgcagtatg gcttggggtt                                                 20

<210> SEQ ID NO 364
<211> LENGTH: 25
<212> TYPE: DNA
<213> ORGANISM: Artificial Sequence
<220> FEATURE:
<223> OTHER INFORMATION: Reverse Primer BAIAP2L1_exon2_3R

<400> SEQUENCE: 364
aggatcatag cgtttacagc tttct                                           25

<210> SEQ ID NO 365
<211> LENGTH: 24
<212> TYPE: DNA
<213> ORGANISM: Artificial Sequence
<220> FEATURE:
<223> OTHER INFORMATION: Reverse Primer BICC1_exon2_3R

<400> SEQUENCE: 365
tgcgtatttg tttcctccat gatc                                            24

<210> SEQ ID NO 366
<211> LENGTH: 20
<212> TYPE: DNA
<213> ORGANISM: Artificial Sequence
<220> FEATURE:
<223> OTHER INFORMATION: Reverse Primer CCDC170_exon2_R

<400> SEQUENCE: 366
agtggtttaa ctgctcccgc                                                 20

<210> SEQ ID NO 367
<211> LENGTH: 20
```

```
<212> TYPE: DNA
<213> ORGANISM: Artificial Sequence
<220> FEATURE:
<223> OTHER INFORMATION: Reverse Primer CLDN7_exon2_R

<400> SEQUENCE: 367
gcaccaggga gaccaccatt                                              20

<210> SEQ ID NO 368
<211> LENGTH: 22
<212> TYPE: DNA
<213> ORGANISM: Artificial Sequence
<220> FEATURE:
<223> OTHER INFORMATION: Reverse Primer EGFR_exon14R

<400> SEQUENCE: 368
ggcactgtat gcactcagag tt                                           22

<210> SEQ ID NO 369
<211> LENGTH: 18
<212> TYPE: DNA
<213> ORGANISM: Artificial Sequence
<220> FEATURE:
<223> OTHER INFORMATION: Reverse Primer EGFR_exon15R

<400> SEQUENCE: 369
caggtcttga cgcagtgg                                                18

<210> SEQ ID NO 370
<211> LENGTH: 19
<212> TYPE: DNA
<213> ORGANISM: Artificial Sequence
<220> FEATURE:
<223> OTHER INFORMATION: Reverse Primer EGFR_exon18R

<400> SEQUENCE: 370
gcttggttgg gagcttctc                                               19

<210> SEQ ID NO 371
<211> LENGTH: 20
<212> TYPE: DNA
<213> ORGANISM: Artificial Sequence
<220> FEATURE:
<223> OTHER INFORMATION: Reverse Primer ERBB2_exon17R

<400> SEQUENCE: 371
aagaccacga ccagcagaat                                              20

<210> SEQ ID NO 372
<211> LENGTH: 19
<212> TYPE: DNA
<213> ORGANISM: Artificial Sequence
<220> FEATURE:
<223> OTHER INFORMATION: Reverse Primer ERBB2_ex8-int8_R

<400> SEQUENCE: 372
tgagtgggta cctcacacc                                               19

<210> SEQ ID NO 373
<211> LENGTH: 21
<212> TYPE: DNA
<213> ORGANISM: Artificial Sequence
<220> FEATURE:
<223> OTHER INFORMATION: Reverse Primer ETV1_exon4_R

<400> SEQUENCE: 373
```
cttctgcaag ccatgtttcc t                                                          21

<210> SEQ ID NO 374
<211> LENGTH: 25
<212> TYPE: DNA
<213> ORGANISM: Artificial Sequence
<220> FEATURE:
<223> OTHER INFORMATION: Reverse Primer ETV1_exon6_R

<400> SEQUENCE: 374
tgaacatgga ctgtggggtt cttc                                                       25

<210> SEQ ID NO 375
<211> LENGTH: 20
<212> TYPE: DNA
<213> ORGANISM: Artificial Sequence
<220> FEATURE:
<223> OTHER INFORMATION: Reverse Primer ETV1_exon7_R

<400> SEQUENCE: 375
ggagggcctc attcccactt                                                            20

<210> SEQ ID NO 376
<211> LENGTH: 20
<212> TYPE: DNA
<213> ORGANISM: Artificial Sequence
<220> FEATURE:
<223> OTHER INFORMATION: Reverse Primer ETV1_exon2_R

<400> SEQUENCE: 376
tggtgaccat gtaaggcact                                                            20

<210> SEQ ID NO 377
<211> LENGTH: 24
<212> TYPE: DNA
<213> ORGANISM: Artificial Sequence
<220> FEATURE:
<223> OTHER INFORMATION: Reverse Primer ETV1_exon2b_R

<400> SEQUENCE: 377
agcatttagc tggagatttc ctca                                                       24

<210> SEQ ID NO 378
<211> LENGTH: 27
<212> TYPE: DNA
<213> ORGANISM: Artificial Sequence
<220> FEATURE:
<223> OTHER INFORMATION: Reverse Primer ETV1_exon5_R

<400> SEQUENCE: 378
aactttcagc ctgatagtct ggtacaa                                                    27

<210> SEQ ID NO 379
<211> LENGTH: 28
<212> TYPE: DNA
<213> ORGANISM: Artificial Sequence
<220> FEATURE:
<223> OTHER INFORMATION: Reverse Primer ETV1_exon3_R

<400> SEQUENCE: 379
ttttcttttc ctgacatttg ttggtttc                                                   28

<210> SEQ ID NO 380
<211> LENGTH: 25
<212> TYPE: DNA
<213> ORGANISM: Artificial Sequence

```
<220> FEATURE:
<223> OTHER INFORMATION: Reverse Primer ETV1_exon11_R

<400> SEQUENCE: 380
agttcatagc tggcctgttt ttctg                                         25

<210> SEQ ID NO 381
<211> LENGTH: 24
<212> TYPE: DNA
<213> ORGANISM: Artificial Sequence
<220> FEATURE:
<223> OTHER INFORMATION: Reverse Primer ETV1_exon12_R

<400> SEQUENCE: 381
agaaaagggc ttctggatca caca                                          24

<210> SEQ ID NO 382
<211> LENGTH: 18
<212> TYPE: DNA
<213> ORGANISM: Artificial Sequence
<220> FEATURE:
<223> OTHER INFORMATION: Reverse Primer ETV4_exon1_2_R

<400> SEQUENCE: 382
cgagacctgc tcccagga                                                 18

<210> SEQ ID NO 383
<211> LENGTH: 18
<212> TYPE: DNA
<213> ORGANISM: Artificial Sequence
<220> FEATURE:
<223> OTHER INFORMATION: Reverse Primer ETV4_exon3_R

<400> SEQUENCE: 383
catgagcttc cccagcgg                                                 18

<210> SEQ ID NO 384
<211> LENGTH: 26
<212> TYPE: DNA
<213> ORGANISM: Artificial Sequence
<220> FEATURE:
<223> OTHER INFORMATION: Reverse Primer ETV4_exon5_R

<400> SEQUENCE: 384
ctgaatggaa atcaggaaca aactgc                                        26

<210> SEQ ID NO 385
<211> LENGTH: 18
<212> TYPE: DNA
<213> ORGANISM: Artificial Sequence
<220> FEATURE:
<223> OTHER INFORMATION: Reverse Primer ETV4_exon4_R

<400> SEQUENCE: 385
agcgagccac gtctcctg                                                 18

<210> SEQ ID NO 386
<211> LENGTH: 23
<212> TYPE: DNA
<213> ORGANISM: Artificial Sequence
<220> FEATURE:
<223> OTHER INFORMATION: Reverse Primer ETV5_exon2_R

<400> SEQUENCE: 386
cagcattgag taatttctgg ggg                                           23
```

<210> SEQ ID NO 387
<211> LENGTH: 21
<212> TYPE: DNA
<213> ORGANISM: Artificial Sequence
<220> FEATURE:
<223> OTHER INFORMATION: Reverse Primer ETV5_exon8_R

<400> SEQUENCE: 387
aactcctggc tgaggaggga a                                         21

<210> SEQ ID NO 388
<211> LENGTH: 21
<212> TYPE: DNA
<213> ORGANISM: Artificial Sequence
<220> FEATURE:
<223> OTHER INFORMATION: Reverse Primer FGFR1_exon8_R

<400> SEQUENCE: 388
agcacctcca tctctttgtc g                                         21

<210> SEQ ID NO 389
<211> LENGTH: 20
<212> TYPE: DNA
<213> ORGANISM: Artificial Sequence
<220> FEATURE:
<223> OTHER INFORMATION: Reverse Primer FGFR1_exon6_R

<400> SEQUENCE: 389
tgtcagaggg caccacagag                                           20

<210> SEQ ID NO 390
<211> LENGTH: 23
<212> TYPE: DNA
<213> ORGANISM: Artificial Sequence
<220> FEATURE:
<223> OTHER INFORMATION: Reverse Primer FGFR1_exon9_R

<400> SEQUENCE: 390
agatgatgat ctccaggtac agg                                       23

<210> SEQ ID NO 391
<211> LENGTH: 23
<212> TYPE: DNA
<213> ORGANISM: Artificial Sequence
<220> FEATURE:
<223> OTHER INFORMATION: Reverse Primer FGFR1_exon10_R

<400> SEQUENCE: 391
gaaccagaag aaccccagag ttc                                       23

<210> SEQ ID NO 392
<211> LENGTH: 29
<212> TYPE: DNA
<213> ORGANISM: Artificial Sequence
<220> FEATURE:
<223> OTHER INFORMATION: Reverse Primer JAK2_exon9_R

<400> SEQUENCE: 392
ccatcaatta atgacacgaa agacaaagc                                 29

<210> SEQ ID NO 393
<211> LENGTH: 22
<212> TYPE: DNA
<213> ORGANISM: Artificial Sequence
<220> FEATURE:
<223> OTHER INFORMATION: Reverse Primer JAK2_exon10_R

```
<400> SEQUENCE: 393
acagtccagt ctgattacct gc                                              22

<210> SEQ ID NO 394
<211> LENGTH: 20
<212> TYPE: DNA
<213> ORGANISM: Artificial Sequence
<220> FEATURE:
<223> OTHER INFORMATION: Reverse Primer JAK2_exon11_R

<400> SEQUENCE: 394
tgtcccactg aggttgtact                                                 20

<210> SEQ ID NO 395
<211> LENGTH: 22
<212> TYPE: DNA
<213> ORGANISM: Artificial Sequence
<220> FEATURE:
<223> OTHER INFORMATION: Reverse Primer JAK2_exon12_R

<400> SEQUENCE: 395
tggtgaggtt ggtacatcag aa                                              22

<210> SEQ ID NO 396
<211> LENGTH: 23
<212> TYPE: DNA
<213> ORGANISM: Artificial Sequence
<220> FEATURE:
<223> OTHER INFORMATION: Reverse Primer JAK2_exon13_R

<400> SEQUENCE: 396
tgaccgtagt ctcctacttc tct                                             23

<210> SEQ ID NO 397
<211> LENGTH: 27
<212> TYPE: DNA
<213> ORGANISM: Artificial Sequence
<220> FEATURE:
<223> OTHER INFORMATION: Reverse Primer JAK2_exon14_R

<400> SEQUENCE: 397
ttaaaaccaa atgcttgtga gaaagct                                         27

<210> SEQ ID NO 398
<211> LENGTH: 30
<212> TYPE: DNA
<213> ORGANISM: Artificial Sequence
<220> FEATURE:
<223> OTHER INFORMATION: Reverse Primer JAK2_exon15_R

<400> SEQUENCE: 398 tcttttcag atatgtatct agtgatccaa                                       30

<210> SEQ ID NO 399
<211> LENGTH: 29
<212> TYPE: DNA
<213> ORGANISM: Artificial Sequence
<220> FEATURE:
<223> OTHER INFORMATION: Reverse Primer JAK2_exon16_R

<400> SEQUENCE: 399
tctctgataa gcagaatatt tttggcaca                                       29

<210> SEQ ID NO 400
```

```
<211> LENGTH: 25
<212> TYPE: DNA
<213> ORGANISM: Artificial Sequence
<220> FEATURE:
<223> OTHER INFORMATION: Reverse Primer JAK2_exon17_R

<400> SEQUENCE: 400
gcattcaggt ggtacccatg gtatt                                              25

<210> SEQ ID NO 401
<211> LENGTH: 22
<212> TYPE: DNA
<213> ORGANISM: Artificial Sequence
<220> FEATURE:
<223> OTHER INFORMATION: Reverse Primer JAK2_exon18_R

<400> SEQUENCE: 401
ccactttggt gcaggaagct ga                                                 22

<210> SEQ ID NO 402
<211> LENGTH: 27
<212> TYPE: DNA
<213> ORGANISM: Artificial Sequence
<220> FEATURE:
<223> OTHER INFORMATION: Reverse Primer JAK2_exon19_R

<400> SEQUENCE: 402
agggcaccta tcctcatatt tggtaac                                            27

<210> SEQ ID NO 403
<211> LENGTH: 25
<212> TYPE: DNA
<213> ORGANISM: Artificial Sequence
<220> FEATURE:
<223> OTHER INFORMATION: Reverse Primer MET_exon11R

<400> SEQUENCE: 403
ggagtggtac aacagattat ctctg                                              25

<210> SEQ ID NO 404
<211> LENGTH: 20
<212> TYPE: DNA
<213> ORGANISM: Artificial Sequence
<220> FEATURE:
<223> OTHER INFORMATION: Reverse Primer MET_exon15R

<400> SEQUENCE: 404
ctgcacttgt cggcatgaac                                                    20

<210> SEQ ID NO 405
<211> LENGTH: 21
<212> TYPE: DNA
<213> ORGANISM: Artificial Sequence
<220> FEATURE:
<223> OTHER INFORMATION: Reverse Primer NOP2_exon16_R

<400> SEQUENCE: 405
ggatgacctg aggcaagtct a                                                  21

<210> SEQ ID NO 406
<211> LENGTH: 22
<212> TYPE: DNA
<213> ORGANISM: Artificial Sequence
<220> FEATURE:
<223> OTHER INFORMATION: Reverse Primer NRG1_exon6R

<400> SEQUENCE: 406
```

```
ctccgcacat tttacaagat gg                                              22
```

<210> SEQ ID NO 407
<211> LENGTH: 28
<212> TYPE: DNA
<213> ORGANISM: Artificial Sequence
<220> FEATURE:
<223> OTHER INFORMATION: Reverse Primer NRG1_exon5_6R

<400> SEQUENCE: 407

```
gtggtggatg tagatgtaga tgaagaag                                        28
```

<210> SEQ ID NO 408
<211> LENGTH: 19
<212> TYPE: DNA
<213> ORGANISM: Artificial Sequence
<220> FEATURE:
<223> OTHER INFORMATION: Reverse Primer NRG1_exon2R

<400> SEQUENCE: 408

```
aacctgcagc cgattcctg                                                  19
```

<210> SEQ ID NO 409
<211> LENGTH: 22
<212> TYPE: DNA
<213> ORGANISM: Artificial Sequence
<220> FEATURE:
<223> OTHER INFORMATION: Reverse Primer NRG1_exon3R

<400> SEQUENCE: 409

```
gaatcagcca gtgatgcttt gt                                              22
```

<210> SEQ ID NO 410
<211> LENGTH: 20
<212> TYPE: DNA
<213> ORGANISM: Artificial Sequence
<220> FEATURE:
<223> OTHER INFORMATION: Reverse Primer NRG1_exon4R

<400> SEQUENCE: 410

```
tgctccttca gttgaggctg                                                 20
```

<210> SEQ ID NO 411
<211> LENGTH: 23
<212> TYPE: DNA
<213> ORGANISM: Artificial Sequence
<220> FEATURE:
<223> OTHER INFORMATION: Reverse Primer NTRK1-exon10R_rdsgn

<400> SEQUENCE: 411

```
gtgtttcgtc cttcttctcc acc                                             23
```

<210> SEQ ID NO 412
<211> LENGTH: 23
<212> TYPE: DNA
<213> ORGANISM: Artificial Sequence
<220> FEATURE:
<223> OTHER INFORMATION: Reverse Primer NTRK1-exon12R

<400> SEQUENCE: 412

```
tgtcatgaaa tgcagggaca tgg                                             23
```

<210> SEQ ID NO 413
<211> LENGTH: 18
<212> TYPE: DNA

```
<213> ORGANISM: Artificial Sequence
<220> FEATURE:
<223> OTHER INFORMATION: Reverse Primer NTRK1-exon9R

<400> SEQUENCE: 413
accagtggtg catctcca                                                   18

<210> SEQ ID NO 414
<211> LENGTH: 22
<212> TYPE: DNA
<213> ORGANISM: Artificial Sequence
<220> FEATURE:
<223> OTHER INFORMATION: Reverse Primer NTRK1-exon11R

<400> SEQUENCE: 414
agcgtagaaa ggaagaggca gg                                              22

<210> SEQ ID NO 415
<211> LENGTH: 20
<212> TYPE: DNA
<213> ORGANISM: Artificial Sequence
<220> FEATURE:
<223> OTHER INFORMATION: Reverse Primer NTRK2_exon13_R_rdsgn

<400> SEQUENCE: 415
tggtgtcccc gatgtcattc                                                 20

<210> SEQ ID NO 416
<211> LENGTH: 22
<212> TYPE: DNA
<213> ORGANISM: Artificial Sequence
<220> FEATURE:
<223> OTHER INFORMATION: Reverse Primer NTRK2_exon16_R_rdsgn

<400> SEQUENCE: 416
gctggcagag tcatcatcat tg                                              22

<210> SEQ ID NO 417
<211> LENGTH: 21
<212> TYPE: DNA
<213> ORGANISM: Artificial Sequence
<220> FEATURE:
<223> OTHER INFORMATION: Reverse Primer NTRK3_exon14R

<400> SEQUENCE: 417
gtcctcctca ccactgatga c                                               21

<210> SEQ ID NO 418
<211> LENGTH: 25
<212> TYPE: DNA
<213> ORGANISM: Artificial Sequence
<220> FEATURE:
<223> OTHER INFORMATION: Reverse Primer NTRK3_exon15R

<400> SEQUENCE: 418
cttcagcacg atgtctctcc tctta                                           25

<210> SEQ ID NO 419
<211> LENGTH: 23
<212> TYPE: DNA
<213> ORGANISM: Artificial Sequence
<220> FEATURE:
<223> OTHER INFORMATION: Reverse Primer NTRK3_exon11_12R

<400> SEQUENCE: 419
ggactcactt cgtcaaacaa gat                                             23
```

<210> SEQ ID NO 420
<211> LENGTH: 24
<212> TYPE: DNA
<213> ORGANISM: Artificial Sequence
<220> FEATURE:
<223> OTHER INFORMATION: Reverse Primer PAWR_exon3_R

<400> SEQUENCE: 420
taattgcatc ttctcgtttc cgct                                              24

<210> SEQ ID NO 421
<211> LENGTH: 18
<212> TYPE: DNA
<213> ORGANISM: Artificial Sequence
<220> FEATURE:
<223> OTHER INFORMATION: Reverse Primer PBX1_exon3_R

<400> SEQUENCE: 421
ctgggggtct gtgggttc                                                     18

<210> SEQ ID NO 422
<211> LENGTH: 22
<212> TYPE: DNA
<213> ORGANISM: Artificial Sequence
<220> FEATURE:
<223> OTHER INFORMATION: Reverse Primer PCDH11X_exon11_R

<400> SEQUENCE: 422
cttgagtgca gttgtcagag gc                                                22

<210> SEQ ID NO 423
<211> LENGTH: 21
<212> TYPE: DNA
<213> ORGANISM: Artificial Sequence
<220> FEATURE:
<223> OTHER INFORMATION: Reverse Primer PDGFRA_exon12_R

<400> SEQUENCE: 423
tgattcaatg accctccagc g                                                 21

<210> SEQ ID NO 424
<211> LENGTH: 25
<212> TYPE: DNA
<213> ORGANISM: Artificial Sequence
<220> FEATURE:
<223> OTHER INFORMATION: Reverse Primer PDGFRB_exon11_R

<400> SEQUENCE: 424
ggatgataag ggagatgatg gtgag                                             25

<210> SEQ ID NO 425
<211> LENGTH: 21
<212> TYPE: DNA
<213> ORGANISM: Artificial Sequence
<220> FEATURE:
<223> OTHER INFORMATION: Reverse Primer PDGFRB_exon9_R

<400> SEQUENCE: 425
tgtctgttcc ccactgtcag g                                                 21

<210> SEQ ID NO 426
<211> LENGTH: 20
<212> TYPE: DNA
<213> ORGANISM: Artificial Sequence
<220> FEATURE:

```
<223> OTHER INFORMATION: Reverse Primer PDGFRB_exon10_R

<400> SEQUENCE: 426
agctggctct cctcttcgga                                               20

<210> SEQ ID NO 427
<211> LENGTH: 23
<212> TYPE: DNA
<213> ORGANISM: Artificial Sequence
<220> FEATURE:
<223> OTHER INFORMATION: Reverse Primer PDGFRB_exon12_R

<400> SEQUENCE: 427
agctcacaga ctcaatcacc ttc                                           23

<210> SEQ ID NO 428
<211> LENGTH: 24
<212> TYPE: DNA
<213> ORGANISM: Artificial Sequence
<220> FEATURE:
<223> OTHER INFORMATION: Reverse Primer PLAG1_exon4_R

<400> SEQUENCE: 428
gctttaggtg gcttctcaag tttc                                          24

<210> SEQ ID NO 429
<211> LENGTH: 22
<212> TYPE: DNA
<213> ORGANISM: Artificial Sequence
<220> FEATURE:
<223> OTHER INFORMATION: Reverse Primer PLAG1_exon3_R

<400> SEQUENCE: 429
gactcttcgt ggaagagagt gg                                            22

<210> SEQ ID NO 430
<211> LENGTH: 21
<212> TYPE: DNA
<213> ORGANISM: Artificial Sequence
<220> FEATURE:
<223> OTHER INFORMATION: Reverse Primer PLAG1_exon2_R

<400> SEQUENCE: 430
gaatgaagca ttctgggtgc c                                             21

<210> SEQ ID NO 431
<211> LENGTH: 20
<212> TYPE: DNA
<213> ORGANISM: Artificial Sequence
<220> FEATURE:
<223> OTHER INFORMATION: Reverse Primer POLH_exon2_R

<400> SEQUENCE: 431
gtccatgtcc acgagagcaa                                               20

<210> SEQ ID NO 432
<211> LENGTH: 21
<212> TYPE: DNA
<213> ORGANISM: Artificial Sequence
<220> FEATURE:
<223> OTHER INFORMATION: Reverse Primer PPARG_exon2R

<400> SEQUENCE: 432
aatggcatct ctgtgtcaac c                                             21
```

```
<210> SEQ ID NO 433
<211> LENGTH: 21
<212> TYPE: DNA
<213> ORGANISM: Artificial Sequence
<220> FEATURE:
<223> OTHER INFORMATION: Reverse Primer PPARGC1A_exon2R

<400> SEQUENCE: 433
aggaagatct gggcaaagag g                                              21

<210> SEQ ID NO 434
<211> LENGTH: 23
<212> TYPE: DNA
<213> ORGANISM: Artificial Sequence
<220> FEATURE:
<223> OTHER INFORMATION: Reverse Primer PPHLN1_exon3R

<400> SEQUENCE: 434
gtctagcagt ggtggtttct ttg                                            23

<210> SEQ ID NO 435
<211> LENGTH: 21
<212> TYPE: DNA
<213> ORGANISM: Artificial Sequence
<220> FEATURE:
<223> OTHER INFORMATION: Reverse Primer RAD51_exon4R_rdsg

<400> SEQUENCE: 435
ggtggaattc agttgcagtg g                                              21

<210> SEQ ID NO 436
<211> LENGTH: 19
<212> TYPE: DNA
<213> ORGANISM: Artificial Sequence
<220> FEATURE:
<223> OTHER INFORMATION: Reverse Primer RUNX1_Exon4_R

<400> SEQUENCE: 436
cctcgctcat cttgcctgg                                                 19

<210> SEQ ID NO 437
<211> LENGTH: 18
<212> TYPE: DNA
<213> ORGANISM: Artificial Sequence
<220> FEATURE:
<223> OTHER INFORMATION: Reverse Primer SHC1_exon2R_rdsgn

<400> SEQUENCE: 437
cccttccacc cgagtcct                                                  18

<210> SEQ ID NO 438
<211> LENGTH: 28
<212> TYPE: DNA
<213> ORGANISM: Artificial Sequence
<220> FEATURE:
<223> OTHER INFORMATION: Reverse Primer KIAA1598_exon7_R

<400> SEQUENCE: 438
ttctctgttc aagaacttct gaatttaa                                       28

<210> SEQ ID NO 439
<211> LENGTH: 22
<212> TYPE: DNA
<213> ORGANISM: Artificial Sequence
<220> FEATURE:
<223> OTHER INFORMATION: Reverse Primer KIAA1598_exon8_R
```

```
<400> SEQUENCE: 439
gctccaggtt tacttgcatc tc                                          22

<210> SEQ ID NO 440
<211> LENGTH: 20
<212> TYPE: DNA
<213> ORGANISM: Artificial Sequence
<220> FEATURE:
<223> OTHER INFORMATION: Reverse Primer KIAA1598_exon9_R

<400> SEQUENCE: 440
agcagaaggt ggctttgtct                                             20

<210> SEQ ID NO 441
<211> LENGTH: 19
<212> TYPE: DNA
<213> ORGANISM: Artificial Sequence
<220> FEATURE:
<223> OTHER INFORMATION: Reverse Primer TACC1_exon7_R

<400> SEQUENCE: 441
tccacaggac accgacaca                                              19

<210> SEQ ID NO 442
<211> LENGTH: 20
<212> TYPE: DNA
<213> ORGANISM: Artificial Sequence
<220> FEATURE:
<223> OTHER INFORMATION: Reverse Primer TACC3_exon11R

<400> SEQUENCE: 442
ttcttcccgt ggagctcctc                                             20

<210> SEQ ID NO 443
<211> LENGTH: 20
<212> TYPE: DNA
<213> ORGANISM: Artificial Sequence
<220> FEATURE:
<223> OTHER INFORMATION: Reverse Primer TACC3_exon10R

<400> SEQUENCE: 443
gagcaggtcc actataggtc                                             20

<210> SEQ ID NO 444
<211> LENGTH: 20
<212> TYPE: DNA
<213> ORGANISM: Artificial Sequence
<220> FEATURE:
<223> OTHER INFORMATION: Reverse Primer TACC3_exon8R

<400> SEQUENCE: 444
tctaccagga ctgtccctca                                             20

<210> SEQ ID NO 445
<211> LENGTH: 21
<212> TYPE: DNA
<213> ORGANISM: Artificial Sequence
<220> FEATURE:
<223> OTHER INFORMATION: Reverse Primer TACC3_exon14R_rdsgn2

<400> SEQUENCE: 445
gggtgatcct tgccaggtaa t                                           21

<210> SEQ ID NO 446
<211> LENGTH: 21
```

```
<212> TYPE: DNA
<213> ORGANISM: Artificial Sequence
<220> FEATURE:
<223> OTHER INFORMATION: Reverse Primer TACC3_exon6R

<400> SEQUENCE: 446
tcactgcctg gacagcttgt g                                              21

<210> SEQ ID NO 447
<211> LENGTH: 21
<212> TYPE: DNA
<213> ORGANISM: Artificial Sequence
<220> FEATURE:
<223> OTHER INFORMATION: Reverse Primer YAP1_exon4_R

<400> SEQUENCE: 447
tcctgagtca tggcttgttc c                                              21

<210> SEQ ID NO 448
<211> LENGTH: 21
<212> TYPE: DNA
<213> ORGANISM: Artificial Sequence
<220> FEATURE:
<223> OTHER INFORMATION: Reverse Primer ABL1_E5_R_rdsgn

<400> SEQUENCE: 448
gcaccaggtt agggtgtttg a                                              21

<210> SEQ ID NO 449
<211> LENGTH: 20
<212> TYPE: DNA
<213> ORGANISM: Artificial Sequence
<220> FEATURE:
<223> OTHER INFORMATION: Reverse Primer AFF1_E4_R_redsgn

<400> SEQUENCE: 449
ccaggcgatg agtgtgagac                                                20

<210> SEQ ID NO 450
<211> LENGTH: 23
<212> TYPE: DNA
<213> ORGANISM: Artificial Sequence
<220> FEATURE:
<223> OTHER INFORMATION: Reverse Primer AFF1_E8_R

<400> SEQUENCE: 450
cgttccttgc tgagaatttg agt                                            23

<210> SEQ ID NO 451
<211> LENGTH: 21
<212> TYPE: DNA
<213> ORGANISM: Artificial Sequence
<220> FEATURE:
<223> OTHER INFORMATION: Reverse Primer CCAR2_exon4_R

<400> SEQUENCE: 451
agtcatgcaa gctggtaaca a                                              21

<210> SEQ ID NO 452
<211> LENGTH: 28
<212> TYPE: DNA
<213> ORGANISM: Artificial Sequence
<220> FEATURE:
<223> OTHER INFORMATION: Reverse Primer CCDC170_exon10_R

<400> SEQUENCE: 452
```
ggatttgttt agatcttcaa tggcttta                                28

<210> SEQ ID NO 453
<211> LENGTH: 27
<212> TYPE: DNA
<213> ORGANISM: Artificial Sequence
<220> FEATURE:
<223> OTHER INFORMATION: Reverse Primer CCDC170_exon6_R

<400> SEQUENCE: 453
taacttccct ttcaagagct tcttttg                                 27

<210> SEQ ID NO 454
<211> LENGTH: 22
<212> TYPE: DNA
<213> ORGANISM: Artificial Sequence
<220> FEATURE:
<223> OTHER INFORMATION: Reverse Primer CCDC170_exon7_R

<400> SEQUENCE: 454
caactgttca acaagctcag at                                      22

<210> SEQ ID NO 455
<211> LENGTH: 25
<212> TYPE: DNA
<213> ORGANISM: Artificial Sequence
<220> FEATURE:
<223> OTHER INFORMATION: Reverse Primer CCDC170_exon8_R

<400> SEQUENCE: 455
gccatctggt ccaacttcat tttct                                   25

<210> SEQ ID NO 456
<211> LENGTH: 27
<212> TYPE: DNA
<213> ORGANISM: Artificial Sequence
<220> FEATURE:
<223> OTHER INFORMATION: Reverse Primer CCDC170_exon9_R

<400> SEQUENCE: 456
ggaggctcat gtgtaattct ttgctct                                 27

<210> SEQ ID NO 457
<211> LENGTH: 21
<212> TYPE: DNA
<213> ORGANISM: Artificial Sequence
<220> FEATURE:
<223> OTHER INFORMATION: Reverse Primer CIT_exon23_R

<400> SEQUENCE: 457
agctgttacg aagagcatca a                                       21

<210> SEQ ID NO 458
<211> LENGTH: 19
<212> TYPE: DNA
<213> ORGANISM: Artificial Sequence
<220> FEATURE:
<223> OTHER INFORMATION: Reverse Primer EGFR_exon17a_R

<400> SEQUENCE: 458
gtggcgatgg acgggatct                                          19

<210> SEQ ID NO 459
<211> LENGTH: 19
<212> TYPE: DNA
<213> ORGANISM: Artificial Sequence

```
<220> FEATURE:
<223> OTHER INFORMATION: Reverse Primer EGFR_exon17b_R

<400> SEQUENCE: 459
gcatgaagag gccgatccc                                                    19

<210> SEQ ID NO 460
<211> LENGTH: 21
<212> TYPE: DNA
<213> ORGANISM: Artificial Sequence
<220> FEATURE:
<223> OTHER INFORMATION: Reverse Primer EGFR_exon8_R

<400> SEQUENCE: 460
tcctccatct catagctgtc g                                                 21

<210> SEQ ID NO 461
<211> LENGTH: 20
<212> TYPE: DNA
<213> ORGANISM: Artificial Sequence
<220> FEATURE:
<223> OTHER INFORMATION: Reverse Primer ERBB4_exon18_R

<400> SEQUENCE: 461
gagcttgatt gggtgctgtg                                                   20

<210> SEQ ID NO 462
<211> LENGTH: 21
<212> TYPE: DNA
<213> ORGANISM: Artificial Sequence
<220> FEATURE:
<223> OTHER INFORMATION: Reverse Primer ERG_exon6R

<400> SEQUENCE: 462
ttctttcacc gcccactcca g                                                 21

<210> SEQ ID NO 463
<211> LENGTH: 23
<212> TYPE: DNA
<213> ORGANISM: Artificial Sequence
<220> FEATURE:
<223> OTHER INFORMATION: Reverse Primer ERG_exon7R

<400> SEQUENCE: 463
ccgtggagag ttttgtaagg ctt                                               23

<210> SEQ ID NO 464
<211> LENGTH: 21
<212> TYPE: DNA
<213> ORGANISM: Artificial Sequence
<220> FEATURE:
<223> OTHER INFORMATION: Reverse Primer ETV1_exon10R

<400> SEQUENCE: 464
atcctcgccg ttggtatgtg g                                                 21

<210> SEQ ID NO 465
<211> LENGTH: 20
<212> TYPE: DNA
<213> ORGANISM: Artificial Sequence
<220> FEATURE:
<223> OTHER INFORMATION: Reverse Primer ETV1_exon8R

<400> SEQUENCE: 465
tcgtcggcaa aggaggaaag                                                   20
```

<210> SEQ ID NO 466
<211> LENGTH: 21
<212> TYPE: DNA
<213> ORGANISM: Artificial Sequence
<220> FEATURE:
<223> OTHER INFORMATION: Reverse Primer ETV1_exon9R

<400> SEQUENCE: 466
ggacaacaca ggtgtcatca t                                    21

<210> SEQ ID NO 467
<211> LENGTH: 19
<212> TYPE: DNA
<213> ORGANISM: Artificial Sequence
<220> FEATURE:
<223> OTHER INFORMATION: Reverse Primer FGFR1_exon7R

<400> SEQUENCE: 467
gccactgttt tgttggcgg                                       19

<210> SEQ ID NO 468
<211> LENGTH: 20
<212> TYPE: DNA
<213> ORGANISM: Artificial Sequence
<220> FEATURE:
<223> OTHER INFORMATION: Reverse Primer FLI1_exon3_R

<400> SEQUENCE: 468
agcttgctgc atttgctaac                                      20

<210> SEQ ID NO 469
<211> LENGTH: 21
<212> TYPE: DNA
<213> ORGANISM: Artificial Sequence
<220> FEATURE:
<223> OTHER INFORMATION: Reverse Primer FLI1_exon4_R

<400> SEQUENCE: 469
ttatggccca ctccagccat t                                    21

<210> SEQ ID NO 470
<211> LENGTH: 20
<212> TYPE: DNA
<213> ORGANISM: Artificial Sequence
<220> FEATURE:
<223> OTHER INFORMATION: Reverse Primer FLI1_exon5_R

<400> SEQUENCE: 470
atcgtgagga ttggtcggtg                                      20

<210> SEQ ID NO 471
<211> LENGTH: 21
<212> TYPE: DNA
<213> ORGANISM: Artificial Sequence
<220> FEATURE:
<223> OTHER INFORMATION: Reverse Primer FLI1_exon6_R

<400> SEQUENCE: 471
gttattgccc caagctcctc t                                    21

<210> SEQ ID NO 472
<211> LENGTH: 24
<212> TYPE: DNA
<213> ORGANISM: Artificial Sequence
<220> FEATURE:
<223> OTHER INFORMATION: Reverse Primer FLI1_exon7_R

<400> SEQUENCE: 472
tattcttact gatcgtttgt gccc                                    24

<210> SEQ ID NO 473
<211> LENGTH: 18
<212> TYPE: DNA
<213> ORGANISM: Artificial Sequence
<220> FEATURE:
<223> OTHER INFORMATION: Reverse Primer FLI1_exon8_R

<400> SEQUENCE: 473
gttggctagg cgactgct                                           18

<210> SEQ ID NO 474
<211> LENGTH: 23
<212> TYPE: DNA
<213> ORGANISM: Artificial Sequence
<220> FEATURE:
<223> OTHER INFORMATION: Reverse Primer FLI1_exon9_R

<400> SEQUENCE: 474
gagagcagct ccaggaggaa ttg                                     23

<210> SEQ ID NO 475
<211> LENGTH: 21
<212> TYPE: DNA
<213> ORGANISM: Artificial Sequence
<220> FEATURE:
<223> OTHER INFORMATION: Reverse Primer FOXO1_exon2_R

<400> SEQUENCE: 475
tctgcacacg aatgaacttg c                                       21

<210> SEQ ID NO 476
<211> LENGTH: 23
<212> TYPE: DNA
<213> ORGANISM: Artificial Sequence
<220> FEATURE:
<223> OTHER INFORMATION: Reverse Primer GPHN_exon11_R

<400> SEQUENCE: 476
gacatgcgat gtcttctagc cac                                     23

<210> SEQ ID NO 477
<211> LENGTH: 25
<212> TYPE: DNA
<213> ORGANISM: Artificial Sequence
<220> FEATURE:
<223> OTHER INFORMATION: Reverse Primer MBIP_exon4_R

<400> SEQUENCE: 477
cattgatttc agcttgcttt ctttc                                   25

<210> SEQ ID NO 478
<211> LENGTH: 20
<212> TYPE: DNA
<213> ORGANISM: Artificial Sequence
<220> FEATURE:
<223> OTHER INFORMATION: Reverse Primer MLLT3_E6_R_redsgn

<400> SEQUENCE: 478
tggtctggga tggtgtgaag                                         20

<210> SEQ ID NO 479

<211> LENGTH: 27
<212> TYPE: DNA
<213> ORGANISM: Artificial Sequence
<220> FEATURE:
<223> OTHER INFORMATION: Reverse Primer MX1_exon12_R

<400> SEQUENCE: 479
ccacgatact gattttcaaa tttctgg                               27

<210> SEQ ID NO 480
<211> LENGTH: 21
<212> TYPE: DNA
<213> ORGANISM: Artificial Sequence
<220> FEATURE:
<223> OTHER INFORMATION: Reverse Primer MX1_exon9_R

<400> SEQUENCE: 480 aagttttct gccaggcagg g                                      21

<210> SEQ ID NO 481
<211> LENGTH: 20
<212> TYPE: DNA
<213> ORGANISM: Artificial Sequence
<220> FEATURE:
<223> OTHER INFORMATION: Reverse Primer MYH11_E31_R_rdsgn

<400> SEQUENCE: 481
ctcttccaga gcttccacgg                                       20

<210> SEQ ID NO 482
<211> LENGTH: 24
<212> TYPE: DNA
<213> ORGANISM: Artificial Sequence
<220> FEATURE:
<223> OTHER INFORMATION: Reverse Primer NCOA3_exon14_R

<400> SEQUENCE: 482
ctgctcggtt atatggagga cgaa                                  24

<210> SEQ ID NO 483
<211> LENGTH: 22
<212> TYPE: DNA
<213> ORGANISM: Artificial Sequence
<220> FEATURE:
<223> OTHER INFORMATION: Reverse Primer NCOA3_exon15_R

<400> SEQUENCE: 483
taagccccag tctcctgagg aa                                    22

<210> SEQ ID NO 484
<211> LENGTH: 20
<212> TYPE: DNA
<213> ORGANISM: Artificial Sequence
<220> FEATURE:
<223> OTHER INFORMATION: Reverse Primer NFIB_exon10_R

<400> SEQUENCE: 484
gggcttagtc ccacatatcg                                       20

<210> SEQ ID NO 485
<211> LENGTH: 20
<212> TYPE: DNA
<213> ORGANISM: Artificial Sequence
<220> FEATURE:
<223> OTHER INFORMATION: Reverse Primer NFIB_exon11_R

<400> SEQUENCE: 485

```
ggggtataaa tgcctgccgt                                               20

<210> SEQ ID NO 486
<211> LENGTH: 26
<212> TYPE: DNA
<213> ORGANISM: Artificial Sequence
<220> FEATURE:
<223> OTHER INFORMATION: Reverse Primer NFIB_exon12_R

<400> SEQUENCE: 486
agatgggtgt cctatttgac acttgg                                        26

<210> SEQ ID NO 487
<211> LENGTH: 20
<212> TYPE: DNA
<213> ORGANISM: Artificial Sequence
<220> FEATURE:
<223> OTHER INFORMATION: Reverse Primer NFIB_exon9_R

<400> SEQUENCE: 487
gccaggcact ttccctacta                                               20

<210> SEQ ID NO 488
<211> LENGTH: 22
<212> TYPE: DNA
<213> ORGANISM: Artificial Sequence
<220> FEATURE:
<223> OTHER INFORMATION: Reverse Primer NTRK2_exon14R

<400> SEQUENCE: 488
aaaggcaaaa tcccaccaca ga                                            22

<210> SEQ ID NO 489
<211> LENGTH: 28
<212> TYPE: DNA
<213> ORGANISM: Artificial Sequence
<220> FEATURE:
<223> OTHER INFORMATION: Reverse Primer NTRK2_exon15R

<400> SEQUENCE: 489
caacaccttg tcttgatttt actttccc                                      28

<210> SEQ ID NO 490
<211> LENGTH: 20
<212> TYPE: DNA
<213> ORGANISM: Artificial Sequence
<220> FEATURE:
<223> OTHER INFORMATION: Reverse Primer NTRK2_exon17_R

<400> SEQUENCE: 490
ttcgcctagc tccctttca                                                20

<210> SEQ ID NO 491
<211> LENGTH: 21
<212> TYPE: DNA
<213> ORGANISM: Artificial Sequence
<220> FEATURE:
<223> OTHER INFORMATION: Reverse Primer NTRK3_exon13R

<400> SEQUENCE: 491
agaaccacca acaggacaca g                                             21

<210> SEQ ID NO 492
<211> LENGTH: 21
<212> TYPE: DNA
```

```
<213> ORGANISM: Artificial Sequence
<220> FEATURE:
<223> OTHER INFORMATION: Reverse Primer PDGFRA_exon2_R

<400> SEQUENCE: 492
acagcctaag accaggaacg c                                              21

<210> SEQ ID NO 493
<211> LENGTH: 27
<212> TYPE: DNA
<213> ORGANISM: Artificial Sequence
<220> FEATURE:
<223> OTHER INFORMATION: Reverse Primer PPARG_exon7_R

<400> SEQUENCE: 493
aggttgtctt gaatgtcttc aatgggc                                        27

<210> SEQ ID NO 494
<211> LENGTH: 22
<212> TYPE: DNA
<213> ORGANISM: Artificial Sequence
<220> FEATURE:
<223> OTHER INFORMATION: Reverse Primer RET_exon10_R

<400> SEQUENCE: 494
gtgccatagc cagctttaat cc                                             22

<210> SEQ ID NO 495
<211> LENGTH: 19
<212> TYPE: DNA
<213> ORGANISM: Artificial Sequence
<220> FEATURE:
<223> OTHER INFORMATION: Reverse Primer RET_exon9_R

<400> SEQUENCE: 495
caggtcttgg tgctgggag                                                 19

<210> SEQ ID NO 496
<211> LENGTH: 28
<212> TYPE: DNA
<213> ORGANISM: Artificial Sequence
<220> FEATURE:
<223> OTHER INFORMATION: Reverse Primer ROS1_exon32_R_rdsgn

<400> SEQUENCE: 496
gaatttttac tcccttctag taatttgg                                       28

<210> SEQ ID NO 497
<211> LENGTH: 22
<212> TYPE: DNA
<213> ORGANISM: Artificial Sequence
<220> FEATURE:
<223> OTHER INFORMATION: Reverse Primer ROS1_exon33R

<400> SEQUENCE: 497
ttccatgtgc aaacactact gc                                             22

<210> SEQ ID NO 498
<211> LENGTH: 23
<212> TYPE: DNA
<213> ORGANISM: Artificial Sequence
<220> FEATURE:
<223> OTHER INFORMATION: Reverse Primer SEPT14_exon10_R

<400> SEQUENCE: 498
gcttccttat ctcctcctgt tga                                            23
```

<210> SEQ ID NO 499
<211> LENGTH: 21
<212> TYPE: DNA
<213> ORGANISM: Artificial Sequence
<220> FEATURE:
<223> OTHER INFORMATION: Reverse Primer SSX1_exon4_R

<400> SEQUENCE: 499
ctggaagtct gtggcctgtt t                                          21

<210> SEQ ID NO 500
<211> LENGTH: 20
<212> TYPE: DNA
<213> ORGANISM: Artificial Sequence
<220> FEATURE:
<223> OTHER INFORMATION: Reverse Primer SSX1_exon5_R

<400> SEQUENCE: 500
gggatgattc tgtggagcct                                            20

<210> SEQ ID NO 501
<211> LENGTH: 20
<212> TYPE: DNA
<213> ORGANISM: Artificial Sequence
<220> FEATURE:
<223> OTHER INFORMATION: Reverse Primer SSX1_exon6_R

<400> SEQUENCE: 501
tgcttctgac actcccttcg                                            20

<210> SEQ ID NO 502
<211> LENGTH: 27
<212> TYPE: DNA
<213> ORGANISM: Artificial Sequence
<220> FEATURE:
<223> OTHER INFORMATION: Reverse Primer SSX2_exon3_R

<400> SEQUENCE: 502
tcatcttttc ccactcttcc ttagaga                                    27

<210> SEQ ID NO 503
<211> LENGTH: 22
<212> TYPE: DNA
<213> ORGANISM: Artificial Sequence
<220> FEATURE:
<223> OTHER INFORMATION: Reverse Primer SSX2_exon4_R

<400> SEQUENCE: 503
agtcttcggc ccgtttatta ca                                         22

<210> SEQ ID NO 504
<211> LENGTH: 21
<212> TYPE: DNA
<213> ORGANISM: Artificial Sequence
<220> FEATURE:
<223> OTHER INFORMATION: Reverse Primer SSX2_exon5_R

<400> SEQUENCE: 504
cttcggggag attccctgga g                                          21

<210> SEQ ID NO 505
<211> LENGTH: 20
<212> TYPE: DNA
<213> ORGANISM: Artificial Sequence
<220> FEATURE:

<223> OTHER INFORMATION: Reverse Primer SSX2_exon6_R

<400> SEQUENCE: 505
ctggcacttc ctccgaatca                                               20

<210> SEQ ID NO 506
<211> LENGTH: 21
<212> TYPE: DNA
<213> ORGANISM: Artificial Sequence
<220> FEATURE:
<223> OTHER INFORMATION: Reverse Primer TACC3_exon13a_R

<400> SEQUENCE: 506
ccttctgctt ctgaacttcc t                                             21

<210> SEQ ID NO 507
<211> LENGTH: 30
<212> TYPE: DNA
<213> ORGANISM: Artificial Sequence
<220> FEATURE:
<223> OTHER INFORMATION: Reverse Primer TACC3_exon13b_R

<400> SEQUENCE: 507
ttggtctttt tcttttagaa ctttctggat                                    30

<210> SEQ ID NO 508
<211> LENGTH: 18
<212> TYPE: DNA
<213> ORGANISM: Artificial Sequence
<220> FEATURE:
<223> OTHER INFORMATION: Reverse Primer TACC3_exon5_R

<400> SEQUENCE: 508
tgccaactgc accacagg                                                 18

<210> SEQ ID NO 509
<211> LENGTH: 25
<212> TYPE: DNA
<213> ORGANISM: Artificial Sequence
<220> FEATURE:
<223> OTHER INFORMATION: Reverse Primer TACC3_exon7R

<400> SEQUENCE: 509
aggaagttcc aaactgctcc aggta                                         25

<210> SEQ ID NO 510
<211> LENGTH: 21
<212> TYPE: DNA
<213> ORGANISM: Artificial Sequence
<220> FEATURE:
<223> OTHER INFORMATION: Reverse Primer TACC3_exon9R

<400> SEQUENCE: 510
aagaaatcga actccacaag c                                             21

<210> SEQ ID NO 511
<211> LENGTH: 21
<212> TYPE: DNA
<213> ORGANISM: Artificial Sequence
<220> FEATURE:
<223> OTHER INFORMATION: Reverse Primer TACC3_midExon4_R

<400> SEQUENCE: 511
tctccgcttt gcattcttcc t                                             21

```
<210> SEQ ID NO 512
<211> LENGTH: 20
<212> TYPE: DNA
<213> ORGANISM: Artificial Sequence
<220> FEATURE:
<223> OTHER INFORMATION: Reverse Primer YAP1_exon5_R

<400> SEQUENCE: 512
gtggctgttt cactggagca                                               20

<210> SEQ ID NO 513
<211> LENGTH: 23
<212> TYPE: DNA
<213> ORGANISM: Artificial Sequence
<220> FEATURE:
<223> OTHER INFORMATION: Forward Primer TBP_F_rdsgn

<400> SEQUENCE: 513
ctttgcagtg acccagcatc act                                           23

<210> SEQ ID NO 514
<211> LENGTH: 20
<212> TYPE: DNA
<213> ORGANISM: Artificial Sequence
<220> FEATURE:
<223> OTHER INFORMATION: Forward Primer ITGB7-F

<400> SEQUENCE: 514
gcacgcacct atgtggaaac                                               20

<210> SEQ ID NO 515
<211> LENGTH: 22
<212> TYPE: DNA
<213> ORGANISM: Artificial Sequence
<220> FEATURE:
<223> OTHER INFORMATION: Forward Primer PSMB2_F_rdsgn

<400> SEQUENCE: 515
tcttcggagt cggaccccat at                                            22

<210> SEQ ID NO 516
<211> LENGTH: 22
<212> TYPE: DNA
<213> ORGANISM: Artificial Sequence
<220> FEATURE:
<223> OTHER INFORMATION: Forward Primer EMC7_A_F

<400> SEQUENCE: 516
tcggtttcct taagacagat gg                                            22

<210> SEQ ID NO 517
<211> LENGTH: 25
<212> TYPE: DNA
<213> ORGANISM: Artificial Sequence
<220> FEATURE:
<223> OTHER INFORMATION: Forward Primer EMC7_B_F_rdsgn

<400> SEQUENCE: 517
actttctaat gaacccaatg gttat                                         25

<210> SEQ ID NO 518
<211> LENGTH: 20
<212> TYPE: DNA
<213> ORGANISM: Artificial Sequence
<220> FEATURE:
<223> OTHER INFORMATION: Forward Primer GPI_F
```

```
<400> SEQUENCE: 518
gcatcacaag atcctcctgg                                                    20

<210> SEQ ID NO 519
<211> LENGTH: 23
<212> TYPE: DNA
<213> ORGANISM: Artificial Sequence
<220> FEATURE:
<223> OTHER INFORMATION: Forward Primer REEP5_F

<400> SEQUENCE: 519
ccagcctaca tctcaattaa agc                                                23

<210> SEQ ID NO 520
<211> LENGTH: 18
<212> TYPE: DNA
<213> ORGANISM: Artificial Sequence
<220> FEATURE:
<223> OTHER INFORMATION: Forward Primer RRP1_F_rdsgn

<400> SEQUENCE: 520
cgggccgcag gtggtttt                                                      18

<210> SEQ ID NO 521
<211> LENGTH: 23
<212> TYPE: DNA
<213> ORGANISM: Artificial Sequence
<220> FEATURE:
<223> OTHER INFORMATION: Forward Primer CHFR_F

<400> SEQUENCE: 521
agtattgtga ttacagggtc tgg                                                23

<210> SEQ ID NO 522
<211> LENGTH: 24
<212> TYPE: DNA
<213> ORGANISM: Artificial Sequence
<220> FEATURE:
<223> OTHER INFORMATION: Forward Primer REL_F

<400> SEQUENCE: 522
gaatcaatcc attcaatgtc cctg                                               24

<210> SEQ ID NO 523
<211> LENGTH: 27
<212> TYPE: DNA
<213> ORGANISM: Artificial Sequence
<220> FEATURE:
<223> OTHER INFORMATION: Forward Primer NASP_F_rdsgn

<400> SEQUENCE: 523
caggaagcag ctagtctttt aggtaag                                            27

<210> SEQ ID NO 524
<211> LENGTH: 23
<212> TYPE: DNA
<213> ORGANISM: Artificial Sequence
<220> FEATURE:
<223> OTHER INFORMATION: Forward Primer POMK_F_rdsgn_2

<400> SEQUENCE: 524
gaaggagctg taaagagagt ctt                                                23

<210> SEQ ID NO 525
<211> LENGTH: 22
```

```
<212> TYPE: DNA
<213> ORGANISM: Artificial Sequence
<220> FEATURE:
<223> OTHER INFORMATION: Forward Primer FRMD8_F

<400> SEQUENCE: 525
gatagcagag agaagcatgt cc                                              22

<210> SEQ ID NO 526
<211> LENGTH: 19
<212> TYPE: DNA
<213> ORGANISM: Artificial Sequence
<220> FEATURE:
<223> OTHER INFORMATION: Forward Primer SLC4A1AP_A_F_rdsgn

<400> SEQUENCE: 526
tcggcaggaa gcagtatct                                                  19

<210> SEQ ID NO 527
<211> LENGTH: 22
<212> TYPE: DNA
<213> ORGANISM: Artificial Sequence
<220> FEATURE:
<223> OTHER INFORMATION: Forward Primer SNAP29_F

<400> SEQUENCE: 527
gatcgacagc aacctagatg ag                                              22

<210> SEQ ID NO 528
<211> LENGTH: 28
<212> TYPE: DNA
<213> ORGANISM: Artificial Sequence
<220> FEATURE:
<223> OTHER INFORMATION: Forward Primer TUBGCP2_A_F_rdsgn

<400> SEQUENCE: 528
catccacgac ccatacagtg agtttatg                                        28

<210> SEQ ID NO 529
<211> LENGTH: 26
<212> TYPE: DNA
<213> ORGANISM: Artificial Sequence
<220> FEATURE:
<223> OTHER INFORMATION: Forward Primer SNRPD3_F_rdsgn

<400> SEQUENCE: 529
gacaacatga actgccagat gtccaa                                          26

<210> SEQ ID NO 530
<211> LENGTH: 25
<212> TYPE: DNA
<213> ORGANISM: Artificial Sequence
<220> FEATURE:
<223> OTHER INFORMATION: Forward Primer PUM1_F

<400> SEQUENCE: 530
tcagaccagc aggtaattaa tgaga                                           25

<210> SEQ ID NO 531
<211> LENGTH: 24
<212> TYPE: DNA
<213> ORGANISM: Artificial Sequence
<220> FEATURE:
<223> OTHER INFORMATION: Forward Primer CIAO1_F

<400> SEQUENCE: 531
```

```
cgtttgggtc tgggaagttg atga                                              24

<210> SEQ ID NO 532
<211> LENGTH: 21
<212> TYPE: DNA
<213> ORGANISM: Artificial Sequence
<220> FEATURE:
<223> OTHER INFORMATION: Forward Primer SRSF4_F

<400> SEQUENCE: 532
tggaactgaa gtcaatggga g                                                 21

<210> SEQ ID NO 533
<211> LENGTH: 20
<212> TYPE: DNA
<213> ORGANISM: Artificial Sequence
<220> FEATURE:
<223> OTHER INFORMATION: Forward Primer VCP_E1-2_F_new

<400> SEQUENCE: 533
gcttctggag ccgattcaaa                                                   20

<210> SEQ ID NO 534
<211> LENGTH: 20
<212> TYPE: DNA
<213> ORGANISM: Artificial Sequence
<220> FEATURE:
<223> OTHER INFORMATION: Forward Primer RER1_E3_F_new

<400> SEQUENCE: 534
ggctagacaa gtccacaccc                                                   20

<210> SEQ ID NO 535
<211> LENGTH: 20
<212> TYPE: DNA
<213> ORGANISM: Artificial Sequence
<220> FEATURE:
<223> OTHER INFORMATION: Forward Primer CHMP2A_E2-3_F

<400> SEQUENCE: 535
aagcaaggcc agatggatgc                                                   20

<210> SEQ ID NO 536
<211> LENGTH: 20
<212> TYPE: DNA
<213> ORGANISM: Artificial Sequence
<220> FEATURE:
<223> OTHER INFORMATION: Forward Primer RAB7A_E1_F

<400> SEQUENCE: 536
gtttagtctc ctcctcggcg                                                   20

<210> SEQ ID NO 537
<211> LENGTH: 15
<212> TYPE: DNA
<213> ORGANISM: Artificial Sequence
<220> FEATURE:
<223> OTHER INFORMATION: Forward Primer ACTB_F

<400> SEQUENCE: 537
gagaccgcgt ccgcc                                                        15

<210> SEQ ID NO 538
<211> LENGTH: 20
<212> TYPE: DNA
<213> ORGANISM: Artificial Sequence
```

```
<220> FEATURE:
<223> OTHER INFORMATION: Reverse Primer TBP-R

<400> SEQUENCE: 538
gcatctccag cacactcttc                                                    20

<210> SEQ ID NO 539
<211> LENGTH: 22
<212> TYPE: DNA
<213> ORGANISM: Artificial Sequence
<220> FEATURE:
<223> OTHER INFORMATION: Reverse Primer ITGB7-R

<400> SEQUENCE: 539
agccaaacag gaaacagacc ag                                                 22

<210> SEQ ID NO 540
<211> LENGTH: 22
<212> TYPE: DNA
<213> ORGANISM: Artificial Sequence
<220> FEATURE:
<223> OTHER INFORMATION: Reverse Primer PSMB2-R

<400> SEQUENCE: 540
aggtagtcca tgtaatacag cg                                                 22

<210> SEQ ID NO 541
<211> LENGTH: 22
<212> TYPE: DNA
<213> ORGANISM: Artificial Sequence
<220> FEATURE:
<223> OTHER INFORMATION: Reverse Primer EMC7_A-R

<400> SEQUENCE: 541
acgggatcaa atctgtaagc tg                                                 22

<210> SEQ ID NO 542
<211> LENGTH: 22
<212> TYPE: DNA
<213> ORGANISM: Artificial Sequence
<220> FEATURE:
<223> OTHER INFORMATION: Reverse Primer EMC7_B-R

<400> SEQUENCE: 542
gtctcatgtc aggatcactt gt                                                 22

<210> SEQ ID NO 543
<211> LENGTH: 20
<212> TYPE: DNA
<213> ORGANISM: Artificial Sequence
<220> FEATURE:
<223> OTHER INFORMATION: Reverse Primer GPI-R

<400> SEQUENCE: 543
aaggtcctct ggactcttgc                                                    20

<210> SEQ ID NO 544
<211> LENGTH: 25
<212> TYPE: DNA
<213> ORGANISM: Artificial Sequence
<220> FEATURE:
<223> OTHER INFORMATION: Reverse Primer REEP5-R

<400> SEQUENCE: 544
ccatgacagg aagatatcag agaag                                              25
```

<210> SEQ ID NO 545
<211> LENGTH: 18
<212> TYPE: DNA
<213> ORGANISM: Artificial Sequence
<220> FEATURE:
<223> OTHER INFORMATION: Reverse Primer RRP1_R

<400> SEQUENCE: 545
ctggaggagt ggcttgtc                                                 18

<210> SEQ ID NO 546
<211> LENGTH: 20
<212> TYPE: DNA
<213> ORGANISM: Artificial Sequence
<220> FEATURE:
<223> OTHER INFORMATION: Reverse Primer CHFR-R

<400> SEQUENCE: 546
ctttctgtct gggagagctg                                               20

<210> SEQ ID NO 547
<211> LENGTH: 25
<212> TYPE: DNA
<213> ORGANISM: Artificial Sequence
<220> FEATURE:
<223> OTHER INFORMATION: Reverse Primer REL-R

<400> SEQUENCE: 547
catgttcatc agggagaaaa acttg                                         25

<210> SEQ ID NO 548
<211> LENGTH: 20
<212> TYPE: DNA
<213> ORGANISM: Artificial Sequence
<220> FEATURE:
<223> OTHER INFORMATION: Reverse Primer NASP-R

<400> SEQUENCE: 548
cttgccaact ccagaagtga                                               20

<210> SEQ ID NO 549
<211> LENGTH: 22
<212> TYPE: DNA
<213> ORGANISM: Artificial Sequence
<220> FEATURE:
<223> OTHER INFORMATION: Reverse Primer POMK-R

<400> SEQUENCE: 549
ccttggagag atttcagcat ct                                            22

<210> SEQ ID NO 550
<211> LENGTH: 19
<212> TYPE: DNA
<213> ORGANISM: Artificial Sequence
<220> FEATURE:
<223> OTHER INFORMATION: Reverse Primer FRMD8-R

<400> SEQUENCE: 550
gaactccagc cacaagatg                                                19

<210> SEQ ID NO 551
<211> LENGTH: 22
<212> TYPE: DNA
<213> ORGANISM: Artificial Sequence
<220> FEATURE:
<223> OTHER INFORMATION: Reverse Primer SLC4A1AP_A-R

<400> SEQUENCE: 551
tcagacgctt cttctcaatc ag                                            22

<210> SEQ ID NO 552
<211> LENGTH: 24
<212> TYPE: DNA
<213> ORGANISM: Artificial Sequence
<220> FEATURE:
<223> OTHER INFORMATION: Reverse Primer SNAP29-R

<400> SEQUENCE: 552
tgtcatcttg ctcctcaatt tctg                                          24

<210> SEQ ID NO 553
<211> LENGTH: 22
<212> TYPE: DNA
<213> ORGANISM: Artificial Sequence
<220> FEATURE:
<223> OTHER INFORMATION: Reverse Primer TUBGCP2_A-R

<400> SEQUENCE: 553
acttgtcgtt gtaatcctcc tg                                            22

<210> SEQ ID NO 554
<211> LENGTH: 19
<212> TYPE: DNA
<213> ORGANISM: Artificial Sequence
<220> FEATURE:
<223> OTHER INFORMATION: Reverse Primer SNRPD3-R

<400> SEQUENCE: 554
gattttgctg ccacggatg                                                19

<210> SEQ ID NO 555
<211> LENGTH: 20
<212> TYPE: DNA
<213> ORGANISM: Artificial Sequence
<220> FEATURE:
<223> OTHER INFORMATION: Reverse Primer PUM1_R

<400> SEQUENCE: 555
accacgtgat tgccattctg                                               20

<210> SEQ ID NO 556
<211> LENGTH: 20
<212> TYPE: DNA
<213> ORGANISM: Artificial Sequence
<220> FEATURE:
<223> OTHER INFORMATION: Reverse Primer CIAO1_R

<400> SEQUENCE: 556
gccaaaccac atgcttgaca                                               20

<210> SEQ ID NO 557
<211> LENGTH: 22
<212> TYPE: DNA
<213> ORGANISM: Artificial Sequence
<220> FEATURE:
<223> OTHER INFORMATION: Reverse Primer SRSF4_R

<400> SEQUENCE: 557
cttcgagagc gagaccttga at                                            22

<210> SEQ ID NO 558

<211> LENGTH: 21
<212> TYPE: DNA
<213> ORGANISM: Artificial Sequence
<220> FEATURE:
<223> OTHER INFORMATION: Reverse Primer VCP_E2_R_new

<400> SEQUENCE: 558
acaattaacc gattgggacg g    21

<210> SEQ ID NO 559
<211> LENGTH: 21
<212> TYPE: DNA
<213> ORGANISM: Artificial Sequence
<220> FEATURE:
<223> OTHER INFORMATION: Reverse Primer RER1_E3-4_R_new

<400> SEQUENCE: 559
gtcacaatgt accaaccctg c    21

<210> SEQ ID NO 560
<211> LENGTH: 20
<212> TYPE: DNA
<213> ORGANISM: Artificial Sequence
<220> FEATURE:
<223> OTHER INFORMATION: Reverse Primer CHMP2A_E3_R

<400> SEQUENCE: 560
ttgagggaca cagcctggat    20

<210> SEQ ID NO 561
<211> LENGTH: 20
<212> TYPE: DNA
<213> ORGANISM: Artificial Sequence
<220> FEATURE:
<223> OTHER INFORMATION: Reverse Primer RAB7A_E1-2_R

<400> SEQUENCE: 561
aggtcatcct tcaaacgcgg    20

<210> SEQ ID NO 562
<211> LENGTH: 20
<212> TYPE: DNA
<213> ORGANISM: Artificial Sequence
<220> FEATURE:
<223> OTHER INFORMATION: Reverse Primer ACTB_R

<400> SEQUENCE: 562
atcatccatg gtgagctggc    20

<210> SEQ ID NO 563
<211> LENGTH: 26
<212> TYPE: DNA
<213> ORGANISM: Artificial Sequence
<220> FEATURE:
<223> OTHER INFORMATION: Forward Primer CD274_3UTR_F

<400> SEQUENCE: 563
caaagaagca aagtgataca catttg    26

<210> SEQ ID NO 564
<211> LENGTH: 24
<212> TYPE: DNA
<213> ORGANISM: Artificial Sequence
<220> FEATURE:
<223> OTHER INFORMATION: Forward Primer CD274_EXON4_F

<400> SEQUENCE: 564

```
gtgaaagtca atgccccata caac                                              24

<210> SEQ ID NO 565
<211> LENGTH: 24
<212> TYPE: DNA
<213> ORGANISM: Artificial Sequence
<220> FEATURE:
<223> OTHER INFORMATION: Forward Primer CD274_EXON3_F

<400> SEQUENCE: 565
ggcatttgct gaacgcattt actg                                              24

<210> SEQ ID NO 566
<211> LENGTH: 20
<212> TYPE: DNA
<213> ORGANISM: Artificial Sequence
<220> FEATURE:
<223> OTHER INFORMATION: Forward Primer PDCD1-EXON3_4_5_F

<400> SEQUENCE: 566
ccgcacgagg gacaatagga                                                   20

<210> SEQ ID NO 567
<211> LENGTH: 23
<212> TYPE: DNA
<213> ORGANISM: Artificial Sequence
<220> FEATURE:
<223> OTHER INFORMATION: Forward Primer CTLA4-EXON1_2_F

<400> SEQUENCE: 567
cttctcttca tccctgtctt ctg                                               23

<210> SEQ ID NO 568
<211> LENGTH: 28
<212> TYPE: DNA
<213> ORGANISM: Artificial Sequence
<220> FEATURE:
<223> OTHER INFORMATION: Forward Primer CTLA4-EXON4_F

<400> SEQUENCE: 568
gctgtttctt tgagcaaaat gctaaaga                                          28

<210> SEQ ID NO 569
<211> LENGTH: 22
<212> TYPE: DNA
<213> ORGANISM: Artificial Sequence
<220> FEATURE:
<223> OTHER INFORMATION: Forward Primer CD47-EXON3_F

<400> SEQUENCE: 569
gaaggtgaaa cgatcatcga gc                                                22

<210> SEQ ID NO 570
<211> LENGTH: 25
<212> TYPE: DNA
<213> ORGANISM: Artificial Sequence
<220> FEATURE:
<223> OTHER INFORMATION: Forward Primer CD47-EXON9_10_11_F

<400> SEQUENCE: 570
gaggaacccc ttaatgcatt caaag                                             25

<210> SEQ ID NO 571
<211> LENGTH: 22
<212> TYPE: DNA
```

```
<213> ORGANISM: Artificial Sequence
<220> FEATURE:
<223> OTHER INFORMATION: Forward Primer LAG3-EXON8_F

<400> SEQUENCE: 571
ctttggagaa gacagtggcg ac                                              22

<210> SEQ ID NO 572
<211> LENGTH: 20
<212> TYPE: DNA
<213> ORGANISM: Artificial Sequence
<220> FEATURE:
<223> OTHER INFORMATION: Forward Primer LAG3_EXON2-F_rdsgn

<400> SEQUENCE: 572
tttgggtggc tccagtgaag                                                 20

<210> SEQ ID NO 573
<211> LENGTH: 23
<212> TYPE: DNA
<213> ORGANISM: Artificial Sequence
<220> FEATURE:
<223> OTHER INFORMATION: Forward Primer HAVCR2_EXON3-F_rdsgn

<400> SEQUENCE: 573
agttggtcat caaaccagcc aag                                             23

<210> SEQ ID NO 574
<211> LENGTH: 30
<212> TYPE: DNA
<213> ORGANISM: Artificial Sequence
<220> FEATURE:
<223> OTHER INFORMATION: Forward Primer HAVCR2_EXON7-F_rdsgn

<400> SEQUENCE: 574
caaagagaag atacagaatt taagcctcat                                      30

<210> SEQ ID NO 575
<211> LENGTH: 22
<212> TYPE: DNA
<213> ORGANISM: Artificial Sequence
<220> FEATURE:
<223> OTHER INFORMATION: Forward Primer PDCD1_EXON2-F_rdsgn

<400> SEQUENCE: 575
gccaggatgg ttcttagact cc                                              22

<210> SEQ ID NO 576
<211> LENGTH: 22
<212> TYPE: DNA
<213> ORGANISM: Artificial Sequence
<220> FEATURE:
<223> OTHER INFORMATION: Forward Primer CD14_exon1_1F

<400> SEQUENCE: 576
gaagacttat cgaccatgga gc                                              22

<210> SEQ ID NO 577
<211> LENGTH: 20
<212> TYPE: DNA
<213> ORGANISM: Artificial Sequence
<220> FEATURE:
<223> OTHER INFORMATION: Forward Primer CD27_exon1-2_1F

<400> SEQUENCE: 577
cagatgtgtg agccaggaac                                                 20
```

-continued

<210> SEQ ID NO 578
<211> LENGTH: 22
<212> TYPE: DNA
<213> ORGANISM: Artificial Sequence
<220> FEATURE:
<223> OTHER INFORMATION: Forward Primer CD39_exon1_1F

<400> SEQUENCE: 578
cttgagaaag gattgctggt ca                                            22

<210> SEQ ID NO 579
<211> LENGTH: 21
<212> TYPE: DNA
<213> ORGANISM: Artificial Sequence
<220> FEATURE:
<223> OTHER INFORMATION: Forward Primer CD40_exon6-7_1F

<400> SEQUENCE: 579
gactgatgtt gtctgtggtc c                                             21

<210> SEQ ID NO 580
<211> LENGTH: 19
<212> TYPE: DNA
<213> ORGANISM: Artificial Sequence
<220> FEATURE:
<223> OTHER INFORMATION: Forward Primer CD70_exon1_2F

<400> SEQUENCE: 580
cttggtgatc tgcctcgtg                                                19

<210> SEQ ID NO 581
<211> LENGTH: 22
<212> TYPE: DNA
<213> ORGANISM: Artificial Sequence
<220> FEATURE:
<223> OTHER INFORMATION: Forward Primer CD80_exon1_1F

<400> SEQUENCE: 581
tctcagaagt ggagtcttac cc                                            22

<210> SEQ ID NO 582
<211> LENGTH: 21
<212> TYPE: DNA
<213> ORGANISM: Artificial Sequence
<220> FEATURE:
<223> OTHER INFORMATION: Forward Primer FOXP3_exon6-7_1F

<400> SEQUENCE: 582
agaggacttc ctcaagcact g                                             21

<210> SEQ ID NO 583
<211> LENGTH: 20
<212> TYPE: DNA
<213> ORGANISM: Artificial Sequence
<220> FEATURE:
<223> OTHER INFORMATION: Forward Primer ICOS_exon3_1F

<400> SEQUENCE: 583
tgtgcagcct ttgttgtagt                                               20

<210> SEQ ID NO 584
<211> LENGTH: 22
<212> TYPE: DNA
<213> ORGANISM: Artificial Sequence
<220> FEATURE:

<223> OTHER INFORMATION: Forward Primer ICOS_exon1-2_2F

<400> SEQUENCE: 584
gcattaaagt tttaacagga ga                                              22

<210> SEQ ID NO 585
<211> LENGTH: 20
<212> TYPE: DNA
<213> ORGANISM: Artificial Sequence
<220> FEATURE:
<223> OTHER INFORMATION: Forward Primer TIGIT_exon3_1F

<400> SEQUENCE: 585
agattccatt gcttggagcc                                                 20

<210> SEQ ID NO 586
<211> LENGTH: 22
<212> TYPE: DNA
<213> ORGANISM: Artificial Sequence
<220> FEATURE:
<223> OTHER INFORMATION: Forward Primer TNFRSF18_exon2-3_1F

<400> SEQUENCE: 586
tacagtccca ggggaaattc ag                                              22

<210> SEQ ID NO 587
<211> LENGTH: 20
<212> TYPE: DNA
<213> ORGANISM: Artificial Sequence
<220> FEATURE:
<223> OTHER INFORMATION: Forward Primer VISTA_exon4-5_1F

<400> SEQUENCE: 587
tgcggatgga cagcaacatt                                                 20

<210> SEQ ID NO 588
<211> LENGTH: 23
<212> TYPE: DNA
<213> ORGANISM: Artificial Sequence
<220> FEATURE:
<223> OTHER INFORMATION: Forward Primer VISTA_exon2-3_2F

<400> SEQUENCE: 588
cctcccagga tagtgaaaac atc                                             23

<210> SEQ ID NO 589
<211> LENGTH: 23
<212> TYPE: DNA
<213> ORGANISM: Artificial Sequence
<220> FEATURE:
<223> OTHER INFORMATION: Reverse Primer CD274_3UTR_R

<400> SEQUENCE: 589
gaacccctaa accacaggtt gag                                             23

<210> SEQ ID NO 590
<211> LENGTH: 24
<212> TYPE: DNA
<213> ORGANISM: Artificial Sequence
<220> FEATURE:
<223> OTHER INFORMATION: Reverse Primer CD274_EXON4_R

<400> SEQUENCE: 590
ctcagcctga catgtcagtt catg                                            24

```
<210> SEQ ID NO 591
<211> LENGTH: 26
<212> TYPE: DNA
<213> ORGANISM: Artificial Sequence
<220> FEATURE:
<223> OTHER INFORMATION: Reverse Primer CD274_EXON3_R

<400> SEQUENCE: 591
ctactgggaa tttgcattca attgtc                                      26

<210> SEQ ID NO 592
<211> LENGTH: 20
<212> TYPE: DNA
<213> ORGANISM: Artificial Sequence
<220> FEATURE:
<223> OTHER INFORMATION: Reverse Primer PDCD1_EXON2_R

<400> SEQUENCE: 592
agaagctgca ggtgaaggtg                                             20

<210> SEQ ID NO 593
<211> LENGTH: 22
<212> TYPE: DNA
<213> ORGANISM: Artificial Sequence
<220> FEATURE:
<223> OTHER INFORMATION: Reverse Primer PDCD1-EXON3_4_5_R

<400> SEQUENCE: 593
ggaaatccag ctccccatag tc                                          22

<210> SEQ ID NO 594
<211> LENGTH: 22
<212> TYPE: DNA
<213> ORGANISM: Artificial Sequence
<220> FEATURE:
<223> OTHER INFORMATION: Reverse Primer CTLA4-EXON1_2_R

<400> SEQUENCE: 594
gcatactcac acacaaagct gg                                          22

<210> SEQ ID NO 595
<211> LENGTH: 23
<212> TYPE: DNA
<213> ORGANISM: Artificial Sequence
<220> FEATURE:
<223> OTHER INFORMATION: Reverse Primer CTLA4-EXON4_R

<400> SEQUENCE: 595
ttgcttttca cattctggct ctg                                         23

<210> SEQ ID NO 596
<211> LENGTH: 23
<212> TYPE: DNA
<213> ORGANISM: Artificial Sequence
<220> FEATURE:
<223> OTHER INFORMATION: Reverse Primer CD47-EXON3_R

<400> SEQUENCE: 596
ctgtccccag aacaggagta tag                                         23

<210> SEQ ID NO 597
<211> LENGTH: 24
<212> TYPE: DNA
<213> ORGANISM: Artificial Sequence
<220> FEATURE:
<223> OTHER INFORMATION: Reverse Primer CD47-EXON9_10_11_R
```

-continued

```
<400> SEQUENCE: 597
cctttcacgt cttactactc tcca                                          24

<210> SEQ ID NO 598
<211> LENGTH: 21
<212> TYPE: DNA
<213> ORGANISM: Artificial Sequence
<220> FEATURE:
<223> OTHER INFORMATION: Reverse Primer LAG3-EXON2_R

<400> SEQUENCE: 598
cagaaggctg agatcctgga g                                             21

<210> SEQ ID NO 599
<211> LENGTH: 20
<212> TYPE: DNA
<213> ORGANISM: Artificial Sequence
<220> FEATURE:
<223> OTHER INFORMATION: Reverse Primer LAG3-EXON8_R

<400> SEQUENCE: 599
ggttcttgct ccagctcctc                                               20

<210> SEQ ID NO 600
<211> LENGTH: 20
<212> TYPE: DNA
<213> ORGANISM: Artificial Sequence
<220> FEATURE:
<223> OTHER INFORMATION: Reverse Primer HAVCR2-EXON3_R

<400> SEQUENCE: 600
ccatgtcccc tggtggtaag                                               20

<210> SEQ ID NO 601
<211> LENGTH: 25
<212> TYPE: DNA
<213> ORGANISM: Artificial Sequence
<220> FEATURE:
<223> OTHER INFORMATION: Reverse Primer HAVCR2-EXON7_R

<400> SEQUENCE: 601
ggtatagatg ttttcttctg agcga                                         25

<210> SEQ ID NO 602
<211> LENGTH: 20
<212> TYPE: DNA
<213> ORGANISM: Artificial Sequence
<220> FEATURE:
<223> OTHER INFORMATION: Reverse Primer CD14_exon2_1R

<400> SEQUENCE: 602
cgcagcggaa atcttcatcg                                               20

<210> SEQ ID NO 603
<211> LENGTH: 20
<212> TYPE: DNA
<213> ORGANISM: Artificial Sequence
<220> FEATURE:
<223> OTHER INFORMATION: Reverse Primer CD27_exon2_1R

<400> SEQUENCE: 603
gtcaggagag aaggagaccc                                               20

<210> SEQ ID NO 604
<211> LENGTH: 22
```

```
<212> TYPE: DNA
<213> ORGANISM: Artificial Sequence
<220> FEATURE:
<223> OTHER INFORMATION: Reverse Primer CD39_exon1-2_1R

<400> SEQUENCE: 604
tcacgttaga ctcttgaaac cc                                          22

<210> SEQ ID NO 605
<211> LENGTH: 22
<212> TYPE: DNA
<213> ORGANISM: Artificial Sequence
<220> FEATURE:
<223> OTHER INFORMATION: Reverse Primer CD40_exon7_1R

<400> SEQUENCE: 605
gataaagacc agcaccaaga gg                                          22

<210> SEQ ID NO 606
<211> LENGTH: 18
<212> TYPE: DNA
<213> ORGANISM: Artificial Sequence
<220> FEATURE:
<223> OTHER INFORMATION: Reverse Primer CD70_exon1-2_2R

<400> SEQUENCE: 606
agctacgtcc cacccaag                                               18

<210> SEQ ID NO 607
<211> LENGTH: 23
<212> TYPE: DNA
<213> ORGANISM: Artificial Sequence
<220> FEATURE:
<223> OTHER INFORMATION: Reverse Primer CD80_exon1-2_1R

<400> SEQUENCE: 607
gtggatttag tttcacagct tgc                                         23

<210> SEQ ID NO 608
<211> LENGTH: 22
<212> TYPE: DNA
<213> ORGANISM: Artificial Sequence
<220> FEATURE:
<223> OTHER INFORMATION: Reverse Primer FOXP3_exon7_1R

<400> SEQUENCE: 608
tctctctctg gaggagacat tg                                          22

<210> SEQ ID NO 609
<211> LENGTH: 23
<212> TYPE: DNA
<213> ORGANISM: Artificial Sequence
<220> FEATURE:
<223> OTHER INFORMATION: Reverse Primer ICOS_exon3-4_1R

<400> SEQUENCE: 609
gcacactgga tgaatacttc ttt                                         23

<210> SEQ ID NO 610
<211> LENGTH: 20
<212> TYPE: DNA
<213> ORGANISM: Artificial Sequence
<220> FEATURE:
<223> OTHER INFORMATION: Reverse Primer ICOS_exon2_2R

<400> SEQUENCE: 610
```

```
tttgtacacc tccgttgtga                                                  20
```

<210> SEQ ID NO 611
<211> LENGTH: 22
<212> TYPE: DNA
<213> ORGANISM: Artificial Sequence
<220> FEATURE:
<223> OTHER INFORMATION: Reverse Primer TIGIT_exon3-4_1R

<400> SEQUENCE: 611

```
ggattctgag ggctttcttc tt                                               22
```

<210> SEQ ID NO 612
<211> LENGTH: 21
<212> TYPE: DNA
<213> ORGANISM: Artificial Sequence
<220> FEATURE:
<223> OTHER INFORMATION: Reverse Primer TNFRSF18_exon3-4_1R

<400> SEQUENCE: 612

```
cagcagtctg tccaaggttt g                                                21
```

<210> SEQ ID NO 613
<211> LENGTH: 18
<212> TYPE: DNA
<213> ORGANISM: Artificial Sequence
<220> FEATURE:
<223> OTHER INFORMATION: Reverse Primer VISTA_exon5_1R

<400> SEQUENCE: 613

```
aggacagggg gtgcctga                                                    18
```

<210> SEQ ID NO 614
<211> LENGTH: 20
<212> TYPE: DNA
<213> ORGANISM: Artificial Sequence
<220> FEATURE:
<223> OTHER INFORMATION: Reverse Primer VISTA_exon3_2R

<400> SEQUENCE: 614

```
ctgcctttgc ttgtagacca                                                  20
```

<210> SEQ ID NO 615
<211> LENGTH: 10
<212> TYPE: DNA
<213> ORGANISM: Artificial Sequence
<220> FEATURE:
<223> OTHER INFORMATION: Barcode sequence
<220> FEATURE:
<221> NAME/KEY: misc_feature
<222> LOCATION: (1)..(10)
<223> OTHER INFORMATION: n is a, c, g, or t

<400> SEQUENCE: 615

```
nnnnnnnnnn                                                             10
```

<210> SEQ ID NO 616
<211> LENGTH: 70
<212> TYPE: DNA
<213> ORGANISM: Artificial Sequence
<220> FEATURE:
<223> OTHER INFORMATION: Universal indexed forward primer

<400> SEQUENCE: 616

```
aatgatacgg cgaccaccga gatctacacc tagcgctaca ctctttccct acacgacgct      60
cttccgatct                                                             70
```

```
<210> SEQ ID NO 617
<211> LENGTH: 66
<212> TYPE: DNA
<213> ORGANISM: Artificial Sequence
<220> FEATURE:
<223> OTHER INFORMATION: Universal indexed reverse primer

<400> SEQUENCE: 617
caagcagaag acggcatacg agataaccgc gggtgactgg agttcagacg tgtgctcttc    60
cgatct                                                              66
```